US006869775B2

(12) United States Patent
Bertin

(10) Patent No.: US 6,869,775 B2
(45) Date of Patent: Mar. 22, 2005

(54) CARD RELATED PROTEIN AND USES THEREOF

(75) Inventor: John Bertin, Watertown, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 82 days.

(21) Appl. No.: 09/728,721

(22) Filed: Dec. 1, 2000

(65) Prior Publication Data

US 2002/0061845 A1 May 23, 2002

Related U.S. Application Data

(63) Continuation-in-part of application No. 09/340,620, filed on Jun. 28, 1999, now Pat. No. 6,482,933, which is a continuation-in-part of application No. 09/245,281, filed on Feb. 5, 1999, now Pat. No. 6,369,196, which is a continuation-in-part of application No. 09/207,359, filed on Dec. 8, 1998, now Pat. No. 6,469,140, which is a continuation-in-part of application No. 09/099,041, filed on Jun. 17, 1998, now Pat. No. 6,340,576, which is a continuation-in-part of application No. 09/019,942, filed on Feb. 6, 1998, now Pat. No. 6,033,855.

(51) Int. Cl.$^7$ .................. C07H 21/04; C12N 15/00; C12N 15/85
(52) U.S. Cl. ............ 435/69.1; 435/6; 435/320.1; 435/325; 435/252.3; 536/23.1
(58) Field of Search ................. 536/23.1; 435/6, 435/69.1, 320.1, 325, 252.3

(56) References Cited

FOREIGN PATENT DOCUMENTS

| WO | WO99/55134 | 4/1999 |
|----|-----------|--------|
| WO | WO 99/40102 | 8/1999 |
| WO | WO 00/06728 | 2/2000 |
| WO | WO 01/00826 A2 | 1/2001 |

OTHER PUBLICATIONS

Conway et al., "TMS1, a Novel Proapoptotic Caspase Recruitment Domain Protein, Is a Target of Methylation–induced Gene Silencing in Human Breast Cancers," Cancer Research 60:6236–6242 (2000).
McConnell et al., "Activation of a Caspase–9–mediated Apoptotic Pathway by Subcellular Redistribution of the Novel Caspase Recruitment Domain Protein TMS1, " Cancer Research 60:6243–6247 (2000).
Srinivasula et al., "The Pyrin–CARD Protein ASC Is an Activating Adaptor for Caspase–1," J. Biological Chemistry 277(24):21119–21122 (2002).
Accession No. AB032249 (Oct. 14, 2000).
Accession No. AF184072 (Aug. 22, 2000).
Accession No. AF184073 (Aug. 22, 2000).
Accession No. AF310103 (Nov. 6, 2000).
Accession No. AF310104 (Nov. 6, 2000).
Accession No. BF302423 (Nov. 23, 2000).
Bertin et al., Human CARD4 Protein Is A Novel CED–4/Apaf–1 Cell Death Family Member . . . J. of Biol. Chem. 274:12955–12958, 1999.

Inohara et al., "NOD1, an Apaf–1 like Activator of Caspase–9 and Nuclear Factor kB" J. of Biol. Chem. 274:14560–14567, 1999.
Marra et al., EMBL Accession No. AA620157, Sep. 12, 1996.
Baker et al., "Transducers of life and death: TNF receptor superfamily and associated proteins" Oncogene 12:1–9, 1996.
Chinnaiyan et al., "The cell–death machine" Current Biology 6:555–562, 1996.
Duan et al., "RAIDD is a new death adaptor molecule" Nature 385:86–89, 1997.
Epstein, F., "Nuclear factor–kB–A pivotal transcription factor in chronic inflammatory diseases" The New England J. of Medicine 336:1066–1071, 1997.
Hofman et al., "The CARD domain: a new apoptotic signalling motif" TIBS 22:155–156, 1997.
Hu et al., "Bcl–X$^L$ interacts with Apaf–1 and inhibits Apaf–1–dependent caspase–9 activation" Proc. Nat'l. Acad. Sci. USA 95:4386–4391, 1998.
Humke et al., "Iceberg: A Novel Inhibitor of Interleukin–1β Generation" Cell 103:99–111, Sep. 29, 2000.
Inohara et al., "Rick, a novel protein kinase conataining a caspase recruitment domain, interacts with . . . " J. of Biol. Chem. 273(20):12296–12300, 1998.
Li et al., "Cytochrome c and dATP–dependent formation of Apaf–1/caspase–9 complex initiates and apoptotic protease cascade" Cell 91:479–489, 1997.
Masumoto et al., "ASC, a Novel 22–kDa Protein, Aggregates During Apoptosis of . . . " J. of Biol. Chem. 274(48):33835–33838, 1999.

(List continued on next page.)

Primary Examiner—Sean McGarry
(74) Attorney, Agent, or Firm—Fish & Richardson P.C.

(57) ABSTRACT

Novel CARD-3, CARD-4L, CARD-4S, CARD-4Y, CARD-4Z, CARD-5, and CARD-6 polypeptides, proteins, and nucleic acid molecules are disclosed. In addition to isolated CARD-3, CARD-4L, CARD-4S, CARD-4Y, CARD-4Z, CARD-5, and CARD-6 proteins, and the invention further provides CARD-3, CARD-4L, CARD-4S, CARD-4Y, CARD-4Z, CARD-5, and CARD-6 fusion proteins, antigenic peptides and anti-CARD-3, anti-CARD-4L and anti-CARD-4S, anti-CARD-4Y, anti-CARD-4Z, anti-CARD-5, and anti-CARD-6 antibodies. The invention also provides CARD-3, CARD-4L, CARD-4S, CARD-4Y, CARD-4Z, CARD-5, and CARD-6 nucleic acid molecules, recombinant expression vectors containing a nucleic acid molecule of the invention, host cells into which the expression vectors have been introduced and non-human transgenic animals in which a CARD-3, CARD-4L, CARD-4S, CARD-4Y, CARD-4Z, CARD-5, and CARD-6 gene has been introduced or disrupted. Diagnostic, screening and therapeutic methods utilizing compositions of the invention are also provided.

32 Claims, 58 Drawing Sheets

OTHER PUBLICATIONS

McCarthy et al., "RIP2 is a novel NF–kB–activating and cell death–inducing kinase" J. of Biol. Chem. 273(27): 16968–16975, 1998.

Miura et al., "Induction of apoptosis in fibroblasts by IL–1β–converting enzyme, a mammalian homolog . . . " Cell 75:653–660, 1993.

Navab et al., "Pathogenesis of Atherosclerosis" American J. of Cardiology 76:18c–23c, 1995.

Reed, J., "Cytochrome c: Can't live with it–Can't live without it" Cell 91:559–562, 1997.

Wallach, D., "Cell death induction by TNF: a matter of self control" TIBS 22:107–109, 1997.

Yan et al., "mE10, a novel caspase recruitment domain–containing proapoptotic molecule" J. of Bio. Chem. 274(15)10287–10292, 1999.

GenBank Accession No. AA160647, Hillier et al., Dec. 1996.

GenBank Accession No. AA160649, Hillier et al., Dec. 1996.

GenBank Accession No. AA278825, Strausberg, Aug. 15, 1997.

GenBank Accession No. AA302352, Kerlavage, Apr. 18, 1997.

GenBank Accession No. AA528254, Strausberg, Aug. 5, 1997.

GenBank Accession No. AA573948, Strausberg, Sep. 12, 1997.

GenBank Accession No. AA582937, Strausberg, Sep. 26, 1997.

GenBank Accession No. AA723533, Hillier et al., Jan. 1998.

GenBank Accession No. AB023416, Masumoto et al., Dec. 1, 1999.

GenBank Accession No. AI148558, Strausberg, Oct. 28, 1998.

GenBank Accession No. AI262374, Strausberg, Nov. 13, 1998.

GenBank Accession No. AI346818, Strausberg, Feb. 2, 1999.

GenBank Accession No. AI570067, Strausberg, May 14, 19999.

GenBank Accession No. AI587178, Strausberg, May 14, 1999.

GenBank Accession No. AI821342, Strausberg, Jul. 9, 1999.

GenBank Accession No. AW192194, Strausberg, Nov. 29, 1999.

GenBank Accession No. AW196663, Strausberg, Nov. 29, 1999.

GenBank Accession No. R84288, Wilson, Aug. 14, 1995.

```
CCACGCGTCCGGTCAGTCTCTGGTTCGGAGAAGCAGCGCTGGCGCTGGCCATCCGGGAATGGGC
GCCCTCGTGACCTAGTGTTGCGGGGTGGAGCGTCTTGCCGGCCTCGCTCGTGCAGGGCGTAT
CTGGGCGCCCTGAGCGCGGCGGGGACCATGAACGGGAGGCCATCTGCAGGGCCTGCCACCGGAACCG
GCCTGAGCGCCCGGACCTGCGCTACCTGGAGCCGGGCCCTCTGCAGTGTCTGCCCGCCACG
CAAACTCGCCGACCTGCCTGCCAGTGGCCGCGTGAAGCACCTGCACATCCACACTCCGCTGTCGTCCGCCACG
CAGACTGGCGCGCGTCAGTGTCTTAAGAGAAGCTGAAATTTTACACAAAGCTAGATTTAGTTACATTCTTCCAAT
AGAAAGGATGTCTTAAGAGAAGCTGAAATTTTACACAAAGCTAGATTTAGTTACATTCTTCCAAT
TTTGGAATTGCAATGAGCCTGAATTTTGGGAATAGTTACTGAATACATGCCAAATGGATCAT
TAAATGAACTCCTACATAGGAAAACTGAATATCCTGATGTTGCTTGGCCATTGAGATTTCGCATC
CTGCATGAAATTGCCCTTGGTGTAAATTACCTGCACATATGACTCCTCCTTTACTTCATCATGA
CTTGAAGACTCAGAATATCTTATTGGACAATGAATTTCATGTTAAGATTGCAGATTTTGGTTTAT
CAAAGTGGCGCATGATGTCCCTCTCACAGTCAAGTAGCAAATCTCACCAGAAGGAGGGACA
ATTATCTATATGCCACCTGAAAACTATGAACCTGACAAGTGTTATCCAGAAAACAGCCAGTATCAAGCACGA
TATATATAGCTATGCAGTTATCACATGGGAAGTGTCACAAGGACATTGACCTGTTATTAAGTGAAGATGTCA
CCAATCCTTTGCAGATAATGTATATACCTCACCGAGCACGTATGATCTCTAATAGAAGTGAACCAGTTTTGAGAACATTTG
TTGCCATATGATGAAAGACCATCTTTCTTAAGACTGTTATTCAGCTAAAATGTTAATGCTAAGAAACAAAATTATCTCTGAACATACCTGTAAATCATGGTCC
TCCAGATGAAAGATAACTTTCTTGAAGCTGTATTATTCAGCTAAAATGTTAATGCTAAGAAACAAAATTATCTCTGAACATACCTGTAAATCATGGTCC
AAGAGATAACTTTCTTGAAGCTGTATTATTCAGCTAAAATGTTAATGCTAAGAAACAAAATTATCTCTGAACATACCTGTAAATCATGGTCC
GCCATTCACCTATGTGACAAGAAGAAGAAATGAATTATCTGAAATATGTGTTCTCCTGAAACTTCAAGT
ACAAGAGGAATCATGTGGATCCTCTGCAGCTCCATGAGTCCATGAAATATGTGTTCTCCTGAAACTTCAAGT
CCCTGCCAGTCCTCGAAGACAGTCTGGAAATCACAGTTGGGATAGCAATAGCAATAATCCACTCTCAACTGCAGGAAACT
CTGCATCACTGTCCTGGAAATCACAGTTGGGATAGCAATAGCAATAATCCACTCTCAACTGCAGGAAACT
CTGTGATCACAAGACCATTCCATGCTCTTCACAGCTCTGGATCCAGCAGAGTGGATCCAGGAGCTGATCATGAA
CAGAACGTCTGGAGCCTGGTATAGCCCAGAGTCGCTAACCAGTGCCCTTCGTCCAGGACTTGATCATGAA
CAAATGACAGAAGCCTGCTTAAGCCTTAGTACCAAGCCTACAAGACCTCAAAGTCAAAGTCAGACAATTACTAGACA
AGAGGACTATGAACTTGTTAGTAGCAAGAAGAATTTGCCAAAGTTATAGTACAAAAATTGAAAGATAACAACAA
CTACTGACATCCAAGGACTGTTTAGTACCAAGAAGAATTGCCAAAGTTATAGTACAAAAATTGAAAGATAACAACAA
ATGGGTCTTCAGCTTACCGGAAATATCTGTGGTTTCCAAGAGAAATGTGTTTCATAAAGGATATTTACTTCA
AATAAAAGCATGTAAGTGACTGTTTTCAAGAGAAATGTGTTTCATAAAGGATATTTATAAAA
AAAAAAAAAAAAAAAAAAAAAAAAAAAAAAAAAAAAAAAAAAA (SEQ ID NO: 1)
```

FIG. 1

| | | | | | | | | | |
|---|---|---|---|---|---|---|---|---|---|
| Met | Asn | Gly | Glu | Ala | Ile | Cys | Ser | Ala | Leu | Pro | Thr | Ile | Pro | Tyr | His | Lys | Leu | Ala | Asp | 20
| Leu | Arg | Tyr | Leu | Ser | Arg | Val | Lys | Gly | Ala | Ser | Gly | Thr | Val | Ser | Ala | Arg | His | Ala | Asp | Trp | 40
| Arg | Val | Gln | Val | Ala | Val | Lys | His | Leu | His | Ile | His | Thr | Pro | Leu | Leu | Asp | Ser | Glu | Arg | 60
| Lys | Asp | Val | Leu | Arg | Glu | Ala | Glu | Ile | Leu | His | Lys | Ala | Arg | Phe | Ser | Tyr | Ile | Leu | Pro | 80
| Ile | Leu | Gly | Ile | Cys | Asn | Glu | Pro | Glu | Phe | Leu | Gly | Ile | Val | Thr | Glu | Tyr | Met | Pro | Asn | 100
| Gly | Ser | Leu | Asn | Glu | Leu | Leu | His | Arg | Lys | Thr | Glu | Tyr | Pro | Asp | Val | Ala | Trp | Pro | Leu | 120
| Arg | Phe | Arg | Ile | Leu | His | Glu | Ile | Ala | Leu | Gly | Val | Asn | Tyr | Leu | His | Asn | Met | Thr | Pro | 140
| Pro | Leu | Leu | His | His | Asp | Leu | Lys | Thr | Gln | Asn | Ile | Leu | Leu | Asp | Asn | Glu | Phe | His | Val | 160
| Lys | Ile | Ala | Asp | Phe | Gly | Leu | Ser | Lys | Trp | Arg | Met | Met | Ser | Leu | Ser | Gln | Ser | Arg | Ser | 180
| Ser | Lys | Ser | Ala | Pro | Glu | Gly | Gly | Thr | Ile | Ile | Tyr | Met | Pro | Pro | Glu | Asn | Tyr | Glu | Pro | 200
| Gly | Gln | Lys | Ser | Arg | Ala | Ser | Ile | Lys | His | Asp | Ile | Tyr | Ser | Tyr | Ala | Val | Ile | Thr | Trp | 220
| Glu | Val | Leu | Ser | Arg | Lys | Gln | Pro | Phe | Glu | Asp | Val | Thr | Asn | Pro | Leu | Gln | Ile | Met | Tyr | 240
| Ser | Val | Ser | Gln | Gly | His | Arg | Pro | Val | Ile | Asn | Glu | Glu | Ser | Leu | Pro | Tyr | Asp | Ile | Pro | 260
| His | Arg | Ala | Arg | Met | Ile | Ser | Leu | Ile | Glu | Ser | Gly | Trp | Ala | Gln | Asn | Pro | Asp | Glu | Arg | 280
| Pro | Ser | Phe | Leu | Lys | Cys | Leu | Ile | Glu | Leu | Glu | Pro | Val | Leu | Arg | Thr | Phe | Glu | Glu | Ile | 300
| Thr | Phe | Leu | Glu | Ala | Val | Ile | Gln | Leu | Lys | Lys | Thr | Lys | Leu | Gln | Ser | Val | Ser | Ser | Ala | 320
| Ile | His | Leu | Cys | Asp | Lys | Lys | Lys | Met | Glu | Leu | Ser | Leu | Asn | Ile | Pro | Val | Asn | His | Gly | 340
| Pro | Gln | Glu | Glu | Ser | Cys | Gly | Ser | Ser | Gln | Leu | His | Glu | Asn | Ser | Gly | Ser | Pro | Glu | Thr | 360
| Ser | Arg | Ser | Leu | Pro | Ala | Pro | Gln | Asp | Asn | Asp | Phe | Leu | Ser | Arg | Lys | Ala | Gln | Asp | Cys | 380
| Tyr | Phe | Met | Lys | Leu | His | His | Cys | Pro | Gly | Asn | His | Ser | Trp | Asp | Ser | Thr | Ile | Ser | Gly | 400
| Ser | Gln | Arg | Ala | Ala | Phe | Cys | Asp | His | Lys | Thr | Ile | Pro | Cys | Ser | Ser | Ala | Ile | Ile | Asn | 420
| Pro | Leu | Ser | Thr | Ala | Gly | Asn | Ser | Glu | Arg | Leu | Gln | Pro | Gly | Ile | Ala | Gln | Gln | Trp | Ile | 440
| Gln | Ser | Lys | Arg | Glu | Asp | Ile | Val | Asn | Gln | Met | Thr | Glu | Ala | Cys | Leu | Asn | Gln | Ser | Leu | 460
| Asp | Ala | Leu | Leu | Ser | Arg | Asp | Leu | Ile | Met | Lys | Glu | Asp | Tyr | Glu | Leu | Val | Ser | Thr | Lys | 480
| Pro | Thr | Arg | Thr | Ser | Lys | Val | Arg | Gln | Leu | Leu | Asp | Thr | Thr | Asp | Ile | Gln | Gly | Glu | Glu | 500
| Phe | Ala | Lys | Val | Ile | Val | Gln | Lys | Leu | Lys | Asp | Asn | Lys | Gln | Met | Gly | Leu | Gln | Pro | Tyr | 520
| Pro | Glu | Ile | Leu | Val | Val | Ser | Arg | Ser | Pro | Ser | Leu | Asn | Leu | Leu | Gln | Asn | Lys | Ser | Met | 540

(SEQ ID NO: 2)

FIG. 2

```
TTTTTATGGG AATCGCAGCT TGGAAGAGAC AGARCAATTC CAGAAWTAAA TTGRAATTGA
AGATTTAACC AATGTTGTTT TAAAATATTC TAACTTCAAA GAATGATGCC AGAACTTWAA
AAGGGRCTGC GCAGAGTAGC AGGGGCCCTG GAGGGCGCGG CCTGAATCCT GATTGCCCTT
CTGCTGAGAG GACACACGCA GCTGAAGATG AATTTGGGAA AAGTAGCCGC TTGCTACTTT
AACTATGGAA GAGCAGGGCC ACAGTGAGAT GGAAATAATC CCATCAGAGT CTCACCCCCA
CATTCAATTA CTGAAAAGCA ATCGGGAACT TCTGGTCACT CACATCCGCA ATACTCAGTG
TCTGGTGGAC AACTTGCTGA AGAATGACTA CTTCTCGGCC GAAGATGCGG AGATTGTGTG
TGCCTGCCCC ACCCAGCCTG ACAAGGTCCG CAAAATTCTG GACCTGGTAC AGAGCAAGGG
CGAGGAGGTG TCCGAGTTCT TCCTCTACTT GCTCCAGCAA CTCGCAGATG CCTACGTGGA
CCTCAGGCCT TGGCTGCTGG AGATCGGCTT CTCCCCTTCC CTGCTCACTC AGAGCAAAGT
CGTGGTCAAC ACTGACCCAG TGAGCAGGTA TACCCAGCAG CTGCGACACC ATCTGGGCCG
TGACTCCAAG TTCGTGCTGT GCTATGCCCA GAAGGAGGAG CTGCTGCTGG AGGAGATCTA
CATGGACACC ATCATGGAGC TGGTTGGCTT CAGCAATGAG AGCCTGGGCA GCCTGAACAG
CCTGGCCTGC CTCCTGGACC ACACCACCGG CATCCTCAAT GAGCAGGGTG AGACCATCTT
CATCCTGGGT GATGCTGGGG TGGGCAAGTC CATGCTGCTA CAGCGGCTGC AGAGCCTCTG
GGCCACGGGC CGGCTAGACG CAGGGGTCAA ATTCTTCTTC CACTTTCGCT GCCGCATGTT
CAGCTGCTTC AAGGAAAGTG ACAGGCTGTG TCTGCAGGAC CTGCTCTTCA GCACTACTG
CTACCCAGAG CGGGACCCCG AGGAGGTGTT TGCCTTCCTG CTGCGCTTCC CCACGTGGC
CCTCTTCACC TTCGATGGCC TGGACGAGCT GCACTCGGAC TTGGACCTGA GCCGCGTGCC
TGACAGCTCC TGCCCCTGGG AGCCTGCCCA CCCCCTGGTC TTGCTGGCCA ACCTGCTCAG
TGGGAAGCTG CTCAAGGGGG CTAGCAAGCT GCTCACAGCC CGCACAGGCA TCGAGGTCCC
GCGCCAGTTC CTGCGGAAGA AGGTGCTTCT CCGGGGCTTC TCCCCAGCC ACCTGCGCGC
CTATGCCAGG AGGATGTTCC CCGAGCGGGC CCTGCAGGAC CGCCTGCTGA GCCAGCTGGA
GGCCAACCCC AACCTCTGCA GCCTGTGCTC TGTGCCCCTC TTCTGCTGGA TCATCTTCCG
GTGCTTCCAG CACTTCCGTG CTGCCTTTGA AGGCTCACCA CAGCTGCCCG ACTGCACGAT
GACCCTGACA GATGTCTTCC TCCTGGTCAC TGAGGTCCAT CTGAACAGGA TGCAGCCCAG
CAGCCTGGTG CAGCGGAACA CACGCAGCCC AGTGGAGACC CTCCACGCCG GCCGGGACAC
TCTGTGCTCG CTGGGGCAGG TGGCCCACCG GGGCATGGAG AAGAGCCTCT TTGTCTTCAC
CCAGGAGGAG GTGCAGGCCT CCGGGCTGCA GGAGAGAGAC ATGCAGCTGG GCTTCCTGCG
GGCTTTGCCG GAGCTGGGCC CCGGGGGTGA CCAGCAGTCC TATGAGTTTT TCCACCTCAC
CCTCCAGGCC TTCTTTACAG CCTTCTTCCT CGTGCTGGAC GACAGGGTGG GCACTCAGGA
GCTGCTCAGG TTCTTCCAGG AGTGGATGCC CCCTGCGGGG GCAGCGACCA CGTCCTGCTA
```

FIG. 3A

```
TCCTCCCTTC CTCCCGTTCC AGTGCCTGCA GGGCAGTGGT CCGGCGCGGG AAGACCTCTT
CAAGAACAAG GATCACTTCC AGTTCACCAA CCTCTTCCTG TGCGGGCTGT TGTCCAAAGC
CAAACAGAAA CTCCTGCGGC ATCTGGTGCC CGCGGCAGCC CTGAGGAGAA AGCGCAAGGC
CCTGTGGGCA CACCTGTTTT CCAGCCTGCG GGCTACCTG AAGAGCCTGC CCGCGTTCA
GGTCGAAAGC TTCAACCAGG TGCAGGCCAT GCCCACGTTC ATCTGGATGC TGCGCTGCAT
CTACGAGACA CAGAGCCAGA AGGTGGGGCA GCTGGCGGCC AGGGGCATCT GCGCCAACTA
CCTCAAGCTG ACCTACTGCA ACGCCTGCTC GGCCGACTGC AGCGCCCTCT CCTTCGTCCT
GCATCACTTC CCCAAGCGGC TGGCCCTAGA CCTAGACAAC AACAATCTCA ACGACTACGG
CGTGCGGGAG CTGCAGCCCT GCTTCAGCCG CCTCACTGTT CTCAGACTCA GCGTAAACCA
GATCACTGAC GGTGGGGTAA AGGTGCTAAG CGAAGAGCTG ACCAAATACA AAATTGTGAC
CTATTTGGGT TTATACAACA ACCAGATCAC CGATGTCGGA GCCAGGTACG TCACCAAAAT
CCTGGATGAA TGCAAAGGCC TCACGCATCT TAAACTGGGA AAAAACAAAA TAACAAGTGA
AGGAGGGAAG TATCTCGCCC TGGCTGTGAA GAACAGCAAA TCAATCTCTG AGGTTGGGAT
GTGGGGCAAT CAAGTTGGGG ATGAAGGAGC AAAAGCCTTC GCAGAGGCTC TGCGGAACCA
CCCCAGCTTG ACCACCCTGA GTCTTGCGTC CAACGGCATC TCCACAGAAG GAGGAAAGAG
CCTTGCGAGG GCCCTGCAGC AGAACACGTC TCTAGAAATA CTGTGGCTGA CCCAAAATGA
ACTCAACGAT GAAGTGGCAG AGAGTTTGGC AGAAATGTTG AAAGTCAACC AGACGTTAAA
GCATTTATGG CTTATCCAGA ATCAGATCAC AGCTAAGGGG ACTGCCCAGC TGGCAGATGC
GTTACAGAGC AACACTGGCA TAACAGAGAT TTGCCTAAAT GGAAACCTGA TAAAACCAGA
GGAGGCCAAA GTCTATGAAG ATGAGAAGCG GATTATCTGT TTCTGAGAGG ATGCTTTCCT
GTTCATGGGG TTTTTGCCCT GGAGCCTCAG CAGCAAATGC CACTCTGGGC AGTCTTTTGT
GTCAGTGTCT TAAAGGGGCC TGCGCAGGCG GGACTATCAG GAGTCCACTG CCTYCATGAT
GCAAGCCAGC TTCCTGTGCA GAAGGTCTGG TCGGCAAACT CCCTAAGTAC CCGCTACAAT
TCTGCAGAAA AAGAATGTGT CTTGCGAGCT GTTGTAGTTA CAGTAAATAC ACTGTGAAGA
GAAAAAAAAA ACGGACGCGT GG   (SEQ ID NO: 7)
```

FIG. 3B

MEEQGHSEMEIIPSESHPHIQLLKSNRELLVTHIRNTQCLVDNLLKNDYFSAEDAEIVCACPTQP

DKVRKILDLVQSKGEEVSEFFLYLLQQLADAYVDLRPWLLEIGFSPSLLTQSKVVVNTDPVSRYT

QQLRHHLGRDSKFVLCYAQKEELLLEEIYMDTIMELVGFSNESLGSLNSLACLLDHTTGILNEQG

ETIFILGDAGVGKSMLLQRLQSLWATGRLDAGVKFFFHFRCRMFSCFKESDRLCLQDLLFKHYCY

PERDPEEVFAFLLRFPHVALFTFDGLDELHSDLDLSRVPDSSCPWEPAHPLVLLANLLSGKLLKG

ASKLLTARTGIEVPRQFLRKKVLLRGFSPSHLRAYARRMFPERALQDRLLSQLEANPNLCSLCSV

PLFCWIIPRCFQHFRAAFEGSPQLPDCTMTLTDVFLLVTEVHLNRMQPSSLVQRNTRSPVETLHA

GRDTLCSLGQVAHRGMEKSLFVFTQEEVQASGLQERDMQLGFLRALPELGPGGDQQSYEFFHLTL

QAFFTAFFLVLDDRVGTQELLRFFQEWMPPAGAATTSCYPPFLPFQCLQGSPAREDLFKNKDHF

QFTNLFLCGLLSKAKQKLLRHLVPAAALRRKRKALWAHLFSSLRGYLKSLPRVQVESFNQVQAMP

TFIWMLRCIYETQSQKVGQLAARGICANYLKLTYCNACSADCSALSFVLHHFPKRLALDLDNNNL

NDYGVRELQPCFSRLTVLRLSVNQITDGGVKVLSEELTKYKIVTYLGLYNNQITDVGARYVTKIL

DECKGLTHLKLGKNKITSEGGKYLALAVKNSKSISEVGMWGNQVGDEGAKAFAEALRNHPSLTTL

SLASNGISTEGGKSLARALQQNTSLEILWLTQNELNDEVAESLAEMLKVNQTLKHLWLIQNQITA

KGTAQLADALQSNTGITEICICLNGNLIKPEEAKVYEDEKRIICF (SEQ ID NO: 8) FIG. 4

```
CACGCGTCCGACTTGCTGAAGAATGACTACTTCTCGGCCGAAGATGCGGAGATTGTGT
GTGCCTGCCCCACCCAGCCTGACAAGGTCCGCAAAATTCTGGACCTGGTACAGAGCAAG
GGCGAGGAGGTGTCCGAGTTCTTCCTCTACTTGCTCCAGCAACTCGCAGATGCCTACGT
GGACCTCAGGCCTTGGCTGCTGGAGATCGGCTTCTCCCCTTCCCTGCTCACTCAGAGCA
AAGTCGTGGTCAACACTGACCCAGTGAGCAGGTATACCCAGCAGCTGCGACACCATCTG
GGCCGTGACTCCAAGTTCGTGCTGTGCTATGCCCAGAAGGAGGAGCTGCTGCTGGAGGA
GATCTACATGGACACCATCATGGAGCTGGTTGGCTTCAGCAATGAGAGCCTGGGCAGCC
TGAACAGCCTGGCCTGCCTCCTGGACCACACCACCGGCATCCTCAATGAGCAGGGTGAG
ACCATCTTCATCCTGGGTGATGCTGGGGTGGGCAAGTCCATGCTGCTACAGCGGCTGCA
GAGCCTCTGGGCCACGGGCCGGCTAGACGCAGGGGTCAAATTCTTCTTCCACTTTCGCT
GCCGCATGTTCAGCTGCTTCAAGGAAAGTGACAGGCTGTGTCTGCAGGACCTGCTCTTC
AAGCACTACTGCTACCCAGAGCGGGACCCCGAGGAGGTGTTTGCCTTCCTGCTGCGCTT
CCCCCACGTGGCCCTCTTCACCTTCGATGGCCTGGACGAGCTGCACTCGGACTTGGACC
TGAGCCGCGTGCCTGACAGCTCCTGCCCCTGGGAGCCTGCCCACCCCTGGTCTTGCTG
GCCAACCTGCTCAGTGGGAAGCTGCTCAAGGGGCTAGCAAGCTGCTCACAGCCCGCAC
AGGCATCGAGGTCCCGCGCCAGTTCCTGCGGAAGAAGGTGCTTCTCCGGGGCTTCTCCC
CCAGCCACCTGCGCGCCTATGCCAGGAGGATGTTCCCGAGCGGGCCCTGCAGGACCGC
CTGCTGAGCCAGCTGGAGGCCAACCCCAACCTCTGCAGCCTGTGCTCTGTGCCCCTCTT
CTGCTGGATCATCTTCCGGTGCTTCCAGCACTTCCGTGCTGCCTTTGAAGGCTCACCAC
AGCTGCCCGACTGCACGATGACCCTGACAGATGTCTTCCTCCTGGTCACTGAGGTCCAT
CTGAACAGGATGCAGCCCAGCAGCCTGGTGCAGCGGAACACACGCAGCCCAGTGGAGAC
CCTCCACGCCGGCCGGGACACTCTGTGCTCGCTGGGGCAGGTGGCCCACCGGGGCATGG
AGAAGAGCCTCTTTGTCTTCACCCAGGAGGAGGTGCAGGCCTCCGGGCTGCAGGAGAGA
GACATGCAGCTGGGCTTCCTGCGGGCTTTGCCGGAGCTGGGCCCCGGGGGTGACCAGCA
GTCCTATGAGTTTTTCCACCTCAGCCTCCTCACCTGTAAAACTGGGATCCCAGTATAGA
CTTTGGAAATCAGTAGACACCATATGCTTCAAAAAACAGGGGCTATTAAAATGACATCA
GGAGCCAGAAAGTCTCATGGCTGTGCTTTCTCTTGAAGTTTATACAACAACCAGATCAC
CGATGTCGGAGCCAGACTGGGAAAAAACAAAATAACAAGTGAAGGAGGGAAGTATCTCG
CCCTGGCTGTGAAGAACAGCAAATCAATCTCTGAGGTTGGGATGTGGGGCAATCAAGTT
GGGGATGAAGGAGCAAAAGCCTTCGCAGAGGCTCTGCGGAACCACCCCAGCTTGACCAC
CCTGAGTCTTGCGTCCAACGGCATCTCCACAGAAGGAGGAAAGAGCCTTGCGAGGGCCC
TGCAGCAGAACACGTCTCTAGAAATACTGTGGCTGACCCAAAATGAACTCAACGATGAA
GTGGCAGAGAGTTTGGCAGAAATGTTGAAAGTCAACCAGACGTTAAAGCATTTATGGCT
TATCCAGAATCAGATCACAGTCTTTTGTGTCAGTGTCTTAAAGGGGCCTGCGCAGGCGG
GACTATCAGGAGTCCACTGCCTCCATGATGCAAGCCAGCTTCCTGTGCAGAAGGTCTGG
TCGGCAAACTCCCTAAGTACCCGCTACAATTCTGCAGAAAAAGAATGTGTCTTGCGAGC
TGTTGTAGTTACAGTAAATACACTGTGAAGAGACTTTATTGCCTATTATAATTATTTTT
ATCTGAAGCTAGAGGAATAAAGCTGTGAGCAAACAGAGGAGGCCAGCCTCACCTCATTC
CAACACCTGCCATAGGGACCAACGGGAGCGAGTTGGTCACCGCTCTTTTCATTGAAGAG
TTGAGGATGTGGCACAAAGTTGGTGCCAAGCTTCTTGAATAAAACGTGTTTGATGGATT
AGTATTATACCTGAAATATTTTCTTCCTTCTCAGCACTTTCCATGTATTGATACTGGT
CCCACTTCACAGCTGGAGACACCGGAGTATGTGCAGTGTGGGATTTGACTCCTCCAAGG
TTTTGTGGAAAGTTAATGTCAAGGAAAGGATGCACCACGGGCTTTTAATTTTAATCCTG
GAGTCTCACTGTCTGCTGGCAAAGATAGAGAATGCCCTCAGCTCTTAGCTGGTCTAAGA
ATGACGATGCCTTCAAAATGCTGCTTCCACTCAGGGCTTCTCCTCTGCTAGGCTACCCT
CCTCTAGAAGGCTGAGTACCATGGGCTACAGTGTCTGGCCTTGGGAAGAAGTGATTCTG
TCCCTCCAAAGAAATAGGGCATGGCTTGCCCCTGTGGCCCTGGCATCCAAATGGCTGCT
TTTGTCTCCCTTACCTCGTGAAGAGGGGAAGTCTCTTCCTGCCTCCCAAGCAGCTGAAG
GGTGACTAAACGGGCGCCAAGACTCAGGGGATCGGCTGGGAACTGGGCCAGCAGAGCAT
GTTGGACACCCCCACCATGGTGGGCTTGTGGTGGCTGCTCCATGAGGGTGGGGGTGAT
ACTACTAGATCACTTGTCCTCTTGCCAGCTCATTTGTTAATAAAATACTGAAAACACAA
AAAAAAAAAAAAAAAAAAAAAAAAAAAAAAAAAAAAAAAAAAAAAAAAAAAAAAAAAAA
AAAAAAAAAAAAA (SEQ ID NO: 25)
```

FIG. 5

HASDLLKNDYFSAEDAEIVCACPTQPDKVRKILDLVQSKGEEVSEFFLYLL
QQLADAYVDLRPWLLEIGFSPSLLTQSKVVVNTDPVSRYTQQLRHHLGRDS
KFVLCYAQKEELLLEEIYMDTIMELVGFSNESLGSLNSLACLLDHTTGILN
EQGETIFILGDAGVGKSMLLQRLQSLWATGRLDAGVKFFHFRCRMFSCFK
ESDRLCLQDLLFKHYCYPERDPEEVFAFLLRFPHVALFTFDGLDELHSDLD
LSRVPDSSCPWEPAHPLVLLANLLSGKLLKGASKLLTARTGIEVPRQFLRK
KVLLRGFSPSHLRAYARRMFPERALQDRLLSQLEANPNLCSLCSVPLFCWI
IFRCFQHFRAAFEGSPQLPDCTMTLTDVFLLVTEVHLNRMQPSSLVQRNTR
SPVETLHAGRDTLCSLGQVAHRGMEKSLFVFTQEEVQASGLQERDMQLGFL
RALPELGPGGDQQSYEFFHLSLLTCKTGIPV (SEQ ID NO: 26)

```
CCCGCGTCCGCGTCCCCGGACCATGGCGCTCTCCGGGCTCTTCTCTAGCTCTCAGCGGCT
GCGAAGTCTGTNAACCTGGTGGCCAAGTGATTGTAAGTCAGGAGACTTTCCTTCGGTTTC
TGCCTTTGATGGCAAGAGGTGGAGATTGTGGCGGCGATTACAGAAAACATCTGGGAAGAC
AAGTTGCTGTTTTTATGGGAATCGCAGGCTTGGAAGAGACAGAAGCAATTCCAGAAATAA
ATTGGAAATTGAAGATTTAAACAATGTTGTTTTAAAATATTCTAACTTCAAAGAATGATG
CCAGAAACTTAAAAAGGGGCTGCGCAGAGTAGCAGGGGCCCTGGAGGGCGCGGCCTGAAT
CCTGATTGCCCTTCTGCTGAGAGGACACACGCAGCTGAAGATGAATTTGGGAAAAGTAGC
CGCTTGCTACTTTAACTATGGAAGAGCAGGGCCACAGTGAGATGGAAATAATCCCATCAG
AGTCTCACCCCACATTCAATTACTGAAAAGCAATCGGGAACTTCTGGTCACTCACATCC
GCAATACTCAGTGTCTGGTGGACAACTTGCTGAAGAATGACTACTTCTCGGCCGAAGATG
CGGAGATTGTGTGTGCCTGCCCCACCCAGCCTGACAAGGTCCGCAAAATTCTGGACCTGG
TACAGAGCAAGGGCGAGGAGGTGTCCGAGTTCTTCCTCTACTTGCTCCAGCAACTCGCAG
ATGCCTACGTGGACCTCAGGCCTTGGCTGCTGGAGATCGGCTTCTCCCCTTCCCTGCTCA
CTCAGAGCAAAGTCGTGGTCAACACTGACCCAGTGAGCAGGTATACCCAGCAGCTGCGAC
ACCATCTGGGCCGTGACTCCAAGTTCGTGCTGTGCTATGCCCAGAAGGAGGAGCTGCTGC
TGGAGGAGATCTACATGGACACCATCATGGAGCTGGTTGGCTTCAGCAATGAGAGCCTGG
GCAGCCTGAACAGCCTGGCCTGCCTCCTGGACCACACCACCGGCATCCTCAATGAGCAGG
CTGCTTCAAGGAAAGTGACAGGCTGTGTCTGCAGGACCTGCTCTTCAAGCACTACTGCTA
CCCAGAGCGGGACCCCGAGGAGGTGTTTGCCTTCCTGCTGCGCTTCCCCCACGTGGCCCT
CTTCACCTTCGATGGCCTGGACGAGCTGCACTCGGACTTGGACCTGAGCCGCGTGCCTGA
CAGCTCCTGCCCCTGGGAGCCTGCCCACCCCCTGGTCTTGCTGGCCAACCTGCTCAGTGG
GAAGCTGCTCAAGGGGGCTAGCAAGCTGCTCACAGCCCGCACAGGCATCGAGGTCCCGCG
CCAGTTCCTGCGGAAGAAGGTGCTTCTCCGGGGCTTCTCCCCCAGCCACCTGCGCGCCTA
TGCCAGGAGGATGTTCCCCGAGCGGGCCCTGCAGGACCGCCTGCTGAGCCAGCTGGAGGC
CAACCCCAACCTCTGCAGCCTGTGCTCTGTGCCCCTCTTCTGCTGGATCATCTTCCGGTG
CTTCCAGCACTTCCGTGCTGCCTTTGAAGGCTCACCACAGCTGCCCGACTGCACGATGAC
CCTGACAGATGTCTTCCTCCTGGTCACTGAGGTCCATCTGAACAGGATGCAGCCCAGCAG
CCTGGTGCAGCGGAACACACGCAGCCCAGTGGAGACCCTCCACGCCGGCCGGGACACTCT
GTGCTCGCTGGGGCAGGTGGCCCACCGGGGCATGGAGAAGAGCCTCTTTGTCTTCACCCA
GGAGGAGGTGCAGGCCTCCGGGCTGCAGGAGAGAGACATGCAGCTGGGCTTCCTGCGGGC
TTTGCCGGAGCTGGGCCCCGGGGGTGACCAGCAGTCCTATGAGTTTTTCCACCTCACCCT
```

FIG. 10A

```
CCAGGCCTTCTTTACAGCCTTCTTCCTCGTGCTGGACGACAGGGTGGGCACTCAGGAGCT
GCTCAGGTTCTTCCAGGAGTGGATGCCCCTGCGGGGGCAGCGACCACGTCCTGCTATCC
TCCCTTCCTCCCGTTCCAGTGCCTGCAGGGCAGTGGTCCGGCGCGGGAAGACCTCTTCAA
GAACAAGGATCACTTCCAGTTCACCAACCTCTTCCTGTGCGGGCTGTTGKCCAAAGCCAA
ACAGAAACTCCTGCGGCATCTGGTGCCCGCGGCAGCCCTGAGGAGAAAGCGCAAGGCCCT
GTGGGCACACCTGTTTTCCAGCCTGCGGGGCTACCTGAAGAGCCTGCCCCGCGTTCAGGT
CGAAAGCTTCAACCAGGTGCAGGCCATGCCCACGTTCATCTGGATGCTGCGCTGCATCTA
CGAGACACAGAGCCAGAAGGTGGGGCAGCTGGCGGCCAGGGGCATCTGCGCCAACTACCT
CAAGCTGACCTACTGCAACGCCTGCTCGGCCGACTGCAGCGCCCTCTCCTTCGTCCTGCA
TCACTTCCCCAAGCGGCTGGCCCTAGACCTAGACAACAACAATCTCAACGACTACGGCGT
GCGGGAGCTGCAGCCCTGCTTCAGCCGCCTCACTGTTCTCAGACTCAGCGTAAACCAGAT
CACTGACGGTGGGGTAAAGGTGCTAAGCGAAGAGCTGACCAAATACAAAATTGTGACCTA
TTTGGGTTTATACAACAACCAGATCACCGATGTCGGAGCCAGGTACGTCACCAAAATCCT
GGATGAATGCAAAGGCCTCACGCATCTTAAACTGGGAAAAAACAAAATAACAAGTGAAGG
AGGGAAGTATCTCGCCCTGGCTGTGAAGAACAGCAAATCAATCTCTGAGGTTGGGATGTG
GGGCAATCAAGTTGGGGATGAAGGAGCAAAAGCCTTCGCAGAGGCTCTGCGGAACCACCC
CAGCTTGACCACCCTGAGTCTTGCGTCCAACGGCATCTCCACAGAAGGAGGAAAGAGCCT
TGCGAGGGCCCTGCAGCAGAACACGTCTCTAGAAATACTGTGGCTGACCCAAAATGAACT
CAACGATGAAGTGGCAGAGAGTTTGGCAGAAATGTTGAAAGTCAACCAGACGTTAAAGCA
TTTATGGCTTATCCAGAATCASATCACAGCTWARGGGACTGCCCAGCTGGCAGATGCGTT
ACAGAGCAACACTGGCATAACAGAGATTTGCCTAAATGGAAACCTGATAAAACCAGAGGA
GGCCAAAGTCTATGAAGATGAGAAGCGGATTATCTGTTTCTGAGAGGATGCTTTCCTGTT
CATGGGGTTTTTGCCCTGGAGCCTCAGCAGCAAATGCCACTYTGGGCAGTCTTTTGTGTC
AGTGTCTTAAAGGGGCCTGCGCAGGCGGGACTATCAGGAGTCCACTGCCTCCATGATGCA
AGCCAGCTTCCTGTGCAGAAGGTCTGGTCGGCAAACTCCCTAAGTACCCGCTACAATTCT
GCAGAAAAGAATGTGTCTTGCGAGCTGTTGTAGTTACAGTAAATACACTGTGAAGAGAC
TTTATTGCCTATTATAATTATTTTTATCTGAAGCTAGAGGAATAAAGCTGTGAGCAAACA
GAGGAGGCCAGCCTCACCTCATTCCAACACCTGCCATAGGGACCAACGGGAGCGAGTTGG
TCACCGCTCTTTTCATTGAAGAGTTGAGGATGTGGCACAAAGTTGGTGCCAAGCTTCTTG
AATAAAACGTGTTTGATGGATTAGTATTATACCTGAAATATTTTCTTCCTTCTCAGCACT
TTCCCATGTATTGATACTGGTCCCACTTCACAGCTGGAGACACCGGAGTATGTGCAGTGT
GGGATTTGACTCCTCCAAGGTTTTGTGGAAAGTTAATGTCAAGGAAAGGATGCACCACGG
```

FIG. 10B

```
GCTTTTAATTTTAATCCTGGAGTCTCACTGTCTGCTGGCAAAGATAGAGAATGCCCTCAG
CTCTTAGCTGGTCTAAGAATGACGATGCCTTCAAAATGCTGCTTCCACTCAGGGCTTCTC
CTCTGCTAGGCTACCCTCCTCTAGAAGGCTGAGTACCATGGGCTACAGTGTCTGGCCTTG
GGAAGAAGTGATTCTGTCCCTCCAAAGAAATAGGGCATGGCTTGCCCCTGTGGCCCTGGC
ATCCAAATGGCTGCTTTTGTCTCCCTTACCTCGTGAAGAGGGGAAGTCTCTTCCTGCCTC
CCAAGCAGCTGAAGGGTGACTAAACGGGCGCCAAGACTCAGGGGATCGGCTGGGAACTGG
GCCAGCAGAGCATGTTGGACACCCCCACCATGGTGGGCTTGTGGTGGCTGCTCCATGAG
GGTGGGGGTGATACTACTAGATCACTTGTCCTCTTGCCAGCTCATTTGTTAATAAAATAC
TGAAAACCCAAAAAAAAAAAAAAAAAAAAAAAAAAAAGGGCGG (SEQ ID NO:39)
```

FIG. 10C

```
MEEQGHSEMEIIPSESHPHIQLLKSNRELLVTHIRNTQCLVDNLLKNDYFSAEDAEIVCA
CPTQPDKVRKILDLVQSKGEEVSEFFLYLLQQLADAYVDLRPWLLEIGFSPSLLTQSKVV
VNTDPVSRYTQQLRHHLGRDSKFVLCYAQKEELLLEEIYMDTIMELVGFSNESLGSLNSL
ACLLDHTTGILNEQAASRKVTGCVCRTCSSSTTATQSGTPRRCLPSCCASPTWPSSPSMA
WTSCTRTWT (SEQ ID NO:40)
```

FIG. 11

CACGCGTCCGCGCTACTGCGGGAGCAGCGTCCTCCCGGGCCACGGCGCTTCCCGGCCCCG
GCGTCCCCGGACCATGGCGCTCTCCGGGCTCTTCTCTAGCTCTCAGCGGCTGCGAAGTCT
GTAAACCTGGTGGCCAAGTGATTGTAAGTCAGGAGACTTTCCTTCGGTTTCTGCCTTTGA
TGGCAAGAGGTGGAGATTGTGGCGGCGATTACAGAAAACATCTGGGAAGACAAGTTGCTG
TTTTTATGGGAATCGCAGGCTTGGAAGAGACAGAAGCAATTCCAGAAATAAATTGGAAAT
TGAAGATTTAAACAATGTTGTTTTAAAATATTCTAACTTCAAAGAATGATGCCAGAAACT
TAAAAAGGGGCTGCGCAGAGTAGCAGGGGCCCTGGAGGGCGCGGCCTGAATCCTGATTGC
CCTTCTGCTGAGAGGACACACGCAGCTGAAGATGAATTTGGGAAAAGTAGCCGCTTGCTA
CTTTAACTATGGAAGAGCAGGGCCACAGTGAGATGGAAATAATCCCATCAGAGTCTCACC
CCCACATTCAATTACTGAAAAGCAATCGGGAACTTCTGGTCACTCACATCCGCAATACTC
AGTGTCTGGTGGACAACTTGCTGAAGAATGACTACTTCTCGGCCGAAGATGCGGAGATTG
TGTGTGCCTGCCCCACCCAGCCTGACAAGGTCCGCAAAATTCTGGACCTGGTACAGAGCA
AGGGCGAGGAGGTGTCCGAGTTCTTCCTCTACTTGCTCCAGCAACTCGCAGATGCCTACG
TGGACCTCAGGCCTTGGCTGCTGGAGATCGGCTTCTCCCCTTCCCTGCTCACTCAGAGCA
AGTCGTGGTCAACACTGACCCAGGTAGGAGTCAGCCCAGCAAGACCGCAGGCACCAGT
GCAAGCAGGGCCCTGGGGGGTTTGGTAATGGCTGGGCCAGCCCTGAGTGCCACCTCAGGA
AGCAGGCCCAGGTGCTATTTTGATTTTAGAAAGGAACAGCTGAATCCTGTCTCCCAAGTG
CAGCCCAGGTGGCTGCGATTGAACTGCCCACACCTCGATGGTCTGGTTTATAGAGGGGCC
TTTGGAAGTATGGGAATGGCCTGTGTTCTGACCCCTTGCTTTCTTCCTATTCTGACATAT
GTAGACATTTTAATGGTTGCACAAATTCAAGGTTGTATTTTTTTTCTTTAAAAAAATCT
TTAGCTGGACATGGTAGCACACACCTGTAGTTCCAGCTACTCAGGAGGCTGAGGCAAGAG
GACTGCTTGAGCCCCAGAGTCTAAGGCTGCAGCGAGCTATGATTGTGCCCCTACACTCCA
CAGCCTGGGTTTTAGAGTGAGACCCTGTCTCTAAAAAAAAAAAAAAAAAAAAAAAAAAAAA
AAAAAAAAAAAAANGGGCGG (SEQ ID NO:41)

FIG. 12

MEEQGHSEMEIIPSESHPHIQLLKSNRELLVTHIRNTQCLVDNLLKNDYFSAEDAEIVCA
CPTQPDKVRKILDLVQSKGEEVSEFFLYLLQQLADAYVDLRPWLLEIGFSPSLLTQSKVV
VNTDPGRSQPQQDRRHQCKQGPGGFGNGWASPECHLRKQAQVLF
(SEQ ID NO:42)

FIG. 13

```
                                                              Majority
  1 MEEQGHSEMEIIPSESHPHIQLLKSNRELLVTHIRNTQCL
    ┌──────────────────────────────────────┐
  1 │MEEQGHSEMEIIPSESHPHIQLLKSNRELLVTHIRNTQCL│  CARD4-Y CLONE
  1 │MEEQGHSEMEIIPSESHPHIQLLKSNRELLVTHIRNTQCL│  CARD4-Z CLONE
  1 │MEEQGHSEMEIIPSESHPHIQLLKSNRELLVTHIRNTQCL│  CARD4L
    └──────────────────────────────────────┘
                                                              Majority
 41 VDNLLKNDYFSAEDAEIVCACPTQPDKVRKILDLVQSKGE
    ┌──────────────────────────────────────┐
 41 │VDNLLKNDYFSAEDAEIVCACPTQPDKVRKILDLVQSKGE│  CARD4-Y CLONE
 41 │VDNLLKNDYFSAEDAEIVCACPTQPDKVRKILDLVQSKGE│  CARD4-Z CLONE
 41 │VDNLLKNDYFSAEDAEIVCACPTQPDKVRKILDLVQSKGE│  CARD4L
    └──────────────────────────────────────┘
                                                              Majority
 81 EVSEFFLYLLQQLADAYVDLRPWLLEIGFSPSLLTQSKVV
    ┌──────────────────────────────────────┐
 81 │EVSEFFLYLLQQLADAYVDLRPWLLEIGFSPSLLTQSKVV│  CARD4-Y CLONE
 81 │EVSEFFLYLLQQLADAYVDLRPWLLEIGFSPSLLTQSKVV│  CARD4-Z CLONE
 81 │EVSEFFLYLLQQLADAYVDLRPWLLEIGFSPSLLTQSKVV│  CARD4L
    └──────────────────────────────────────┘
                                                              Majority
121 VNTDPVSRYTQQLRHHLGRDSKFVLCYAQKEELLEEIYM
121  VNTDPVSRYTQQLRH[P]QQ[D]R[R]HLGRDSKFVLCYAQKEELLEEIYM    CARD4-Y CLONE
121  VNTDP[G]R[S]Q[P]QQLRHHLGRDSKFVLCYAQKEELLEEIYM           CARD4-Z CLONE
121  VNTDPVSRYTQQLRHHL-----GRDSKFVLCYAQKEELLEEIYM            CARD4L
```

FIG. 14A

```
                                                                                    Majority
     DTIMELVGFSNESLGSLNSLACLLDHTTGILNEQXXXXX
     |----+----|----+----|----+----|----+----|
              170           180           190           200
161  DTIMELVGFSNESLGSLNSLACLLDHTTGILNEQAASR--    CARD4-Y CLONE
137  ----------------------------------------    CARD4-Z CLONE
161  DTIMELVGFSNESLGSLNSLACLLDHTTGILNEQGETIFI    CARD4L XCKXXX                                      Majority
     |----+----|----+----|----+----|----+----|
              210           220           230           240
199  ---------------------------------------KIVTG        CARD4-Y CLONE
137  ---------------------------------------QCKIQ--      CARD4-Z CLONE
201  LGDAGVGKSMLLQRLQSLWATGRLDAGVKFFHFRCRMFS             CARD4L C              VC              XCXXXX                                          Majority
     |----+----|----+----|----+----|----+----|
              250           260           270           280
203  C------------------------------------                CARD4-Y CLONE
141  C------------------------------------                CARD4-Z CLONE
241  FKESDRLCLQDLLFKHYCYPERDPEEVFAFLLRFPHVAL              CARD4L RTCSSS CPWEPAHPLVLLANLLSG                   Majority
     |----+----|----+----|----+----|----+----|
              290           300           310           320
206  ---------------------------------------              CARD4-Y CLONE
141  ---------------------------------------              CARD4-Z CLONE
281  FTFDGLDELHSDLDLSRVPDSS PWEPAHPLVLLANLLSG             CARD4L
```

FIG. 14B

```
                                                                      Majority
         - - - - - - - - - - - - - T X X T X X X X P R - - - - - - - - - - - - -
         |----------|----------|----------|----------|----------|----------|
                   330        340        350        360
212      - - - - - - - - - - - - - - -ⓉTAⓆSGTⓅR- - - - - - - - - - - - - -     CARD4-Y CLONE
141      - - - - - - - - - - - - - - -ⓉARⓉGIEVPⓇQFLRKKVLLRGFSPSHLRAY            CARD4-Z CLONE
321      KLLKGASKLL                                                              CARD4L Majority
         - - - - - - - - - - - - - - - - - - - - - - - - - - - - - - - R C - -
         |----------|----------|----------|----------|----------|----------|
                   370        380        390        400
222      - - - - - - - - - - - - - - - - - - - - - - - - - - - - - - -ⓇⒸ- -    CARD4-Y CLONE
141      - - - - - - - - - - - - - - - - - - - - - - - - - - - - - - -ⓇⒸ      CARD4-Z CLONE
361      ARRMFPERALQDRLLSQLEANPNLCSLCSVPLFCWIIFⓇⒸ                                CARD4L Majority
         - - - - - - - - - - - - - L P X C - - - - - - - - - - - - - - - - - -
         |----------|----------|----------|----------|----------|----------|
                   410        420        430        440
224      - - - - - - - - - - - -ⓁⓅSⒸ- - - - - - - - - - - - - - - - - - -    CARD4-Y CLONE
141      - - - - - - - - - - - -ⓁⓅⒹⒸTMTLTDVFLLVTEVHLNRMQPSS                   CARD4-Z CLONE
401      FQHFRAAFEGSPQ                                                           CARD4L Majority
         - - - - - - - - - - - - - - - - - - - - - - - - - - - - - - - - - - -
         |----------|----------|----------|----------|----------|----------|
                   450        460        470        480
228                                                                              CARD4-Y CLONE
141                                                                              CARD4-Z CLONE
441      LVQRNTRSPVETLHAGRDTLCSLGQVAHRGMEKSLFVFTQ                                 CARD4L
```

Sequence alignment showing Majority consensus with CARD4-Y CLONE, CARD4-Z CLONE, and CARD4L sequences across positions 481–640.

```
                                                        ---GPGG-----------------  Majority
                   490       500       510       520
                    |         |         |         |
228                                                      CARD4-Y CLONE
141                                                      CARD4-Z CLONE
481  E E V Q A S G L Q E R D M Q L G F L R A L P E L [GPGG] D Q Q S Y E F F H L T L   CARD4L ---FXXXWXXP--------CXX--  Majority
                   530       540       550       560
                    |         |         |         |
228                                            -[C]A S                              CARD4-Y CLONE
145                              -[F]G N G[W]A S[P]-                                CARD4-Z CLONE
521  Q A F F T A F F L V L D D R V G T Q E L L R[F]F Q E[W]M P[P]A G A A T T S[C]Y P   CARD4L P-----------------------  Majority
                   570       580       590       600
                    |         |         |         |
231  [P]-                                                CARD4-Y CLONE
153  [P]-                                                CARD4-Z CLONE
561  [P]F L P F Q C L Q G S G P A R E D L F K N K D H F Q F T N L F L C G L L S K A K   CARD4L ---XWX------------------  Majority
                   610       620       630       640
                    |         |         |         |
232                         T[W]P                        CARD4-Y CLONE
153                                                      CARD4-Z CLONE
601  Q K L L R H L V P A A A L R R K R K A L[W]A H L F S S L R G Y L K S L P R V Q V   CARD4L
```

```
                                                                                          Majority
- - - - - - - - - - - - - - - - - - - - - - - - - - - - - - - - - W X X X X X X X
                    810               820              830              840
                                                                  W T                     CARD4-Y CLONE
- - - - - - - - - - - - - - - - - - - - - - - - - - - - - - - - - - - - -                CARD4-Z CLONE
  248   - - - A R L G K N K I T S E G G K Y L A L A V K N S K S I S E V G M W G N Q V G D E G   CARD4L
  156
  801

Majority
X X X X X X X L R X X X X X X X X X X X X X X X X X X X X X X X X X X X X X X X X
                    850               860              870              880
- - - Q V L - - - - L R K Q A - - - - - - - - - - - - - - - - - - - - - - -              CARD4-Y CLONE
- - - - - - - - - - L R - - - - - - - - - - - - - - - - - - - - - - - - - -              CARD4-Z CLONE
  249   A K A F A E A L R N H P S L T T L S L A S N G I S T E G G K S L A R A L Q Q N T   CARD4L
  156
  841

Majority
X X X X L X X X X X X X X X X X X X X X X X X X X X X X X X X X X X X X X X X X X
                    890               900              910              920
S L E I L W L T Q N E L N D E V A E S L A E M L K V N Q T L K H L W L I Q N Q I          CARD4-Y CLONE
- - - - - - - - - - - - - - - - - - - - - - - - - - - - - - - - - - - - -                CARD4-Z CLONE
  249   - - - - - - - - - - - - - - - - - - - - - - - - - - - - - - - - - - - - -        CARD4L
  161
  881

Majority
X X X X X X X X X X X X X X X X X X X X X X X X X X X X X X X X X X X X X X X X
                    930               940              950              960
- - - T A K G T A Q L A D A L Q S N T G I T E I C L N G N L I K P E E A K V Y E D E K    CARD4-Y CLONE
- - - - - - - - - - - - - - - - - - - - - - - - - - - - - - - - - - - - -                CARD4-Z CLONE
  249                                                                                     CARD4L
  164
  921
```

FIG. 14F

```
         X X X X F
         ─────────
249      - - - - [F]      Majority
164      - - - - [F]      CARD4-Y CLONE
961      R I I C [F]      CARD4-Z CLONE
                          CARD4L
```

Decoration 'Decoration #1': Shade (with solid black) residues that match the Consensus exactly.

FIG. 14G

```
CCACGCGTCCGCGGACCGCGAGCGGTAGCGCCCTCCCTCCCAGCTGTTGTCCCGCCCGAT
CCGCGACCCTAGTCCCCGGATCCCCTTGCTGAGAGTCACCGTACTCCAGGGCCAACTGAG
CCAAAGTCCTGCCAACTTGGGTCAGCAATGAAAGGCAGGATCCTGGGTGGTGGCCCTGAA
TCCTGATTTGTCTGCCCTGCCAGCGAGACACATGTGGTCAAAGATGAATTTGAGAAAGT
AGCTGCTGGCTACTTGAACAATGGAGGAACACGGCCATCATGAGATGGAAGGCACCCCAT
TGGGTTGTCACTCCCACATTAAACTGCTGAAGATCAACAGGGAACATCTGGTCACCAACA
TTCGGAACACTCAGTGTCTGGTGGACAACTTGCTGGAGAATGGCTACTTCTCAGCCGAAG
ATGCAGAGATTGTGTGTGCCTGTCCCACCAAGCCTGACAAGGTCCGAAAGATCCTTGACC
TGGTGCAGAGCAAAGGCGAGGAGGTGTCTGAGTTCTTCCTCTACGTGCTGCAGCAGCTGG
AGGATGCTTACGTGGACCTCAGGCTGTGGCTCTCAGAAATTGGCTTCTCCCCTTCCCAGC
TCATTCGGACCAAAACTATCGTCAATACTGACCCAGTAAGCAGGTATACCCAACAGCTGC
GACACCAACTGGGCCGCGACTCCAAGTTCATGCTGTGCTACGCCCAGAAGGAGGACCTGC
TGCTGGAGGAGACCTATATGGACACACTCATGGGGCTGGTAGGCTTCAACAATGAAAACC
TGGGCAGCCTAGGAGGCCTGGATTGCCTGCTGGACCACAGTACGGGCGTCCTCAACGAGC
ATGGCGAGACTGTCTTCGTGTTCGGGGACGCGGGAGTGGGCAAGTCCATGCTGCTGCAGA
GGTTGCAGAGCCTCTGGGCGTCAGGCAGGTTGACCTCCACAGCCAAATTCTTCTTCCACT
TCCGCTGCCGCATGTTCAGCTGCTTCAAGGAGAGCGACATGCTGAGTCTGCAGGACCTGC
TCTTCAAGCATTTCTGCTACCCGGAGCAGGACCCCGAGGAGGTGTTCTCCTTCTTGCTGC
GCTTTCCCCACACAGCGCTCTTCACTTTTGACGGCCTGGATGAGCTGCACTCAGACTTCG
ACCTGAGCCGCGTGCCGGATAGCTGCTGCCCCTGGGAGCCGGCTCACCCTCTGGTCCTGC
TGGCTAACCTCCTAAGTGGGAGGCTGCTCAAGGGTGCCGGCAAATTGCTCACTGCTCGCA
CAGGCGTGGAGGTCCCCCGCCAGCTCCTGCGCAAAAAGGTGCTGCTCCGGGGCTTCTCCC
CAAGTCACCTGCGCGCCTATGCCCGCCGGATGTTCCCCGAGCGCACAGCGCAGGAGCATC
TGCTGCAGCAGCTGGATGCCAACCCCAACCTCTGCAGCCTGTGCGGGGTGCCGCTCTTCT
GTTGGATCATCTTCCGTTGTTTCCAGCACTTCCAGACGGTCTTCGAGGGCTCCTCTTCAC
AGTTGCCGGACTGTGCTGTGACCCTGACCGATGTCTTTCTGCTGGTCACTGAGGTGCATC
TGAACAGGCCGCAGCCCAGCAGCCTGGTGCAGCGCAACACGCGCAGCCCGGCGGAAACCC
TACGTGCAGGCTGGCGCACGCTGCATGCGCTGGGAGAGGTGGCTCACCGAGGCACCGACA
AGAGCCTCTTTGTGTTTGGCCAGGAGGAGGTGCAGGCGTCGAAGCTGCAGGAAGGAGATC
TGCAGCTGGGCTTCCTGCGGGCTTTGCCCGATGTGGGCCCTGAGCAGGGCCAGTCTTACG
AATTTTTCCACCTTACGCTCCAGGCCTTCTTCACCGCCTTCTTCCTGGTAGCAGATGACA
AAGTGAGCACCCGGGAGTTGCTGAGGTTCTTTCGAGAATGGACGTCTCCTGGAGAGGCAA
```

FIG. 15A

```
CAAGCTCGTCCTGCCATTCTTCCTTCTTCTCCTTCCAGTGCCTGGGCGGCAGAAGCCGGT
TGGGCCCTGATCCTTTCAGGAACAAAGATCACTTCCAGTTCACCAACCTCTTCGTGTGCG
GGCTACTGGCCAAAGCCCGACAGAAACTCCTTCGGCAGCTGGTGCCCAAGGCTATCCTGA
GGAGGAAGCGCAAGGCCCTGTGGGCTCACCTGTTTGCTAGCCTGCGCTCCTACTTGAAGA
GCCTACCTCGGGTCCAGTCTGGAGGCTTTAACCAGGTGCATGCCATGCCCACATTCCTGT
GGATGCTGCGCTGCATCTATGAGACGCAGAGCCAGAAGGTGGGGCGCCTCGCCGCCAGGG
GCATCAGTGCGGACTACCTCAAGCTGGCCTTTTGCAACGCTTGCTCTGCGGACTGCAGCG
CCCTGTCCTTCGTCCTGCATCACTTCCACAGGCAGCTGGCCCTAGACCTGGACAACAACA
ACCTCAATGACTATGGCGTGCAGGAGCTGCAGCCTTGCTTTAGCCGTCTCACGGTTATCA
GACTCAGCGTCAACCAGATCACCGACACGGGGGTGAAGGTGCTATGTGAGGAACTGACCA
AGTATAAGATCGTGACGTTCCTGGGTTTATACAACAACCAGATAACTGATATCGGAGCCA
GGTATGTGGCCCAAATCCTGGATGAATGCAGAGGCCTCAAGCACCTTAAACTAGGGAAAA
ACAGAATAACAAGTGAGGGCGGGAAGTGTGTGGCTTTGGCTGTGAAGAACAGCACCTCCA
TCGTTGATGTTGGGATGTGGGGTAATCAGATTGGAGACGAAGGGGCAAAGGCCTTCGCAG
AGGCATTGAAGGACCACCCCAGCCTGACCACTCTCAGTCTTGCATTCAATGGCATCTCTC
CGGAGGGAGGGAAGAGCCTTGCGCAGGCCCTGAAGCAGAACACCACACTGACAGTAATCT
GGCTGACCAAAAATGAACTTAATGATGAGTCTGCAGAGTGCTTCGCTGAGATGCTGAGAG
TGAACCAGACGCTACGGCATTTATGGCTGATCCAGAATCGCATCACAGCCAAGGGGACAG
CGCAGCTGGCGAGGGCACTGCAGAAGAACACAGCCATAACAGAGATTTGTCTCAATGGAA
ACTTGATTAAGCCCGAGGAGGCCAAAGTCTTCGAGAATGAGAAGAGAATCATCTGCTTCT
GACGGACGCTCCTGGGCAGGATCTTTGTCCTAGGTTGCTCCTCAGTCACAGACAGCACTG
TGCAGTCAGCAGGGTAGCAGGATGCTGTGCAGCGCCTGCAGCAAGGTGCCTGTCAGGAGC
CCACACCTCCACAGTGCACACCGATGTCCCCTGCTCATGCTTGGACTGGTAGCACCCGCG
CCGCGGCTGAGACCCTGCAGACGCAGGGAGTCTTAGGAACCATCGTCACCACTCAAAGCC
AGCAGGGCATCTTCTGTACAAAGATCTCCCTGCATATCCACTAGACGGAAGCTGAAGGAA
CGCAACAGCAGAGGAGGCCAACAGACGCCTGGCTGAAGGCTCCGTGGGACCAACGGTGTC
ACCTTCAGAAAAGAGCTGGGAACTTGAGCAGAGCCGATGGTAACTTCTTGGGGAAAGAAG
GCACCCAGTGACTGCATGGTTATTCTGAGTCCTCCTTCCTCTGCTTAGTCCCTCTCACTG
TACAGGTCTGTTTCTTCCTCGCAGCTGTGGCTGCTGAAGTAGGTCCACTGTGGGGAGAGC
TCATCACAGACTTTGGTTCGGTTCTGGATTCTCAGTGGTGGCAACCGAGAGTCAGACGAT
ACCCTCTAGGTCAGTCTCAGAGGATCTCTATGCTGTGAGAGGGTTGAGGGCCCACCCAGA
ATTTTTTTTTTTTACCAGTTTTTACTGTGCCTGCCCCAGGAGGGAGAATTACTTCCCAGC
```

FIG. 15B

CTCCACAGCAGCAGGCATGGCTTGCCTCAATGGTCCTGAGATCCCAACAAAACTCTCTCC
CTTGCCTGTGAGCAGAAAGTATCTTCATGTCCTCAGAAGTTGGAGGGTGACTGGACACAG
TTAAGACTCAGAGAGCCAGCTGATAGCTCAAAGCAAAGCATGGCACATACCCACCACCAT
ACCATGGTGCGCATGGGATGGGACAGTTGGAATGTTGCAGATAACGTGTTCTTTTGCCAG
TTCATTTGTTAATAAAATATTTAAAACGTTAAAAAAAAAAAAAAAAAAAAAAAAGGGCG
G (SEQ ID NO:43)

FIG. 15C

MEEHGHHEMEGTPLGCHSHIKLLKINREHLVTNIRNTQCLVDNLLENGYFSAEDAEIVCA
CPTKPDKVRKILDLVQSKGEEVSEFFLYVLQQLEDAYVDLRLWLSEIGFSPSQLIRTKTI
VNTDPVSRYTQQLRHQLGRDSKFMLCYAQKEDLLLEETYMDTLMGLVGFNNENLGSLGGL
DCLLDHSTGVLNEHGETVFVFGDAGVGKSMLLQRLQSLWASGRLTSTAKFFHFRCRMFS
CFKESDMLSLQDLLFKHFCYPEQDPEEVFSFLLRFPHTALFTFDGLDELHSDFDLSRVPD
SCCPWEPAHPLVLLANLLSGRLLKGAGKLLTARTGVEVPRQLLRKKVLLRGFSPSHLRAY
ARRMFPERTAQEHLLQQLDANPNLCSLCGVPLFCWIIFRCFQHFQTVFEGSSSQLPDCAV
TLTDVFLLVTEVHLNRPQPSSLVQRNTRSPAETLRAGWRTLHALGEVAHRGTDKSLFVFG
QEEVQASKLQEGDLQLGFLRALPDVGPEQGQSYEFFHLTLQAFFTAFFLVADDKVSTREL
LRFFREWTSPGEATSSSCHSSFFSFQCLGGRSRLGPDPFRNKDHFQFTNLFVCGLLAKAR
QKLLRQLVPKAILRRKRKALWAHLFASLRSYLKSLPRVQSGGFNQVHAMPTFLWMLRCIY
ETQSQKVGRLAARGISADYLKLAFCNACSADCSALSFVLHHFHRQLALDLDNNNLNDYGV
QELQPCFSRLTVIRLSVNQITDTGVKVLCEELTKYKIVTFLGLYNNQITDIGARYVAQIL
DECRGLKHLKLGKNRITSEGGKCVALAVKNSTSIVDVGMWGNQIGDEGAKAFAEALKDHP
SLTTLSLAFNGISPEGGKSLAQALKQNTTLTVIWLTKNELNDESAECFAEMLRVNQTLRH
LWLIQNRITAKGTAQLARALQKNTAITEICLNGNLIKPEEAKVFENEKRIICF
(SEQ ID NO:44)

FIG. 16

```
           MEEQGHSEMEGIPLGSHSHIQLLKINRELLVTNIRNTQCLVDNLLENGYFSAEDAEIVCACPTQPDKVRKILDLVQSKGEEVSEFFLYVL
                   10        20        30        40        50        60        70        80       90
mCARD4Lpep.PRO   MEEHGHHEMEGIPLGCHSSHIKLLKINREHLVTNIRNTQCLVDNLLENGYFSAEDAEIVCACPTKPDKVRKILDLVQSKGEEVSEFFLYVL   90
hCARD4Lpep.PRO   MEEQGHSEMEIIPSESHPHIQLLKSNRELLVTHIRNTQCLVDNILKNDYFSAEDAEIVCACPTQPDKVRKILDLVQSKGEEVSEFFLYLL   90

QQLADAYVDLRLWLLEIGFSPSLLTQSKVYVNTDPVSRYTQQLRHQLGRDSKFYLCYAQKEDLLLEEIYMDTLMGLVGFSNESLGSLGGL
                  100       110       120       130       140       150       160       170      180
mCARD4Lpep.PRO   QQLEDAYVDLRLWLSEIGFSPSQLIRTKTIVNTDPVSRYTQQLRHQLGRDSKFMLCYAQKEDLLLEEIYMDTLMGLVGFNNENLGSLGGL  180
hCARD4Lpep.PRO   QQLADAYVDLRPWLLEIGFSPSLLTQSKVYVNTDPVSRYTQQLRHHLGRDSKFVLCYAQKEELLLEEIYMDTIMELVGFSNESLGSLNSL  180

ACLLDHSTGVLNEQGETVFVLGDAGVGKSMLLQRLQSLWASGRLTAGAKFFHFRCRMFSCFKESDRLSLQDLLEKHFCYPEQDPEEVFA
                  190       200       210       220       230       240       250       260      270
mCARD4Lpep.PRO   DCLLDHSTGVLNEHGETVFVFGDAGVGKSMLLQRLQSLWASGRLTSTAKFFFHFRCRMFSCFKESDMLSLQDLLFKHCYPEQDPEEVFS  270
hCARD4Lpep.PRO   ACLLDHTTGILNEQGETIFILGDAGVGKSMLLQRLQSLWATGRLDAGVKFFFHFRCRMFSCFKESDRLCLQDLLFKHCYPERDPEEVFA  270

FLLREPHVALFTFDGLDELHSDLDLSRVPDSSCPWEPAHPLVLLANLLSGKLLKGAGKLLTARTGVEVPRQLRKKVILRGFSPSHLRAY
                  280       290       300       310       320       330       340       350      360
mCARD4Lpep.PRO   FLLRFPHTALFTFDGLDELHSDFDLSRVPDSSCPWEPAHPLVLLANLLSGRLLKGAGKLLTARTGVEVPRQLLRKKVILRGFSPSHLRAY  360
hCARD4Lpep.PRO   FLLRFPHVALFTFDGLDELHSDLDLSRVPDSSCPWEPAHPLVLLANLLSGKLLKGASKLLTARTGIEVPRQFLRKKVILRGFSPSHLRAY  360

ARRMFPERAAQDHLLSQLDANPNLCSLCGVPLFCWIIFRCFQHFQAAFEGSSSQLPDCAVTLTDVFLLVTEVHLNRMQPSSLVQRNTRSP
                  370       380       390       400       410       420       430       440      450
mCARD4Lpep.PRO   ARRMFPERTAQEHLLQQLDANPNLCSLCGVPLFCWIIFRCFQHFQTVFEGSSSQLPDCAVTLTDVFLLVTEVHLNRPQPSSLVQRNTRSP  450
hCARD4Lpep.PRO   ARRMFPERALQDRLLSQLEANPNLCSLCSVPLFCWIIFRCFQHFRAAFEGSP-QLPDCTMTLTDVFLLVTEVHLNRMQPSSLVQRNTRSP  449

AETLHAGRDTLHALGEVAHRGTDKSLFVFGEEVQASGLQEGDLQLGFLRALPDVGPGDGQSYEFFHLTLQAFFTAFFLVADDKYGTQE
                  460       470       480       490       500       510       520       530     540
mCARD4Lpep.PRO   AETLRAGWRTLHALGEVAHRGTDKSLFVFGEEVQASKLQEGDLQLGFLRALPDVGPE-QGQSYEFFHLTLQAFFTAFFLVADDKVSTRE  539
hCARD4Lpep.PRO   VETLHAGRDTLCSLGQVAHRGMEKSLFVFTQEEVQASGLQERDMQLGFLRALPELGPGGDQQSYEFFHLTLQAFFTAFFLVLDDRVGTQE  539
```

FIG. 17A

```
mCARD4Lpep.PRO  LLRFFQEWTSPGGAASSSCHSSELSFQCLGGSGRAGEDLFKNKDHFQFTNLFVCGLLAKAKQKLLRQLVPAAALRRKRKALWAHLFASLR  629
hCARD4Lpep.PRO  LLRFFREWTSPGEATSSSCHSSFFSFQCLGGRSRLGPDPFRNKDHFQFTNLFVCGLLAKARQKLLVPKAILRRKRKALWAHLFASLR    629
                         550       560       570       580       590       600       610       620    630 mCARD4Lpep.PRO  GYLKSLPRYQVGGFNQVQAMPTFLWMLRCIYETQSQKVGQLAARGISADYLKLAFCNACSADCSALSFVLHHFHKQLALDLDNNNLNDYG  719
hCARD4Lpep.PRO  SYLKSLPRYQSGGFNQVHAMPTFLWMLRCIYETQSQKVGRLAARGISADYLKLAFCNACSADCSALSFVLHHFHRQLALDLDNNNLNDYG  719
                         640       650       660       670       680       690       700       710    720 mCARD4Lpep.PRO  VQELQPCFSRLTVIRLSVNQITDGGVKVLSEELTKYKIVTFLGLYNNQITDGARYVAQILDECKGLTHISLYNNQITDVGAKLGKNKIT    810
hCARD4Lpep.PRO  VQELQPCFSRLTVIRLSVNQITDTGVKVLCEELTKYKIVTFLGLYNNQITDIGARYVAQILDECRGLKHL----KLGKNRIT          797
hCARD4Lpep.PRO  VRELQPCFSRLTVLRLSVNQITDGGVKVLSEELTKYKIVTYLGLYNNQITDVGARYVTKILDECKGLTHISLYNNQITDVGARLGKNKIT  809
                         730       740       750       760       770       780       790       800    810 mCARD4Lpep.PRO  SEGGKYYALAVKNSTSIVDVGMWGNQVGDEGAKAFAEALKDHPSLTTLSLASNGISTEGGKSLAQAALQQNTSLTVLWLTQNELNDEVAES  900
hCARD4Lpep.PRO  SEGGKCVALAVKNSTSIVDVGMMKGNQIGDEGAKAFAEALKDHPSLTTLSLAFNGISPEGGGKSLAQALKQNTTLTVIWLTKNELNDESAEC 887
hCARD4Lpep.PRO  SEGGKYLALAVKNSKSISEVGMWGNQVGDEGAKAFAEALRNHPSLTTLSLASNGISTEGGKSLARALQQNTSLEIILWLTQNELNDEVAES  899
                         820       830       840       850       860       870       880       890    900 mCARD4Lpep.PRO  LAEMLKVNQITLKHLWLIQNQITAKGTAQLADALQSNTIGITEICLNGNLIKPEEAKVFEDEKRIICF  953
hCARD4Lpep.PRO  FAEMLRVNQITLRHLWLIQNRITAKGTAQLARALQKNTAITEICLNGNLIKPEEAKVFENEKRIICF   953
hCARD4Lpep.PRO  LAEMLKVNQITLKHLWLIQNQITAKGTAQLADALQSNTIGITEICLNGNLIKPEEAKVYEDEKRIICF  965
                         910       920       930       940       950       960
```

FIG. 17B

```
gatcatcgttcactgcagccttgaactcttgtgctcatgtgatcctcctgccttagcctcccaa
tagctgggactacaggtgcgccaccatgcctggctaattttttttattttgtagagatgggtgt
ctcactatgttgcacaggttggtctcaaactactggccttacttcaagctatctacccatctcag
cctcccaaagcgctgggattacagtcatgagccaacttgcctggccagataaaggtcttaagcat
ggttccttcctgctctaggtagagaaacccacaaccagtgggaggtggggtgagctctttctgt
agcttttgctttgctgatgatgtcattgatctcttcaggggctgcgcagagtagcaggggccctg
gagggcgcggcctgaatcctgattgccttctgctgagaggacacacgcagctgaagatgaattt
gggaaaagtagccgcttgctactttaactatggaagagcagggccacagtgagatggaaataatc
ccatcagagtctcaccccacattcaattactgaaaagcaatcgggaacttctggtcactcacat
ccgcaatactcagtgtctggtggacaacttgctgaagaatgactacttctcggccgaagatgcgg
agattgtgtgtgcctgccccacccagcctgacaaggtgccccggggacagggacgggcatggcat
tgtgtggaccccgggagctagaagaggcctctccctgctgatctgagtgaagagcgtgggagttt
agtccagcgggcagggctgcattttggggtactaatagcacacaaatgcctgggttagcaggttg
cacagtcaggtatttttacttctgtgtttgtgtctggagcaaaccctgacatctcagttctcattg
ctgtgtgtattggttcccagacacttcatttttagatcccctttaaattaggagggaaaaagaac
ataagcataagagcatccccagcagcgatgttcattcagtgcctctgaaggctggagggctgctt
gttgctgggtgagactcggaggggaaccgactcagggtcaggaatgatgacatcccacggtgggt
ccacagtgaagaatcttccccgctccactgtgggacgccttaacagcccttacttccacttacgc
tttgcgttatctcctgaaaaataaaatggagaccacaaattccttcttggttagaggaatgacac
aactcatttatgacatgaccccgctgggactcagaagagaccaggacggtttctgggggaagcag
tagcacactcgtgtgctttgttctcttctcttgatttgttttcccacatttttaacaagaaaaaa
agccgttttaatatatggcctatcgccctcctactgtgtggcccaggtgcctacctcattatgc
ccaaggggtggttctcacctctccactctcattcctgcacagcagttgtgtcaggttaagaggga
caaggagaaggctgggcaccgtggctcacgcctgtaatcccagcactttgggaggccgaggcagg
cagatcacctaaggtcaggagtttgagaccagcctggccaacatggggaaaacccgtctctaata
aaaacacaaaaattagtcgggcatggtggtgggtgcctgtaatcccagccacttgggaggctgag
gaaagagaattccttgaacctgggaggtggaggttgcagtgagccaagattgtgccattgcactc
cagccctccagcctgggtgacagagcaagactctgtctcaaaaaagaaaaaaaaaaaaagaggt
agagaagtccatggctatttgtctgtccttttattttaggctcatggaagcctcctggttttct
tagagctgagtggttttatttcttgctcaggaggtcatttcacagatttcgggctccaatatgt
tgactgtcacagcagctgggggatggcatagctaccggctgtactaagaactcagagccctgcc
ctgagcctgcctgagggtccttatggtaggaggatgcccctcatgccagcccgtgccctcatgct
tgtgtcacctccaggtccgcaaaattctggacctggtacagagcaagggcgaggaggtgtccgag
ttcttcctctacttgctccagcaactcgcagatgcctacgtggacctcaggccttggctgctgga
gatcggcttctcccctccctgctcactcagagcaaagtcgtggtcaacactgacccaggtagga
gtcagccccagcaagaccgcaggcaccagtgcaagcagggccctggggggtttggtaatggctgg
gccagccctgagtgccacctcaggaagcaggccaggtgctattttgatttagaaaggaacagc
tgaatcctgtctcccaagtgcagcccaggtggctgcgattgaactgcccacacctcgatggtctg
gtttatagaggggcctttggaagtatgggaatggcctgtgttctgaccccttgctttcttcctat
tctgacatatgtagacattttaatggttgcacaaattcaaggttgtattttttttctttttaaaa
aaatctttagctggacatggtagcacacacctgtagttccagctactcaggaggctgaggcaaga
ggactgcttgagcccagagtctaaggctgcagcgagctatgattgtgcccctacactccagcct
gggtgacagagtgagaccctgtctctaaaaaaggaaagaaaaaaattaaaaagccttgccaggtt
tgattctaggcaaagtattctgtcaccgttgagtgccagtccttatttccaaactaatggaagac
cccatcagttaactgattagttcaataagtatttttgctgtatccaccacatgccaagaccta
cactgtgctggatgtcagggagacagtggtgagcagacacagacagggttcctgccctcagggag
cttcaagtcagctggaagagaccaccagtcagcaatctcaaaaatgtgtcaggacagcggcagtc
caaggcatgtgagaacatatcattagggccaggatctgctctggggcaggagtcttctttccctg
cttttgaactctccactttgagacagctgttggtaacataccagcaccaaggacctaagtcctgc
cttttaaagaatccaatatgttgttggaaacagaagcacaagacaggtgtgtgcttagggaaac
aaggccagccggcagagtgtcagtgctaggctccagcttccacagccctgcaggtgcctgccag
ccactgctagcttctgactctgtctgctccttcctgtctccccttgtttccttcccccatgaaaa
aaaagaaagtattcccatgaggaatcattctttcgaaagacttctctgttggttccgttagcca
gctactttactagcttttacagtgtaattcactctacaagcagtctcacacaaaagactacatat
```

FIG. 18A

```
tgtatgattctgtttatatgaaatgtccagaaaaggtaaatctatagacaaagcaaatcagtagt
tgcctacggcccagggattggctacaaataggctccagaaaactctgggaagatggtagagatgt
tctagacctggactgtggtgaggtttgcacaactttgtaaacttactaaaaattactgacaaata
tataacactccctaacactttgggaggccgaggtgggcagatcgcttgaacccaggaatttgaga
ccagcctgggcaacatggcgagacccgtctctacaaaaaaacacaaaattagttgggcttggt
ggcatatgcctgtgtcccagctacttgggaggctgaggtgggaggattgcttgagcctgggagtt
tgagactgcatgattgggtcactgcaccctagcctgagtgacagagcaggaccctatctctaaca
acaaaaaagcagtgttggtggaggagggccagcgtggccatctggcctggccctcgagtgcgagg
ggcttcagtgtttagctgcagttcagtgatgacactgtgcggaggaataagggtggcctgtctca
gacactgatcccagctgaagtttgtcaccttctttctggcaaatctgaggtcaagcagagagatc
aaagcctggggccctcagggtcaggaatgctggctctgtgacgctcccaggtcctgcatctgag
gagtggctgcgctggcctcagggcccaggttgtgaattttgtttatgcactcgcctctcctcttt
gagacctccctgtttgatgctgtttctgcctctctcctcaccctgctgctgtgccctgccacccc
ctccctccagtgagcaggtatacccagcagctgcgacaccatctgggccgtgactccaagttcgt
gctgtgctatgcccagaaggaggagctgctgctggaggagatctacatggacaccatcatggagc
tggttggcttcagcaatgagagcctgggcagcctgaacagcctggcctgcctcctggaccacacc
accggcatcctcaatgagcagggtgagaccatcttcatcctgggtgatgctgggtgggcaagtc
catgctgctacagcggctgcagagcctctgggccacgggccggctagacgcagggtcaaattct
tcttccactttcgctgccgcatgttcagctgcttcaaggaaagtgacaggctgtgtctgcaggac
ctgctcttcaagcactactgctacccagagcgggaccccgaggaggtgtttgccttcctgctgcg
cttcccccacgtggccctcttcaccttcgatggcctggacgagctgcactcggacttggacctga
gccgcgtgcctgacagctcctgccctgggagcctgccaccccctggtcttgctggccaacctg
ctcagtgggaagctgctcaaggggctagcaagctgctcacagcccgcacaggcatcgaggtccc
gcgccagttcctgcggaagaaggtgcttctccggggcttctcccccagccacctgcgcgcctatg
ccaggaggatgttccccgagcgggccctgcaggaccgcctgctgagccagctggaggccaacccc
aacctctgcagcctgtgctctgtgcccctcttctgctggatcatcttccggtgcttccagcactt
ccgtgctgcctttgaaggctcaccacagctgcccgactgcacgatgaccctgacagatgtcttcc
tcctggtcactgaggtccatctgaacaggatgcagcccagcagcctggtgcagcggaacacacgc
agcccagtggagaccctccacgccggccgggacactctgtgctcgctggggcaggtggcccaccg
gggcatggagaagagcctctttgtcttcacccaggaggaggtgcaggcctccgggctgcaggaga
gagacatgcagctgggcttcctgcgggctttgcggagctgggccccgggggtgaccagcagtcc
tatgagttttccacctcaccctccaggccttctttacagccttcttcctcgtgctggacacag
ggtgggcactcaggagctgctcaggttcttccaggagtggatgcccctgcgggggcagcgacca
cgtcctgctatcctccctcctcccgttccagtgcctgcagggcagtggtccggcgcgggaagac
ctcttcaagaacaaggatcacttccagttcaccaacctcttcctgtgcgggctgttgtccaaagc
caaacagaaactccttcggcatctggtgcccgcggcagccctgaggagaaagcgcaaggccctgt
gggcacacctgttttccagcctgcggggctacctgaagagcctgccccgcgttcaggtcgaaagc
ttcaaccaggtgcaggccatgcccacgttcatctggatgctgcgctgcatctacgagacacagag
ccagaaggtggggcagctggcggccaggggcatctgcgccaactacctcaagctgacctactgca
acgcctgctcggccgactgcagcgccctctccttcgtcctgcatcacttccccaagcggctggcc
ctagacctagacaacaacaatctcaacgactacggcgtgcgggagctgcagccctgcttcagccg
cctcactgttctcaggtgaggctgccaggcaaggggagcaacaggtgggccgggcggccaggct
cggagggcatcgggaatggcatcatggaccaggatcccccaggactcatgaccatggcccttgga
atgtccagaccttttctttcttagcagggcagaggtcaaggtgcaaagcttcgaggcaggtggac
ctggatcagccacagctgggtgcccttgaacaaagtgcttaactctcagagcctccacgccctca
tctggaaaaagaagatgctcataatcctatcaattatggccacagggaccaatgttagttgagaa
tgggtgaagtgcattacaaatattacctaatggaatgctctttacaaccctgtaacttaggtact
gttattgtctctatttggcagataaggaagtagaggcacagagaagttaatagcttgctttagg
tcacacagctcagacatagcagtgccagaatgcataaagaaccttccttttaagattaatgtaag
gctccgagatagccctcaaaaagtttctggaatatgggagcttttattactgcagagaaagcaga
ccttgtgccagttggcactggtgactttctgtgatcaacgctagcagcccttcacactgctagag
acctcagttaaaatgctgactcgtggttgttttcctgttccatagtttacgggaaacagagccca
gtctgtttttcttctattagcatttcctatgtaaaataaaccttgtaaatctctacaggggttaa
atttgccattacttgactcatgcatttctaaaaagcagtagggatttggaactgactcccagtgc
```

FIG. 18B

```
ctgtcacaccagtgtcagagtgtaaataattgcatggggacatggggtgcaggggtcgaaggct
gccctagcctgggaattggaaaacctggagtctgttctctgtactctcagccagtgactctcct
ctgtagccccaggcagtctcacactcagtgccaccctctgtccatctttttttttctccccaa
atggagtcccgctctgttgcccaggctggagtgcagtggcgtgatctcagctcactgcaacctcc
gcctcctgggttcaagcgattctcttgccccagcctcctgagtagctgggattacaggcacacgc
caccatgtccggctaagttttttgtattttagtaggacggggtttcccatgttggccaggctg
gtcttgaaatcctgacctcaggtgatccgcccgcctcggccttccaaaatgttggggttacaggc
atgagccgccacccgaccctctgtccatcttttcaatgggaaactccacaccagtgtggtgg
ccctgcccttcctgctgtccccaggtgaagctttccttcacaccagtgcaagaaaaaacagcttg
taggaaagcagaggatatgggtaaccacgggaagcacactcagttctctggctgcatcagttagg
attagttttagctgagagcgaaaaccccaaatgttggtgagttacaagcttatttctctcatgta
aaagtctagaggtaggtagttcaggactggtatggagtctccatgaccctccggagcccaggctc
tcttctgccttcctgttctgccatcctcactacccggctttcccatcttggccaagagggctg
tcaaactccagccatctagtcgacactctagctatcagtaagaaggaagggcaaagattgagagc
atgcctcaatcttttaagaacacttcttggctattactaattatattgctgcttagatttcagaa
cttaatggtatgggcagaatttaatgagatgggcccagctaaaagatgggggaatctattgctaa
gaaagtatagatattgggaatgtctagcagcctgtgctgtcttgggctggccatgccatgtacat
acacactatttcccagcaccaagctggggactctgagggaaagggtccagagtgtctgacttgat
catttgatgtggcctaaaaatcaagcttttaattgttcagccttttacttgttatcaaggtcag
cttgtgggtctaattgggcccaaggcttgtgtttctaagtaaagttttattggaacgcagccata
cccatttatttacttactggctgcttcacactacacagttgagtagctgtgacagagaccacatg
gcccacagagcctaaaatatttgctgtctgacactttacagaatgacatgagcagtctcctttga
cagtgggactcacagccttttccagtgacaaatcagggttagcccatgtgtttctggatgggggg
aagctgttggcatttgggtataacagttcttgtgagacctgtccagcattttgcaggacccta
acatcattggccctgcctgcaagatgacagggcactccctcctccagtcacaaccactaaaagca
gcccctgacatttccaaacccatgccctccaccatacgagaaccaggtacagggtctggctgaca
cataggtcacacgcaaagggtggatgtcagaggtggctggcctcacacgtcctccctgtgtcctt
cacggtcgtgtgaggagccaggggctgtgctgcagcctcgctcatgggctggtgcaggatgggtc
tggcggccccacgttggccaggctttgtaaggggctatttggctgattgctgtggccattctcca
ggggcgtctatacctgagaaaactccagggcctgaaggcttctggatctttgtaagattaatggt
ccttcataatgagtgcctgccctgactcgtaatttttttgctgttttatttcagactcagcgtaa
accagatcactgacggtggggtaaaggtgctaagcgaagagctgaccaaatacaaaattgtgacc
tatttggggtatgtctttctccagaacactgggccaactacctagtaataatacagagctgcagg
gaattcacattcccataggtccctggatgatcggcacggatggcccagggctgggaagagcgctg
gcccaggagttgagagtcctgggttctctttgtggctcggccagtcatgaagtcttgctgagcct
cagcctcctcacctgtaaaactgggatcccagtataggcaagtaggcttacaactggttattggg
ggatgcaacgagaatataaggggatatatttaataaatgctagaatcctgtttacatattagtct
ggactattttgggtccataatccctcatccagagcctttggggcaagacccgaatggggattctg
agtgcatgctatggcatgacgtggccgcaggggtctaaggcagtgcccattttcaaacactttc
atatttctcccgcagaatgtatgaaacagtcaaaccaagtgtggtaagaaagactaagtagct
ccacatcagttgccaaaagaattgtgagaaactttgggcattcagagcctttgaggttttggagt
ctgagagaagggattgcgggccagccccacacaactggtggctctgcaagctggagcagttgttc
agtttcttggggcctcagtggccttcgatgttaatgaggacggtgacgcaaacgaccccgggcca
cactcggctccagggctctgtgtggctgtggaacccctggaagcctgagcttagctgcctttcaac
ttccatctgctgtactattgaattggcattgagcggtgagatggctgaaaggtagacatcgagaa
gttttaatattcagaatcttttcttctcaagacgctgaatgtaatcttagttgtaaatacccatc
acctgccagtcaccgagcactcatgcaccagggctttgcgttatgtcctaagatcctcataacca
ccctgcaaggggactatcatcattacctctgtattacagatggagaaactgaggcacagagaggt
aacgtgacttgtctcaggccataaagctggggaaagtagtggagctggttttgaacctgagctgt
gagacctcagagccctaaactctggtgcctgtgtgttcccctttcaacccagactttggaaatca
gtagacaccatatgcttcaaaaaacaggggctattaaaatgacatcaggagccagaaagtctcat
ggctgtgctttctcttgaagtttatacaacaaccagatcaccgatgtcggagccaggtacgtcac
caaaatcctggatgaatgcaaaggcctcacgcatcttaagtaagtggggtaggcaccaggttcct
tagtatattctcttgatcaccccttctgttgttcaaagattaaatgtcacagtaaagagctttc
```

FIG. 18C

```
atcctaaagccttccacttgtcccagggccatgttggtcaagtaaagatacctctgtgtgatctg
tgaggcttggattctggaagggcctcccgttattggtaggggaaaggttggcattttgatttca
ttaactactaggccgaagaaaggactaactctcacccttctggtggtcttttgccccaaggga
gtttcctgtcgggttgcaaggaagagcttgggcccttgccctgctgtaggtgtgccctgcgcagg
gggtgacagtgcgccaggcttggagcctctggtcctgccctgacagtggccacataccttgaccc
ttggcagtcaaagtgggacctcccaggtctcccgagggaagtcagtgatgctgctgaggtcaatt
agaggacccagggagggctcaggtccctgagcttctgcagagactgtggaccatctcctggaga
ggaaccctgactgactgtcctcagggcttcagttccctccctgacaggaggcccaggccatggct
cttgtggatcccagaagaaagtgtacggttcccaagatggggctggaaggggctctgtgctgggg
aggagggtgacccacattggagccctgcatagctggaggctgactgtgtgtgactctctctgca
gactgggaaaaaacaaaataacaagtgaaggaggaagtatctcgccctggctgtgaagaacagc
aaatcaatctctgaggttgggtgagtagaaggggatggatgtatgtggtacaacctgctgtgtgt
gtgggggcgggccttgctgttctttcatacatcagtacaccagaaggaccactggggctcgct
gtcggggagagatagtggagagctttcaccatgctgcgaaactgaaaccgtgcccattaagcaat
aactcccccggtcccctcccccctgcctcttgcagccaccctgctacttactctctctatggttt
tgactactctacctcatgtaagtggaatcatacagtatttgccttttggggatggctgatttcac
tagcatcatgtcctcaagattcgtccacatggaagcatgggacaggatttccttttttttttttt
tttttttttttttttgacagagtctcgctctgttgcccaggctggagtgcagtggcatgatctcgg
ctcactgcaacctctgccttctgggttcaagcgattctctcgcctcagccacacgagtagctggg
attataggcacccgccaccaatcccagctaattttttgtatttttagtagaggcggggtttcacca
tgttggccaggctggtctcaaactcctgacctcaaatgatccaccacctcggtctcccaaagtg
tcaggattataggcgtgagccaccgtgccccgccaggatttccttcttttttaaggctgagtaat
actccattgcatggctatgccacattttgttactcattcatccaagaacagacactggcttgct
tctatgctttggctgttgtgaataatgctgctgtgcacatgggcatacaaatgtctcttcaagga
ctgccttcaattcttttttttttttttttttttttttagattcttttttttttttattatactcta
agtttagggtacatgtgcacattgtgcaggttagttacatatgtatacatgtgccatgctggtg
cgctgcacccactaatgtgtcatctagcattaggtatatctcccaatgctatccctcccccctcc
cccgaccccaccacagtccccagagtgtgatattcccttcctgtgtccatgtgatctcattgtt
caattcccacctatgagtgagaatatgcggtgtttggttttttgttcttgcgatagtttactgag
aatgatggtttccaatttcatccatgtccctacaaaggatatgaactcatcattttttatggctg
catagtattccatggtgtatatgtgccacattttcttaatccagtctatcattgttggacatttg
ggttggttccaagtctttgctattgtgaatagtgccacaataaacatacgtgtgcatgtgtcttt
atagcagcatgatttatactcatttgggtatataccagtaatgggatggctgggtcaaatggta
tttctagttctagatccctgaggaatcgccacactgacttccacaatggttgaactagtttacag
tcccaccaacagtgtaaaagtgttcctatttctccgcatcctctccagcacctgctgtttcctga
cttttaatgattgccattctaactggtgtgagatgatatctcatagtggttttgatttgcattt
ctctgatggccagtgatgatgagcatttcttcatgtgtttttggctgcataaatgtcttctttt
gagaagtgtctgttcatgtccttcgcccactttttgatggggttgtttgttttttttcttgtaaat
ttgtttgagttcattgtagattctggatattagccctttgtcagatgagtaggttgcgaaaattt
tctcccatgttgtaggttgcctgttcactctgatggtagtttcttttgctgtgcagaagctcttt
agtttaattagatcccatttgtcaattttgtctttgttgccattgcttttggtgttttggacat
gaagtccttgcccacgcctatgtcctgaatggtaatgcctaggttttcttctagggttttatgg
ttttaggtttaacgtttaaatcttaatccatcttgaattgattttttgtataaggtgtaaggaag
ggatccagtttcagcttctacatatggctagccagttttcccagcaccatttattaaatagggga
atcctttcccattgcttgttttctcaggtttgtcaaagatcagatagttgtagatatgcggca
ttatttctgagggctctgttctgttccattgatctatatctctgttttggtaccagtaccatgct
gttttggttactgtagccttgtagtatagtttgaagtcaggtagtgtgatgcctccagctttgtt
cttttggcttaggattgacttggcgatgcgggctctttttggttccatatgaactttaaagtag
tttttccaattctgtgaagaaagtcattggtagcttgatggggatggcattgaatctgtaaatt
accttgggcagtatggccattttcacgatattgattcttcctacccatgagcatggaatgttctt
ccatttgtttgtgtcctcttttattccttgagcagtggtttgtagttctccttgaagaggtcct
tcacatcccttgtaagttggattcctaggtattttattctctttgaagcaaattgtgaatgggagt
tcacccatgatttggctctctgtttgtctgttgttggtgtataagaatgcttgtgattttttgtac
attgattttgtatcctgagactttgctgaagttgcttatcagcttaaggagattttgggctgaga
```

FIG. 18D

```
cgatggggtttttctagataaacaatcatgtcgtctgcaaacagggacaatttgacttcctctttt
cctaattgaatacccttttatttccttctcctgcctgattgccctggccagaacttccaacactat
gttgaataggagcggtgagagagggcatccctgtcttgtgccagttttcaaagggaatgcttcca
gtttttgcccattcagtatgatattggctgtgggtttgtcatagatagctcttattattttgaaa
tacgtcccatcaatacctaatttattgagagtttttagcatgaagggttgttgaatttgtcaaa
ggcttttctgcatctattgagataatcatgtggttttttgtctttggctctgtttatatgctgga
ttacatttattgatttgcgtatattgaaccagccttgcatcccagggatgaagcccacttgatca
tggtggataagcttttttgatgtgctgctggattcggtttgccagtattttattgaggattttttgc
atcaatgttcatcaaggatattggtctaaaattctcttttttggttgtgtctctgcccggctttg
gtatcagaatgatgctggcctcataaaatgagttagggaggattccctcttttctattgattgg
aatagtttcagaaggaatggtaccagttcctccttgtacctctggtagaattcggctgtgaatcc
atctggtcctggactcttttttggttggtaaactattgattattgccacaatttcagagcctgtta
ttggtctattcagagattcaacttcttcctggtttagtcttgggagagtgtatgtgtcgaggaat
gtatccatttcttctagatttttctagtttatttgcgtagagggtgtttgtagtattctctgatggt
agtttgtatttctgtgggatcggtggtgatatcccctttatcatttttattgtgtctatttgat
tcttctctcttttttttctttattagtcttgctagcggtctatcaatttgttgatcctttcgaaa
aaccagctcctggattcattgattttttgaagggttttttgtgtctctatttccttcagttctgc
tctgatttttagttattttcttgccttctgctagcttttgaatgtgtttgctcttgcttttctagtt
cttttaattgtgatgttagggtgtcaatttggatctttcctgctttctcttgtaggcatttagt
gctataaatttccctctacacactgctttgaatgcgtcccagagattctggtatgtggtgtcttt
gttctcgttggtttcaaagaacatctttatttctgccttcatttcgttatgtacccagtagtcat
tcaggagcaggttgttcagtttccatgtagttgagcggctttgagtgagattcttaatcctgagt
tctagtttgattgcactgtggtctgagagatagtttgttataatttctgttcttttacatttgct
gaggagagctttacttccaactatgtggtcaatttggaataggtgtggtgtggtgctgaaaaaa
atgtatattctgttgatttgggtggagagttctgtagatgtctattaggtctgcttggtgcaga
gctgagttcaattcctgggtatccttgttgacttctctgtctcattgatctgtctaatgttgacag
tggggtgttaaagtctcccattattaatgtgtgggagtctaagtctctttgtaggtcactgagga
cttgctttatgaatctgggtgctcctgtattgggtgcataaatatttaggatagttagctcctct
tgttgaattgatccctttaccattatgtaatggccttctttgtctcttttgatctttgttggttt
aaagtctgttttatcagagactaggattgcaacccctgccttttttttgttttccattggcttggt
agatctctcctccatccttttatttttgagcctatgtgtgtctctgcacgtgagatgggtttcctga
atacagcacactgatgggtcttgactctttatccaacttgccagtctgtgtctttaattgcaga
atttagtccatttatatttaaagttaatattgttatgtgtgaatttgatcctgtcattatgatgt
tagctggcgattttgctcattagttgatgcagtttcttcctagtctcgatgtctttacatttttg
gcatgattttgcagcggctggtaccggttgttcctttccatgtttaccgcttcctcaggagctc
ttttagggcaggcctggtggtgacaaaatctctcagcatttgcttgtctataaagtattttattt
ctccttcacttatgaagcttagtttggctggatatgaaattctgggttgaaaattcttttctttta
agaatgttgaatattggcccccactctcttctggcttgtagggtttctgcgagagatccgctgt
tagtctgatgggctttcctttgagggtaacccgaacttctctctggctgcccttaacatttttt
ccttcatttcaactttggtgaatctgacaattatgtgtcttggagttgctcttctcgaggagtat
ctttgtggcgttctctgtatttcctgaatctgaacgttggcctgccttgctagattgggggaagtt
ctcctggataatatcctgcagagtgttttccaacttggttccattctccacatcactttcaggta
caccaatcagacgtagatttggtcttttcacatagtcccatatttcttggaggctttgctcattt
cttttattcttttttctctaaacttcccttctcgcttcatttcattcattttcatcttccattgc
tgataccctttcttccagttgatcgcatcggctcctgaggcttctgcattcttcacgtagttctc
gagccttggtttttcagctccatcagctccttttaagcacttctctgtattggttattctagttata
cattcttctaaatttttttcaaagttttcaacttctttgcctttggtttgaatgtcctcccgtag
ctcagagtaatttgatcgtctgaagcctttcttctctcagctcgtcaaaatcattctccatccagc
tttgttctgttgctggtgaggaactgcgttcctttggaggaggagaggcgctctgcgttttagag
tttccagttttctgttctgttttttccccatctttgtggttttatctacttttggtctttgatg
atggtgatgtacagatgggttttcagtgtagatgtcctttctggttgttagttttccttctaaca
gacaggaccctcagctgcaggtctgttggaaatacccctgccgtgtgaggtgtcagtgtgcctctgc
tgggggtgcctcccagttaggctgctcgggggtcagggtcagggacccacttgaggaggcagt
ctgcccgttctcagatctccagctgcgtgctgggagaaccactgctctcttcaaagctgtcagac
```

FIG. 18E

```
agggacacttaagtctgcagaggttactgctgtcttttgtttgtctgtgccctgccccagagg
tggagcctacagaggcaggcaggcctccttgagctgtggtgggctccacccagttcgagcttccc
ggctgctttgtttacctaagcaagcctgggctatggcgggcgccctcccccagcctcgttgccg
ccttgcagtttgatctcagactgctgtgctagcaatcagcgagattccgtgggcgtaggaccctc
tgagccaggtgtgggatatagtctcgtggtgcgccgtttcttaagccggtctgaaaagcgcaata
ttcgggtgggagtgacccgatttccaggtgcgtccgtcacccctttctttgactcggaaaggga
actccctgatcccttgcgcttcccaggtgaggcaatgcctcgccctgcttcggctcgcgcacggt
gcgcgcacacactggcctgcgcccactgtctggcgctccctagtgagatgaacccggtacctcag
atggaaatgcagaaatcacccgtcttctgcgtcgctcacgctgggagctgtagaccggagctgtt
cctattcggccatcttggctcctccctccaattcttttgggtatatatccagcagtgggattgct
ggatcacatggtaattttttaattttttgaagaatcatcatactgttttccacggcagcagcacca
ttttatgttcccaccaacagttcattctagtttctccacatccttgccaacacttgctatttct
cttttgacagtacccatcctaatgagtgtgaggtcctgtctcattgtggttttgattcttgagg
cttttaaagcttttgtttcattataattttattggattacaaaaggaacacaggtaatttta
tttggaaactatgaaaaataataaaaattatcttctcagaaaatgattcttgttaacatttaagc
tcagttaagctctctcactttctctcccttctctctctctttgtacaacttttaaaaaatatagtag
gggtgagactatatgtatctatactatagtaggggtgagactatatgtatcctttccttttcact
taatctcatgccttgagtagctttccactttattaaaaatgtgatgccattcaattgtatagtaa
atacatatatgtaagcaaaacactgaaaactcttattctgggttccagcaagccatacctggaat
ggtgtaagcaggtagtttgcttggtgtgaacgtgttgttgaggcagctgccattgtgttgtgagt
gggccacacgaacttgttctgttgtgtgtagacagtgtgtgctgatcctattaggaacagccaac
gctttgtgtgagccacacacggttctaagtgctttgcttctgttaactcagtgaatcctcacaac
tccatgacggaatgctctaattatcccatttttatagatggggcaactgaggtccaagagactac
ataatttcccgaagttcacacaggtagcagatggcagagccgggtcaggagtccaccatcttacc
acgcagactgttttagccagagactctccggatctgctgtaggggacagaatacagctttatcgc
cgcacctgtccaccaagatggccgtagccacagagcttggttgggtaacgtcctctttatgtgac
aggaacgttgctgatggggtttctgaaggtacttcctgctcttttgtctcctggaagactgtgtct
tcaggaatgtctctgaccctgcccagagttgaacggatgctgggaaccagcacctgcacacggc
cttccctccaggactctgcgcacctctgtgctccacaggagacatgcaggtgctttctctcatga
gctcaggctcctgggctgacagctctccgaagctcgtggtgaggctcggtctctaactgtgccac
ttgccgatggcctctgttcacaaggcttccctgctcttcgatcttgcatcaccccttgaatttg
aaatccagagcagcccactcagagaccagtgtgaggaattagtgtccaggccacagatccaggga
ctgggcacaaacatctgcctgttgagtaggaactgagctgtggccattggcaaaaaaggagggt
gagcatggctgtttcttggggagctaacattcactatcttgtctcctccctcaggatgtgggca
atcaagttggggatgaaggagcaaaagccttcgcagaggctctgcggaaccacccccagcttgacc
accctgaggtaactgtggccctgctgtctccagggcaacctggtccctcccagctgctctagg
tttgctggggaagggtgattcgtgctcctaatagaagaggaatttgcatgtgtgatttccttac
tcttgtcaaaccttctttgatgcataagaggccatctagtaaagcacattcttctcttttttta
actttaagttctgggatacatgtagaagatgtgcaggtttgttacataggcaaatgcatgccatg
gtgatttgctgcacctatcaacctgtcatctaggtttaagccctgcatgcattaggtatttgtc
ctaatgcttgccctccccttgcccccaccccaacaggccctggtgtgtgttgttcccctccat
gtgtccatgtgttctcattgttcaactcccacttacgagtgagaacatgcagtgtttggttttt
gttcctgtgttagtttgctgagaatgatggtttccagcttcatccatgtgccagcaaaggacatg
atctcatttttttttatggttgcatagtattccatagtgtgtatgtgccacattttcttttatcca
gtctatcactgatgggcatttgggttggttccaagtctttgctattgtaaatagtgctacaataa
acatacactgtgcttgtgtctttatagcagaatgatttataatcctttgggtaaatacccagtaat
gggattgctgggtcaaatggtatttctggttctagatccctgaggaatcaccttaagtgtttatt
cagctcagtgaattctgcatgtgtcccacaccagccaaccaccacccccatcaagacagaggaca
tttccagcccctcagccatccctgcatgtcccttgctggtagagggagggtttcctaagtgcaga
tgaaacttaataagatgctggccagcagattcctgccccttccttgtcctcaggatgatgctgga
aaagagggactcttcctctctataaatggggatgcacctacccagccccgcttaggctgctggc
caaatcttgggaccttggtatgtccacggctctgctgctgttcttcctaccactgaaaaagagtc
caagaaggtggggacagtagcagaagagactttgccaggtcttgcagatggggtaccttgatggg
gccagcctttagaaggacagcttgccaggcctcgccagcctcctgcccatgtgcagaaacctgag
```

FIG. 18F

```
gtgccgaccccagcccactgttgtgtgagcaggctgtgctgatgacccatttcccgtccagcctg
cccttgtgctctgtgtgtgggctctggggcagcagcgcctgggcactactgctgcagctgaacac
ttctgcatcctgccccgagtgagcctgggctggggccacagccaggcagaggcttccagctgtt
ctgatgttgaagctaagattgaatgtagatgtgtctttaataattcaccccaagtgtgttccttc
ctagtcttgcgtccaacggcatctccacagaaggaggaaagagccttgcgagggccctgcagcag
aacacgtctctagaaatactgtggtaatagctcgagtcatttcatttgtttgtttgttttctgt
gatagggtcttgctttgtcgtccaggcttgagtgcattggtgtgatctcagctcactgcagcctc
cacctcccaggctcattcgaacctcccgccttggccttccgagtcctgagactataggcatgcac
caccacacccagttaattttaaaatttttgtagagatggggtttttgctatgttacccaggctgg
tcttgaactcctgggctcaagcagttctcctgccctggcttctcaaagccctgggattgcaggtg
tgagccactgcacctggcacagagtcattttggagggtttaggtcccaggaattatcccaggggc
tgcacatggcctggaatcttaacagaaaaggtgtctcccaattggaaaggctctaggcctttcag
ttaagttgataatttcctcctagagaagagaatagccacttctacaagcataaacaggtacagga
ggaggaagtgggctccgggagcctggatctgaggccttggccttctaggcccaggagaactaga
acgctggccatgcaagctatccaggtatccttggataccttcagatgtgcttagcagaggccaac
ttccacacacttggctcaaaatttctcccttcctcctcttcatctgccttccccaggcagcct
cctcctcccaggtcttcacatcagggtttggcctttatgctccatccagctcatctgtcactt
gtcacctgaagcccacagtcctcgctccctctgcactctagggcacttactaagtggatgtgg
cctcctgagagtgttttttgttggtgttccctttttatggccacttaatgttttattttgcttt
atttgtatttacatctctgtatcataaattccatacaggtggctgggagcagtgactcacatctg
taatcccagtactttggaaggctgaggtggaggatcgcttgaggccaagagttcgagactagcc
tgggcaatatagcgagaccctctatctacaaaaaaaaaaacattccttacaggttaagtgaggg
agttgtattacaaccctccctatcatctactcagagcccagtgctcatttgatcttgctaaatta
gttactgagaataatgacaatatcctcttcatgagagagttttgacattaggcctgctgtccagt
aagtgcattttaaattctttcccctcaacaaatcatttaacatttgaaaagtagtttatgtttt
ttggaaaaaatgtaagacactaaaggaggacatgaaagtacctcctaaagttcctgctaaaagga
ggaagtgaaagtacctccctttgtgttttccaaaataacctttccttctagccttttgttctat
gtatgttcaaagatatgcaaaacagaatagcattcaagcagtggctctaaaaatattgtaatcac
atactttacatgtctcctttagggtttctccatcttgatgctgttgacattttggtccaagtgat
tcttttattatggtagggctgtcctgtgcatcatagacggtttagccgcatctctgcctgtacct
cccagtggtgaggatcaaaaatgcctccggacatggccaggtgcccatggagagtgaaatcaca
tggatagtagtaatgtcaacacctagaagccctcaagtgctgactgcatgccatgtgttattcta
cacttttccctgtgttaactcactcagcctcacaaccactctatacgatctctactgttaacgt
tcaccagtgagaaaactcagacccaaagaacttaagcctgttgcccgaggtcaccctgctggtgg
gtgatacaaacctgcccaggctgagtccggagtagatgtcaatgctgtgttcttctccctcctca
ttctacctcattctccctacaagctgcacaacatctcgaatagatatcacaatatatttcatcag
ttgtttctgatctaaatttgttcagattttacattaggataataccacaatgcatgctgcaatgt
ataaagctttgtgtgtatatccttgcacactgtagggtaaatttctagaagtctgattgtcttaa
aatgaagcacattaaaaatttgggcaggcacatccaaactgcccttcaaggaattttttttttta
aatgttctttctgttctattcttcttcctaatgattctttcgtccactggcacaagtgggtccta
ccctgtttacaccaaggagctttggtgctttatccagaccacttctggttctaaggaccattgag
agacttcctgaactttcagtcacttaacttgggtccctcacaagttaactgagagcaaagtactg
aacacattttaatgtgcagtcagtgactgtttcaggtcttcaaactaacttggataacacactgt
cagtggtgttcaagggaccctgggactagaggagaactgagaagcaggcattggccctttgtttt
ccgtgggcccccatcttccatgaaatctgagggctcagcaaaggtggggagggagggtgggctcc
tctacaggtagctgggctaagaaataggagcccaggtacaggatttgcattaaaaatgagtccca
ttgaccttctgtggggctgacaggctgggcttggagcctggctgttttctgggttctcagcaagt
gatcatctgcatagctggagagccttggctgagctcccgctcctgtgaactctaaaacaatgtc
tgccaagtaggctctcttgagtaaatacttccttttttttccttaggctgacccaaaatgaactc
aacgatgaagtggcagagagtttggcagaaatgttgaaagtcaaccagacgttaaagcatttatg
gtaactcagagagccttacaatttcagactgtgctacttttcaaaagtatttttgagataaaat
ttacatactgtaaaattcactctcttaaagtatacaattcagaggtttttagtgcaaccatcacc
acctaattctagaacattttcactcctcctccccactccaaaaagccctggtatccattaagcag
tcactccctgtcctcctcccagaccctggcaaccactaatccgctttctgtctctatggatttg
```

FIG. 18G

```
cctactctgggcatttcatataaatggaatcaagcaatatgtgacctttcgtctctgtgttctag
catgtttcattcctttttatggctaaatgataattcactctaaggaaattttgcagtttattaat
cagttgatgggacatttggggttgtttctacttttcgactattatgcgtaatgctactgtgaacac
tcctgttcatgcttttgggtgaacatatgttttcatctcttttgggaatatacctgggaatagaa
tttctgggtcatatggcaattctgtaactttttgaggagccaccaaactgttttctaaagtggat
gtactatttacattctcgccagcaatgtatgtggattccaatttctccacatcctcaccaacac
ttattattgtccatcttttaaaatctagttatactagtggatgtgaagtaatattgtggttttga
tttgcatttccctgatgacaacaatgttgaatgtcttttatgtgcctactgggagtctgtatag
cttcttggagaaatgtctccatatcctttgcccatttaaaattgggtttgtcttctaatgctg
agttatagggggttctctatatattctgggtgctagacctttactagatacaggttttgcaagtat
tttctttctttctgtggagttttttcctctttcttgatagtgacctttaaaggacaacagttttta
atttttgtttttttgagatggagtcttgctcttgtcacccagacaggagtgcagtggcatgatc
tcagctctctgcaacctccacctcctgggttcaagcgattcttctgcctcagcctcctgagtagt
tgggattacaggcatcagccaccatgcctgtctcattttgtatttaatagagatggggtttca
ccattaggcccaggctggtcttgaactcctgacctcaggtgatccacctgcctcagcctcccaa
agtgctgggattacaggcgaaaagccactgcacctggccaatagttttaatttgatgaagtcc
aatttatctatttttcttggttgcttgtgctttcagtgtcttatctaagaaatgattgccta
atccaagatcacaaagaactccacctaagttttctgttaagcgttatagttgtttcccctcacat
ataggtctgcaatccattttgagttaattttgtatagtgtaaagtgagggttaacctcattctc
ttgcacgtggatatccagctgtcccggcagcaccacgtgttaacagattatcttttcctattga
atggccttgacacccttgtcaaaaatcaattgaccataaatgtatgggtttatttctgaattctc
tgttctggtccattgatttatatgtctctcctatgccaggaccattgctgtagctttgtgtagta
cattttgaaatcaggaggtgtgagttctactttgttcttctttctcaagattgtttagaccattc
tgggttctttgcatttcttatgaattcagactcaccttgtcaatttctgcaaaaagactagactc
tgctacatattgtttttctttccttttagcctgcagaattatttgatcccattccctaagtgc
aggccagcctctccagggagagcagagctaggacagggtcagaaagagagtcttggctgctttgt
gcattcccaacctgcactggccctagtgaaggcagcccgagtgggtggatgtgcctggacactgc
aggcttttaggggcattaggtgctctccttcctggcctcctgccacatcttggttggaggctgc
cttccctgccttcaaaaaagcctaagtggtgactagaaaacagcagagtgtaactgaatacagaa
cttggtgcccacttcctggttctattttgtccttttgaaagggaaggtcattacctctgccat
tgaacccaggggccctagcccttgtggggtatggctgggagcaccagatcctggctgcagcccag
ccaccagtggtcctgtgtgcttggcagtaacagtgacaagagctcccttcccctggacactgt
gcctaatacctcctcttgaaatctcacacacccagtggatgggggcactctatagttattct
cagtttacagatgacacaactgaggcacagacagatgcgtttatttcttcaaggttctgtagctg
aacagtggggagggagggtttaagaggagctgcaccgctctgcaatactgctctcacgaggga
gtcctcttcattcatgacagcatagggccctcgtcttcctggtaagggcttccttcttgggtcag
tgccaggatttctaagggtcatgtttagcaggagcctattctacaaacagccaggagcagggaat
gactctgtgatgaagcggagacactacagcctcttgatgcatttatttcctggttgggttagaag
cgtagctgcccaagggagcatttcaggagaggcctggcttcctagcgatagctgaaaactttgtt
tcatttgaatcactgctacccagaacaatggggtgcattctcagagtcccattattaaagcttt
tccactgagcccatgagaactattcatgagaactatttcatggcagcataactgtttctcctcc
ctccctcttgcatgttggtagcctcttaactttaaaacctgccttgcctttccctagctacctgg
aaggagacgtcagacttcctgtcccatggtgtgtttcttacaatttgttgttcagattggtggtc
tcccaaatatatataaaaatataaatggagtctcactctgtcacccagctggagtgcagtggca
cgatcttggctcactgcaacctccacctcccagttcaagcaattctcctacctcagtctcccgag
tagctgggagtacaggtgcacaccaccatgcccagctaattttttgtatttaatagagacag
gttggccaggatggtatcgatctcctgagctcgtgatccacccacctcggcctcccaaagtgctg
ggattacaggtgtgagccactgcacccggccccaaatatttgattatgcacctctgcagtgaaa
aatgcaaacacacacatcagttcatgtattacattatgttcactataaaacaaacagaaaattt
aaaaaatatcaagctatcctttactctagtggatcttacctggacactttagccagatacaaag
tcacatggactcagttcttcccctgaccaacttgtctcttatcccaaaacaccttgcaactccc
ttacgaaggggtcaaatttgatccagtattatggattttatacaagttatgttcttctttcaggc
ttatccagaatcagatcacagctaaggggactgcccagctggcagatgcgttacagagcaacact
ggcataacagagatttggtaagatcccagcgtttgtcacagtaataacaccagtgactgtttact
```

FIG. 18H

```
caccaccactgactgtgcaaggcacaacgcagggtggtttctgtttattcctccagcaaccctgc
acagtaatggtattacctctgttttacagaggtagacagaggcccagaccagtgaaataaggttg
cccaaggtcactacgagagaagctagaattcagcccagaatgcctgattccatattctgtgctct
cctgccctgggccccgccctcatctaccttcattgggtgggatgggggaagtggccagtgaaat
gatttcctagtggaagtaaatcccctgggactcagcaattgagagatgactgtgttggccagga
gtttggagctcattcttcccttttctgggttccgtaagacatttccaggctgacttgaactgac
ctgtgctctttgtctacttcttttttctgctttgagaacttccttatgctaatagaagaaaaaa
gtttgctttactgtgacattgagcgccatgccacttctttcttgcctcccataaggcacagacac
tccccactcagcagctcccttaacaacttaattgcctgggtgacgtgggactgggtggatgctgg
gagaggggccttattaactatgtcctcctttcatgactggggagaatttcatagccaattaaaaa
aaaacaaaaaacagctccttggccaacacaggctcctcatacagtgttttttaaactttgcttta
gaacttgtttggaacttgtcataaaatcgatcagtttggtgaattgcaaccaacaatatttaaaa
agaaaacagaacagaacaaaatatcaggatgcaatgtgcatggtatgaaagtatcatttcattca
tcttagttcatgcttgcatgtgagtgggtgtgtgtttgcataagtgttggttcacaacataaaat
gtaattcttatttaggggttgtagacaaaaggttttttttaaaaaaaacactgttggctaggcat
ggtggctcatgcctgtaataccagcactttgggaggccaagatgggcagatctcttgagcacagg
agtttgagaccagcctgggcaacatgcgaaacccgtcactacaaaaattagcccgacatggtgc
tatgtgcctgtagtcccagctactcaggaagctgatgtgggaggatggatgcatgggagatcaag
gctgcagtgagccaggatcatgccactgcaatccagcctgggtgccagagaccctgtctcaaaaa
acaaaaaagaaaaaagaaaaacaccatcatagagaatagagcccagatctaaacagacacctgt
ggcctgtgtgcctgcgaagcccagcctgcccagcagcctgggaagcactggagggcactggaact
gtttgcatgggtgtttgccctcaggccactccgtttctgctgattcttaagtttgaggacagca
ggcagaggggagaggaaggagactgccagactacagaacagtttgcagagcacagttggcttcc
actttttctctgtagctggtcaggcgggtagtaaagacctacagttgctttaattctgtcaagttt
caaaatctgcattgcttccctcttgagggtcaccattcctacacaaggaaccatttagtagggc
caggagacttcagcttcaaggcctgcacttgtgtcagggtggagaggggaactggccaccaattc
agagagggcaggacaggcggcatgggtgctggtcttgggagtgtcttcacttaggtccctggctt
gttctgggagcctccagagcatgctcctctgtgtgtgacttcatgggactgggctctgagaaggc
tgtggctttgttggccctgccagggactgccacaccaggccacagggttgtggttgagctggccg
gggagccacgttcagggagcagctctgcttggagccaacacttacagagtaagccttctccttgg
acttgttaactgtactgacacttatttctacctcattcctttctgaaaataacttggaagtctga
agtcccttgatgagttctgtctttaagaacagaaattagaggtgaacaatgaacactgtaaatta
cagaaatgtatcccactccagtataacagctttctgtgaggctatctcctccagactgtggctct
gggagggtggggcctgagtcaaggtcctagggactagtgctgtgtcttcatttattccttgaata
acgaaacgcttgagcatcagggactgtgctagcaccaaaaatccagtggtgaacaacatggcttc
atgggttcactgtctagaaagggagaagcacattaaagaaaaaatcatttgcgtaattatttaat
tacaactgtgatgggtactatcacaaaggggaaggccaagagggaacctgatttagatgaggttg
cagggaaggcctctctgaggaagcagcacttacactaagccatgaaggatgaataggagctagtc
agctgaggtgagtattctgcgtagggaacagcatgtgcaaagggtctggggcaggagggagtgtg
gtgtcctggaagaactgccagaagctgctgtgcccagggttcagacagtgtggaagagggact
acaggaggctgaggagataggcagggactggaccataaagatctgtgggtcatgatgtgcattt
tggtctttatcctaaaagtgatggaaagtcagtgaacagtttgaagcaggagaggcatgtgatca
gatctgcaatgcaaaagaccaattcttggctcttctaggaaactgaattggagaaggccagagt
acgtggaaatgacctgtcagtaggacattgtactgatgcagggaagagatgatgggtgctcagac
caagatggccggccaaagacatagaggttccagggaggcattctagattcttaggaattagggga
gaactttgtgatacaaggaacatggggatgagaaggaaggtgtccaggttgaccccaggttact
aacctgctcagcaggatgagagtggtccattcactaagccaggggaccctaggaggtgtggctac
tttgaggtgtggggagaggtccaagtgaggatgccaagcaggtaactgcctccacggacataca
aacaaggccgtggcattgatgagatcgggtggggaaaagggcttagccccaaacctggaggaaat
ctcagatgtagaggtcacatggaggagaatataggaaaggaaattgaagtagagtgctcagatgc
aggagaaaaatcagcgcatataaccaagccaaggggagggagtgcctcaagaaggagggagagga
gaggtcaggacagccaaaatcctgagggccaagaaagacaagacctggaaaatgtcattaaattc
aggcttatggaggctacaggtgaccttagtgagacccagtgaacagagggatggcagctggagag
gatccatgctaatatgaaggaactatctgcaaagggtatgttccttaatttcagggatacatgtg
```

FIG. 18I

```
tattgtgtgatacacgagtgtgtgctatgaacacaccttgggaaggagtgtgcgaggatccttaa
cattttacctgtgtacttttgtcttcctccttttcaacagcctaaatggaaacctgataaaacca
gaggaggccaaagtctatgaagatgagaagcggattatctgtttctgagaggatgctttcctgtt
catggggttttgccctggagcctcagcagcaaatgccactctgggcagtcttttgtgtcagtgt
cttaaagggcctgcgcaggcgggactatcaggagtccactgcctccatgatgcaagccagcttc
ctgtgcagaaggtctggtcggcaaactccctaagtacccgctacaattctgcagaaaaagaatgt
gtcttgcgagctgttgtagttacagtaaatacactgtgaagagactttattgcctattataa
```

FIG. 18J

```
  1 GTCGACCCACGCGTCCGGCAGCAGGCAGGCTGCAGCAGGCGAGCAGCAGCAAGAGTAAAAGG
    CAGCTGGGTGCGCAGGCCGTCGTCCGTCCGACGTCGTCCGCTCGTCGTCGTTCTCATTTTCC

63 TGACCGCGGCTGCCCACCCCAGAGCCATGGGGCGGGCACGAGATGCCATCCTGGACGCTCTT
    ACTGGCGCCGACGGGTGGGGTCTCGGTACCCCGCCCGTGCTCTACGGTAGGACCTGCGAGAA
                             1▶ M  G  R  A  R  D  A  I  L  D  A  L

125 GAAAACTTGTCAGGGGATGAACTCAAAAAGTTCAAGATGAAGCTGCTGACAGTGCAACTGCG
    CTTTTGAACAGTCCCCTACTTGAGTTTTTCAAGTTCTACTTCGACGACTGTCACGTTGACGC
    13▶ E  N  L  S  G  D  E  L  K  K  F  K  M  K  L  L  T  V  Q  L  R

187 AGAAGGCTATGGGCGCATCCCACGCGGGGCCCTGCTGCAGATGGACGCCATAGATCTCACTG
    TCTTCCGATACCCGCGTAGGGTGCGCCCCGGGACGACGTCTACCTGCGGTATCTAGAGTGAC
    33▶ E  G  Y  G  R  I  P  R  G  A  L  L  Q  M  D  A  I  D  L  T

249 ACAAACTTGTCAGCTACTATCTGGAGTCGTATGGCTTGGAGCTCACAATGACTGTGCTTAGA
    TGTTTGAACAGTCGATGATAGACCTCAGCATACCGAACCTCGAGTGTTACTGACACGAATCT
    54▶ D  K  L  V  S  Y  Y  L  E  S  Y  G  L  E  L  T  M  T  V  L  R

311 GACATGGGCTTACAGGAGCTGGCTGAGCAGCTGCAAACGACTAAAGAAGAGTCTGGAGCTGT
    CTGTACCCGAATGTCCTCGACCGACTCGTCGACGTTTGCTGATTTCTTCTCAGACCTCGACA
    75▶ D  M  G  L  Q  E  L  A  E  Q  L  Q  T  T  K  E  E  S  G  A  V

373 GGCAGCTGCAGCCAGTGTCCCTGCTCAGAGTACAGCCAGAACAGGACACTTTGTGGACCAGC
    CCGTCGACGTCGGTCACAGGGACGAGTCTCATGTCGGTCTTGTCCTGTGAAACACCTGGTCG
    95▶ A  A  A  A  S  V  P  A  Q  S  T  A  R  T  G  H  F  V  D  Q

435 ACAGGCAAGCACTCATTGCCAGGGTCACAGAAGTGGACGGAGTGCTGGATGCTTTGCATGGC
    TGTCCGTTCGTGAGTAACGGTCCCAGTGTCTTCACCTGCCTCACGACCTACGAAACGTACCG
    116▶ H  R  Q  A  L  I  A  R  V  T  E  V  D  G  V  L  D  A  L  H  G

497 AGTGTGCTGACTGAAGGACAGTACCAGGCAGTTCGTGCAGAGACCACCAGCCAAGACAAGAT
    TCACACGACTGACTTCCTGTCATGGTCCGTCAAGCACGTCTCTGGTGGTCGGTTCTGTTCTA
    137▶ S  V  L  T  E  G  Q  Y  Q  A  V  R  A  E  T  T  S  Q  D  K  M

559 GAGGAAGCTCTTCAGCTTTGTTCCATCCTGGAACCTGACCTGCAAGGACTCCCTCCTCCAGG
    CTCCTTCGAGAAGTCGAAACAAGGTAGGACCTTGGACTGGACGTTCCTGAGGGAGGAGGTCC
    157▶ R  K  L  F  S  F  V  P  S  W  N  L  T  C  K  D  S  L  L  Q

621 CCTTGAAGGAAATACATCCCTACTTGGTGATGGACCTGGAGCAGAGCTGAGGTATCTTTTCC
    GGAACTTCCTTTATGTAGGGATGAACCACTACCTGGACCTCGTCTCGACTCCATAGAAAAGG
    178▶ A  L  K  E  I  H  P  Y  L  V  M  D  L  E  Q  S  -

683 AGCTACATTATCTAGCTCCTGACTTTGTATACACAATTTTTGAAAAAACAATTTGTATTTGT
    TCGATGTAATAGATCGAGGACTGAAACATATGTGTTAAAAACTTTTTTGTTAAACATAAACA

745 GTTTAAAAAAAAAAAAAAAAAAAAAAGGGCGGCCGC
    CAAATTTTTTTTTTTTTTTTTTTTTTCCCGCCGGCG
```

FIG. 19

Appl. No.: 09/728,721
Reply to Action dated December 28, 2004
Replacement Sheet

```
  1 CGCGTCCGGCTGCAGCGGGGTGAGCGGCGGCAGCGGCCGGGGATCCTGGAGCCATGGGGC
    GCGCAGGCCGACGTCGCCCCACTCGCCGCCGTCGCCGGCCCCTAGGACCTCGGTACCCCG
                                                          1▶ M  G

61 GCGCGCGCGACGCCATCCTGGATGCGCTGGAGAACCTGACCGCCGAGGAGCTCAAGAAGT
    CGCGCGCGCTGCGGTAGGACCTACGCGACCTCTTGGACTGGCGGCTCCTCGAGTTCTTCA
  3▶R  A  R  D  A  I  L  D  A  L  E  N  L  T  A  E  E  L  K  K

121 TCAAGCTGAAGCTGCTGTCGGTGCCGCTGCGCGAGGGCTACGGGCGCATCCCGCGGGGCG
    AGTTCGACTTCGACGACAGCCACGGCGACGCGCTCCCGATGCCCGCGTAGGGCGCCCCGC
 23▶F  K  L  K  L  L  S  V  P  L  R  E  G  Y  G  R  I  P  R  G

181 CGCTGCTGTCCATGGACGCCTTGGACCTCACCGACAAGCTGGTCAGCTTCTACCTGGAGA
    GCGACGACAGGTACCTGCGGAACCTGGAGTGGCTGTTCGACCAGTCGAAGATGGACCTCT
 43▶A  L  L  S  M  D  A  L  D  L  T  D  K  L  V  S  F  Y  L  E

241 CCTACGGCGCCGAGCTCACCGCTAACGTGCTGCGCGACATGGGCCTGCAGGAGATGGCCG
    GGATGCCGCGGCTCGAGTGGCGATTGCACGACGCGCTGTACCCGGACGTCCTCTACCGGC
 63▶T  Y  G  A  E  L  T  A  N  V  L  R  D  M  G  L  Q  E  M  A

301 GGCAGCTGCAGGCGGCCACGCACCAGGGCTCTGGAGCCGCGCCAGCTGGGATCCAGGCCC
    CCGTCGACGTCCGCCGGTGCGTGGTCCCGAGACCTCGGCGCGGTCGACCCTAGGTCCGGG
 83▶G  Q  L  Q  A  A  T  H  Q  G  S  G  A  A  P  A  G  I  Q  A

361 CTCCTCAGTCGGCAGCCAAGCCAGGCCTGCACTTTATAGACCAGCACCGGGCTGCGCTTA
    GAGGAGTCAGCCGTCGGTTCGGTCCGGACGTGAAATATCTGGTCGTGGCCCGACGCGAAT
103▶P  P  Q  S  A  A  K  P  G  L  H  F  I  D  Q  H  R  A  A  L

421 TCGCGAGGGTCACAAACGTTGAGTGGCTGCTGGATGCTCTGTACGGGAAGGTCCTGACGG
    AGCGCTCCCAGTGTTTGCAACTCACCGACGACCTACGAGACATGCCCTTCCAGGACTGCC
123▶I  A  R  V  T  N  V  E  W  L  L  D  A  L  Y  G  K  V  L  T

481 ATGAGCAGTACCAGGCAGTGCGGGCCGAGCCCACCAACCCAAGCAAGATGCGGAAGCTCT
    TACTCGTCATGGTCCGTCACGCCCGGCTCGGGTGGTTGGGTTCGTTCTACGCCTTCGAGA
143▶D  E  Q  Y  Q  A  V  R  A  E  P  T  N  P  S  K  M  R  K  L

541 TCAGTTTCACACCAGCCTGGAACTGGACCTGCAAGGACTTGCTCCTCCAGGCCCTAAGGG
    AGTCAAAGTGTGGTCGGACCTTGACCTGGACGTTCCTGAACGAGGAGGTCCGGGATTCCC
163▶F  S  F  T  P  A  W  N  W  T  C  K  D  L  L  L  Q  A  L  R

601 AGTCCCAGTCCTACCTGGTGGAGGACCTGGAGCGGAGCTGAGGCTCCTTCCCAGCAACAC
    TCAGGGTCAGGATGGACCACCTCCTGGACCTCGCCTCGACTCCGAGGAAGGGTCGTTGTG
183▶E  S  Q  S  Y  L  V  E  D  L  E  R  S

661 TCCGGTCAGCCCCTGGCAATCCCACCAAATCATCCTGAATCTGATCTTTTTATACACAAT
    AGGCCAGTCGGGGACCGTTAGGGTGGTTTAGTAGGACTTAGACTAGAAAAATATGTGTTA

721 ATACGAAAAGCCAGCTTGAA
    TATGCTTTTCGGTCGAACTT
```

FIG. 21

ALIGN calculates a global alignment of two sequences
version 2.0uPlease cite: Myers and Miller, CABIOS (1989)
> hCARD5-DNA                                          740 aa vs.
> mCARD5-DNA                                          763 aa
scoring matrix: pam120.mat, gap penalties: -12/-4
68.2% identity;     Global alignment score: 2377

```
                    10        20        30
inputs  C---GCGTCCGGCTGCAG-CGGGGTG-----AGCG-GCGGCAGC-------------GGC
          :::::::::.::::  :.::  ::      .:::  ::.:::::            :..:
        CCACGCGTCCGGCAGCAGGCAGGCTGCAGCAGGCGAGCAGCAGCAAGAGTAAAAGGTGAC
            10        20        30        40        50        60

40        50        60        70        80        90
inputs  CGGGGAT------CCTGGAGCCATGGGGCGCGCGCGCGACGCCATCCTGGATGCGCTGGA
        ::  ::  :       ::  .:::::::::::  ::..::  ::  :::::::::::  ::  ::  ::
        CGCGGCTGCCCACCCCAGAGCCATGGGGCGGGCACGAGATGCCATCCTGGACGCTCTTGA
            70        80        90        100       110       120

100       110       120       130       140       150
inputs  GAACCTGACCGCCGAGGAGCTCAAGAAGTTCAAGCTGAAGCTGCTGTCGGTGCCGCTGCG
         .:::  ::.:  :    ::  ::.:::::.:::::::::  :::::::::::..:::: .:::::
        AAACTTGTCAGGGGATGAACTCAAAAAGTTCAAGATGAAGCTGCTGACAGTGCAACTGCG
            130       140       150       160       170       180

160       170       180       190       200       210
inputs  CGAGGGCTACGGGCGCATCCCGCGGGGCGCGCTGCTGTCCATGGACGCCTTGGACCTCAC
        ::.:::::  :::::::::::::::.::  ::  ::  ::::::      :::::::::::.:.::   :::::
        AGAAGGCTATGGGCGCATCCCACGCGGGGCCCTGCTGCAGATGGACGCCATAGATCTCAC
            190       200       210       220       230       240

220       230       240       250       260       270
inputs  CGACAAGCTGGTCAGCTTCTACCTGGAGACCTACGGCGCCGAGCTCACCGCTAAC-GTGC
        :::::.::   :::::::.:::   :::::::.:   ::   :::        :::::::::   .   :.::   ::::
        TGACAAACTTGTCAGCTACTATCTGGAGTCGTATGGCTTGGAGCTCAC-AATGACTGTGC
            250       .260       270       280       290

280       290       300       310       320       330
inputs  TGCGCGACATGGGCCTGCAGGAGATGGCCGGGCAGCTGCAGGCGGCCACGCACCAGGGCT
        :   :  ::::::::::  :..::::::  ::::  ..::::::::::::..::.:   :  .  :   ::.:  :
        TTAGAGACATGGGCTTACAGGAGCTGGCTGAGCAGCTGCAAACGACTAAAGA--AGAG-T
        300       310       320       330       340       350

340       350       360       370       380       390
inputs  CTGGAGCCGCGCCAGCTGGGATCCAGGCCCCTCCTCAGTCGGCAGCCAAGCCAGGCCTGC
        ::::::::  :  :  ::::::::  ..  :  .  :  ::::  :::::.    .:::::::..  ::::      .:
        CTGGAGCTGTGGCAGCTGCAGCCAGTGTCCCTGCTCAGAGTACAGCCAGAACAGG---AC
        360       370       380       390       400       410

```
inputs ACTTTATAGACCAGCACCGGGCTGCGCTTATCGCGAGGGTCACAAACGTTGAGTGGCTGC
       ::::::.:.:::::::::: ::  .::.:: :: :: :::::::::.: :: ::  :. :::
       ACTTTGTGGACCAGCACAGGCAAGCACTCATTGCCAGGGTCACAGAAGTGGACGGAGTGC
          420       430       440       450       460       470

460       470       480       490       500       510
inputs TGGATGCTCTGTACGGGAAGGTCCTGACGGATGAGCAGTACCAGGCAGTGCGGGCCGAGC
       ::::::::: :: : :: :.. :: ::::: ::.:..:::::::::::::: :: :: :::
       TGGATGCTTTGCATGGCAGTGTGCTGACTGAAGGACAGTACCAGGCAGTTCGTGCAGAGA
          480       490       500       510       520       530

520       530       540       550       560       570
inputs CCACCAACCCAAGCAAGATGCGGAAGCTCTTCAGTTTCACACCAGCCTGGAACTGGACCT
       ::::::.:: :,..:::::::: ::::::::::::: ::  . .::: :::::::: :::::
       CCACCAGCCAAGACAAGATGAGGAAGCTCTTCAGCTTTGTTCCATCCTGGAACCTGACCT
          540       550       560       570       580       590

580       590       600       610       620       630
inputs GCAAGGACTTGCTCCTCCAGGCCCTAAGGGAGTCCCAGTCCTACCTGGTGGAGGACCTGG
       :::::::::   :::::::::::::: :.:.::::.. :: ::::: :::::..:::::::::
       GCAAGGACTCCCTCCTCCAGGCCTTGAAGGAAATACATCCCTACTTGGTGATGGACCTGG
          600       610       620       630       640       650

640       650       660       670       680
inputs AGCGGAGCTGAGGC-TCCTTCCCAGCAACACTCCGGTC-AGCCCTGGCAAT-CCCAC-C
       :::.:::::::::: :: :: :::::.::: :  .:: ::: ::::.:...:  ::  :
       AGCAGAGCTGAGGTATCTTTTCCAGCTACATT---ATCTAGCTCCTGACTTTGTATACAC
          660       670       680       690       700       710

690       700       710       720       730       740
inputs AAATCATCCTGAATCTGATCTTTTTATACACAATATACGAAAAGCCAGCTTGAA
       ::.: .::  ..::.:....: : :.:.:. ,  ...:.: .::::.  :.  .....:
       AATTTTTGAAAAAACAATT-TGTATTTGTGTTTAAAAAAAAAAAAAAAAAAAGG
          720       730       740       750       760
```

FIG. 23B

Appl. No.: 09/728,721
Reply to Action dated December 28, 2004
Replacement Sheet

```
ALIGN calculates a global alignment of two sequences
 version 2.0uPlease cite: Myers and Miller, CABIOS (1989)
> hCARD5-protein                                    195 aa vs.
> mCARD5-protein                                    193 aa
 scoring matrix: pam120.mat, gap penalties: -12/-4
 71.8% identity;   Global alignment score: 712

10         20         30         40         50         60
inputs  MGRARDAILDALENLTAEELKKFKLKLLSVPLREGYGRIPRGALLSMDALDLTDKLVSFY
        ::::::::::::::...::::::...:.:::::::::::::: :::.::::::::.:
        MGRARDAILDALENLSGDELKKFKMKLLTVQLREGYGRIPRGALLQMDAIDLTDKLVSYY
               10         20         30         40         50         60

70         80         90        100        110        120
inputs  LETYGAELTANVLRDMGLQEMAGQLQAATHQGSGAAPAGIQAPPQSAAKPGLHFIDQHRA
        ::.::  :::  .:::::::::: :::. : . :::..:.  .:.::.:  : ::.:::
        LESYGLELTMTVLRDMGLQELAEQLQT-TKEESGAVAAAASVPAQSTARTG-HFVDQHRQ
               70         80         90        100        110

130        140        150        160        170        180
inputs  ALIARVTNVEWLLDALYGKVLTDEQYQAVRAEPTNPSKMRKLFSFTPAWNWTCKDLLLQA
        ::::::::.:.  :::: :  :::. :::::::::  :..:::::::.:.:: ::::  ::::
        ALIARVTEVDGVLDALHGSVLTEGQYQAVRAETTSQDKMRKLFSFVPSWNLTCKDSLLQA
              120        130        140        150        160        170

190
inputs  LRESQSYLVEDLERS
        :.: ..::: :::.:
        LKEIHPYLVMDLEQS
              180        190
```

FIG. 24

Page 43 of 58
Appl. No.: 09/728,721
Reply to Action dated December 28, 2004
Replacement Sheet

```
  1 CCCGCGTCCGGACTTCCCTTCCAGTGTTTGTTCCTCTCTGCTCTCTCCAACAGAAGGTATTTTTG
    GGGCGCAGGCCTGAAGGGAAGGTCACAAACAAGGAGAGACGAGAGAGGTTGTCTTCCATAAAAAC

66 GCATGTTTTATCTTTGCTAAGTAGGATTTCTGTCTTTCTTTGTTAACACAGATTTCTTTCTGTGC
    CGTACAAAATAGAAACGATTCATCCTAAAGACAGAAAGAAACAATTGTGTCTAAAGAAAGACACG

131 CAGAATGACCTGATCCATTTCCTGGTTTGTAGAAAGCCATGGCTTCAGAGGGTGCTTCCTCAGAA
    GTCTTACTGGACTAGGTAAAGGACCAAACATCTTTCGGTACCGAAGTCTCCCACGAAGGAGTCTT
    1▸ M  A  S  E  G  A  S  S  E

196 ATCATAGAAAAACAGCGAACAAAGTTGCTCAGTGTCCTCCAACAAGATCCCGACTCTATCTTGGA
    TAGTATCTTTTTGTCGCTTGTTTCAACGAGTCACAGGAGGTTGTTCTAGGGCTGAGATAGAACCT
    10▸ I  I  E  K  Q  R  T  K  L  L  S  V  L  Q  Q  D  P  D  S  I  L  D

261 CACGTTAACCTCTCGGAGACTGATTTCTGAGGAGGAGTATGAGACTCTAGAGGCAATTACAGATC
    GTGCAATTGGAGAGCCTCTGACTAAAGACTCCTCCTCATACTCTGAGATCTCCGTTAATGTCTAG
    31▸ T  L  T  S  R  R  L  I  S  E  E  E  Y  E  T  L  E  A  I  T  D

326 CTCTGAAGAAAAGCCGGAAGCTGTTAATTTTGATCCAGAAGAAGGGAGAGGACAGCTGTTGTTGT
    GAGACTTCTTTTCGGCCTTCGACAATTAAAACTAGGTCTTCTTCCCTCTCCTGTCGACAACAACA
    53▸ P  L  K  K  S  R  K  L  L  I  L  I  Q  K  K  G  E  D  S  C  C  C

391 TTCCTCAAGTGTCTGTCTAATGCCTTTCCACAGTCAGCTTCCACCTTGGGTTTAAAGCAGGAAGT
    AAGGAGTTCACAGACAGATTACGGAAAGGTGTCAGTCGAAGGTGGAACCCAAATTCGTCCTTCA
    75▸ F  L  K  C  L  S  N  A  F  P  Q  S  A  S  T  L  G  L  K  Q  E  V

456 TCCACGGCAGGGGACTGGAGAGGTTGTCGAGGTGAGCAGGGGTTTGGAAGATCCCTTTTCTCTTG
    AGGTGCCGTCCCCTGACCTCTCCAACAGCTCCACTCGTCCCCAAACCTTCTAGGGAAAAGAGAAC
    96▸ P  R  Q  G  T  G  E  V  V  E  V  S  R  G  L  E  D  P  F  S  L

521 GGACCATAACCCCAGAAATAGCAGAGCTCTCAGAAGAGAAAGAATGCCCGGGTCTGGGAGCTCCG
    CCTGGTATTGGGGTCTTTATCGTCTCGAGAGTCTTCTCTTTCTTACGGGCCCAGACCCTCGAGGC
    118▸ G  T  I  T  P  E  I  A  E  L  S  E  E  K  E  C  P  G  L  G  A  P

586 GAGTTCTTCACCTGCAAGGAAAGCAGCCACAGGGAACCGGAAGTACCTTCTTGGGAGAATCAGGA
    CTCAAGAAGTGGACGTTCCTTTCGTCGGTGTCCCTTGGCCTTCATGGAAGAACCCTCTTAGTCCT
    140▸ E  F  F  T  C  K  E  S  S  H  R  E  P  E  V  P  S  W  E  N  Q  E

651 AGGGCGTGGTGCACAGCAAGTCACCGCTCCGCGTTCAGTCAAAGGAGTTGAGTATGAAGTTCCAG
    TCCCGCACCACGTGTCGTTCAGTGGCGAGGCGCAAGTCAGTTTCCTCAACTCATACTTCAAGGTC
    161▸ G  R  G  A  Q  Q  V  T  A  P  R  S  V  K  G  V  E  Y  E  V  P
```

FIG. 25A

```
716  CAAGTATCTCCCTCTTAAGCGACGGGCAGAGATACGAGGAGCCAGATGATTCGCTGTACTTAGAA
     GTTCATAGAGGGAGAATTCGCTGCCCGTCTCTATGCTCCTCGGTCTACTAAGCGACATGAATCTT
 183▶ A  S  I  S  L  L  S  D  G  Q  R  Y  E  E  P  D  D  S  L  Y  L  E

781  GAAGGGGAAGGTGAAGAGTCTCTTGGGTACCCTGAAGATGTTTTGGAGGAAGGGGCCGGCGATGA
     CTTCCCCTTCCACTTCTCAGAGAACCCATGGGACTTCTACAAAACCTCCTTCCCCGGCCGCTACT
 205▶ E  G  E  G  E  E  S  L  G  Y  P  E  D  V  L  E  E  G  A  G  D  D

846  CCCACAGTGCTTTGTATATGATAGTGAGGAGGAATGCGAGTATGAGGAAAACATGGGCTCCTCCG
     GGGTGTCACGAAACATATACTATCACTCCTCCTTACGCTCATACTCCTTTTGTACCCGAGGAGGC
 226▶ P  Q  C  F  V  Y  D  S  E  E  E  C  E  Y  E  E  N  M  G  S  S

911  GTGAAGACAGTAGCTGCGACGACACTTCAGAGACCTGCGTTCCATTGGAAGGGGAGAAAAGCGCT
     CACTTCTGTCATCGACGCTGCTGTGAAGTCTCTGGACGCAAGGTAACCTTCCCCTCTTTTCGCGA
 248▶ G  E  D  S  S  C  D  D  T  S  E  T  C  V  P  L  E  G  E  K  S  A

976  GAAGAAAGAAAAAGAGTGTTTCAACACGTCCTGTCCTGTTTGAACATGGATAGAAACAGAAAGCT
     CTTCTTTCTTTTTCTCACAAAGTTGTGCAGGACAGGACAAACTTGTACCTATCTTTGTCTTTCGA
 270▶ E  E  R  K  R  V  F  Q  H  V  L  S  C  L  N  M  D  R  N  R  K  L

1041 TCTCCCAGAGTTCGTGAGGCAGTTTTCCATAGACCGAGGATGTGAGTGGACACCCAAGACCCCAG
     AGAGGGTCTCAAGCACTCCGTCAAAAGGTATCTGGCTCCTACACTCACCTGTGGGTTCTGGGGTC
 291▶ L  P  E  F  V  R  Q  F  S  I  D  R  G  C  E  W  T  P  K  T  P

1106 GAGACTTAGCTTGGAATTTCTTGATGAAAGTTCAGGCTTTAGACTCGACAGCCAGAGATTCTATC
     CTCTGAATCGAACCTTAAAGAACTACTTTCAAGTCCGAAATCTGAGCTGTCGGTCTCTAAGATAG
 313▶ G  D  L  A  W  N  F  L  M  K  V  Q  A  L  D  S  T  A  R  D  S  I

1171 CTGAGGCCCGAGGTGGCGGGTGAAGAGAATGAAGAATTGCCGGCTGGAATAGAGAAGTTAGGCAT
     GACTCCGGGCTCCACCGCCCACTTCTCTTACTTCTTAACGGCCGACCTTATCTCTTCAATCCGTA
 335▶ L  R  P  E  V  A  G  E  E  N  E  E  L  P  A  G  I  E  K  L  G  I

1236 TGGAGACCCCCAAACCATCCATCCCCTGGATGTCCTCTGCGCCTGCATGCTTTGTGCAGACAGCT
     ACCTCTGGGGGTTTGGTAGGTAGGGGACCTACAGGAGACGCGGACGTACGAAACACGTCTGTCGA
 356▶ G  D  P  Q  T  I  H  P  L  D  V  L  C  A  C  M  L  C  A  D  S

1301 CCTTGCAGCGTGAAGTCATGTCAAACATGTACCAATGCCAGTTTGCTCTCTTCCCCTGCTACTGCCA
     GGAACGTCGCACTTCAGTACAGTTTGTACATGGTTACGGTCAAACGAGAAGGGGACGATGACGGT
 378▶ S  L  Q  R  E  V  M  S  N  M  Y  Q  C  Q  F  A  L  P  L  L  L  P

1366 GATGCTGAGAACAACAAAAACCTCTTAATGGTAGGGGCCATGAAGGACTTAAAGCAGCCCTCAGC
     CTACGACTCTTGTTGTTTTTGGAGAATTACCATCCCCGGTACTTCCTGAATTTCGTCGGGAGTCG
 400▶ D  A  E  N  N  K  N  L  L  M  V  G  A  M  K  D  L  K  Q  P  S  A
```

FIG. 25B

```
1431  ACAGTCCTCAGGAGGGCCCCTCAGGGAAACAGACACATTTCTGGGTCTCACAAAGATGCCTGTCA
      TGTCAGGAGTCCTCCCGGGGAGTCCCTTTGTCTGTGTAAAGACCCAGAGTGTTTCTACGGACAGT
 421▶ Q  S  S  G  G  P  L  R  E  T  D  T  F  L  G  L  T  K  M  P  V

1496  TCTCTTTTGTGCGACTAGGACGCTGCAGCTTCTCCAAGTCCAGAATTGTTAACACACTGCTCAGC
      AGAGAAAACACGCTGATCCTGCGACGTCGAAGAGGTTCAGGTCTTAACAATTGTGTGACGAGTCG
 443▶ I  S  F  V  R  L  G  R  C  S  F  S  K  S  R  I  V  N  T  L  L  S

1561  TCCTCCCAGCAGAAACCATACCCGATTTTCCTCCATCAGGATCTGTCTGTCCCTGTGCTTCCTCG
      AGGAGGGTCGTCTTTGGTATGGGCTAAAAGGAGGTAGTCCTAGACAGACAGGGACACGAAGGAGC
 465▶ S  S  Q  Q  K  P  Y  P  I  F  L  H  Q  D  L  S  V  P  V  L  P  R

1626  GCAAATTTCTGACGGCCTGGTGGAAGTGACATGGTGCTTTCCTGACAAGTTGCTGAAGGAAAGCC
      CGTTTAAAGACTGCCGGACCACCTTCACTGTACCACGAAAGGACTGTTCAACGACTTCCTTTCGG
 486▶ Q  I  S  D  G  L  V  E  V  T  W  C  F  P  D  K  L  L  K  E  S

1691  CGCATGCTTTCCAGAAACCTGTTGCTGTGGCCAACCTTCGTGGAGATTTAGAAAGCTTTTGGATA
      GCGTACGAAAGGTCTTTGGACAACGACACCGGTTGGAAGCACCTCTAAATCTTTCGAAAACCTAT
 508▶ P  H  A  F  Q  K  P  V  A  V  A  N  L  R  G  D  L  E  S  F  W  I

1756  CAATTTGGTTTCCTGGTAGAAGTTTCCTCCGGTCTTTTCTTTTTCACAGACTGCCTTGGTGAGAA
      GTTAAACCAAAGGACCATCTTCAAAGGAGGCCAGAAAAGAAAAAGTGTCTGACGGAACCACTCTT
 530▶ Q  F  G  F  L  V  E  V  S  S  G  L  F  F  F  T  D  C  L  G  E  K

1821  GGAATGGGACTTGCTAATGTTTTTAGGAGAGGACACCATTGAACGGTGCTACTTTATCCTCAGTC
      CCTTACCCTGAACGATTACAAAAATCCTCTCCTGTGGTAACTTGCCACGATGAAATAGGAGTCAG
 551▶ E  W  D  L  L  M  F  L  G  E  D  T  I  E  R  C  Y  F  I  L  S

1886  CCCAGGCTAAGGAGAGTGAAGAAGCCCAGATTTTCCAAAGGATCCTAAAACTGAAGCCATCTCAG
      GGGTCCGATTCCTCTCACTTCTTCGGGTCTAAAAGGTTTCCTAGGATTTTGACTTCGGTAGAGTC
 573▶ P  Q  A  K  E  S  E  E  A  Q  I  F  Q  R  I  L  K  L  K  P  S  Q

1951  CTACTGTTTTGGGAAGCTGAGGAAGCTGGGGATAGAAGGAAGACTATGGAGGCCCTTCAAGCTGC
      GATGACAAAACCCTTCGACTCCTTCGACCCCTATCTTCCTTCTGATACCTCCGGGAAGTTCGACG
 595▶ L  L  F  W  E  A  E  E  A  G  D  R  R  K  T  M  E  A  L  Q  A  A

2016  CCTCCAGGAAGTAATGTCCTCTCCACTCAGATGTGTGTCCCTTGAAGAGATGGCCTCTCTGGCCA
      GGAGGTCCTTCATTACAGGAGAGGTGAGTCTACACACAGGGAACTTCTCTACCGGAGAGACCGGT
 616▶ L  Q  E  V  M  S  S  P  L  R  C  V  S  L  E  E  M  A  S  L  A

2081  GGGAGCTGGGCATTCAGGTAGACCAAGACTTTGAAGTTACTCAAGATATTCAAGTTTCCCCCACA
      CCCTCGACCCGTAAGTCCATCTGGTTCTGAAACTTCAATGAGTTCTATAAGTTCAAAGGGGGTGT
 638▶ R  E  L  G  I  Q  V  D  Q  D  F  E  V  T  Q  D  I  Q  V  S  P  T
```

FIG. 25C

```
2146 ACAGTTGAAGGTGAAAACCAACAACCATGTAGTCAGACCAAAAGCCCGGCTGAAAGCGGAGCTCA
     TGTCAACTTCCACTTTTGGTTGTTGGTACATCAGTCTGGTTTTCGGGCCGACTTTCGCCTCGAGT
 660▸ T  V  E  G  E  N  Q  Q  P  C  S  Q  T  K  S  P  A  E  S  G  A  Q

2211 GGAGCCAATCAGAGAGCCAGGGGCTCAATGTGACGACAGTCAGAATGCTCCGGTTTTCCATCAGA
     CCTCGGTTAGTCTCTCGGTCCCCGAGTTACACTGCTGTCAGTCTTACGAGGCCAAAAGGTAGTCT
 681▸ E  P  I  R  E  P  G  A  Q  C  D  D  S  Q  N  A  P  V  F  H  Q

2276 CTCCAGTATACATGCCTTATCCAGCACACCCATGGGCTTTGGCCATCAAAGCTGGAGGTAACTTT
     GAGGTCATATGTACGGAATAGGTCGTGTGGGTACCCGAAACCGGTAGTTTCGACCTCCATTGAAA
 703▸ T  P  V  Y  M  P  Y  P  A  H  P  W  A  L  A  I  K  A  G  G  N  F

2341 TACCACGTTCCTTTGAATGCCCCCTGGTTATGGGCTCCCACTTTGGATCACAGCAGAGGGCTAAG
     ATGGTGCAAGGAAACTTACGGGGGACCAATACCCGAGGGTGAAACCTAGTGTCGTCTCCCGATTC
 725▸ Y  H  V  P  L  N  A  P  W  L  W  A  P  T  L  D  H  S  R  G  L  S

2406 TGGTTCTTTCCATTCCCATGCTAAACCCACTCACTCTAAGGCCTTCCAAGCTAACTGCCACCATC
     ACCAAGAAAGGTAAGGGTACGATTTGGGTGAGTGAGATTCCGGAAGGTTCGATTGACGGTGGTAG
 746▸ G  S  F  H  S  H  A  K  P  T  H  S  K  A  F  Q  A  N  C  H  H

2471 CCCATCCCTCCCATGCTAAACCCACTCATGTGAATCCCTCTCATGCTAACCCCACTCATGTGCAG
     GGGTAGGGAGGGTACGATTTGGGTGAGTACACTTAGGGAGAGTACGATTGGGGTGAGTACACGTC
 768▸ P  H  P  S  H  A  K  P  T  H  V  N  P  S  H  A  N  P  T  H  V  Q

2536 CCTTGCATGCTAAACCCACTCACTCTAAGGCCTTCCAAGCTAAACCCACTCCCTCTCAGACCTCT
     GGAACGTACGATTTGGGTGAGTGAGATTCCGGAAGGTTCGATTTGGGTGAGGGAGAGTCTGGAGA
 790▸ P  C  M  L  N  P  L  T  L  R  P  S  K  L  N  P  L  P  L  R  P  L

2601 TGGAGCCAAGCTAACTGCAATCATGCCCATCCCTCCCTTGCTAAACCCTCTCATACGAATCCCTC
     ACCTCGGTTCGATTGACGTTAGTACGGGTAGGGAGGGAACGATTTGGGAGAGTATGCTTAGGGAG
 811▸ G  A  K  L  T  A  I  M  P  I  P  P  L  L  N  P  L  I  R  I  P

2666 TGATGCTAACCCCACTCATGTGCAGCCTTCCCATGCTAAACCCGCTCATCTACAGTCTTCCCAAA
     ACTACGATTGGGGTGAGTACACGTCGGAAGGGTACGATTTGGGCGAGTAGATGTCAGAAGGGTTT
 833▸ L  M  L  T  P  L  M  C  S  L  P  M  L  N  P  L  I  Y  S  L  P  K

2731 CAAAACCCTCCCCATCCCAATCTACTGCAGTTCACGGCACACAAACCTCAGCAGTCCCAGTCTAA
     GTTTTGGGAGGGGTAGGGTTAGATGACGTCAAGTGCCGTGTGTTTGGAGTCGTCAGGGTCAGATT
 855▸ Q  N  P  P  H  P  N  L  L  Q  F  T  A  H  K  P  Q  Q  S  Q  S  K

2796 GCCTTCTCAGCAGAGACCCAGTCAGCCTAAATCATTCCAGACCAAGCCTTCACAGGCCAGGGCCT
     CGGAAGAGTCGTCTCTGGGTCAGTCGGATTTAGTAAGGTCTGGTTCGGAAGTGTCCGGTCCCGGA
 876▸ P  S  Q  Q  R  P  S  Q  P  K  S  F  Q  T  K  P  S  Q  A  R  A
```

FIG. 25D

```
2861 GCCACCCAAGAGCAGGGAGACGTTAAAGAACATACTCTGGAGATCTGGGAAATAAAGTATGGGCT
     CGGTGGGTTCTCGTCCCTCTGCAATTTCTTGTATGAGACCTCTAGACCCTTTATTTCATACCCGA
 898 C  H  P  R  A  G  R  R

2926 TTGCTTAAGTATTCTTTTTCATATAGCAAGCTGAAGAAAAGTTTTAGTGAAAGACTGATAAAAGT
     AACGAATTCATAAGAAAAAGTATATCGTTCGACTTCTTTTCAAAATCACTTTCTGACTATTTTCA

2991 AGCAAAACCCAAAAAAAGGTATGCAAAGTCTTAAGTGCATAGCAAAGTATCCAAGTGTGGGAAATA
     TCGTTTTGGGTTTTTTCCATACGTTTCAGAATTCACGTATCGTTTCATAGGTTCACACCCTTTAT

3056 TGGAAGCAGTTAAAAGTAGAATCTGGCTGGGCATGGTGGCACACATCTACAGGGTTTAGCATGGG
     ACCTTCGTCAATTTTCATCTTAGACCGACCCGTACCACCGTGTGTAGATGTCCCAAATCGTACCC

3121 AGGGCTCTGTCATCCCAACTCAGAGAAGCAGGCAGATCTCTGTGTGTTTGAGGCCAGTCTGGTCT
     TCCCGAGACAGTAGGGTTGAGTCTCTTCGTCCGTCTAGAGACACACAAACTCCGGTCAGACCAGA

3186 ACATAACAACGACACAAGCAAGTCCTACATCAGCCATACTACAAAATGAGACCCCATCTGGGGAC
     TGTATTGTTGCTGTGTTCGTTCAGGATGTAGTCGGTATGATGTTTTACTCTGGGGTAGACCCCTG

3251 AAAAGGGTTGGATCTAACATCAAACCAAAGAAATCAGTCAAGTATTCCAGAAGGCATCATTAATT
     TTTTCCCAACCTAGATTGTAGTTTGGTTTCTTTAGTCAGTTCATAAGGTCTTCCGTAGTAATTAA

3316 ACACTCAGTGGGTTACCACAACCAAACCATACTCGACAACTAACCCCCTAAAGGAGCAAGAAGGA
     TGTGAGTCACCCAATGGTGTTGGTTTGGTATGAGCTGTTGATTGGGGATTTCCTCGTTCTTCCT

3381 GTTGGGTGGGTGTTAGGCTGAACATGATTGGGGAAGAACTGAAGATAGATAAGGTCATTCGTAAT
     CAACCCACCCACAATCCGACTTGTACTAACCCCTTCTTGACTTCTATCTATTCCAGTAAGCATTA

3446 ACAGGTTATGGGACTTGTCAAATCCATTAAATGCAATATTAAGAAGCAGTGGGAATCTTAAGGCT
     TGTCCAATACCCTGAACAGTTTAGGTAATTTACGTTATAATTCTTCGTCACCCTTAGAATTCCGA

3511 ACATTAAGCTCCAGTGAGTCGCAACCCTCCCCTATTAGATGATGTGAGATTTGAACCCCAGTGAA
     TGTAATTCGAGGTCACTCAGCGTTGGGAGGGGATAATCTACTACACTCTAAACTTGGGGTCACTT

3576 TGGGGTGTGTCTGATAGCCCGTGTGTGTGACAAACTGTGTAATTATAAAGTGATGAAAACGTGGG
     ACCCCACACAGACTATCGGGCACACACACTGTTTGACACATTAATATTTCACTACTTTTGCACCC

3641 AGTTCAGCTTATCTGTGTTGAAGAAAGGCTGCTTCAGAGGTGCCTTGGTTTTGGGTTTATGATCA
     TCAAGTCGAATAGACACAACTTCTTTCCGACGAAGTCTCCACGGAACCAAAACCCAAATACTAGT
```

FIG. 25E

3706 GCCACTGAGCAGATACTCTGCACCATTGGTACAGTTAAATCAGCTTGCTTCTGGTAATAGCCCCA
     CGGTGACTCGTCTATGAGACGTGGTAACCATGTCAATTTAGTCGAACGAAGACCATTATCGGGT

3771 ATCTACCACATTTATCCCTTACAGGCGGAAATAATGAATGATCAGCAAAACATCCAATTTTACCT
     TAGATGGTGTAAATAGGGAATGTCCGCCTTTATTACTTACTAGTCGTTTTGTAGGTTAAAATGGA

3836 TAACCTTGGTACTGATTTGTATATGTATCATTCTTTATATAATAGCTAAGAAAATTTAGCTCATT
     ATTGGAACCATGACTAAACATATACATAGTAAGAAATATATTATCGATTCTTTTAAATCGAGTAA

3901 AGGGGTTCTGATATATTAGTTTAATGGTTTGAAGTCAGAAATGTGTTAGTTTTTAATTTTAGAGT
     TCCCCAAGACTATATAATCAAATTACCAAACTTCAGTCTTTACACAATCAAAAATTAAAATCTCA

3966 TAATTGAAAATATTGAGATGAATTTACAAAGGCTATAAGTAATGTTTGAGAGGGTTATAATTTTT
     ATTAACTTTTATAACTCTACTTAAATGTTTCCGATATTCATTACAAACTCTCCCAATATTAAAAA

4031 GTAGACTCATACTGTTCTGAACATTTGGATAGCTTCTCGTAGTTAGCAGTGTTATAGAAGAATAT
     CATCTGAGTATGACAAGACTTGTAAACCTATCGAAGAGCATCAATCGTCACAATATCTTCTTATA

4096 ATTTGATTCAGGTATTTAACCAGAGCTGCTCTTAGTTTTTAAGTGTCACCAAGAGTCAATAAAAG
     TAAACTAAGTCCATAAATTGGTCTCGACGAGAATCAAAAATTCACAGTGGTTCTCAGTTATTTTC

4161 GCTACATTATCTGAACATGTGGGAACACAACTGTGACCTTACACTTAAGAGACTGAGGAAGGGAA
     CGATGTAATAGACTTGTACACCCTTGTGTTGACACTGGAATGTGAATTCTCTGACTCCTTCCCTT

4226 ATCAAGGTTCAAGCCAGCAGCACATAGTGAGACCAGGTCTCAAGACACAAAAACTATCCACCTTA
     TAGTTCCAAGTTCGGTCGTCGTGTATCACTCTGGTCCAGAGTTCTGTGTTTTTGATAGGTGGAAT

4291 AGGAAGATTTTAAAATTTGCCTCATTAAGAAATAAAGTAAGATTTATAAATTGGACTAAATGTCA
     TCCTTCTAAAATTTTAAACGGAGTAATTCTTTATTTCATTCTAAATATTTAACCTGATTTACAGT

4356 CATCTTTGAACTTATGACTGTTTAATTTTTTTGACTTAAAGTTTAATTTTATTATTGTATGCGTGT
     GTAGAAACTTGAATACTGACAAATTAAAAAACTGAATTTCAAATTAAAATAATAACATACGCACA

4421 GTTGTATGTGTGTGCACATGTGTGCCACTGCATGTATGTGGAGGCCATCAGACAATGTTGTAGAG
     CAACATACACACACGTGTACACACGGTGACGTACATACACCTCCGGTAGTCTGTTACAACATCTC

4486 TCTGTTCTTTCCTCTTAGCCCTATGTGTTTTTACCCACTGAGCTAGGCCACCTACTCCTATAAGTC
     AGACAAGAAAGGAGAATCGGGATACACAAAATGGGTGACTCGATCCGGTGGATGAGGATATTCAG

FIG. 25F

```
4551 TAATTTTAAATAGTAAAATAGTTCTAAGAAGTCAATCAGGGAAAAAAATGGCTGTCAAAGTCTCA
     ATTAAAATTTATCATTTTATCAAGATTCTTCAGTTAGTCCCTTTTTTTACCGACAGTTTCAGAGT

4616 AAGAAAAATCGTATTAGCCATGGATAGAGACTCACCTCTTGAATCATTTGTGTCTGAGAATAGCC
     TTCTTTTTAGCATAATCGGTACCTATCTCTGAGTGGAGAACTTAGTAAACACAGACTCTTATCGG

4681 TAATATCACAATAATGTGTTTGTACATGTGTTAGTTAATATTGTTTTCAGAGTATTTAATCTCTC
     ATTATAGTGTTATTACACAAACATGTACACAATCAATTATAACAAAAGTCTCATAAATTAGAGAG

4746 ATGATTATTGTAAAGATGAAAAAAGAAATAGTGGGCAATGTATGTGAGTATTTAATTTTGCCTGA
     TACTAATAACATTTCTACTTTTTTCTTTATCACCCGTTACATACACTCATAAATTAAAACGGACT

4811 CAATTCTGTCTTTTAGAATGATAAATGTAAGAAGTAAAATAAAACGGTTCATTCTCAGAACAACT
     GTTAAGACAGAAAATCTTACTATTTACATTCTTCATTTTATTTTGCCAAGTAAGAGTCTTGTTGA

4876 AAGCCAGCTCACTTAAGTCTGGGCCCTGCTGGCATTGGCTAGTCTAGCTACCCCCACCCAAACAC
     TTCGGTCGAGTGAATTCAGACCCGGGACGACCGTAACCGATCAGATCGATGGGGGTGGGTTTGTG

4941 AAAAGTTTAGAGAAGAAAATGACTGAGTCAAGCTTGCCTAATGACTTTTGGACATAAAGTTTATG
     TTTTCAAATCTCTTCTTTTACTGACTCAGTTCGAACGGATTACTGAAAACCTGTATTTCAAATAC

5006 GTCCTAGAAAGCCTTAAAATAAGTAGGATATAAAACATGTAAATTAACCCACACATTATGTGGGT
     CAGGATCTTTCGGAATTTTATTCATCCTATATTTTGTACATTTAATTGGGTGTGTAATACACCCA

5071 TGAGAAGCAGAAAAATGTCAGTAGAACACTCGGCCAGTGCATAAAGAAGGAAGAGACCTCTGTTC
     ACTCTTCGTCTTTTTACAGTCATCTTGTGAGCCGGTCACGTATTTCTTCCTTCTCTGGAGACAAG

5136 TGGGTTATAAAACTGCTCTTTGTGCTCAATTTGTCCCCTGCTTTTGTTTGCCAGAATGTACAAGA
     ACCCAATATTTTGACGAGAAACACGAGTTAAACAGGGACGAAAACAAACGGTCTTACATGTTCT

5201 TTATAAAATAAACTCACTTTTACTTTTAAAAAAAAAAAAAAAAAAAAGGGCGG
     AATATTTTATTTGAGTGAAAATGAAAATTTTTTTTTTTTTTTTTCCCGCC
```

FIG. 25G

```
CACGCGTCCGCCGGATCAGAGAGTGCTCCGAGCTGGGTTGCCCCACTGTGCTTGTATCTGCACTCTCCAACACTAGGC  79

ATCATTGACATGTTAAAGCTTAGCCAAATAGAATTGTTCTTTGTCATTCTTTTTTTAACTTTTACTTATTCATTAGGAT 158

M   A   T   E   S   T   P   S   E     9
GATTTCATAATATATTTCCTGGTTTAGAGGAAACAGGAACA  ATG GCT ACC GAG AGT ACT CCC TCA GAG  226

I   I   E   R   E   R   K   K   L   L   E   I   L   Q   H   D   P   D   S   I    29
ATC ATA GAA AGA GAA AGA AAA AAG TTG CTT GAA ATC CTT CAA CAT GAT CCT GAT TCT ATC  286

L   D   T   L   T   S   R   R   L   I   S   E   E   E   Y   E   T   L   E   N    49
TTA GAC ACG TTA ACT TCT CGG AGG CTG ATT TCT GAG GAA GAG TAT GAG ACT CTG GAG AAT  346

V   T   D   L   L   K   K   S   R   K   L   L   I   L   V   Q   K   K   G   E    69
GTT ACA GAT CTC CTG AAG AAA AGT CGG AAG CTG TTA ATT TTG GTA CAG AAA AAG GGA GAG  406

A   T   C   Q   H   F   L   K   C   L   F   S   T   F   P   Q   L   A   A   I    89
GCG ACC TGT CAG CAT TTT CTC AAG TGT TTA TTT AGT ACT TTT CCA CAG TTA GCT GCC ATT  466

C   G   L   R   H   E   V   L   K   H   E   N   T   V   P   P   Q   S   M   G   109
TGC GGC TTA AGG CAT GAA GTT TTA AAA CAT GAG AAT ACA GTA CCT CCT CAA TCT ATG GGG  526

A   S   S   N   S   E   D   A   F   S   P   G   I   K   Q   P   E   A   P   E   129
GCA AGC AGT AAT TCA GAA GAT GCT TTT TCT CCT GGA ATA AAA CAG CCT GAA GCC CCT GAG  586

I   T   V   F   F   S   E   K   E   H   L   D   L   E   T   S   E   F   F   R   149
ATC ACA GTG TTC TTC AGT GAG AAG GAA CAC TTG GAT TTG GAA ACC TCT GAG TTT TTC AGG  646

D   K   K   T   S   Y   R   E   T   A   L   S   A   R   K   N   E   K   E   Y   169
GAC AAG AAA ACT AGT TAT AGG GAA ACA GCT TTG TCT GCC AGG AAG AAT GAG AAG GAA TAT  706

D   T   P   E   V   T   L   S   Y   S   V   E   K   V   G   C   E   V   P   A   189
GAC ACA CCA GAA GTC ACA TTA TCA TAT TCA GTT GAG AAA GTT GGA TGT GAA GTT CCA GCA  766

T   I   T   Y   I   K   D   G   Q   R   Y   E   E   L   D   D   S   L   Y   L   209
ACT ATT ACA TAT ATA AAA GAT GGA CAG AGA TAT GAG GAG CTA GAT GAT TCT TTA TAC TTA  826

G   K   E   E   Y   L   G   S   V   D   T   P   E   D   A   E   A   T   V   E   229
GGA AAA GAG GAA TAT CTA GGA TCT GTT GAC ACC CCT GAA GAT GCA GAA GCC ACT GTG GAA  886

E   E   V   Y   D   D   P   E   H   V   G   Y   D   G   E   E   D   F   E   N   249
GAG GAG GTT TAT GAT GAC CCA GAG CAC GTT GGA TAT GAT GGT GAA GAG GAC TTC GAG AAT  946

S   E   T   T   E   F   S   G   E   E   P   S   Y   E   G   S   E   T   S   L   269
TCA GAA ACC ACA GAG TTC TCT GGT GAA GAA CCA AGT TAT GAG GGA TCA GAA ACC AGC CTT 1006

S   L   E   E   E   Q   E   K   S   I   E   E   R   K   K   V   F   K   D   V   289
TCA TTG GAG GAG GAA CAG GAG AAA AGT ATA GAA GAA AGA AAA AAG GTG TTT AAA GAT GTC 1066

L   L   C   L   N   M   D   R   S   R   K   V   L   P   D   F   V   K   Q   F   309
CTG TTA TGT TTG AAC ATG GAT AGA AGC AGA AAG GTT CTG CCA GAT TTT GTT AAA CAA TTC 1126

S   L   D   R   G   C   K   W   T   P   E   S   P   G   D   L   A   W   N   F   329
TCC TTA GAT CGA GGA TGT AAG TGG ACC CCT GAG AGT CCA GGA GAC TTA GCC TGG AAT TTC 1186

L   M   K   V   Q   A   R   D   V   T   A   R   D   S   I   L   S   H   K   V   349
CTG ATG AAA GTT CAA GCA CGA GAT GTG ACG GCT AGG GAT TCA ATC CTC AGT CAC AAG GTT 1246

L   D   E   D   S   K   E   D   L   L   A   G   V   E   N   L   E   I   R   D   369
CTG GAT GAA GAT AGC AAG GAG GAT TTG CTG GCT GGA GTG GAG AAT TTG GAA ATT CGA GAC 1306
```

FIG. 28A

```
I   Q   T   I   N   P   L   D   V   L   C   A   T   M   L   C   S   D   S   S   389
ATA CAA ACC ATT AAT CCC CTT GAC GTG CTT TGT GCC ACC ATG CTG TGT TCA GAT AGC TCT 1366

L   Q   R   Q   V   M   S   N   M   Y   Q   C   Q   F   A   L   P   L   L   L   409
TTG CAA CGC CAA GTC ATG TCA AAC ATG TAT CAG TGC CAG TTT GCT CTT CCC CTG CTA CTG 1426

P   D   A   E   N   N   K   S   I   L   M   L   G   A   M   K   D   I   V   K   429
CCA GAT GCA GAA AAC AAC AAA AGC ATC TTA ATG CTG GGG GCC ATG AAA GAC ATT GTG AAG 1486

K   Q   S   T   Q   F   S   G   G   P   T   E   D   T   E   K   F   L   T   L   449
AAG CAG TCA ACA CAG TTT TCA GGG GGG CCT ACA GAG GAT ACA GAA AAG TTT CTG ACT CTC 1546

M   K   M   P   V   I   S   F   V   R   L   G   Y   C   S   F   S   K   S   R   469
ATG AAG ATG CCT GTC ATC TCT TTT GTG CGT CTA GGA TAC TGT AGC TTC TCT AAG TCC AGA 1606

I   L   N   T   L   L   S   P   A   Q   L   K   L   H   K   I   F   L   H   Q   489
ATC CTC AAC ACA CTT CTC AGC CCT GCC CAG TTG AAA TTA CAC AAA ATC TTT CTT CAT CAA 1666

D   L   P   L   L   V   L   P   R   Q   I   S   D   G   L   V   E   I   T   W   509
GAT TTG CCT CTT TTG GTG CTT CCC CGG CAA ATC TCT GAT GGC CTG GTT GAG ATA ACA TGG 1726

C   F   P   D   S   D   D   R   K   E   N   P   F   F   Q   K   P   V   A   L   529
TGT TTT CCT GAT AGC GAT GAT AGA AAG GAA AAC CCC TTT TTC CAA AAG CCT GTT GCT CTG 1786

A   N   L   R   G   N   L   E   S   F   W   T   Q   F   G   F   L   M   E   V   549
GCT AAT CTC CGT GGA AAT CTA GAA AGT TTT TGG ACT CAG TTT GGT TTT TTG ATG GAA GTT 1846

S   S   A   V   F   F   F   T   D   C   L   G   E   K   E   W   D   L   L   M   569
TCT TCA GCT GTG TTT TTT TTC ACT GAC TGT TTA GGT GAG AAG GAA TGG GAC TTG CTA ATG 1906

F   L   G   E   A   A   I   E   R   C   Y   F   V   L   S   S   Q   A   R   E   589
TTT TTA GGA GAG GCT GCC ATT GAA AGA TGC TAC TTT GTT CTC AGT TCC CAA GCC AGG GAG 1966

S   E   E   A   Q   I   F   Q   R   I   L   N   L   K   P   A   Q   L   L   F   609
AGT GAA GAG GCT CAA ATT TTT CAG AGG ATA CTG AAC TTG AAG CCA GCA CAG CTA CTG TTT 2026

W   E   R   G   D   A   G   D   R   R   K   N   M   E   G   L   Q   A   A   L   629
TGG GAG AGG GGA GAT GCT GGG GAT AGA AGG AAG AAC ATG GAG GGC CTT CAA GCT GCC CTC 2086

Q   E   V   M   F   S   S   C   L   R   C   V   S   V   E   D   M   A   A   L   649
CAG GAA GTG ATG TTC TCT TCT TGC CTC AGA TGT GTG TCT GTG GAG GAT ATG GCC GCC CTG 2146

A   R   E   L   G   I   Q   V   D   E   D   F   E   N   T   Q   R   I   Q   V   669
GCC AGG GAG CTG GGG ATT CAG GTA GAT GAA GAC TTT GAA AAC ACT CAG AGA ATT CAA GTT 2206

S   S   G   E   N   M   A   G   T   A   E   G   E   G   Q   Q   R   H   S   Q   689
TCC TCT GGA GAA AAC ATG GCT GGG ACA GCT GAA GGT GAG GGT CAG CAA AGA CAC AGT CAG 2266

L   K   S   S   S   K   S   Q   A   L   M   P   I   Q   E   P   G   T   Q   C   709
CTA AAA AGC TCA TCT AAA AGC CAG GCT CTA ATG CCA ATT CAA GAG CCT GGG ACT CAA TGT 2326

E   L   S   Q   N   L   Q   N   L   Y   G   T   P   V   F   R   P   V   L   E   729
GAG CTC AGC CAG AAT CTT CAG AAT CTC TAT GGT ACC CCA GTA TTC AGG CCT GTT CTA GAG 2386

N   S   W   L   F   P   T   R   I   G   G   N   F   N   H   V   S   L   K   A   749
AAC TCC TGG CTC TTT CCA ACC AGA ATT GGA GGT AAC TTT AAC CAT GTT TCC TTG AAA GCC 2446

S   W   V   M   G   R   P   F   G   S   E   Q   R   P   K   W   F   H   P   L   769
TCC TGG GTT ATG GGC CGC CCC TTT GGG TCA GAG CAG AGG CCT AAG TGG TTC CAT CCT TTG 2506
```

FIG. 28B

```
P   F   Q   N   A   G   A   Q   G   R   G   K   S   F   G   I   Q   S   F   H   789
CCT TTT CAG AAT GCA GGG GCC CAG GGC CGA GGT AAA AGT TTT GGT ATT CAA TCC TTC CAT 2566

P   Q   I   F   Y   S   G   E   R   F   M   K   F   S   R   V   A   R   G   C   809
CCC CAG ATA TTT TAT TCA GGT GAA AGA TTC ATG AAA TTT TCC AGA GTT GCT CGG GGA TGT 2626

H   S   N   G   T   F   G   R   L   P   R   P   I   C   Q   H   V   Q   A   C   829
CAC TCG AAT GGA ACA TTT GGG AGA CTG CCA AGA CCC ATT TGT CAG CAT GTA CAG GCC TGC 2686

P   E   R   P   Q   M   M   G   T   L   E   R   S   R   A   V   A   S   K   I   849
CCT GAG AGA CCA CAA ATG ATG GGA ACT CTT GAA AGG TCT AGG GCA GTA GCC TCC AAG ATA 2746

G   H   S   Y   S   L   D   S   Q   P   A   R   A   V   G   K   P   W   P   Q   869
GGT CAC TCC TAT TCC CTG GAT TCA CAG CCA GCA AGA GCA GTA GGG AAG CCA TGG CCT CAG 2806

Q   A   C   T   R   V   T   E   L   T   E   A   T   G   K   L   I   R   T   S   889
CAA GCT TGC ACC AGG GTA ACA GAG TTA ACT GAA GCA ACT GGA AAA CTG ATA AGA ACA TCC 2866

H   I   G   K   P   H   P   Q   S   F   Q   P   A   A   A   T   Q   K   L   R   909
CAT ATT GGA AAG CCT CAC CCT CAG TCC TTT CAA CCA GCA GCA GCC ACA CAA AAA CTA AGA 2926

P   A   S   Q   Q   G   V   Q   M   K   T   Q   G   G   A   S   N   P   A   L   929
CCT GCT TCT CAA CAA GGA GTC CAG ATG AAG ACA CAA GGT GGG GCT TCA AAT CCA GCT CTC 2986

Q   I   G   S   H   P   M   C   K   S   S   Q   F   K   S   D   Q   S   N   P   949
CAA ATA GGG TCC CAT CCC ATG TGC AAG AGC TCT CAG TTC AAA TCC GAT CAG TCC AAC CCA 3046

S   T   V   K   H   S   Q   P   K   P   F   H   S   V   P   S   Q   P   K   S   969
TCC ACA GTC AAA CAC TCC CAG CCT AAA CCC TTC CAT TCT GTG CCC TCT CAA CCT AAA TCC 3106

S   Q   T   K   S   C   Q   S   Q   P   S   Q   T   K   P   S   P   C   K   S   989
TCT CAG ACA AAA TCC TGT CAG TCC CAG CCC TCC CAA ACT AAA CCT TCT CCA TGC AAA TCT 3166

T   Q   P   K   P   S   Q   P   W   P   P   Q   S   K   P   S   Q   P   R   P   1009
ACT CAG CCT AAG CCA AGC CAG CCC TGG CCT CCC CAG TCT AAG CCT TCT CAG CCC AGA CCC 3226

P   Q   P   K   S   S   S   T   N   P   S   Q   A   K   A   H   H   S   K   A   1029
CCT CAA CCT AAG TCA TCC TCA ACC AAT CCT TCA CAA GCT AAG GCA CAC CAC TCA AAA GCA 3286

G   Q   K   R   G   G   K   H   *                                                1038
GGG CAG AAG AGG GGA GGG AAG CAT TAA                                              3313
```

AGAGCTAACTCCAGAGATCTATAAAGCATATCCTTTACCCAGGCCATTCCTATCATATAGTAAGCAGAAGAGTTGCCAT 3392

GAAAGTAAAAGACTACTGTCATTAGCATGTAAAACAAAGAAAGATATACATGACCGAATTGGATATCTTTGTTTGTTTG 3471

TTTGAGACAGAGTTTCACTCTTGTTGCCCAGGCTGGAGTGCAATGGCACGATCTCGGCTCACCGCAACCTCTGCTTCCT 3550

GGCTTAAAGTGATTCTCCTGCCTCAGCCTCTCGAGTAGCTGGGATTACAGGCATGCACCACCACACCCAGCTAATTTTG 3629

TATTTTTAGTAGAGGCAGGGTTTCTCCATGTTGGTCAGGCTGGTCTTGAACTCCCGACCTCAGGTGATCCGCCCACCTA 3708

GGCCTCTCAAAGTGTTGGGATTACGTGTGTAAGCCACAGTGCCCAGCCCGAATTGGATATCTTTAAGATATCTGTAAGT 3787

GTTATATCCCTAACCAAGAAGAAAAATATGAAAATAATTAAGACTAGAATCAAGCAGTAGATAATTGAATCCAATCTTG 3866

GGTATTATTAGATAATGTATAACTTGCACCCAGGGAATGGGGTCTATGAGACAACCCCACTTGGAGAAGAATGGGGTT 3945

AGGGTCTCTAATTGCAAAGTGACTGTACAATAGGACGAAAGTTGCCTCTGTGTCTGAGAAAGTATCTTAGTTGTTGGCT 4024

FIG. 28C

GCTCCAGAGGTATCTTTGTCAAAGCTTCTGGTTCAATATCAGCCACTGAGCAGATAACCCTGCTTATTGGTGTGGTT 4103

AAATCAACTAGCTTCTGCTAATAGCCCCAATTTGCTTGAATGGGAAACTCTCTCATTTGACCCTTATAGGTAGAAATA 4182

ATGAATTAACAACCAATAAAATTAATCATTTGGCATTAAAAAAAAAAAAAAAAAAAAAA 4244

FIG. 28D

```
CONSENSUS        *->maederrilLkknrvrliesLgldvLdeiLdvLlekdvlnlkeeEkik
                 +++    +    ++ r++l+e+L+ d   d +Ld L +++++ ++e E
CARD6       5    STP--SEIERERKKLLEILQHD-PDSILDTLTSRRLISEEEYETLE    48

CONSENSUS        ragakledDKarelvdslqrrgsqafdafidaledTgqsyLAdvLel<-*
                 + l +   r  l++ +q++g.+ ++ f + +l++    LA++  +l
CARD6       49   NVTDLLKK--SRKLLILVQKKGEATCQHFLKCLFS-TFPQLAAICGL    92
```

FIG. 30

CARD RELATED PROTEIN AND USES THEREOF

CROSS REFERENCE TO RELATED APPLICATIONS

This application is a continuation-in-part of U.S. application Ser. No. 09/340,620, filed Jun. 28, 1999 now U.S. Pat. No. 6,482,933, which is a continuation-in-part of U.S. application Ser. No. 09/245,281, filed Feb. 5, 1999 now U.S. Pat. No. 6,369,196, which is a continuation-in-part of U.S. application Ser. No. 09/207,359, filed Dec. 8, 1998 now U.S. Pat. No. 6,469,140, which is a continuation-in-part of U.S. application Ser. No. 09/099,041, filed Jun. 17, 1998 now U.S. Pat. No. 6,340,576, which is a continuation-in-part of U.S. application Ser. No. 09/019,942, filed Feb. 6, 1998 now U.S. Pat. No. 6,033,855. The contents of each of these applications is incorporated herein by reference.

BACKGROUND OF THE INVENTION

In multicellular organisms, homeostasis is maintained by balancing the rate of cell proliferation against the rate of cell death. Cell proliferation is influenced by numerous growth factors and the expression of proto-oncogenes, which typically encourage progression through the cell cycle. In contrast, numerous events, including the expression of tumor suppressor genes, can lead to an arrest of cellular proliferation.

In differentiated cells, a particular type of cell death called apoptosis occurs when an internal suicide program is activated. This program can be initiated by a variety of external signals as well as signals that are generated within the cell in response to, for example, genetic damage. For many years, the magnitude of apoptotic cell death was not appreciated because the dying cells are quickly eliminated by phagocytes, without an inflammatory response.

The mechanisms that mediate apoptosis have been intensively studied. These mechanisms involve the activation of endogenous proteases, loss of mitochondrial function, and structural changes such as disruption of the cytoskeleton, cell shrinkage, membrane blebbing, and nuclear condensation due to degradation of DNA. The various signals that trigger apoptosis are thought to bring about these events by converging on a common cell death pathway that is regulated by the expression of genes that are highly conserved from worms, such as C. elegans, to humans. In fact, invertebrate model systems have been invaluable tools in identifying and characterizing the genes that control apoptosis. Through the study of invertebrates and more evolved animals, numerous genes that are associated with cell death have been identified, but the way in which their products interact to execute the apoptotic program is poorly understood.

Caspases, a class of proteins central to the apoptotic program, are responsible for the degradation of cellular proteins that leads to the morphological changes seen in cells undergoing apoptosis. Caspases (cysteinyl aspartate-specific proteinases) are cysteine proteases having specificity for aspartate at the substrate cleavage site. Generally, caspases are classified as either initiator caspases or effector caspases, both of which are zymogens that are activated by proteolysis that generates an active species. An effector caspase is activated by an initiator caspase which cleaves the effector caspase. Initiator caspases are activated by an autoproteolytic mechanism that is often dependent upon oligomerization directed by association of the caspase with an adapter molecule.

Many caspases and proteins that interact with caspases possess domains of about 60 amino acids called a caspase recruitment domain (CARD). Hofmann et al. (TIBS 22:155, 1997) and others have postulated that certain apoptotic proteins bind to each other via their CARDs and that different subtypes of CARDs may confer binding specificity, regulating the activity of various caspases, for example. The functional significance of CARDs have been repeatedly demonstrated. For example, Duan et al. (Nature 385:86, 1997) showed that deleting the CARD at the N-terminus of RAIDD abolished the ability of RAIDD to bind to caspases.

Caspase-1 is an example of an initiator caspase. Caspase-1 was first discovered as the protease responsible for the conversion of the inactive precursor of IL-1β to the mature proinflammatory cytokine (caspase-1 was originally termed interleukin-1β converting enzyme, ICE). Caspase-1 also processes the inactive precursor of the cytokine IL-18 into an active form. Caspase-1 is synthesized as a single chain zymogen consisting of an N-terminal CARD containing prodomain and a large (p20) and small (p10) catalytic domain. Caspase-1 is thought to oligomerize upon the receipt of a proinflammatory signal and autoprocess to generate an active heterodimeric protease consisting of the p20 and p10 subunits.

RIP2 (CARDIAK/RICK) binds caspase-1 via an interaction between the CARD domain of RIP2 and the CARD domain of caspase-1. This interaction results in the processing and activation of caspase-1. Thus, RIP2 is thought to be an upstream activator adaptor of caspase-1. Conversely, the activation of caspase-1 and subsequent generation of IL-1β is regulated by a CARD domain-containing decoy molecule termed ICEBERG. This decoy attenuates inflammation by binding to the CARD domain of caspase-1 and inhibiting or displacing the upstream activator RIP2. ICEBERG is induced by proinflammatory stimuli and thus appears to be part of a negative feedback loop that shuts off IL-1β generation and thus dampens the inflammatory response (Humke et al., Cell 103:99, 2000).

In addition to its role in inflammation via IL-1β processing, caspase-1 also appears to participate in cell death pathways. For example, overexpression of caspase-1 in Rat-1 fibroblasts induces apoptosis that can be suppressed by overexpression of antiapoptotic genes such as Bcl-2 (Miura et al., Cell 75:653, 1993).

Caspase-9 activation may precede the activation of all other cell death-related caspases in the mitochondrial pathways of apoptosis (Slee et al., J. Cell Biol. 144:281–292, 1999). Inactive procaspase-9 is activated by interaction with a complex which includes Apaf-1, a CARD-containing protein, and other factors (Li et al., Cell 91:479, 1997; Srinivasula et al., Mol. Cell 1:949–959, 1998). Recognition of procaspase-9 by Apaf-1 occurs primarily through the interaction of the CARD of Apaf-1 with the prodomain of caspase-9. The CARD of Apaf-1 shares about 20% sequence identity with the prodomain of procaspase-9. The prodomain of caspase-9 is a member of the CARD family of apoptotic signaling motifs (Hofmann and Bucher, Trends in Biochem. Sci. 22:155–156, 1997). A similar domain is present in caspase activating proteins CED-4 and RAIDD/CRADD as well as in initiator caspases CED-3 and caspase-2/ICH-1 (Duan and Dixit, Nature 385:86–89, 1997; Ahmad et al., Cancer Res. 57:615–619, 1997; Alnemri et al., Cell 87:171, 1996). Apaf-1 can bind several other caspases, e.g., caspase-4 and caspase-8 (Inohara et al., J. Biol. Chem. 273:12296–12300, 1998).

Nuclear factor-κB (NF-κB) is a transcription factor expressed in many cell types and which activates homologous or heterologous genes that have κB sites in their promoters. Molecules that regulate NF-κB activation play a critical role in both apoptosis and inflammation. Quiescent NF-κB resides in the cytoplasm as a heterodimer of proteins referred to as p50 and p65 and is complexed with the regulatory protein IκB. NF-κB binding to IκB causes NF-κB to remain in the cytoplasm. At least two dozen stimuli that activate NF-κB are known (New England Journal of Medicine 336:1066, 1997) and they include cytokines, protein kinase C activators, oxidants, viruses, and immune system stimuli. NF-κB activating stimuli activate specific IκB kinases that phosphorylate IκB leading to its degradation. Once liberated from IκB, NF-κB translocates to the nucleus and activates genes with κB sites in their promoters. The proinflammatory cytokines TNF-α and IL-1 induce NF-κB activation by binding their cell-surface receptors and activating the NF-κB-inducing kinase, NIK, and NF-κB. NIK phosphorylates the IκB kinases α and β which phosphorylate IκB, leading to its degradation.

NF-κB and the NF-κB pathway has been implicated in mediating chronic inflammation in inflammatory diseases such as asthma, ulcerative colitis, rheumatoid arthritis (Epstein, New England Journal of Medicine 336:1066, 1997) and inhibiting NF-κB or NF-κB pathways may be an effective way of treating these diseases. NF-κB and the NF-κB pathway has also been implicated in atherosclerosis (Navab et al., American Journal of Cardiology 76:18C, 1995), especially in mediating fatty streak formation, and inhibiting NF-κB or NF-κB pathways may be an effective therapy for atherosclerosis. Among the genes activated by NF-κB are cIAP-1, cIAP-2, TRAF1, and TRAF2, all of which have been shown to protect cells from TNF-α induced cell death (Wang et al., Science 281:1680–83, 1998). CLAP, a protein which includes a CARD, activates the Apaf-1-caspase-9 pathway and activates NF-κB by acting upstream of NIK and IκB kinase (Srinivasula et al., supra).

Bcl-2 family proteins are important regulators of pathways involved in apoptosis and can act to inhibit or promote cell death. Expression of certain anti-apoptotic Bcl-2 family members is commonly altered in cancerous cells, suppressing programmed cell death and extending tumor growth. Among the anti-apoptotic Bcl-2 family members thus far identified are Boo, Bcl-2, BCl-$x_L$, Bcl-w, NR-13, A1, and Mcl-2. Pro-apoptotic Bcl-2 family members include Bax, Bak, Bad, Bik, Bid, Hrk, Bim, and Bol/Mtd. Significantly, the anti-apoptotic Bcl-2 family member, BCl-$x_L$, has been shown to interact with Apaf-1 and block Apaf-1-dependent caspase-9 activation (Hu et al., Proc. Nat'l. Acad. Sci. 95:4386–4391, 1998). Boo, another anti-apoptotic Bcl-2 family member, interacts with Apaf-1 and caspase-9. Bak and Bik, pro-apoptotic Bcl-2 family members, can disrupt the association of Boo with Apaf-1 (Song et al., EMBO J. 18:167–178, 1999). Boo is thought to be involved in the control of ovarian atresia and sperm maturation. Diva, another member of the Bcl-2 family, inhibits binding of Bcl-$x_L$ to Apf-1, preventing BC1-$x_L$ from binding to Apaf-1.

Neurotrophins (e.g., NGF), which are best know as neuronal survival factors, can mediate apoptosis via the p75 neurotrophin receptor (p75$^{NTR}$). It is thought that p75$^{NTR}$ activation can lead to NF-κB activation (Carter et al., Science 272:542–545, 1996). It has been proposed that p75$^{NTR}$-mediated cell death acts to ensure rapid cell death when a neuron is unable to obtain sufficient neurotropins. This mechanism could, for example, cause the elimination of neurons that reach an inappropriate target or that reach an appropriate target at an inappropriate time (Miller and Kaplan, Cell Death and Diff. 5:343–345, 1998).

SUMMARY OF THE INVENTION

The present invention is based, at least in part, on the discovery of genes encoding CARD-3, CARD-4, CARD-5, and CARD-6. A full-length human CARD-3 cDNA is presented. Several CARD-4 cDNAs are presented. Briefly, the CARD-4 gene can express a long transcript that encodes CARD-4L, a short transcript that encodes partial CARD-4S, or two CARD-4 splice variants (CARD-4Y and CARD-4Z). A full length cDNA sequence for the murine ortholog of CARD-4L is also presented. Full-length cDNAs encoding murine and human CARD-5 are presented. In addition, full-length cDNAs encoding human and rat CARD-6 are presented.

CARD-3, CARD-4, CARD-5, and CARD-6 are intracellular proteins that are predicted to be involved in regulating caspase activation. CARD-4 is found to activate the NF-κB pathway and to enhance caspase 9-mediated cell death. CARD-5 is found to activate the NF-κB pathway and to bind to the CARD domains of caspase-1, CARD-7, and CARD-5 itself. In addition, proteins that bind to CARD-4 are presented including CARD-3 and hNUDC.

The CARD-3 cDNA described below (SEQ ID NO:1) has a 1620 open reading frame (nucleotides 214 to 1833 of SEQ ID NO:1; SEQ ID NO:3) which encodes a 540 amino acid protein (SEQ ID NO:2). CARD-3 contains a kinase domain which extends from amino acid 1 to amino acid 300 of SEQ ID NO:2; SEQ ID NO:4, followed by a linker domain at amino acid 301 to amino acid 431 of SEQ ID NO:2; SEQ ID NO:5 and a CARD at amino acid 432 to amino acid 540 of SEQ ID NO:2; SEQ ID NO:6.

At least four forms of CARD-4 exist in the cell, a long form, CARD-4L, a short form, CARD-4S, and two splice variants, CARD-4Y and CARD-4Z. The cDNA of CARD-4L described below (SEQ ID NO:7) has a 2859 nucleotide open reading frame (nucleotides 245–3103 of SEQ ID NO:7; SEQ ID NO:9) which encodes a 953 amino acid protein (SEQ ID NO:8). CARD-4L protein possesses a CARD domain (amino acids 15–114; SEQ ID NO:10) The nucleotide sequence of the full length cDNA corresponding to the murine ortholog of human CARD-4L is presented (SEQ ID NO:42) as is the predicted amino acid sequence of murine CARD-4L (SEQ ID NO:43). A comparison between the predicted amino acid sequences of human CARD-4L and murine CARD-4L is also depicted in FIG. 17.

Human CARD-4L is also predicted to have a nucleotide binding domain which extends from about amino acid 198 to about amino acid 397 of SEQ ID NO:8; SEQ ID NO:11, a Walker Box "A", which extends from about amino acid 202 to about amino acid 209 of SEQ ID NO:8; SEQ ID NO:12, a Walker Box "B", which extends from about amino acid 280 to about amino acid 284, of SEQ ID NO:8; SEQ ID NO:13, a kinase 1a (P-loop) subdomain, which extends from about amino acid 127 to about amino acid 212 of SEQ ID NO:8; SEQ ID NO:46, a kinase 2 subdomain, which extends from about amino acid 273 to about amino acid 288 of SEQ ID NO:8; SEQ ID NO:47, a kinase 3a subdomain, which extends from about amino acid 327 to about amino acid 338 of SEQ ID NO:8; SEQ ID NO:14, and ten Leucine-rich repeats which extend from about amino acid 674 to about amino acid 950 of SEQ ID NO:8. The first Leucine-rich repeat extends from about amino acid 674 to about amino acid 701 of SEQ ID NO:8; SEQ ID NO:15. The second Leucine-rich repeat extends from about amino acid 702 to about amino acid 727 of SEQ ID NO:8; SEQ ID NO:16. The third Leucine-rich repeat extends from about amino acid 728 to about amino acid 754 of SEQ ID NO:8; SEQ ID NO:17.

The fourth Leucine-rich repeat extends from about amino acid 755 to about amino acid 782 of SEQ ID NO:8; SEQ ID NO:18. The fifth Leucine-rich repeat extends from about amino acid 783 to about amino acid 810 of SEQ ID NO:8; SEQ ID NO:19. The sixth Leucine-rich repeat extends from about amino acid 811 to about amino acid 838 of SEQ ID NO:8; SEQ ID NO:20. The seventh Leucine-rich repeat extends from about amino acid 839 to about amino acid 866 of SEQ ID NO:8; SEQ ID NO:21. The eighth Leucine-rich repeat extends from about amino acid 867 to about amino acid 894 of SEQ ID NO:8; SEQ ID NO:22. The ninth Leucine-rich repeat extends from about amino acid 895 to about amino acid 922 of SEQ ID NO:8; SEQ ID NO:23 and the tenth leucine-rich repeat extends from about amino acid 923 to about amino acid 950 of SEQ ID NO:8; SEQ ID NO:24.

The partial cDNA of CARD-4S described below (SEQ ID NO:25) has a 1470 nucleotide open reading frame (nucleotides 1–1470 of SEQ ID NO:25; SEQ ID NO:27) which encodes a 490 amino acid protein (SEQ ID NO:26). CARD-4S protein possesses a CARD domain (amino acids 1–74 of SEQ ID NO:26; SEQ ID NO:28). CARD-4S is predicted to have a P-Loop which extends from about amino acid 163 to about amino acid 170 of SEQ ID NO:26; SEQ ID NO:29, and a Walker Box "B" which extends form about amino acid 241 to about amino acid 245 of SEQ ID NO:26; SEQ ID NO:30.

A human CARD-4Y nucleotide cDNA sequence is presented (SEQ ID NO:38) as is the amino acid sequence of the predicted CARD-4Y product (SEQ ID NO:39). A human CARD-4Z nucleotide cDNA sequence is presented (SEQ ID NO:40) as is the amino acid sequence of the predicted CARD-4Z product (SEQ ID NO:41). A comparison of the CARD-4Y, CARD-4Z, and human CARD-4L predicted amino acid sequences is also shown in FIG. 14.

The 761 nucleotide murine CARD-5 cDNA described below (SEQ ID NO:60) has a 579 nucleotide open reading frame (nucleotides 89 to 668 of SEQ ID NO:60; SEQ ID NO:62) which encodes a 193 amino acid protein (SEQ ID NO:61). Murine CARD-5 contains a CARD domain which extends from amino acid 110 to amino acid 179 of SEQ ID NO:61 (SEQ ID NO:66).

The 740 nucleotide human CARD-5 cDNA described below (SEQ ID NO:48) has a 585 nucleotide open reading frame (nucleotides 54 to 639 of SEQ ID NO:48; SEQ ID NO:50) which encodes a 195 amino acid protein (SEQ ID NO:49). Human CARD-5 contains a CARD domain which extends from amino acid 111 to amino acid 181 of SEQ ID NO:49 (SEQ ID NO:58).

The 5252 nucleotide rat CARD-6 cDNA described below (SEQ ID NO:51) has a 2715 nucleotide open reading frame (nucleotides 169 to 2883 of SEQ ID NO:51; SEQ ID NO:53) which encodes a 905 amino acid protein (SEQ ID NO:52). Rat CARD-6 contains a CARD domain which extends from amino acid 1 to amino acid 108 of SEQ ID NO:52 (SEQ ID NO:59). Rat CARD-6 also has a proline-rich C-terminus which extends from amino acid 698 to amino acid 905 of SEQ ID NO:52 (SEQ ID NO:65). This proline-rich domain includes five putative SH3 binding sites. These binding sites have the sequence PXXP and are located at amino acids 710 to 713 (PAHP), 806 to 809 (PLRP), 819 to 822 (PIPP), 857 to 860 (PPHP), and 881 to 884 (PSQP) of SEQ ID NO:52.

The 4244 nucleotide human CARD-6 cDNA described below (SEQ ID NO:54) has a 3111 nucleotide open reading frame (nucleotides 200 to 3310 of SEQ ID NO:54, SEQ ID NO:56) which encodes a 1037 amino acid protein (SEQ ID NO:55). Human CARD-6 includes a CARD domain which extends from amino acid 5 to amino acid 92 of SEQ ID NO:55 (SEQ ID NO:64).

Like other proteins containing a CARD domain, CARD-3, CARD-4, CARD-5, and CARD-6 to participate in the network of interactions that lead to caspase activity. Human CARD-4L and CARD-5 likely play functional roles in caspase activation similar to that of Apaf-1 (Zou et al. (1997) Cell 90:405–413). For example, upon activation, CARD-4L and CARD-5 binds a nucleotide, thus allowing CARD-4L or CARD-5 to bind and activate a CARD-containing caspase via a CARD-CARD interaction, leading to apoptotic death of the cell and/or cytokine processing that leads to inflammation. CARD-3, CARD-4, CARD-5, and CARD-6 molecules are useful as modulating agents in regulating a variety of cellular processes including cell growth and cell death. In one aspect, this invention provides isolated nucleic acid molecules encoding CARD-3, CARD-4, CARD-5, or CARD-6 proteins or biologically active portions thereof, as well as nucleic acid fragments suitable as primers or hybridization probes for the detection of CARD-3, CARD-4, CARD-5, or CARD-6 encoding nucleic acids.

The invention encompasses methods of diagnosing and treating patients who are suffering from a disorder associated with an abnormal level or rate (undesirably high or undesirably low) of apoptotic cell death, abnormal activity of the Fas/APO-1 receptor complex, abnormal activity of the TNF receptor complex, abnormal inflammatory response, or abnormal activity of a caspase by administering a compound that modulates the expression of CARD-3, CARD-4, CARD-5, or CARD-6 (at the DNA, mRNA or protein level, e.g., by altering mRNA splicing) or by altering the activity of CARD-3, CARD-4, CARD-5, or CARD-6. Examples of such compounds include small molecules, antisense nucleic acid molecules, ribozymes, and polypeptides.

Certain disorders are associated with an increased number of surviving cells, which are produced and continue to survive or proliferate when apoptosis is inhibited or occurs at an undesirably low rate. Compounds that modulate the expression or activity of CARD-3, CARD-4, CARD-5, or CARD-6 can be used to treat or diagnose such disorders. These disorders include cancer (particularly follicular lymphomas, chronic myelogenous leukemia, melanoma, colon cancer, lung carcinoma, carcinomas associated with mutations in p53, and hormone-dependent tumors such as breast cancer, prostate cancer, and ovarian cancer). Such compounds can also be used to treat viral infections (such as those caused by herpesviruses, poxviruses, and adenoviruses). Failure to remove autoimmune cells that arise during development or that develop as a result of somatic mutation during an immune response can result in autoimmune disease. Thus, autoimmune disorders can be caused by an undesirably low levels of apoptosis. Accordingly, modulators of CARD-3, CARD-4, CARD-5, or CARD-6 activity or expression can be used to treat autoimmune disorders (e.g., systemic lupus erythematosis, immune-mediated glomerulonephritis, and arthritis).

Many diseases are associated with an undesirably high rate of apoptosis. Modulators of CARD-3, CARD04, CARD-5, or CARD-6 expression or activity can be used to treat or diagnose such disorders. For example, populations of cells are often depleted in the event of viral infection, with perhaps the most dramatic example being the cell depletion caused by the human immunodeficiency virus (HIV). Surprisingly, most T cells that die during HIV infections do not appear to be infected with HIV. Although a number of explanations have been proposed, recent evidence suggests that stimulation of the CD4 receptor results in the enhanced susceptibility of uninfected T cells to undergo apoptosis. A wide variety of neurological diseases are characterized by the gradual loss of specific sets of neurons. Such disorders include Alzheimer's disease, Parkinson's disease, amyotrophic lateral sclerosis (ALS) retinitis pigmentosa, spinal muscular atrophy, and various forms of cerebellar degeneration. The cell loss in these diseases does not induce an inflammatory response, and apoptosis appears to be the mechanism of cell death. In addition, a number of hematologic diseases are associated with a decreased production of blood cells. These disorders include anemia associated with chronic disease, aplastic anemia, chronic neutropenia, and the myelodysplastic syndromes. Disorders of blood cell production, such as myelodysplastic syndrome and some forms of aplastic anemia, are associated with increased apoptotic cell death within the bone marrow. These disorders could result from the activation of genes that promote apoptosis, acquired deficiencies in stromal cells or hematopoietic survival factors, or the direct effects of toxins and mediators of immune responses. Two common disorders associated with cell death are myocardial infarctions and stroke. In both disorders, cells within the central area of ischemia, which is produced in the event of acute loss of blood flow, appear to die rapidly as a result of necrosis. However, outside the central ischemic zone, cells die over a more protracted time period and morphologically appear to die by apoptosis.

Proteins containing a CARD domain are thought to be involved in various inflammatory disorders. For example, the CARD domain-containing protein caspase-1 promotes inflammation by converting certain proinflammatory cytokines from an inactive to an active form. Accordingly, CARD-3, CARD-4, CARD-5, and CARD-6 polypeptides, nucleic acids and modulators of CARD-3, CARD-4, CARD-5, or CARD-6 expression or activity can be used to treat immune disorders. Such immune disorders include, but are not limited to, chronic inflammatory diseases and disorders, such as Crohn's disease, reactive arthritis, including Lyme disease, insulin-dependent diabetes, organ-specific autoimmunity, including multiple sclerosis, Hashimoto's thyroiditis and Grave's disease, contact dermatitis, psoriasis, graft rejection, graft versus host disease, sarcoidosis, atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis), certain viral infections, including HIV, and bacterial infections, including tuberculosis and lepromatous leprosy.

In addition to the aforementioned disorders, CARD-3, CARD-4, CARD-5, and CARD-6 polypeptides, nucleic acids, and modulators of CARD-3, CARD-4, CARD-5 or CARD-6 expression or activity can be used to treat disorders of cell signaling and disorders of tissues in which CARD-3, CARD-4, CARD-5 or CARD-6 is expressed.

The invention features a nucleic acid molecule which is at least 45% (or 55%, 65%, 75%, 85%, 95%, or 98%) identical to the nucleotide sequence shown in SEQ ID NO:1, SEQ ID NO:3, SEQ ID NO:7, SEQ ID NO:9, SEQ ID:25, SEQ ID NO:27, SEQ ID NO:38, SEQ ID NO:40, SEQ ID NO:42, SEQ ID NO:48, SEQ ID NO:50, SEQ ID NO:51, SEQ ID NO:53, SEQ ID NO:54, SEQ ID NO:56, SEQ ID NO:60, SEQ ID NO:62, the nucleotide sequence of the cDNA insert of the plasmid deposited with the ATCC as Accession Number 203037 (the "cDNA of ATCC 203037"), the nucleotide sequence of the cDNA insert of the plasmid deposited with the ATCC as Accession Number 203035 (the "cDNA of ATCC 203035"), the nucleotide sequence of the cDNA insert of the plasmid deposited with the ATCC as Accession Number 203036 (the "cDNA of ATCC 203036"), the nucleotide sequence of the cDNA insert of the plasmid deposited with the ATCC as Accession Number PTA-211 (the "cDNA of ATCC PTA-211"), the nucleotide sequence of the cDNA insert of the plasmid deposited with the ATCC as Accession Number PTA-212 ("the cDNA of ATCC PTA-212"), the nucleotide sequence of the cDNA insert of the plasmid deposited with the ATCC as Accession Number PTA-213 (the "cDNA of ATCC PTA-213"), or a complement thereof.

The invention features a nucleic acid molecule which includes a fragment of at least 150 (300, 325, 350, 375, 400, 425, 450, 500, 550, 600, 650, 700, 800, 900, 1000, 1300, 1600 or 1931) nucleotides of the nucleotide sequence shown in SEQ ID NO:1, or SEQ ID NO:3, or the nucleotide sequence of the cDNA ATCC 203037, or a complement thereof.

The invention also features a nucleic acid molecule which includes a fragment of at least 150 (350, 400, 450, 500, 550, 600, 650, 700, 800, 900, 1000, 1300, 1600, 1900, 2100, 2400, 2700, 3000, or 3382) nucleotides of the nucleotide sequence shown in SEQ ID NO:7, SEQ ID NO:9, or the nucleotide sequence of the cDNA ATCC 203035, or a complement thereof.

Also within the invention is a nucleic acid molecule which includes a fragment of at least 150 (350, 400, 450, 500, 550, 600, 650, 700, 800, 900, 1000, 1300, 1600, 1900, 2100, 2400, 2700, and 3080) nucleotides of the nucleotide sequence shown in SEQ ID NO:25, SEQ ID NO:27, SEQ ID NO:38, SEQ ID NO:40, or the nucleotide sequence of the cDNA of ATCC 203036, or a complement thereof.

The invention also features a nucleic acid molecule which includes a fragment of at least 150 (350, 400, 450, 500, 550, 600, 650, 700, and 761) nucleotides of the nucleotide sequence shown in SEQ ID NO:60, SEQ ID NO:62, or the nucleotide sequence of the cDNA of ATCC PTA-212, or a complement thereof.

The invention also features a nucleic acid molecule which includes a fragment of at least 150 (350, 400, 450, 500, 550, 600, 650, 700, and 740) nucleotides of the nucleotide sequence shown in SEQ ID NO:48, SEQ ID NO:50, the cDNA of ATCC PTA-213, or a complement thereof.

The invention also features a nucleic acid molecule which includes a fragment of at least 150 (350, 400, 450, 500, 600, 700, 800, 900, 1000, 1500, 2000, 2500, 3000, 3500, 4000, 4500, 5000, and 5252) nucleotides of the nucleotide sequence shown in SEQ ID NO:51, SEQ ID NO:53, or a complement thereof The invention also features a nucleic acid molecule which includes a fragment of at least 150 (200, 300, 400, 500, 600, 700, 800, 900, 1000, 1400, 1800, 2200, 2600, or 3000) nucleotides of the nucleotide sequence shown in SEQ ID NO:54, SEQ ID NO:56, the cDNA of ATCC PTA-213, or a complement thereof.

The invention features a nucleic acid molecule which includes a nucleotide sequence encoding a protein having an amino acid sequence that is at least 45% (or 55%, 65%, 75%, 85%, 95%, or 98%) identical to the amino acid sequence of SEQ ID NO:2, SEQ ID NO:8, SEQ ID NO:26, SEQ ID NO:39, SEQ ID NO:41, SEQ ID NO:43, SEQ ID NO:49, SEQ ID NO:52, SEQ ID NO:55, SEQ ID NO:61, or the amino acid sequence encoded by the cDNA of ATCC 203037, the amino acid sequence encoded by the cDNA of ATCC 203035, the amino acid sequence encoded by the cDNA of ATCC 203036, the amino acid sequence encoded by the cDNA of ATCC PTA-211, the amino acid sequence encoded by the cDNA of ATCC PTA-212, or the amino acid sequence encoded by the cDNA of ATCC PTA-213.

In an embodiment, a CARD-3 nucleic acid molecule has the nucleotide sequence shown in SEQ ID NO:1, or SEQ ID NO:3, or the nucleotide sequence of the cDNA of ATCC 203037. In another embodiment, a CARD-4L nucleic acid molecule has the nucleotide sequence shown in SEQ ID NO:7, or SEQ ID NO:9, or the nucleotide sequence of the cDNA of ATCC 203035.

In yet another embodiment, a CARD-4S nucleic acid molecule has the nucleotide sequence shown in SEQ ID NO:25, or SEQ ID NO:27, or the nucleotide sequence of the cDNA of ATCC 203036. In another embodiment, a murine CARD-4L nucleic acid molecule has the nucleotide sequence shown in SEQ ID NO:42.

In another embodiment, a CARD-4Y nucleic acid molecule has the nucleotide sequence shown in SEQ ID NO:38.

In another embodiment, a CARD-4Z nucleic acid molecule has the nucleotide sequence shown in SEQ ID NO:40.

In another embodiment, a human CARD-5 nucleic acid molecule has the nucleotide sequence shown in SEQ ID NO:48, SEQ ID NO:50 or the nucleotide sequence of the cDNA of ATCC PTA-213. In another embodiment, a murine CARD-5 nucleic acid molecule has the nucleotide sequence shown in SEQ ID NO:60 or SEQ ID NO:62.

In yet another embodiment, a rat CARD-6 nucleic acid molecule has the nucleotide sequence shown in SEQ ID NO:51, SEQ ID NO:53, or the nucleotide sequence of the cDNA of ATCC PTA-211.

In still another embodiment, a human CARD-6 nucleic acid molecule has the nucleotide sequence shown in SEQ ID NO:54, SEQ ID NO:56, or the nucleotide sequence of the cDNA of ATCC PTA-213.

Also within the invention is a nucleic acid molecule which encodes a fragment of a polypeptide having the amino acid sequence of SEQ ID NO:2, SEQ ID NO:8, SEQ ID NO:26, SEQ ID NO:39, SEQ ID NO:41, SEQ ID NO:43, SEQ ID NO:49, SEQ ID NO:52, SEQ ID NO:55, SEQ ID NO:61, the fragment including at least 15 (25, 30, 50, 100, 150, 300, 400 or 540, 600, 700, 800, 900) contiguous amino acids of SEQ ID NO:2, SEQ ID NO:8, SEQ ID NO:26, SEQ ID NO:39, SEQ ID NO:41, SEQ ID NO:43, SEQ ID NO:49, SEQ ID NO:52, or SEQ ID NO:55, SEQ ID NO:61, the polypeptide encoded by the cDNA of ATCC Accession Number 203037, the polypeptide encoded by the cDNA of ATCC Accession Number 203035, the polypeptide encoded by the cDNA of ATCC Accession Number 203036, the polypeptide encoded by the cDNA of ATCC Accession Number PTA-211, the polypeptide encoded by the cDNA of ATCC Accession Number PTA-212, or the polypeptide encoded by the cDNA of ATCC Accession Number PTA-213.

The invention includes a nucleic acid molecule which encodes a naturally occurring allelic variant of a polypeptide comprising the amino acid sequence of SEQ ID NO:2, SEQ ID NO:8, SEQ ID NO:26, SEQ ID NO:39, SEQ ID NO:41, SEQ ID NO:43, SEQ ID NO:49, SEQ ID NO:52, SEQ ID NO:55, SEQ ID NO:61, or an amino acid sequence encoded by the cDNA of ATCC Accession Number 203037, 203035, 203036, PTA-211 PTA-212, or PTA-213, wherein the nucleic acid molecule hybridizes to a nucleic acid molecule consisting of SEQ ID NO:1, SEQ ID NO:3, SEQ ID NO:7, SEQ ID NO:9, SEQ ID:25, SEQ ID NO:27, SEQ ID NO:38, SEQ ID NO:40, SEQ ID NO:42, SEQ ID NO:48, SEQ ID NO:50, SEQ ID NO:51, SEQ ID NO:53, SEQ ID NO:54, SEQ ID NO:56, SEQ ID NO:60, SEQ ID NO:62, the cDNA of ATCC 203037, the cDNA of ATCC 203035, the cDNA of ATCC 203036, the cDNA of ATCC PTA-211, the cDNA of ATCC PTA-212, or the cDNA of PTA-213 under stringent conditions.

In general, an allelic variant of a gene will be readily identifiable as mapping to the same chromosomal location as said gene. For example, in Example 6, the chromosomal location of the human CARD-4 gene is discovered to be chromosome 7 close to the SHGC-31928 genetic marker. Allelic variants of human CARD-4 will be readily identifiable as mapping to the human CARD-4 locus on chromosome 7 near genetic marker SHGC-31928.

Also within the invention are: an isolated CARD-3 protein having an amino acid sequence that is at least about 65%, preferably 75%, 85%, 95%, or 98% identical to the amino acid sequence of SEQ ID NO:2; an isolated CARD-3 protein having an amino acid sequence that is at least about 85%, 95%, or 98% identical to the kinase domain of SEQ ID NO:2 (e.g., about amino acid residues 1 to 300 of SEQ ID NO:2; SEQ ID NO:4); and an isolated CARD-3 protein having an amino acid sequence that is at least about 85%, 95%, or 98% identical to the linker domain of SEQ ID NO:2 (e.g., about amino acid residues 301 to 431 of SEQ ID NO:2; SEQ ID NO:5); an isolated CARD-3 protein having an amino acid sequence that is at least about 85%, 95%, or 98% identical to the CARD domain of SEQ ID NO:2 (e.g., about amino acid residues 432 to 540 of SEQ ID NO:2; SEQ ID NO:6); an isolated CARD-4L protein having an amino acid sequence that is at least about 65%, preferably 75%, 85%, 95%, or 98% identical to the amino acid sequence of SEQ ID NO:8; an isolated CARD-4L protein having an amino acid sequence that is at least about 85%, 95%, or 98% identical to the CARD domain of SEQ ID NO:8 (e.g., about amino acid residues 15 to 114 of SEQ ID NO:8; SEQ ID NO:10); an isolated CARD-4L protein having an amino acid sequence that is at least about 85%, 95%, or 98% identical to the nucleotide binding domain of SEQ ID NO:8 (e.g., about amino acid residues 198 to 397 of SEQ ID NO:8; SEQ ID NO:11; an isolated CARD-4L protein having an amino acid sequence that is at least about 85%, 95%, or 98% identical to the kinase 1a (P-loop) subdomain SEQ ID NO:8 (e.g., about amino acid 127 to about amino acid 212 of SEQ ID NO:8; SEQ ID NO:46); an isolated CARD-4L protein having an amino acid sequence that is at least about 85%, 95%, or 98% identical to the kinase 2 subdomain of SEQ ID NO:8 (e.g., about amino acid 273 to about amino acid 288 of SEQ ID NO:8; SEQ ID NO:47); an isolated CARD-4L protein having an amino acid sequence that is at least about 85%, 95%, or 98% identical to a kinase 3a subdomain of SEQ ID NO:8 (e.g., about amino acid residues 327 to 338 of SEQ ID NO:8; SEQ ID NO:14); an isolated CARD-4L protein having an amino acid sequence that is at least about 85%, 95%, or 98% identical to the Leucine-rich repeats of SEQ ID NO:8 (e.g., about amino acid residues 674 to 701 of SEQ ID NO:8; SEQ ID NO:15; from amino acid 702 to amino acid 727 of SEQ ID NO:8; SEQ ID NO: 16; which extends from amino acid 728 to amino acid 754 SEQ ID NO:8; SEQ ID NO:17; from amino acid 755 to amino acid 782 of SEQ ID NO:8; SEQ ID NO:18; from amino acid 783 to amino acid 810 of SEQ ID NO:8; SEQ ID NO:19; from amino acid 811 to amino acid 838 of SEQ ID NO:8; SEQ ID NO:20 from amino acid 839 to amino acid 866 of SEQ ID NO:8; SEQ ID NO:21; from amino acid 867 to amino acid 894 of SEQ ID NO:8; SEQ ID NO:22; from amino acid 895 to amino acid 922 of SEQ ID NO:8; SEQ ID NO:23; and from amino acid 923 to amino acid 950 of SEQ ID NO:8; SEQ ID NO:24); an isolated CARD-4S protein having an amino acid sequence that is at least about 65%, preferably 75%, 85%, 95%, or 98% identical to the amino acid sequence of SEQ ID NO:26; an isolated CARD-4S protein having an amino acid sequence that is at least about 85%, 95%, or 98% identical to the CARD domain of SEQ ID NO:26 (e.g., about amino acid residues 1 to 74 of SEQ ID NO:26; SEQ ID NO:28). Also within the invention are: an isolated murine CARD-4L protein having an amino acid sequence that is at least about 65%, preferably 75%, 85%, 95%, or 98% identical to the amino acid sequence of SEQ ID NO:43. Also within the invention area isolated CARD-4Y protein having an amino acid sequence that is at least about 65%, preferably 75%, 85%, 95%, or 98% identical to the amino acid sequence of SEQ ID NO:39. Also within the invention are: an isolated CARD-4Z protein having an amino acid sequence that is at least about 65%, preferably 75%, 85%, 95%, or 98% identical to the amino acid sequence of SEQ ID NO:41.

Also within the invention are: an isolated CARD-5 protein having an amino acid sequence that is at least about 65%, preferably 75%, 85%, 95%, or 98% identical to the amino acid sequence of SEQ ID NO:49 and an isolated CARD-5 protein comprising an amino acid sequence that is at least about 90%, 95%, or 98% identical to SEQ ID NO:58 (CARD domain).

Also within the invention are an isolated CARD-5 protein having an amino acid sequence that is at least about 65%, preferably 75%, 85%, 95%, or 98% identical to the amino acid sequence of SEQ ID NO:60 and an isolated CARD-5 protein comprising an amino acid sequence that is at least about 90%, 95%, or 98% identical to SEQ ID NO:57 (CARD domain).

The invention also includes: an isolated CARD-6 protein having an amino acid sequence that is at least about 65%, preferably 75%, 85%, 95%, or 98% identical to the amino acid sequence of SEQ ID NO:52 and an isolated CARD-6 protein having an amino acid sequence that is at least about 90%, 95%, or 98% identical to SEQ ID NO:59 (CARD domain).

The invention also includes: an isolated CARD-6 protein having an amino acid sequence that is at least about 65%, preferably 75%, 85%, 95%, or 98% identical to the amino acid sequence of SEQ ID NO:55 and an isolated CARD-6 protein having an amino acid sequence that is at least about 90%, 95%, or 98% identical to SEQ ID NO:64 (CARD domain).

Also within the invention are: an isolated CARD-3 protein which is encoded by a nucleic acid molecule having a nucleotide sequence that is at least about 65%, preferably 75%, 85%, or 95% identical to SEQ ID NO:3 or the cDNA of ATCC 203037; an isolated CARD-3 protein which is encoded by a nucleic acid molecule having a nucleotide sequence at least about 65% preferably 75%, 85%, or 95% identical to the kinase domain encoding portion of SEQ ID NO:1 (e.g., about nucleotides 213 to 1113 of SEQ ID NO:1); an isolated CARD-3 protein which is encoded by a nucleic acid molecule having a nucleotide sequence at least about 65% preferably 75%, 85%, or 95% identical the linker domain encoding portion of SEQ ID NO:1 (e.g., about nucleotides 1114 to 1506 of SEQ ID NO:1); and an isolated CARD-3 protein which is encoded by a nucleic acid molecule having a nucleotide sequence at least about 65% preferably 75%, 85%, or 95% identical the CARD domain encoding portion of SEQ ID NO:1 (e.g., about nucleotides 1507 to 1833 of SEQ ID NO:1); and an isolated CARD-3 protein which is encoded by a nucleic acid molecule having a nucleotide sequence which hybridizes under stringent hybridization conditions to a nucleic acid molecule having the nucleotide sequence of SEQ ID NO:3 or the non-coding strand of the cDNA of ATCC 203037. Also within the invention are: an isolated CARD-4Y protein which is encoded by a nucleic acid molecule having a nucleotide sequence that is at least about 65%, preferably 75%, 85%, or 95% identical to SEQ ID NO:38. Also within the invention are nucleic acid molecules which include about nucleotides 2759 to 2842 of SEQ ID NO:7; about nucleotides 2843 to 2926 of SEQ ID NO:7; about nucleotides 2927 to 3010 of SEQ ID NO:7; about nucleotides 3011 to 3094 of SEQ ID NO:7; and an isolated CARD-4L protein which is encoded by a nucleic acid molecule having a nucleotide sequence which hybridizes under stringent hybridization conditions to a nucleic acid molecule having the nucleotide sequence of SEQ ID NO:9, or the non-coding strand of the cDNA of ATCC 203035.

Also within the invention are an isolated CARD-4S protein which is encoded by a nucleic acid molecule having a nucleotide sequence that is at east about 65%, preferably 75%, 85%, or 95% identical to SEQ ID NO:27; an isolated CARD-3 protein which is encoded by a nucleic acid molecule having a nucleotide sequence at least about 65% preferably 75%, 85%, or 95% identical the CARD domain encoding portion of SEQ ID NO:25 (e.g., about nucleotides 1 to 222 of SEQ ID NO:25); an isolated CARD-3 protein which is encoded by a nucleic acid molecule having a nucleotide sequence at least about 65% preferably 75%, 85%, or 95% identical the P-Loop encoding portion of SEQ ID NO:25 (e.g., about nucleotides 485 to 510 of SEQ ID NO:25).

Also within the invention are an isolated CARD-5 protein which is encoded by a nucleic acid molecule having a nucleotide sequence that is at least about 65%, preferably 75%, 85%, or 95% identical to SEQ ID NO:48 or the cDNA of ATCC PTA-213; an isolated CARD-5 protein which is encoded by a nucleic acid molecule having a nucleotide sequence at least about 90% preferably 95%, or 98% identical to the CARD encoding portion of SEQ ID NO:48 (e.g., about nucleotides 383 to 596 of SEQ ID NO:48); and an isolated CARD-5 protein which is encoded by a nucleic acid molecule having a nucleotide sequence which hybridizes under stringent hybridization conditions to a nucleic acid molecule having the nucleotide sequence of SEQ ID NO:48 or the non-coding strand of the cDNA of ATCC PTA-213.

Also within the invention are an isolated CARD-5 protein which is encoded by a nucleic acid molecule having a nucleotide sequence that is at least about 65%, preferably 75%, 85%, or 95% identical to SEQ ID NO:60; an isolated CARD-5 protein which is encoded by a nucleic acid molecule having a nucleotide sequence at least about 90% preferably 95%, or 98% identical to the CARD encoding portion of SEQ ID NO:60 (e.g., about nucleotides 416 to 625 of SEQ ID NO:60); and an isolated CARD-5 protein which is encoded by a nucleic acid molecule having a nucleotide sequence which hybridizes under stringent hybridization conditions to a nucleic acid molecule having the nucleotide sequence of SEQ ID NO:60.

Also within the invention are an isolated CARD-6 protein which is encoded by a nucleic acid molecule having a nucleotide sequence that is at least about 65%, preferably 75%, 85%, or 95% identical to SEQ ID NO:51; an isolated CARD-6 protein which is encoded by a nucleic acid molecule having a nucleotide sequence at least about 90% preferably 95%, or 98% identical to the CARD encoding portion of SEQ ID NO:51 (e.g., about nucleotides 169 to 456 of SEQ ID NO:51); and an isolated CARD-6 protein which is encoded by a nucleic acid molecule having a nucleotide sequence which hybridizes under stringent hybridization conditions to a nucleic acid molecule having the nucleotide sequence of SEQ ID NO:51.

Also within the invention are an isolated CARD-6 protein which is encoded by a nucleic acid molecule having a nucleotide sequence that is at least about 65%, preferably 75%, 85%, or 95% identical to SEQ ID NO:54; an isolated CARD-6 protein which is encoded by a nucleic acid molecule having a nucleotide sequence at least about 90% preferably 95%, or 98% identical to the CARD encoding portion of SEQ ID NO:54; and an isolated CARD-6 protein which is encoded by a nucleic acid molecule having a nucleotide sequence which hybridizes under stringent hybridization conditions to a nucleic acid molecule having the nucleotide sequence of SEQ ID NO:54.

Another embodiment of the invention features CARD-3, CARD-4, CARD-5, or CARD-6 nucleic acid molecules which specifically detect CARD-3, CARD-4, CARD-5, or CARD-6 nucleic acid molecules, relative to nucleic acid molecules encoding other members of the CARD superfamily. For example, in one embodiment, a CARD-4L nucleic acid molecule hybridizes under stringent conditions to a nucleic acid molecule comprising the nucleotide sequence of SEQ ID NO:7, SEQ ID NO:9, or the cDNA of ATCC 203035, or a complement thereof. In another embodiment, the CARD-4L nucleic acid molecule is at least 300 (350, 400, 450, 500, 550, 600, 650, 700, 800, 900, 1000, 1300, 1600, 1900, 2100, 2400, 2700, 3000, or 3382) nucleotides in length and hybridizes under stringent conditions to a nucleic acid molecule comprising the nucleotide sequence shown in SEQ ID NO:7, SEQ ID NO:9, the cDNA of ATCC 203035, or a complement thereof. In another embodiment, an isolated CARD-4L nucleic acid molecule comprises nucleotides 287 to 586 of SEQ ID NO:7, encoding the CARD domain of CARD-4L, or a complement thereof. In yet another embodiment, the invention provides an isolated nucleic acid molecule which is antisense to the coding strand of a CARD-4L nucleic acid.

In another embodiment, a CARD-5 nucleic acid molecule hybridizes under stringent conditions to a nucleic acid molecule comprising the nucleotide sequence of SEQ ID NO:48, SEQ ID NO:50, or the cDNA of ATCC PTA-213, or a complement thereof. In another embodiment, the CARD-5 nucleic acid molecule is at least 300 (350, 400, 450, 500, 550, 585, 600, 650, 700, or 740) nucleotides in length and hybridizes under stringent conditions to a nucleic acid molecule comprising the nucleotide sequence shown in SEQ ID NO:48, SEQ ID NO:50, the cDNA of ATCC PTA-213, or a complement thereof. In another embodiment, an isolated CARD-5 nucleic acid molecule comprises nucleotides 383 to 596 of SEQ ID NO:48, encoding the CARD of CARD-5. In yet another embodiment, the invention provides an isolated nucleic acid molecule which is antisense to the coding strand of a CARD-5 nucleic acid.

Another aspect of the invention provides a vector, e.g., a recombinant expression vector, comprising a CARD-3, CARD-4, CARD-5, or CARD-6 nucleic acid molecule of the invention. In another embodiment the invention provides a host cell containing such a vector. The invention also provides a method for producing CARD-3, CARD-4, CARD-5, or CARD-6 protein by culturing, in a suitable medium, a host cell of the invention containing a recombinant expression vector such that a CARD-3, CARD-4, CARD-5, or CARD-6 protein is produced.

Another aspect of this invention features isolated or recombinant CARD-3, CARD-4, CARD-5, or CARD-6 proteins and polypeptides. Preferred CARD-3, CARD-4, CARD-5, or CARD-6 proteins and polypeptides possess at least one biological activity possessed by naturally occurring human CARD-3, CARD-4, CARD-5, or CARD-6, e.g., (1) the ability to form protein:protein interactions with proteins in the apoptotic signaling pathway; (2) the ability to form CARD-CARD interactions with proteins in the apoptotic signaling pathway, e.g., caspase-1; (3) the ability to bind a CARD-3, CARD-4, CARD-5, or CARD-6 ligand; and (4) the ability to bind to an intracellular target. Other activities include: (1) modulation of cellular proliferation; (2) modulation of cellular differentiation; (3) modulation of cellular death; (4) modulation of the NF-κB pathway; (5) modulation of proinflammatory cytokine activation; and (6) modulation of inflammation.

The CARD-3, CARD-4, CARD-5, or CARD-6 proteins of the present invention, or biologically active portions thereof, can be operatively linked to a non-CARD-3, non-CARD-4, non-CARD-5, or non-CARD-6 polypeptide (e.g., heterologous amino acid sequences) to form CARD-3, CARD-4, CARD-5, or CARD-6 fusion proteins, respectively. The invention further features antibodies that specifically bind CARD-3, CARD-4, CARD-5, or CARD-6 proteins, such as monoclonal or polyclonal antibodies. In addition, the CARD-3, CARD-4, CARD-5, or CARD-6 proteins or biologically active portions thereof can be incorporated into pharmaceutical compositions, which optionally include pharmaceutically acceptable carriers.

In another aspect, the present invention provides a method for detecting the presence of CARD-3, CARD-4, CARD-5, or CARD-6 activity or expression in a biological sample by contacting the biological sample with an agent capable of detecting an indicator of CARD-3, CARD-4, CARD-5, or CARD-6 activity such that the presence of CARD-3, CARD-4, CARD-5, or CARD-6 activity is detected in the biological sample.

In another aspect, the invention provides a method for modulating CARD-3, CARD-4, CARD-5, or CARD-6 activity comprising contacting a cell with an agent that modulates (inhibits or stimulates) CARD-3, CARD-4, CARD-5, or CARD-6 activity or expression such that CARD-3, CARD-4, CARD-5, or CARD-6 activity or expression in the cell is modulated. In one embodiment, the agent is an antibody that specifically binds to CARD-3, CARD-4, CARD-5, or CARD-6 protein. In another embodiment, the agent modulates expression of CARD-3, CARD-4, CARD-5, or CARD-6 by modulating transcription of a CARD-3, CARD-4, CARD-5, or CARD-6 gene, splicing of a CARD-3, CARD-4, CARD-5, or CARD-6 mRNA, or translation of a CARD-3, CARD-4, CARD-5, or CARD-6 mRNA. In yet another embodiment, the agent is a nucleic acid molecule having a nucleotide sequence that is antisense to the coding strand of the CARD-3, CARD-4, CARD-5, or CARD-6 mRNA or the CARD-3, CARD-4, CARD-5, or CARD-6 gene.

In one embodiment, the methods of the present invention are used to treat a subject having a disorder characterized by aberrant CARD-3, CARD-4, CARD-5, or CARD-6 protein or nucleic acid expression or activity or related to CARD-3, CARD-4, CARD-5, or CARD-6 expression or activity by administering an agent which is a CARD-3, CARD-4, CARD-5, or CARD-6 modulator to the subject. In one embodiment, the CARD-3, CARD-4, CARD-5, or CARD-6 modulator is a CARD-3, CARD-4, CARD-5, or CARD-6 protein. In another embodiment the CARD-3, CARD-4, CARD-5, or CARD-6 modulator is a CARD-3, CARD-4, CARD-5, or CARD-6 nucleic acid molecule. In other embodiments, the CARD-3, CARD-4, CARD-5, or CARD-6 modulator is a peptide, peptidomimetic, or other small molecule.

The present invention also provides a diagnostic assay for identifying the presence or absence of a genetic lesion or mutation characterized by at least one of: (i) aberrant modification or mutation of a gene encoding a CARD-3, CARD-4, CARD-5, or CARD-6 protein; (ii) mis-regulation of a gene encoding a CARD-3, CARD-4, CARD-5, or CARD-6 protein; (iii) aberrant RNA splicing; and (iv) aberrant post-translational modification of a CARD-3, CARD-4, CARD-5, or CARD-6 protein, wherein a wild-type form of the gene encodes a protein with a CARD-3, CARD-4, CARD-5, or CARD-6 activity.

In another aspect, the invention provides a method for identifying a compound that binds to or modulates the activity of a CARD-3, CARD-4, CARD-5, or CARD-6 protein. In general, such methods entail measuring a biological activity of a CARD-3, CARD-4, CARD-5, or CARD-6 protein in the presence and absence of a test compound and identifying those compounds which alter the activity of the CARD-3, CARD-4, CARD-5, or CARD-6 protein.

The invention also features assays for identifying compounds that block the interaction of CARD-5 with a CARD-5 ligand, e.g., caspase-1, CARD-7, or CARD-5. Isolated CARD domains of CARD-5, caspase-1, and/or CARD-7 can be used in these assays.

The invention also features methods for identifying a compound which modulates the expression of CARD-3, CARD-4, CARD-5, or CARD-6 by measuring the expression of CARD-3, CARD-4, CARD-5, or CARD-6 in the presence and absence of a compound.

Other features and advantages of the invention will be apparent from the following detailed description and claims.

BRIEF DESCRIPTION OF THE DRAWINGS

FIG. 1 depicts the cDNA sequence (SEQ ID NO:1) of human CARD-3. The open reading frame of CARD-3 (SEQ ID NO:1) extends from nucleotide 213 to nucleotide 1833 nucleotide (SEQ ID NO:3).

FIG. 2 depicts the predicted amino acid sequence (SEQ ID NO:2) of human CARD-3.

FIG. 3 depicts the cDNA sequence (SEQ ID NO:7) of CARD-4L. The open reading frame of SEQ ID NO:7 extends from nucleotide 245 to nucleotide 3103 (SEQ ID NO:9).

FIG. 4 depicts the predicted amino acid sequence (SEQ ID NO:8) of human CARD-4L.

FIG. 5 depicts the partial cDNA sequence (SEQ ID NO:25) of CARD-4S and the predicted amino acid sequence (SEQ ID NO:25) of human CARD-4S. The open reading frame of CARD-4 (SEQ ID NO:25) extends from nucleotide 1 to nucleotide 1470 (SEQ ID NO:27).

FIG. 6 depicts the predicted amino acid sequence (SEQ ID NO:26) of human CARD-4S.

FIG. 7 depicts an alignment of the CARD domains of CARD-4 (SEQ ID NO:10), CARD-3 (SEQ ID NO:6), ARC-CARD (SEQ ID NO:31), cIAP1-CARD (SEQ ID NO:32), and cIAP2-CARD (SEQ ID NO:33).

FIG. 10 depicts the cDNA sequence (SEQ ID NO:38) of the human CARD-4Y splice variant clone. The predicted open reading frame of the human CARD-4Y splice variant clone extends from nucleotide 438 to nucleotide 1184.

FIG. 11 depicts the amino acid sequence (SEQ ID NO:39) of the protein predicted to be encoded by the human CARD-4Y cDNA open reading frame.

FIG. 12 depicts the cDNA sequence (SEQ ID NO:40) of the human CARD-4Z splice variant clone. The predicted open reading frame of the human CARD-4Z splice variant clone extends from nucleotide 489 to nucleotide 980.

FIG. 13 depicts the amino acid sequence (SEQ ID NO:41) of the protein predicted to be encoded by the human CARD-4Z cDNA open reading frame.

FIG. 15 depicts the nucleotide sequence of the murine CARD-4L cDNA (SEQ ID NO:42).

FIG. 16 depicts the predicted amino acid sequence of murine CARD-4L (SEQ ID NO:43).

FIG. 17 depicts an alignment of human CARD-4L (SEQ ID NO:8) and the predicted amino acid sequence of murine CARD-4L (SEQ ID NO:43).

FIG. 18 depicts a 32042 nucleotide genomic sequence of CARD-4.

FIG. 19 depicts the nucleotide sequence of a murine CARD-5 cDNA (SEQ ID NO:60). The open reading frame of this cDNA extends from nucleotide 89 to nucleotide 667 of SEQ ID NO:60 (SEQ ID NO:62) and encodes a 193 amino acid protein (SEQ ID NO:61).

FIG. 21 depicts the nucleotide sequence of a human CARD-5 cDNA (SEQ ID NO:48). The open reading frame of this cDNA extends from nucleotide 53 to nucleotide 638 of SEQ ID NO:48 (SEQ ID NO:50) and encodes a 195 amino acid protein SEQ ID NO:49).

FIG. 23 depicts an alignment of the cDNA sequences of murine CARD-5 (SEQ ID NO:60) and human CARD-5 (SEQ ID NO:48). This alignment was created using ALIGN (version 2.0; PAM120 scoring matrix; −12/−4 gap penalty). In this alignment the sequences are 68.2% identical.

FIG. 24 depicts an alignment of the amino acid sequences of murine CARD-5 (SEQ ID NO:61) and human CARD-5 (SEQ ID NO:49). This alignment was created using ALIGN (version 2.0; PAM120 scoring matrix; −12/−4 gap penalty). In this alignment the sequences are 71.8% identical.

FIG. 25 depicts the nucleotide sequence of a rat CARD-6 cDNA (SEQ ID NO:51). The open reading frame of this cDNA extends from nucleotide 169 to nucleotide 2883 of SEQ ID NO:51 (SEQ ID NO:53) and encodes a 505 amino acid protein (SEQ ID NO:52).

FIG. 28 depicts the nucleotide sequence of a human CARD-6 cDNA (SEQ ID NO:54). The open reading frame of this cDNA extends from nucleotide 200 to 3310 of SEQ ID NO:54 (SEQ ID NO:56) and encodes a 1037 amino acid protein (SEQ ID NO:55).

FIG. 30 depicts an alignment of the CARD domain of human CARD-6 (SEQ ID NO:64) with a consensus CARD domain (SEQ ID NO:67). In this depiction of the consensus sequence, more conserved residues are indicated by uppercase letters and less conserved residues are indicated by lowercase letters.

DETAILED DESCRIPTION OF THE INVENTION

The present invention is based, in part, on the discovery of cDNA molecules encoding human CARD-3, human CARD-4, partial murine CARD-4L, murine CARD-5, human CARD-5, rat CARD-6, and human CARD-6 proteins.

TABLE 1

Summary of CARD-3, CARD-4, CARD-5, and CARD-6 Sequence Information.

| Gene | cDNA | Protein | ORF | Figure | Accession Number |
|---|---|---|---|---|---|
| human CARD-3 | SEQ ID NO:1 | SEQ ID NO:2 | SEQ ID NO:3 | FIGS. 1-2 | 203037 |
| human CARD-4L | SEQ ID NO:7 | SEQ ID NO:8 | SEQ ID NO:9 | FIGS. 3-4 | 203035 |
| human CARD-4S | SEQ ID NO:25 | SEQ ID NO:26 | SEQ ID NO:27 | FIGS. 5-6 | 203036 |
| human CARD-4Y | SEQ ID NO:38 | SEQ ID NO:39 | | FIGS. 10-11 | |
| human CARD-4Z | SEQ ID NO:40 | SEQ ID NO:41 | | FIGS. 12-13 | |
| murine CARD-4L | SEQ ID NO:42 | SEQ ID NO:43 | | FIGS. 15-16 | |
| human CARD-5 | SEQ ID NO:48 | SEQ ID NO:49 | SEQ ID NO:50 | FIG. 21 | PTA-213 |
| murine CARD-5 | SEQ ID NO:60 | SEQ ID NO:61 | SEQ ID NO:62 | FIG. 19 | PTA-212 |
| human CARD-6 | SEQ ID NO:54 | SEQ ID NO:55 | SEQ ID NO:56 | FIG. 28 | PTA-213 |
| rat CARD-6 | SEQ ID NO:51 | SEQ ID NO:52 | SEQ ID NO:53 | FIG. 25 | PTA-211 |

A nucleotide sequence encoding a human CARD-3 protein is shown in FIG. 1 (SEQ ID NO:1; SEQ ID NO:3 includes the open reading frame only). A predicted amino acid sequence of CARD-3 protein is also shown in FIG. 2 (SEQ ID NO:2).

Figure 14E:
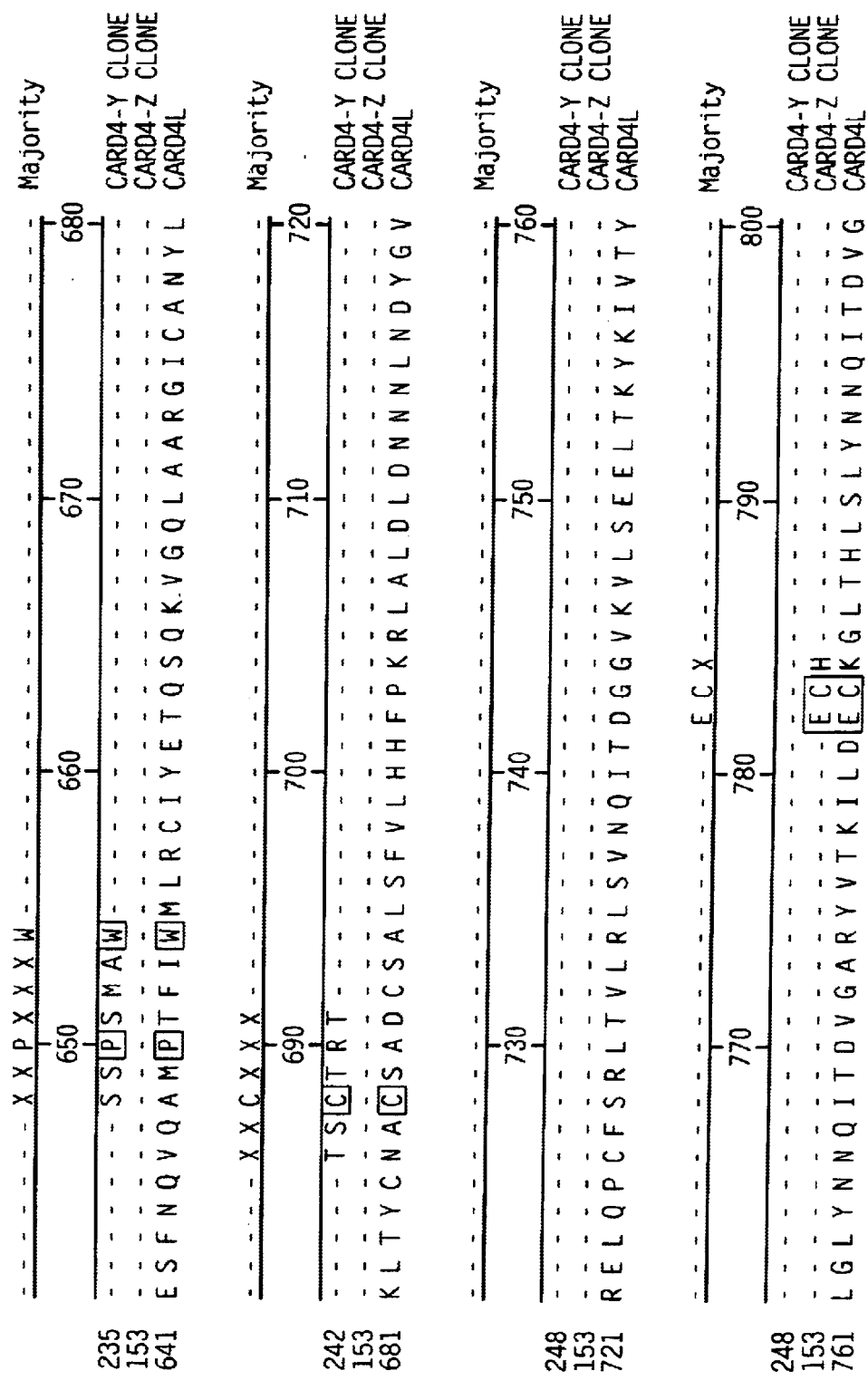
FIG. 14 depicts an alignment of human CARD-4L (SEQ ID NO:8), the predicted amino acid sequence of human CARD-4Y (SEQ ID NO:39), and the predicted amino acid sequence of human CARD-4Z (SEQ ID NO:41).

CARD-4 has at least two forms, a long form, CARD-4L, and a short form, CARD-4S, as well as two or more splice variants. A nucleotide sequence encoding a human CARD-4L protein is shown in FIG. 3 (SEQ ID NO:7; SEQ ID NO:9 includes the open reading frame only). A predicted amino acid sequence of CARD-4L protein is also shown in FIG. 4 (SEQ ID NO:8). A nucleotide sequence encoding a human CARD-4S protein is shown in FIG. 5 (SEQ ID NO:25; SEQ ID NO:27 includes the open reading frame only). A predicted amino acid sequence of CARD-4S protein is shown in FIG. 6 (SEQ ID NO:26). Two additional splice variants of human CARD-4 are provided in FIGS. 10 and 11 (human CARD-4Y) and FIGS. 12 and 13 (human CARD-4Z) (predicted amino acid sequences: SEQ ID NO:39 and SEQ ID NO:41 and nucleic acid sequences: SEQ ID NO:38 and SEQ ID NO:40). These two splice variants are predicted to contain 249 and 164 amino acids, respectively. An alignment of human CARD-4Y, human CARD-4Z and human CARD-4L is shown in FIG. 14.

In addition to the human CARD-4 proteins, a full length nucleotide sequence of the murine ortholog of human CARD-4L is provided in FIG. 15 (SEQ ID NO:42). An alignment of murine CARD-4L with human CARD-4L is shown in FIG. 17.

A nucleotide sequence encoding a murine CARD-5 protein is shown in FIG. 19 (SEQ ID NO:60; SEQ ID NO:62 includes the open reading frame only). A predicted amino acid sequence of murine CARD-5 protein is also shown in FIG. 19 (SEQ ID NO:61).

A nucleotide sequence encoding a human CARD-5 protein is shown in FIG. 21 (SEQ ID NO:48; SEQ ID NO:50 includes the open reading frame only). A predicted amino acid sequence of human CARD-5 protein is also shown in FIG. 21 (SEQ ID NO:49).

A nucleotide sequence encoding a rat CARD-6 protein is shown in FIG. 25 (SEQ ID NO:51; SEQ ID NO:53 includes the open reading frame only). A predicted amino acid sequence of rat CARD-6 protein is also shown in FIG. 25 (SEQ ID NO:52).

The human CARD-3 cDNA of FIG. 1 (SEQ ID NO:1), which is approximately 1931 nucleotides long including untranslated regions, encodes a protein having a molecular weight of approximately 61 kDa (excluding post-translational modifications).

A plasmid containing a cDNA encoding human CARD-3 (pXE17A) was deposited with the American Type Culture Collection (ATCC), Manasass, Va. on May 14, 1998, and assigned Accession Number 203037. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

The human CARD-4L cDNA of FIG. 3 (SEQ ID NO:7), which is approximately 3382 nucleotides long including untranslated regions, encodes a protein having a molecular weight of approximately 108 kDa (excluding post-translational modifications).

A plasmid containing a cDNA encoding human CARD-4L (pC4L1) was deposited with the American Type Culture Collection (ATCC), Manasass, Va. on Jul. 7, 1998, and assigned Accession Number 203035. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

The human CARD-4S cDNA of FIG. 5 (SEQ ID NO:25), which is 3082 nucleotides long including untranslated regions.

A plasmid containing a cDNA encoding human CARD-4S (pDB33E) was deposited with the American Type Culture Collection (ATCC), Manasass, Va. on May 14, 1998, and assigned Accession Number 203036. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

The human CARD-5 cDNA of FIG. 21 (SEQ ID NO:48), which is approximately 740 nucleotides long including untranslated regions, encodes a protein having a molecular weight of approximately 21.6 kD.

A plasmid containing a cDNA encoding human CARD-5 (EpHC5) was deposited with the American Type Culture Collection (ATCC), Manasass, Va. on Jun. 11, 1999, and assigned Accession Number PTA-2 13. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

The murine CARD-5 cDNA of FIG. 19 (SEQ ID NO:60), which is approximately 778 nucleotides long, including untranslated regions, encodes a protein having a molecular weight of approximately 21.5 kD.

A plasmid containing a cDNA encoding murine CARD-5 (EpMC5) was deposited with the American Type Culture Collection (ATCC), Manassas, Va. on Jun. 11, 1999, and assigned Accession Number PTA-212. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

The human CARD-6 cDNA of FIG. 28 (SEQ ID NO:54), which is approximately 4244 nucleotides long encodes a protein having a molecular weight of approximately 116.5 kD (excluding post-translational modifications).

A plasmid containing a cDNA encoding an amino terminal portion of human CARD-6 (EpHC6e), a plasmid encoding a carboxy terminal portion of human CARD-6 (EpHC6c), and a plasmid containing cDNA encoding human CARD-6 (EpHC6) were deposited with the American Type Culture Collection (ATCC), Manasass, Va. on Jun. 11, 1999, and assigned Accession Number PTA-213. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

The rat CARD-6 cDNA of FIG. 25 (SEQ ID NO:51), which is approximately 5252 nucleotides long including untranslated regions, encodes a protein having a molecular weight of approximately 100.7 kD.

A plasmid containing a cDNA encoding rat CARD-6 (EpMR5) was deposited with the American Type Culture Collection (ATCC), Manassas, Va. on Jun. 10, 1999, and assigned Accession Number PTA-211. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

A region of human CARD-4L protein (SEQ ID NO:8), the CARD domain (SEQ ID NO:10), bears some similarity to a CARD domain of CARD-3 (SEQ ID NO:6), ARC-CARD (SEQ ID NO:31), cIAP1-CARD (SEQ ID NO:32), and cIAP2-CARD (SEQ ID NO:33). This comparison is depicted in FIG. 7.

Figure 27:
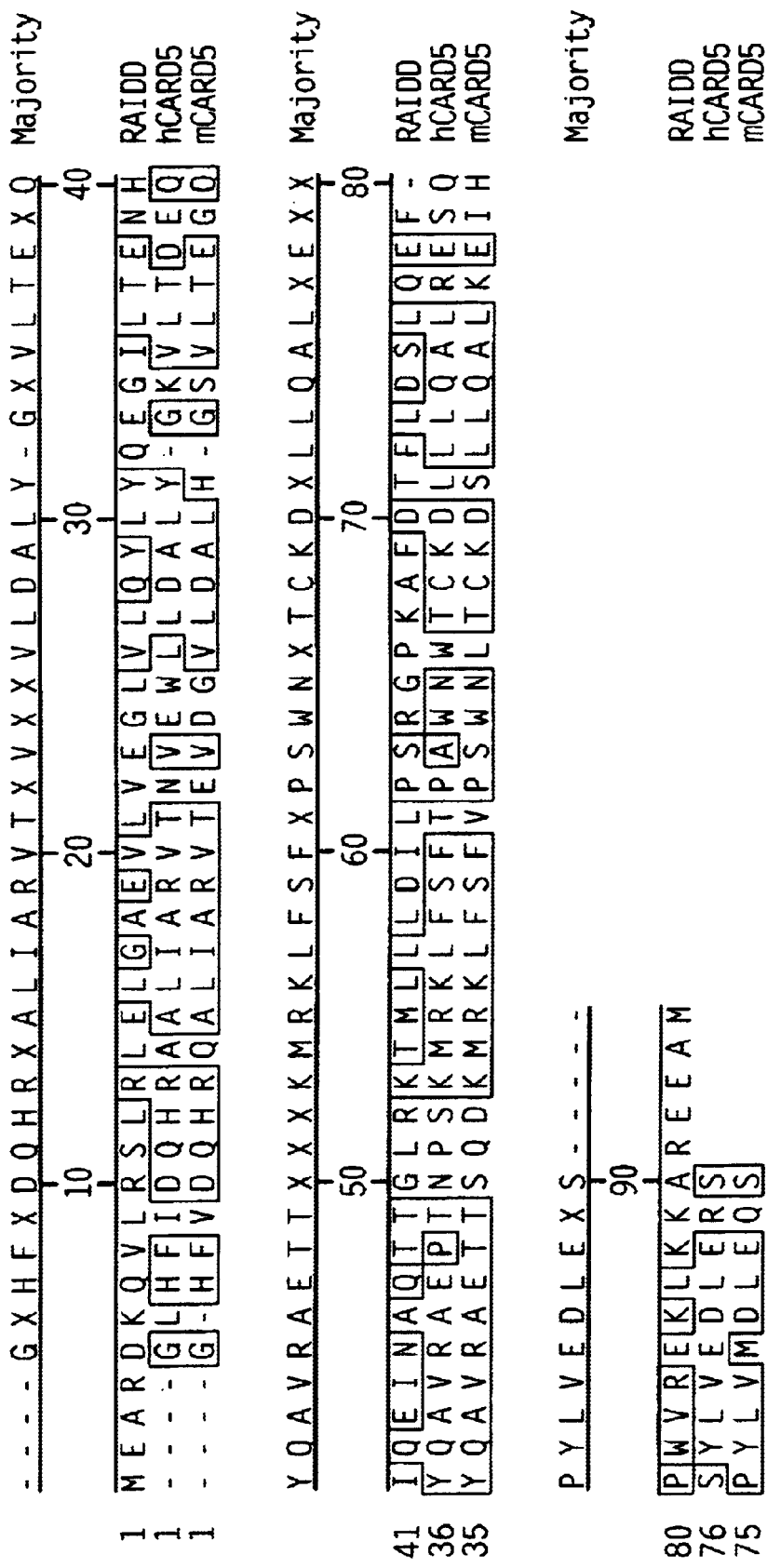
FIG. 27 depicts an alignment of the CARD domains of murine CARD-5 (SEQ ID NO:57), human CARD-5 (SEQ ID NO:58), and RAIDD (SEQ ID NO:70).

A region, the CARD domain (SEQ ID NO:58), of human CARD-5 protein (SEQ ID NO:48) and a region, the CARD domain (SEQ ID NO:57), of murine CARD-5 protein (SEQ ID NO:61) bear some similarity to the CARD of RAIDD (SEQ ID NO:70). This comparison is depicted in FIG. 27.

Each of CARD-3, CARD-4, CARD-5, and CARD-6 are members of a family of molecules (the "CARD-3 family", the "CARD-4 family", the "CARD-5 family", and the "CARD-6 family" respectively) having certain conserved structural and functional features. The term "family" when referring to the protein and nucleic acid molecules of the invention is intended to mean two or more proteins or nucleic acid molecules having a common structural domain and having sufficient amino acid or nucleotide sequence identity as defined herein. Such family members can be naturally occurring and can be from either the same or different species. For example, a family can contain a first protein of human origin and a homologue of that protein of murine origin, as well as a second, distinct protein of human origin and a murine homologue of that protein. Members of a family may also have common functional characteristics.

In one embodiment, a CARD-3, CARD-4, CARD-5, or CARD-6 protein includes a CARD domain having at least about 65%, preferably at least about 75%, and more preferably about 85%, 95%, or 98% amino acid sequence identity to the CARD domain of SEQ ID NO:6 or the CARD domain of SEQ ID NO:10 or the CARD domain of SEQ ID NO:28, the CARD domain of SEQ ID NO:57, the CARD domain of SEQ ID NO:58, the CARD domain of SEQ ID NO:59, or the CARD domain of SEQ ID NO:64.

Preferred CARD-3, CARD-4, CARD-5, or CARD-6 polypeptides of the present invention have an amino acid sequence sufficiently identical to the CARD domain amino acid sequence of SEQ ID NO:6, SEQ ID NO:10, SEQ ID NO:57, SEQ ID NO:58, SEQ ID NO:59, and SEQ ID NO:64, respectively.

The CARD-3 polypeptide also has an amino acid sequence sufficiently identical to the kinase domain sequence of SEQ ID NO:4, and an amino acid sequence that is sufficiently identical to the linker domain of SEQ ID NO:5. The CARD-4L polypeptide has an amino acid sequence sufficiently identical to the nucleotide binding domain of SEQ ID NO:11, an amino acid sequence sufficiently identical to the Walker Box "A" of SEQ ID NO:12 or Walker Box "B" of SEQ ID NO:13, an amino acid sequence sufficiently identical to the kinase 1a subdomain of SEQ ID NO:46, an amino acid sequence sufficiently identical to the kinase 2 subdomain of SEQ ID NO:47, or an amino acid sequence sufficiently identical to the kinase 3a subdomain of SEQ ID NO: 14, or an amino acid sequence sufficiently identical to the Leucine-rich repeats of SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, and SEQ ID NO:24.

As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences have a common structural domain and/or common functional activity. For example, amino acid or nucleotide sequences which contain a common structural domain having about 65% identity, preferably 75% identity, more preferably 85%, 95%, or 98% identity are defined herein as sufficiently identical.

As used interchangeably herein a "CARD-3, CARD-4, CARD-5, or CARD-6 activity", "biological activity of CARD-3, CARD-4, CARD-5, or CARD-6" or "functional activity of CARD-3, CARD-4, CARD-5, or CARD-6", refers to an activity exerted by a CARD-3, CARD-4, CARD-5, or CARD-6 protein, polypeptide or nucleic acid molecule on a CARD-3, CARD-4, CARD-5, or CARD-6 responsive cell as determined in vivo, or in vitro, according to standard techniques. A CARD-3, CARD-4, CARD-5, or CARD-6 activity can be a direct activity, such as an association with or an enzymatic activity on a second protein or an indirect activity, such as a cellular signaling activity mediated by interaction of the CARD-3, CARD-4, CARD-5, or CARD-6 protein with a second protein. In one embodiment, a CARD-3, CARD-4, CARD-5, or CARD-6 activity includes at least one or more of the following activities: (i) the ability to interact with proteins in an apoptotic signaling pathway (ii) the ability to interact with a CARD-3, CARD-4, CARD-5, or CARD-6 ligand; (iii) the ability to interact with an intracellular target protein; (iv) the ability to interact, directly or indirectly with one or more with caspases, e.g., caspase-1; (v) the ability to modulate the activity of a caspase, e.g., caspase-9; (vi) the ability to modulate the activity of NF-κB; (vii) the ability to modulate Apaf-1; (viii) the ability to be modulated by a Bcl-2 family member; (ix) the ability to be modulated by the p75 neurotrophin receptor; and (x) the ability to modulate the activity of a stress activated kinase (e.g., JNK/p38). For example, in Example 4, CARD-3-containing proteins were shown to associate with CARD-4-containing proteins. In example 9, CARD-4 proteins were shown to induce NF-κB-mediated transcription. In example 10, CARD-3 and CARD-4 were shown to enhance caspase-9 activity. In example 17, CARD-5 was shown to bind the CARD domains of caspase-1, CARD-7, and CARD-5. In example 18, CARD-5 was shown to induce NF-κB-mediated transcription.

CARD-5 may modulate caspase-l activation by binding to caspase-1. CARD-5 binding to caspase-1 may effect an oligomerizaton-based activation of the molecule. This caspase-1 activation can lead to the activation of inflammatory and/or apoptotic pathways. Alternatively, CARD-5 binding of caspase-1 may attenuate caspase-1 activation mediated by other activator adaptors such as RIP2.

CARD-3 may bind to the p75 neurotrophin receptor. CARD-3 may transduce the activity of the p75 neurotrophin receptor and thus modulate apoptosis of neuronal cells. Accordingly, CARD-3 nucleic acids and polypeptides as well as modulators of CARD-3 activity or expression can be used to modulate apoptosis of neurons (e.g., for treatment of neurological disorders, particularly neurodegenerative disorders).

Accordingly, another embodiment of the invention features isolated CARD-3, CARD-4, CARD-5, or CARD-6 proteins and polypeptides having a CARD-3, CARD-4, CARD-5, or CARD-6 activity.

Various aspects of the invention are described in further detail in the following subsections.

I. Isolated Nucleic Acid Molecules

One aspect of the invention pertains to isolated nucleic acid molecules that encode CARD-3, CARD-4, CARD-5, or CARD-6 proteins or biologically active portions thereof, as well as nucleic acid molecules sufficient for use as hybridization probes to identify CARD-3, CARD-4, CARD-5, or CARD-6-encoding nucleic acids (e.g., CARD-3, CARD-4, CARD-5, or CARD-6 mRNA) and fragments for use as PCR primers for the amplification or mutation of CARD-3, CARD-4, CARD-5, or CARD-6 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. Preferably, an "isolated" nucleic acid is free of sequences (preferably protein encoding sequences) which naturally flank the nucleic acid (i.e., sequences located at the 5' and 3' ends of the nucleic acid) in the genomic DNA of the organism from which the nucleic acid is derived. For example, in various embodiments, the isolated CARD-3, CARD-4, CARD-5, or CARD-6 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, SEQ ID NO:3, SEQ ID NO:7, SEQ ID NO:9, SEQ ID:25, SEQ ID NO:27, SEQ ID NO:38, SEQ ID NO:40, SEQ ID NO:42, SEQ ID NO:48, SEQ ID NO:50, SEQ ID NO:51, SEQ ID NO:53, SEQ ID NO:54, SEQ ID NO:56, SEQ ID NO:60, SEQ ID NO:62, the cDNA of ATCC 203037, the cDNA of ATCC 203035, the cDNA of ATCC 203036, the cDNA of ATCC PTA-211, the cDNA of ATCC PTA-212, or the cDNA of ATCC PTA-213, or a complement of any of these nucleotide sequences, can be isolated using standard molecular biology techniques and the sequence information provided herein. Using all or portion of the nucleic acid sequences of SEQ ID NO:1, SEQ ID NO:3, SEQ ID NO:7, SEQ ID NO:9, SEQ ID:25, SEQ ID NO:27, SEQ ID NO:38, SEQ ID NO:40, SEQ ID NO:42, SEQ ID NO:48, SEQ ID NO:50, SEQ ID NO:51, SEQ ID NO:53, SEQ ID NO:54, SEQ ID NO:56, SEQ ID NO:60, SEQ ID NO:62, the cDNA of ATCC 203037 the cDNA of ATCC 203035, the cDNA of ATCC 203036, the cDNA of ATCC PTA-211, the cDNA of ATCC PTA-212, or the cDNA of PTA-213, as a hybridization probe, CARD-3, CARD-4, CARD-5, or CARD-6 nucleic acid molecules can be isolated using standard hybridization and cloning techniques (e.g., as described in Sambrook et al., eds., Molecular Cloning: A Laboratory Manual. 2nd, ed., Cold Spring Harbor Laboratory, Cold Spring Harbor Laboratory Press, Cold Spring Harbor, N.Y., 1989).

A nucleic acid of the invention can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to CARD-3, CARD-4, CARD-5, or CARD-6 nucleotide sequences can be prepared by standard synthetic techniques, e.g., using an automated DNA synthesizer.

In another embodiment, an isolated nucleic acid molecule of the invention comprises a nucleic acid molecule which is a complement of the nucleotide sequence shown in SEQ ID NO:1, SEQ ID NO:3, SEQ ID NO:7, SEQ ID NO:9, SEQ ID:25, SEQ ID NO:27, SEQ ID NO:38, SEQ ID NO:40, SEQ ID NO:42, SEQ ID NO:48, SEQ ID NO:50, SEQ ID NO:51, SEQ ID NO:53, SEQ ID NO:54, SEQ ID NO:56, SEQ ID NO:60, SEQ ID NO:62, the cDNA of ATCC 203037, the cDNA of ATCC 203035, or the cDNA of ATCC 203036, or the cDNA of ATCC PTA-211, the cDNA of PTA-212, or the cDNA of PTA-213, or a portion thereof. A nucleic acid molecule which is complementary to a given nucleotide sequence is one which is sufficiently complementary to the given nucleotide sequence that it can hybridize to the given nucleotide sequence thereby forming a stable duplex.

Moreover, the nucleic acid molecule of the invention can comprise only a portion of a nucleic acid sequence encoding CARD-3, CARD-4, CARD-5, or CARD-6, for example, a fragment which can be used as a probe or primer or a fragment encoding a biologically active portion of CARD-3, CARD-4, CARD-5, or CARD-6. The nucleotide sequence determined from the cloning of the human CARD-3, CARD-4, CARD-5, or CARD-6, and the partial murine CARD-4 gene allows for the generation of probes and primers designed for use in identifying and/or cloning CARD-3, CARD-4, CARD-5, or CARD-6 homologues in other cell types, e.g., from other tissues, as well as CARD-3, CARD-4, CARD-5, or CARD-6 homologues and orthologs from other mammals. The probe/primer typically comprises substantially purified oligonucleotide. The oligonucleotide typically comprises a region of nucleotide sequence that hybridizes under stringent conditions to at least about 12, preferably about 25, more preferably about 50, 75, 100, 125, 150, 175, 200, 250, 300, 350 or 400 consecutive nucleotides of the sense or anti-sense sequence of SEQ ID NO:1, SEQ ID NO:3, SEQ ID NO:7, SEQ ID NO:9, SEQ ID:25, SEQ ID NO:27, SEQ ID NO:38, SEQ ID NO:40, SEQ ID NO:42, SEQ ID NO:48, SEQ ID NO:50, SEQ ID NO:51, SEQ ID NO:53, SEQ ID NO:54, SEQ ID NO:56, SEQ ID NO:60, SEQ ID NO:62, the cDNA of ATCC 203037, the cDNA of ATCC 203035, or the cDNA of ATCC 203036, or the cDNA of ATCC PTA-211, the cDNA of PTA-212, or the cDNA of PTA-213, or of a naturally occurring mutant of one of SEQ ID NO:1, SEQ ID NO:3, SEQ ID NO:7, SEQ ID NO:9, SEQ ID:25, SEQ ID NO:27, SEQ ID NO:38, SEQ ID NO:40, SEQ ID NO:42, SEQ ID NO:48, SEQ ID NO:50, SEQ ID NO:51, SEQ ID NO:53, SEQ ID NO:54, SEQ ID NO:56, SEQ ID NO:60, SEQ ID NO:62, the cDNA of ATCC 203037, the cDNA of ATCC 203035, the cDNA of ATCC 203036, or the cDNA of ATCC PTA-211, the cDNA of PTA-212, or the cDNA of PTA-213.

Probes based on the CARD-3, CARD-4, CARD-5, or CARD-6 nucleotide sequence can be used to detect transcripts or genomic sequences encoding the same or similar proteins. The probe comprises a label group attached thereto, e.g., a radioisotope, a fluorescent compound, an enzyme, or an enzyme co-factor. Such probes can be used as a part of a diagnostic test kit for identifying allelic variants and orthologs of the CARD-3, CARD-4, CARD-5, or CARD-6 proteins of the present invention, identifying cells or tissue which mis-express a CARD-3, CARD-4, CARD-5, or CARD-6 protein, such as by measuring a level of a CARD-3, CARD-4, CARD-5, or CARD-6-encoding nucleic acid in a sample of cells from a subject, e.g., detecting CARD-3, CARD-4, CARD-5, or CARD-6 mRNA levels or determining whether a genomic CARD-3, CARD-4, CARD-5, or CARD-6 gene has been mutated or deleted.

A nucleic acid fragment encoding a "biologically active portion" of CARD-3, CARD-4, CARD-5, or CARD-6 can be prepared by isolating a portion of SEQ ID NO:1, SEQ ID NO:3, SEQ ID NO:7, SEQ ID NO:9, SEQ ID:25, SEQ ID NO:27, SEQ ID NO:38, SEQ ID NO:40, SEQ ID NO:42, SEQ ID NO:48, SEQ ID NO:50, SEQ ID NO:51, SEQ ID NO:53, SEQ ID NO:54, SEQ ID NO:56, SEQ ID NO:60, SEQ ID NO:62, the cDNA of ATCC 203037, the cDNA of ATCC 203035, the cDNA of ATCC 203036, or the cDNA of ATCC PTA-211, the cDNA of PTA-212, or the cDNA of PTA-213, which encodes a polypeptide having a CARD-3, CARD-4, CARD-5, or CARD-6 biological activity, expressing the encoded portion of CARD-3, CARD-4, CARD-5, or CARD-6 protein (e.g., by recombinant expression in vitro) and assessing the activity of the encoded portion of CARD-3, CARD-4, CARD-5, or CARD-6. For example, a nucleic acid fragment encoding a biologically active portion of CARD-3, CARD-4, CARD-5, or CARD-6 includes a CARD domain, e.g., SEQ ID NO:6, SEQ ID NO:10, SEQ ID NO:28, SEQ ID NO:57, SEQ ID NO:58, SEQ ID NO:59, or SEQ ID NO:62.

The invention further encompasses nucleic acid molecules that differ from the nucleotide sequence of SEQ ID NO:1, SEQ ID NO:3, SEQ ID NO:7, SEQ ID NO:9, SEQ ID:25, SEQ ID NO:27, SEQ ID NO:38, SEQ ID NO:40, SEQ ID NO:42, SEQ ID NO:48, SEQ ID NO:50, SEQ ID NO:51, SEQ ID NO:53, SEQ ID NO:54, SEQ ID NO:56, SEQ ID NO:60, SEQ ID NO:62, the cDNA of ATCC 203037, the cDNA of ATCC 203035, the cDNA of ATCC 203036, or the cDNA of ATCC PTA-211, the cDNA of PTA-212, or the cDNA of PTA-213, due to degeneracy of the genetic code and thus encode the same CARD-3, CARD-4, CARD-5, or CARD-6 protein as that encoded by the nucleotide sequence shown in SEQ ID NO:1, SEQ ID NO:3, SEQ ID NO:7, SEQ ID NO:9, SEQ ID:25, SEQ ID NO:27, SEQ ID NO:38, SEQ ID NO:40, SEQ ID NO:42, SEQ ID NO:48, SEQ ID NO:50, SEQ ID NO:51, SEQ ID NO:53, SEQ ID NO:54, SEQ ID NO:56, SEQ ID NO:60, SEQ ID NO:62, the cDNA of ATCC 203037, the cDNA of ATCC 203035, the cDNA of ATCC 203036, or the cDNA of ATCC PTA-211, the cDNA of ATCC PTA-212, or the cDNA of ATCC PTA-213.

In addition to the CARD-3, CARD-4, CARD-5, or CARD-6 nucleotide sequence shown in SEQ ID NO:1, SEQ ID NO:3, SEQ ID NO:7, SEQ ID NO:9, SEQ ID:25, SEQ ID NO:27, SEQ ID NO:38, SEQ ID NO:40, SEQ ID NO:42, SEQ ID NO:48, SEQ ID NO:50, SEQ ID NO:51, SEQ ID NO:53, SEQ ID NO:54, SEQ ID NO:56, SEQ ID NO:60, SEQ ID NO:62, the cDNA of ATCC 203037, the cDNA of ATCC 203035, the cDNA of ATCC 203036, the cDNA of ATCC PTA-211, the cDNA of ATCC PTA-212, or the cDNA of ATCC PTA-213, it will be appreciated by those skilled in the art that DNA sequence polymorphisms that lead to changes in the amino acid sequences of CARD-3, CARD-4, CARD-5, or CARD-6 may exist within a population (e.g., the human population). Such genetic polymorphism in the CARD-3, CARD-4, CARD-5, or CARD-6 gene may exist among individuals within a population due to natural allelic variation. As used herein, the terms "gene" and "recombinant gene" refer to nucleic acid molecules comprising an open reading frame encoding a CARD-3, CARD-4, CARD-5, or CARD-6 protein, preferably a mammalian CARD-3, CARD-4, CARD-5, or CARD-6 protein. Such natural allelic variations can typically result in 1–5% variance in the nucleotide sequence of the CARD-3, CARD-4, CARD-5, or CARD-6 gene. Any and all such nucleotide variations and resulting amino acid polymorphisms in CARD-3, CARD-4, CARD-5, or CARD-6 that are the result of natural allelic variation and that do not alter the functional activity of CARD-3, CARD-4, CARD-5, or CARD-6 are intended to be within the scope of the invention. Thus, e.g., 1%, 2%, 3%, 4%, or 5% of the amino acids in CARD-3, CARD-4, CARD-5, or CARD-6 are replaced by another amino acid, preferably the amino acids are replaced by conservative substitutions.

Moreover, nucleic acid molecules encoding CARD-3, CARD-4, CARD-5, or CARD-6 proteins from other species (CARD)-3, CARD-4, CARD-5, or CARD-6 orthologs/homologues), which have a nucleotide sequence which differs from that of a CARD-3, CARD-4, CARD-5, or CARD-6 disclosed herein, are intended to be within the scope of the invention.

For example, Example 5 describes the murine CARD-4 ortholog and Example 14 describes the murine CARD-5 ortholog. Nucleic acid molecules corresponding to natural allelic variants and homologues of the CARD-3, CARD-4, CARD-5, or CARD-6 cDNA of the invention can be isolated based on their similarity to the nucleic acids disclosed herein using the human or murine cDNAs, or a portion thereof, as a hybridization probe according to standard hybridization techniques under stringent hybridization conditions.

In general, an allelic variant of a gene will be readily identifiable as mapping to the same chromosomal location as said gene. For example, in Example 6, the chromosomal location of the human CARD-4 gene is discovered to be chromosome 7 close to the SHGC-31928 genetic marker. Allelic variants of human CARD-4 will be readily identifiable as mapping to the human CARD-4 locus on chromosome 7 near genetic marker SHGC-31928.

Accordingly, in another embodiment, an isolated nucleic acid molecule of the invention is at least 300 (325, 350, 375, 400, 425, 450, 500, 550, 600, 650, 700, 800, 900, 1000, 1300, 1600 or 1931) nucleotides in length and hybridizes under stringent conditions to the nucleic acid molecule comprising the nucleotide sequence, preferably the coding sequence, of SEQ ID NO:1, SEQ ID NO:3, or the cDNA of ATCC 203037. In yet another embodiment, an isolated nucleic acid molecule of the invention is at least 300 (325, 350, 375, 400, 425, 450, 500, 550, 600, 650, 700, 800, 900, 1000, or 1300, 1640, 1900, 2200, 2500, 2800, 3100, or 3382) nucleotides in length and hybridizes under stringent conditions to the nucleic acid molecule comprising the nucleotide sequence, preferably the coding sequence, of SEQ ID NO:7, SEQ ID NO:9, SEQ ID NO:25, SEQ ID NO:27, SEQ ID NO:38, SEQ ID NO:40, the cDNA of ATCC 203035, or the cDNA of ATCC 203036. Accordingly, in another embodiment, an isolated nucleic acid molecule of the invention is at least 300 (325, 350, 375, 400, 425, 450, 500, 550, 600, 650, 700, 800, 900, 1000, or 1300, 1640, 1900, 2200, 2500, 2800, 3100, 3300, 3600, 3900, 4200 or 4209) nucleotides in length and hybridizes under stringent conditions to the nucleic acid molecule comprising the nucleotide sequence, preferably the coding sequence, of SEQ ID NO:42.

In yet another embodiment, an isolated nucleic acid molecule of the invention is at least 300 (350, 400, 450, 500, 550, 600, 650, 700, or 740) nucleotides in length and hybridizes under stringent conditions to a nucleic acid molecule consisting of the nucleotide sequence of SEQ ID NO:48 or SEQ ID NO:50.

In yet another embodiment, an isolated nucleic acid molecule of the invention is at least 300 (350, 400, 450, 500, 550, 600, 650, 700, or 761) nucleotides in length and hybridizes under stringent conditions to a nucleic acid molecule consisting of the nucleotide sequence of SEQ ID NO:60 or SEQ ID NO:62.

In yet another embodiment, an isolated nucleic acid molecule of the invention is at least 300 (350, 400, 450, 500, 550, 600, 650, 700, 1000, 1500, 2000, 2500, 3000, 3500, 4000, 4500, 5000, 5200, or 5252) nucleotides in length and hybridizes under stringent conditions to a nucleic acid molecule consisting of the nucleotide sequence of SEQ ID NO:51 or SEQ ID NO:53.

In yet another embodiment, an isolated nucleic acid molecule of the invention is at least 300 (350, 400, 450, 500, 550, 600, 650, 700, 1000, 1500, 2000, 2500, 3000, 3500, 4000, 4500, or 5000) nucleotides in length and hybridizes under stringent conditions to a nucleic acid molecule consisting of the nucleotide sequence of SEQ ID NO:54 or SEQ ID NO:56.

As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in Current Protocols in Molecular Biology, John Wiley & Sons, N.Y. (1989), 6.3.1–6.3.6. An, non-limiting example of stringent hybridization conditions are hybridization in 6× sodium chloride/sodium citrate (SSC) at about 45° C., followed by one or more washes in 0.2×SSC, 0.1% SDS at 50–65° C. (e.g., 50° C. or 60° C. or 65° C.). Preferably, the isolated nucleic acid molecule of the invention that hybridizes under stringent conditions corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the CARD-3, CARD-4, CARD-5, or CARD-6 sequence that may exist in the population, the skilled artisan will further appreciate that changes can be introduced by mutation into the nucleotide sequence of SEQ ID NO:1, SEQ ID NO:3, SEQ ID NO:7, SEQ ID NO:9, SEQ ID:25, SEQ ID NO:27, SEQ ID NO:38, SEQ ID NO:40, SEQ ID NO:42, SEQ ID NO:48, SEQ ID NO:50, SEQ ID NO:51, SEQ ID NO:53, SEQ ID NO:54, SEQ ID NO:56, SEQ ID NO:60, SEQ ID NO:62, the cDNA of ATCC 203037, the cDNA of ATCC 203035, the cDNA of ATCC 203036, the cDNA of ATCC PTA-211, the cDNA of ATCC PTA-212, or the cDNA of ATCC PTA-213, thereby leading to changes in the amino acid sequence of the encoded protein without altering the functional ability of the protein. For example, one can make nucleotide substitutions leading to amino acid substitutions at "non-essential" amino acid residues. A "non-essential" amino acid residue is a residue that can be altered from the wild-type sequence of CARD-3, CARD-4L/S, CARD-4 splice variant, murine CARD-4 protein, human CARD-5 protein, murine CARD-5 protein, or rat CARD-6 protein without altering the biological activity, whereas an "essential" amino acid residue is required for biological activity.

For example, amino acid residues that are conserved among the CARD-3, CARD-4L/S, CARD-4 splice variant, CARD-4, CARD-5, or CARD-6 proteins of various species are predicted to be particularly unamenable to alteration.

For example, preferred CARD-3, CARD-4, CARD-5, and CARD-6 proteins of the present invention, contain at least one CARD domain. Additionally, a CARD-3 protein also contains at least one kinase domain or at least one linker domain. A CARD domain contains at least one nucleotide binding domain or Leucine-rich repeats. Such conserved domains are less likely to be amenable to mutation. Other amino acid residues, however, (e.g., those that are not conserved or only semi-conserved among CARD-3, CARD-4, CARD-5, or CARD-6 of various species) may not be essential for activity and thus are likely to be amenable to alteration.

Accordingly, another aspect of the invention pertains to nucleic acid molecules encoding CARD-3, CARD-4, CARD-5, or CARD-6 proteins that contain changes in amino acid residues that are not essential for activity. Such CARD-3, CARD-4, CARD-5, or CARD-6 proteins differ in amino acid sequence from SEQ ID NO:2, SEQ ID NO:8, SEQ ID NO:25, SEQ ID NO:39, SEQ ID NO:41, SEQ ID NO:43, SEQ ID NO:49, SEQ ID NO:52, SEQ ID NO:55, or SEQ ID NO:61, and yet retain biological activity. In one embodiment, the isolated nucleic acid molecule includes a nucleotide sequence encoding a protein that includes an amino acid sequence that is at least about 45% identical, 65%, 75%, 85%, 95%, or 98% identical to the amino acid sequence of SEQ ID NO:2, SEQ ID NO:8, SEQ ID NO:26, SEQ ID NO:39, SEQ ID NO:41, SEQ ID NO:43, SEQ ID NO:49, SEQ ID NO:52, SEQ ID NO:55, or SEQ ID NO:61.

An isolated nucleic acid molecule encoding a CARD-3, CARD-4, CARD-5, or CARD-6 protein having a sequence which differs from that of SEQ ID NO:1, SEQ ID NO:3, SEQ ID NO:7, SEQ ID NO:9, SEQ ID:25, SEQ ID NO:27, SEQ ID NO:38, SEQ ID NO:40, SEQ ID NO:42, SEQ ID NO:48, SEQ ID NO:50, SEQ ID NO:51, SEQ ID NO:53, SEQ ID NO:54, SEQ ID NO:56, SEQ ID NO:60, SEQ ID NO:62, the cDNA of ATCC 203037, the cDNA of ATCC 203035, the cDNA of ATCC 203036, the cDNA of ATCC PTA-211, the cDNA of ATCC PTA-212, or the cDNA of ATCC PTA-213, can be created by introducing one or more nucleotide substitutions, additions or deletions into the nucleotide sequence of CARD-3 (SEQ ID NO:1, SEQ ID NO:3, the cDNA of ATCC 203037) or CARD-4L (SEQ ID NO:7, SEQ ID NO:9, the cDNA of ATCC 203035), or CARD-4S (SEQ ID NO:25, SEQ ID NO:27, the cDNA of ATCC 203036), or human CARD-4 splice variants (SEQ ID NO:38, SEQ ID NO:40, or murine CARD-4 (SEQ ID NO:42), or murine CARD-5 (SEQ ID NO:60, SEQ ID NO:62, the cDNA of PTA-211), or human CARD-5 (SEQ ID NO:48, SEQ ID NO:50, the cDNA of ATCC PTA-213), rat CARD-6 (SEQ ID NO:51, SEQ ID NO:53, the cDNA of ATCC PTA-211), or human CARD-6 (SEQ ID NO:54, SEQ ID NO:56, the cDNA of ATCC PTA-213) such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. Thus, for example, 1%, 2%, 3%, 5%, or 10% of the amino acids can be replaced by conservative substitution. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in CARD-3, CARD-4, CARD-5, or CARD-6 is preferably replaced with another amino acid residue from the same side chain family. Alternatively, mutations can be introduced randomly along all or part of a CARD-3, CARD-4, CARD-5, or CARD-6 coding sequence, such as by saturation mutagenesis, and the resultant mutants can be screened for CARD-3, CARD-4, CARD-5, or CARD-6 biological activity to identify mutants that retain activity. Following mutagenesis, the encoded protein can be expressed recombinantly and the activity of the protein can be determined.

In an embodiment, a mutant CARD-3, CARD-4, CARD-5, or CARD-6 protein can be assayed for: (1) the ability to form protein:protein interactions with proteins in the apoptotic signaling pathway; (2) the ability to bind a CARD-3, CARD-4, CARD-5, or CARD-6 ligand; or (3) the ability to bind to an intracellular target protein. For example, (1) in Example 7, a two-hybrid screening assay for the physical interaction of CARD-3 and CARD-4 is shown, (2) in Example 8, a two-hybrid system assay for the interaction between CARD-4 and its ligand hNUDC is described, (3) in Example 12, a coimmunoprecipitation assay for the interaction of CARD-3 with its ligand CARD-4 is shown, and (4) in Example 17, a two-hybrid screening assay for the physical interaction of CARD-5 and caspase-1, CARD-7, or CARD-5 is shown. In yet another embodiment, a mutant CARD-3, CARD-4, CARD-5, or CARD-6 protein can be assayed for the ability to modulate cellular proliferation, cellular differentiation, or cellular death. For example, in Example 10, assays for the regulation of cellular death (apoptosis) by CARD-3 or CARD-4 are described. In yet another embodiment, a mutant CARD-3 or CARD-4 protein can be assayed for regulation of a cellular signal transduction pathway. For example, in Examples 9 and 18, an assay for the regulation of the NF-κB pathway by CARD-4 and CARD-5 is described.

The present invention encompasses antisense nucleic acid molecules, i.e., molecules which are complementary to a sense nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire CARD-3, CARD-4, CARD-5, or CARD-6 coding strand, or to only a portion thereof, e.g., all or part of the protein coding region (or open reading frame). An antisense nucleic acid molecule can be antisense to a noncoding region of the coding strand of a nucleotide sequence encoding CARD-3, CARD-4, CARD-5, or CARD-6. The noncoding regions ("5' and 3' untranslated regions") are the 5' and 3' sequences which flank the coding region and are not translated into amino acids. Given the coding strand sequences encoding CARD-3, CARD-4, CARD-5, and CARD-6 disclosed herein, antisense nucleic acids of the invention can be designed according to the rules of Watson and Crick base pairing. The antisense nucleic acid molecule can be complementary to the entire coding region of CARD- 3, CARD-4, CARD-5, or CARD-6L/S mRNA, but more preferably is an oligonucleotide which is antisense to only a portion of the coding or noncoding region of CARD-3, CARD-4, CARD-5, or CARD-6 mRNA. For example, the antisense oligonucleotide can be complementary to the region surrounding the translation start site of CARD-3 mRNA, e.g., an oligonucleotide having the sequence CCCTGGTACTTGCCCCTCCGGTAG (SEQ ID NO:34) or CCTGGTACTTGCCCCTCC (SEQ ID NO:35) or of the CARD-4L mRNA, e.g., TCGTTAAGCCCTTGAAGA-CAGTG (SEQ ID NO:36) and TCGTTAGCCCTTGAA-GACCAGTGAGTGTAG (SEQ ID NO:37) or of the human CARD-5 mRNA, e.g., TAGGACCTCGGTAC-CCGCGCGCGCG (SEQ ID NO:68) or CGCCGGCCCC TAGGACCTCGGTACC (SEQ ID NO:69). An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-aino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a CARD-3, CARD-4, CARD-5, or CARD-6 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) Nucleic Acids. Res. 15:6625–6641). The antisense nucleic acid molecule can also comprise a 2'-o-methylribonucleotide (Inoue et al. (1987) Nucleic Acids Res. 15:6131–6148) or a chimeric RNA-DNA analogue (Inoue et al. (1987) FEBS Lett. 215:327–330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) Nature 334:585–591)) can be used to catalytically cleave CARD-3, CARD-4, CARD-5, or CARD-6 mRNA transcripts to thereby inhibit translation of CARD-3, CARD-4, CARD-5, or CARD-6 mRNA. A ribozyme having specificity for a CARD-3, CARD-4, CARD-5, or CARD-6-encoding nucleic acid can be designed based upon the nucleotide sequence of a CARD-3, CARD-4, CARD-5, or CARD-6 cDNA disclosed herein. For example, a derivative of a Tetrahymena L-19 IVS RNA can be constructed in which the nucleotide sequence of the active site is complementary to the nucleotide sequence to be cleaved in a CARD-3, CARD-4, CARD-5, or CARD-6-encoding mRNA. See, e.g., Cech et al. U.S. Pat. No. 4,987,071; and Cech et al. U.S. Pat. No. 5,116,742. Alternatively, CARD-3, CARD-4, CARD-5, or CARD-6 mRNA can be used to select a catalytic RNA having a specific ribonuclease activity from a pool of RNA molecules. See, e.g., Bartel and Szostal (1993) Science 261:1411–1418.

The invention also encompasses nucleic acid molecules which form triple helical structures. For example, CARD-3, CARD-4, CARD-5, or CARD-6 gene expression can be inhibited by targeting nucleotide sequences complementary to the regulatory region of the CARD-3, CARD-4, CARD-5, or CARD-6 (e.g., the CARD-3, CARD-4, CARD-5, or CARD-6 promoter and/or enhancers) to form triple helical structures that prevent transcription of the CARD-3, CARD-4, CARD-5, or CARD-6 gene in target cells. See generally, Helene (1991) Anticancer Drug Des. 6(6):569–84; Helene (1992) Ann. N.Y. Acad. Sci. 660:27–36; and Maher (1992) Bioassays 14(12):807–15.

In embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) Bioorganic & Medicinal Chemistry 4(1):5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) supra; Perry-O'Keefe et al. (1996) Proc. Natl. Acad. Sci. USA 93:14670–675.

PNAs of CARD-3, CARD-4, CARD-5, or CARD-6 can be used for therapeutic and diagnostic applications. For example, PNAs can be used as antisense or antigene agents for sequence-specific modulation of gene expression by, e.g., inducing transcription or translation arrest or inhibiting replication. PNAs of CARD-3, CARD-4, CARD-5, or CARD-6 can also be used, e.g., in the analysis of single base pair mutations in a gene by, e.g., PNA directed PCR clamping; as artificial restriction enzymes when used in combination with other enzymes, e.g., S1 nucleases (Hyrup (1996) supra; or as probes or primers for DNA sequence and hybridization (Hyrup (1996) supra; Perry-O'Keefe et al. (1996) Proc. Natl. Acad. Sci. USA 93:14670–675).

In another embodiment, PNAs of CARD-3, CARD-4, CARD-5, or CARD-6 can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of CARD-3, CARD-4, CARD-5, or CARD-6 can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) supra). The synthesis of PNA-DNA chimeras can be performed as described in Hyrup (1996) supra and Finn et al. (1996) Nucleic Acids Research 24(17):3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag et al. (1989) Nucleic Acid Res. 17:5973–88). PNA monomers are then coupled in a stepwise manner to produce a chimeric molecule with a 5' PNA segment and a 3' DNA segment (Finn et al. (1996) Nucleic Acids Research 24(17):3357–63). Alternatively, chimeric molecules can be synthesized with a 5' DNA segment and a 3' PNA segment (Peterser et al. (1975) Bioorganic Med. Chem. Lett. 5:1119–11124).

In other embodiments, the oligonucleotide may include other appended groups such as peptides (e.g., for targeting host cell receptors in vivo), or agents facilitating transport across the cell membrane (see, e.g., Letsinger et al. (1989) Proc. Natl. Acad. Sci. USA 86:6553–6556; Lemaitre et al. (1987) Proc. Natl. Acad. Sci. USA 84:648–652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) Bio/Techniques 6:958–976) or intercalating agents (see, e.g., Zon (1988) Pharm. Res. 5:539–549). To this end, the oligonucleotide may be conjugated to another molecule, e.g., a peptide, hybridization triggered cross-linking agent, transport agent, hybridization-triggered cleavage agent, etc.

II. Isolated CARD-3, CARD-4, CARD-5, and CARD-6 Proteins and Anti-CARD-3, CARD-4, CARD-5, and CARD-6 Antibodies.

One aspect of the invention pertains to isolated CARD-3, CARD-4, CARD-5, and CARD-6 proteins, and biologically active portions thereof, as well as polypeptide fragments suitable for use as immunogens to raise anti-CARD-3, CARD-4, CARD-5, or CARD-6 antibodies. In one embodiment, native CARD-3, CARD-4, CARD-5, or CARD-6 proteins can be isolated from cells or tissue sources by an appropriate purification scheme using standard protein purification techniques. In another embodiment, CARD-3, CARD-4, CARD-5, or CARD-6 proteins are produced by recombinant DNA techniques. Alternative to recombinant expression, a CARD-3, CARD-4, CARD-5, or CARD-6 protein or polypeptide can be synthesized chemically using standard peptide synthesis techniques.

An "isolated" or "purified" protein or biologically active portion thereof is substantially free of cellular material or other contaminating proteins from the cell or tissue source from which the CARD-3, CARD-4, CARD-5, or CARD-6 protein is derived, or substantially free from chemical precursors or other chemicals when chemically synthesized. The language "substantially free of cellular material" includes preparations of CARD-3, CARD-4, CARD-5, or CARD-6 protein in which the protein is separated from cellular components of the cells from which it is isolated or recombinantly produced. Thus, CARD-3, CARD-4, CARD-5, or CARD-6 protein that is substantially free of cellular material includes preparations of CARD-3, CARD-4, CARD-5, or CARD-6 protein having less than about 30%, 20%, 10%, or 5% (by dry weight) of non-CARD-3, CARD-4, CARD-5, or CARD-6 protein (also referred to herein as a "contaminating protein"). When the CARD-3, CARD-4, CARD-5, or CARD-6 protein or biologically active portion thereof is recombinantly produced, it is also preferably substantially free of culture medium, i.e., culture medium represents less than about 20%, 10%, or 5% of the volume of the protein preparation. When CARD-3, CARD-4, CARD-5, or CARD-6 protein is produced by chemical synthesis, it is preferably substantially free of chemical precursors or other chemicals, i.e., it is separated from chemical precursors or other chemicals which are involved in the synthesis of the protein. Accordingly such preparations of CARD-3, CARD-4, CARD-5, or CARD-6 protein have less than about 30%, 20%, 10%, 5% (by dry weight) of chemical precursors or non-CARD-3, CARD-4, CARD-5, or CARD-6 chemicals.

Biologically active portions of a CARD-3, CARD-4, CARD-5, or CARD-6 protein include peptides comprising amino acid sequences sufficiently identical to or derived from the amino acid sequence of the CARD-3, CARD-4, CARD-5, or CARD-6 protein (e.g., the amino acid sequence shown in SEQ ID NO:2, SEQ ID NO:8, SEQ ID NO:26, SEQ ID NO:39, SEQ ID NO:41, SEQ ID NO:43, SEQ ID NO:49, SEQ ID NO:52, SEQ ID NO:55, or SEQ ID NO:61), which include less amino acids than the full length CARD-3, CARD-4, CARD-5, or CARD-6 protein, and exhibit at least one activity of a CARD-3, CARD-4, CARD-5, or CARD-6 protein. Typically, biologically active portions comprise a domain or motif with at least one activity of the CARD-3, CARD-4, CARD-5, or CARD-6 protein. A biologically active portion of a CARD-3, CARD-4, CARD-5, or CARD-6 protein can be a polypeptide which is, for example, 10, 25, 50, 100 or more amino acids in length. Preferred biologically active polypeptides include one or more identified CARD-3, CARD-4, CARD-5, or CARD-6 structural domains, e.g., the CARD domain (SEQ ID NO:6, SEQ ID NO:10, SEQ ID NO:27, SEQ ID NO:66, SEQ ID NO:67, or SEQ ID NO:68).

Moreover, other biologically active portions, in which other regions of the protein are deleted, can be prepared by recombinant techniques and evaluated for one or more of the functional activities of a native CARD-3, CARD-4, CARD-5, or CARD-6 protein.

CARD-3, CARD-4, CARD-5, or CARD-6 protein has the amino acid sequence shown of SEQ ID NO:2, SEQ ID NO:8, SEQ ID NO:26, SEQ ID NO:39, SEQ ID NO:41, SEQ ID NO:43, SEQ ID NO:49, SEQ ID NO:52, SEQ ID NO:55, or SEQ ID NO:61. Other useful CARD-3, CARD-4, CARD-5, or CARD-6 proteins are substantially identical to SEQ ID NO:2, SEQ ID NO:8, SEQ ID NO:26, SEQ ID NO:39, SEQ ID NO:41, SEQ ID NO:43, SEQ ID NO:49, SEQ ID NO:52, or SEQ ID NO:55, or SEQ ID NO:61, and retain the functional activity of the protein of SEQ ID NO:2, SEQ ID NO:8, SEQ ID NO:26, SEQ ID NO:39, SEQ ID NO:41, SEQ ID NO:43, SEQ ID NO:49, SEQ ID NO:52, SEQ ID NO:55, or SEQ ID NO:61, yet differ in amino acid sequence due to natural allelic variation or mutagenesis. CARD-3 and CARD-4 are involved in activating caspases in the apoptotic pathway. For example, in Example 10, CARD-4 is shown to enhance caspase 9 activity. In example 17, CARD-5 is shown to bind to the CARD domain of caspase-1.

A useful CARD-3, CARD-4, CARD-5, or CARD-6 protein is a protein which includes an amino acid sequence at least about 45%, preferably 55%, 65%, 75%, 85%, 95%, or 99% identical to the amino acid sequence of SEQ ID NO:2, SEQ ID NO:8, SEQ ID NO:26, SEQ ID NO:39, SEQ ID NO:41, SEQ ID NO:43, SEQ ID NO:49, SEQ ID NO:52, SEQ ID NO:55, or SEQ ID NO:61, and retains the functional activity of the CARD-3, CARD-4, CARD-5, or CARD-6 proteins of SEQ ID NO:2, SEQ ID NO:8, SEQ ID NO:26, SEQ ID NO:39, SEQ ID NO:41, SEQ ID NO:43, SEQ ID NO:49, SEQ ID NO:52, SEQ ID NO:55, or SEQ ID NO:61.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions× 100).

The determination of percent homology between two sequences can be accomplished using a mathematical algorithm. A preferred, non-limiting example of a mathematical algorithm utilized for the comparison of two sequences is the algorithm of Karlin and Altschul (1990) Proc. Nat'l Acad. Sci. USA 87:2264–2268, modified as in Karlin and Altschul (1993) Proc. Nat'l Acad. Sci. USA 90:5873–5877. Such an algorithm is incorporated into the NBLAST and XBLAST programs of Altschul, et al. (1990) J. Mol. Biol. 215:403–410. BLAST nucleotide searches can be performed with the NBLAST program, score=100, wordlength=12 to obtain nucleotide sequences similar or homologous to CARD-3, CARD-4, CARD-5, or CARD-6 nucleic acid molecules of the invention. For example, Example 5 describes the use of the TBLASTN program to query a database of sequences of full length and partial cDNA sequences with the human CARD-4 polypeptide sequence leading to the discovery of murine CARD-4 and Example 4 describes the use of BLASTN to query a proprietary EST database with the 5' untranslated sequence of CARD-4 leading to the discovery of two human CARD-4 splice variants. BLAST protein searches can be performed with the XBLAST program, score=50, wordlength=3 to obtain amino acid sequences homologous to CARD-3, CARD-4, CARD-5, or CARD-6 protein molecules of the invention. To obtain gapped alignments for comparison purposes, Gapped BLAST can be utilized as described in Altschul et al. (1997) Nucleic Acids Res. 25:3389–3402. When utilizing BLAST and Gapped BLAST programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically exact matches are counted.

The invention also provides CARD-3, CARD-4, CARD-5, or CARD-6 chimeric or fusion proteins. As used herein, a CARD-3, CARD-4, CARD-5, or CARD-6 "chimeric protein" or "fusion protein" comprises a CARD-3, CARD-4, CARD-5, or CARD-6 polypeptide operatively linked to a non-CARD-3, CARD-4, CARD-5, or CARD-6 polypeptide. A "CARD-3, CARD-4, CARD-5, or CARD-6 polypeptide" refers to a polypeptide having an amino acid sequence corresponding to all or a portion (preferably a biologically active portion) of a CARD-3, CARD-4, CARD-5, or CARD-6, whereas a "non-CARD-3, CARD-4, CARD-5, or CARD-6 polypeptide" refers to a polypeptide having an amino acid sequence corresponding to a protein which is not substantially identical to the CARD-3, CARD-4, CARD-5, or CARD-6 protein, e.g., a protein which is different from the CARD-3, CARD-4, CARD-5, or CARD-6 proteins and which is derived from the same or a different organism. Within the fusion protein, the term "operatively linked" is intended to indicate that the CARD-3, CARD-4, CARD-5, or CARD-6 polypeptide and the non-CARD-3, CARD-4, CARD-5, or CARD-6 polypeptide are fused in-frame to each other. The heterologous polypeptide can be fused to the N-terminus or C-terminus of the CARD-3, CARD-4, CARD-5, or CARD-6 polypeptide.

One useful fusion protein is a GST fusion protein in which the CARD-3, CARD-4, CARD-5, or CARD-6 sequences are fused to the C-terminus of the GST sequences. Such fusion proteins can facilitate the purification of recombinant CARD-3, CARD-4, CARD-5, or CARD-6. In another embodiment, the fusion protein contains a signal sequence from another protein. In certain host cells (e.g., mammalian host cells), expression and/or secretion of CARD-3, CARD-4, CARD-5, or CARD-6 can be increased through use of a heterologous signal sequence. For example, the gp67 secretory sequence of the baculovirus envelope protein can be used as a heterologous signal sequence (Current Protocols in Molecular Biology, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Molecular cloning, Sambrook et al, second edition, Cold spring harbor laboratory press, 1989) and the protein A secretory signal (Pharmacia Biotech; Piscataway, N.J.).

In yet another embodiment, the fusion protein is a CARD-3, CARD-4, CARD-5, or CARD-6-immunoglobulin fusion protein in which all or part of CARD-3, CARD-4, CARD-5, or CARD-6 is fused to sequences derived from a member of the immunoglobulin protein family. The CARD-3, CARD-4, CARD-5, or CARD-6-immunoglobulin fusion proteins of the invention can be incorporated into pharmaceutical compositions and administered to a subject to inhibit an interaction between a CARD-3, CARD-4, CARD-5, or CARD-6 ligand and a CARD-3, CARD-4, CARD-5, or CARD-6 protein on the surface of a cell, to thereby suppress CARD-3, CARD-4, CARD-5, or CARD-6-mediated signal transduction in vivo. The CARD-3, CARD-4, CARD-5, or CARD-6-immunoglobulin fusion proteins can be used to affect the bioavailability of a CARD-3, CARD-4, CARD-5, or CARD-6 cognate ligand. Inhibition of the CARD-3 ligand/CARD-3, CARD-4 ligand/CARD-4, CARD-5 ligand/CARD-5, or CARD-6 ligand/CARD-6 interaction may be useful therapeutically for both the treatment of proliferative and differentiative disorders, as well as modulating (e.g., promoting or inhibiting) cell survival. Moreover, the CARD-3, CARD-4, CARD-5, or CARD-6-immunoglobulin fusion proteins of the invention can be used as immunogens to produce anti-CARD-3, CARD-4, CARD-5, or CARD-6 antibodies in a subject, to purify CARD-3, CARD-4, CARD-5, or CARD-6 ligands and in screening assays to identify molecules which inhibit the interaction of CARD-3, CARD-4, CARD-5, or CARD-6 with a CARD-3, CARD-4, CARD-5, or CARD-6 ligand.

Preferably, a CARD-3, CARD-4, CARD-5, or CARD-6 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., Current Protocols in Molecular Biology, Ausubel et al. eds., John Wiley & Sons: 1992). Moreover, many expression vectors are commercially available that already encode a fusion moiety (e.g., a GST polypeptide). A CARD-3, CARD-4, CARD-5, or CARD-6-encoding nucleic acid can be cloned into such an expression vector such that the fusion moiety is linked in-frame to the CARD-3, CARD-4, CARD-5, or CARD-6 protein.

The present invention also pertains to variants of the CARD-3, CARD-4, CARD-5, or CARD-6 proteins which function as either CARD-3, CARD-4, CARD-5, or CARD-6 agonists (mimetics) or as CARD-3, CARD-4, CARD-5, or CARD-6 antagonists. Variants of the CARD-3, CARD-4, CARD-5, or CARD-6 protein can be generated by mutagenesis, e.g., discrete point mutation or truncation of the CARD-3, CARD-4, CARD-5, or CARD-6 protein. An agonist of the CARD-3, CARD-4, CARD-5, or CARD-6 protein can retain substantially the same, or a subset, of the biological activities of the naturally occurring form of the CARD-3, CARD-4, CARD-5, or CARD-6 protein. An antagonist of the CARD-3, CARD-4, CARD-5, or CARD-6 protein can inhibit one or more of the activities of the naturally occurring form of the CARD-3, CARD-4, CARD-5, or CARD-6 protein by, for example, competitively binding to a downstream or upstream member of a cellular signaling cascade which includes the CARD-3, CARD-4, CARD-5, or CARD-6 protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the CARD-3, CARD-4, CARD-5, or CARD-6 proteins.

Variants of the CARD-3, CARD-4, CARD-5, or CARD-6 protein which function as either CARD-3, CARD-4, CARD-5, or CARD-6 agonists (mimetics) or as CARD-3, CARD-4, CARD-5, or CARD-6 antagonists can be identified by screening combinatorial libraries of mutants, e.g., truncation mutants of the CARD-3, CARD-4, CARD-5, or CARD-6 protein for CARD-3, CARD-4, CARD-5, or CARD-6 protein agonist or antagonist activity. In one embodiment, a variegated library of CARD-3, CARD-4, CARD-5, or CARD-6 variants is generated by combinatorial mutagenesis at the nucleic acid level and is encoded by a variegated gene library. A variegated library of CARD-3, CARD-4, CARD-5, or CARD-6 variants can be produced by, for example, enzymatically ligating a mixture of synthetic oligonucleotides into gene sequences such that a degenerate set of potential CARD-3, CARD-4, CARD-5, or CARD-6 sequences is expressible as individual polypeptides, or alternatively, as a set of larger fusion proteins (e.g., for phage display) containing the set of CARD-3, CARD-4, CARD-5, or CARD-6 sequences therein. There are a variety of methods which can be used to produce libraries of potential CARD-3, CARD-4, CARD-5, or CARD-6 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential CARD-3, CARD-4, CARD-5, or CARD-6 sequences. Methods for synthesizing degenerate oligonucleotides are known in the art (see, e.g., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477).

Useful fragments of CARD-3, CARD-4, CARD-5, and CARD-6, include fragments comprising or consisting of a domain or subdomain described herein, e.g., a kinase domain or a CARD domain.

In addition, libraries of fragments of the CARD-3, CARD-4, CARD-5, or CARD-6 protein coding sequence can be used to generate a variegated population of CARD-3, CARD-4, CARD-5, or CARD-6 fragments for screening and subsequent selection of variants of a CARD-3, CARD-4, CARD-5, or CARD-6 protein. In one embodiment, a library of coding sequence fragments can be generated by treating a double stranded PCR fragment of a CARD-3, CARD-4, CARD-5, or CARD-6 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the CARD-3, CARD-4, CARD-5, or CARD-6 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of CARD-3, CARD-4, CARD-5, or CARD-6 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify CARD-3, CARD-4, CARD-5, or CARD-6 variants (Arkin and Yourvan (1992) Proc. Natl. Acad. Sci. USA 89:7811–7815; Delgrave et al. (1993) Protein Engineering 6(3):327–331).

An isolated CARD-3, CARD-4, CARD-5, or CARD-6 protein, or a portion or fragment thereof, can be used as an immunogen to generate antibodies that bind CARD-3, CARD-4, CARD-5, or CARD-6 using standard techniques for polyclonal and monoclonal antibody preparation. The full-length CARD-3, CARD-4, CARD-5, or CARD-6 protein can be used or, alternatively, the invention provides antigenic peptide fragments of CARD-3, CARD-4, CARD-5, or CARD-6 for use as immunogens. The antigenic peptide of CARD-3, CARD-4, CARD-5, or CARD-6 comprises at least 8 (preferably 10, 15, 20, or 30) amino acid residues of the amino acid sequence shown in SEQ ID NO:2, SEQ ID NO:8, SEQ ID NO:26, SEQ ID NO:39, SEQ ID NO:41, SEQ ID NO:43, SEQ ID NO:49, SEQ ID NO:52, SEQ ID NO:55, or SEQ ID NO:61 or polypeptides including amino acids 128–139 or 287–298 of human CARD-4L and encompasses an epitope of CARD-3, CARD-4, CARD-5, or CARD-6 such that an antibody raised against the peptide forms a specific immune complex with CARD-3, CARD-4, CARD-5, or CARD-6.

Useful antibodies include antibodies which bind to a domain or subdomain of CARD-3, CARD-4, CARD-5, or CARD-6 described herein (e.g., a kinase domain, a CARD domain, or a leucine-rich domain).

Figure 8:
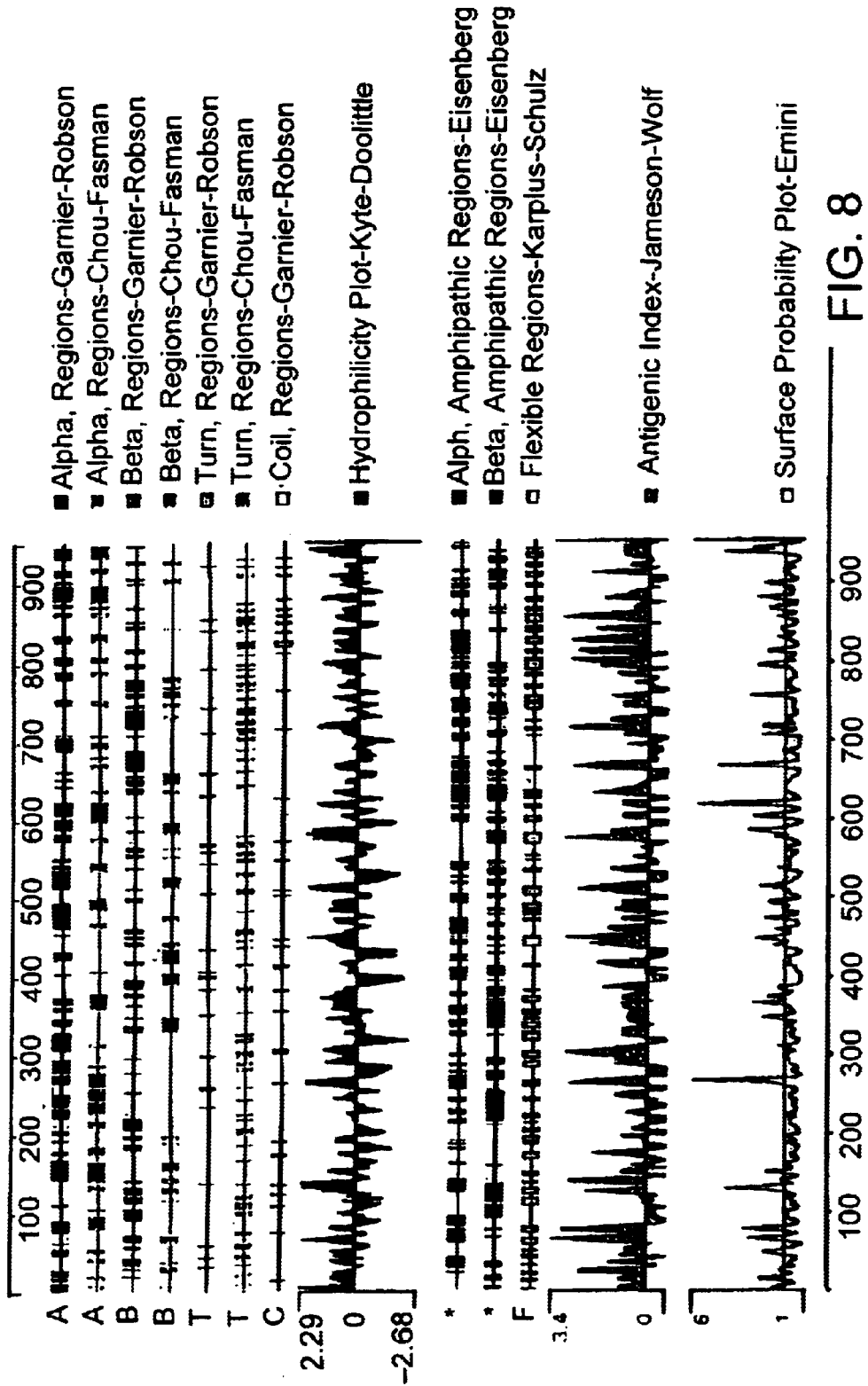
FIG. 8 is a plot showing predicted structural features of human CARD-4L.
Figure 9:
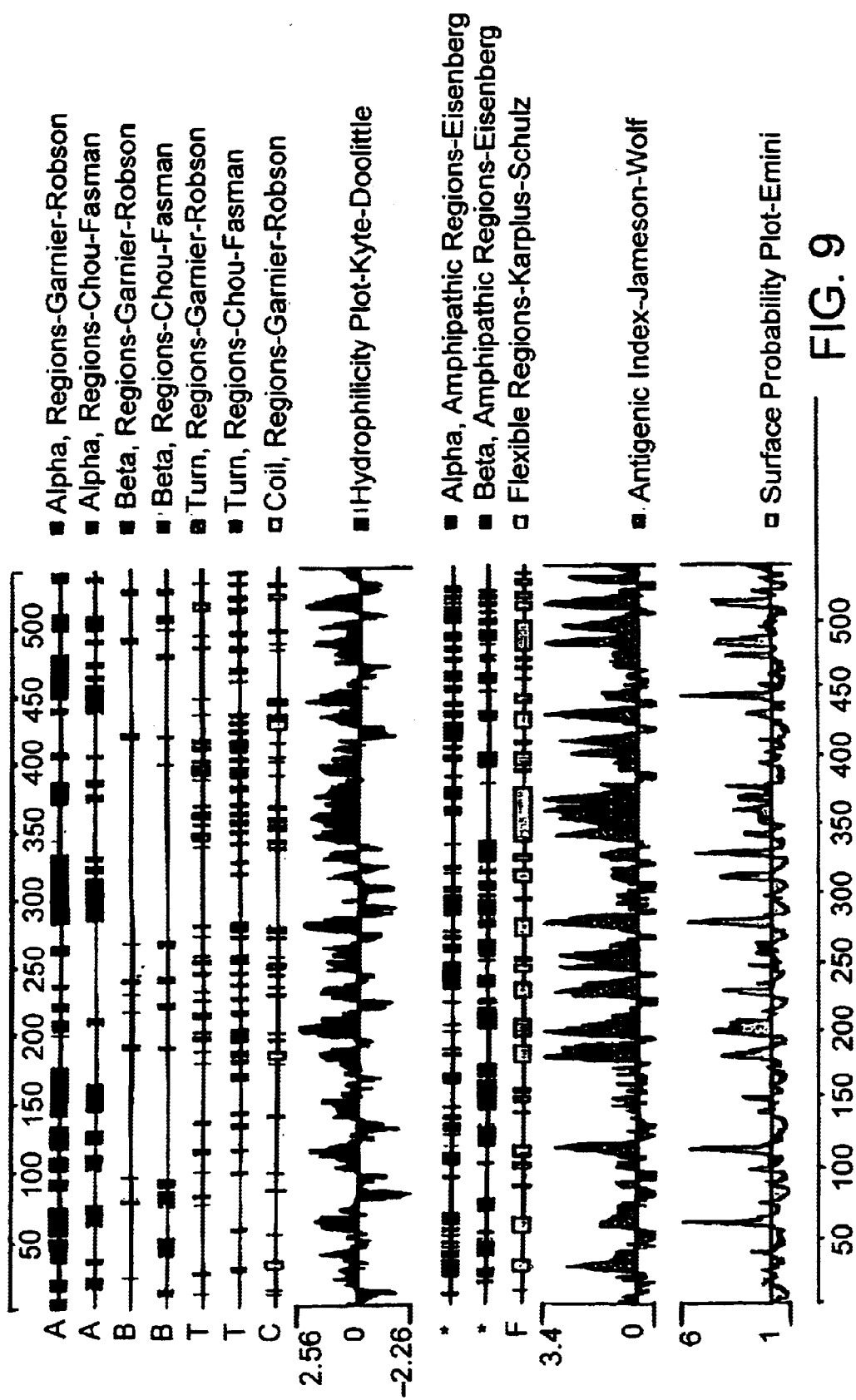
FIG. 9 is a plot showing predicted structural features of human CARD-4S.

Preferred epitopes encompassed by the antigenic peptide are regions of CARD-3, CARD-4, CARD-5, or CARD-6 that are located on the surface of the protein, e.g., hydrophilic regions. Other important criteria include a preference for a terminal sequence, high antigenic index (e.g., as predicted by Jameson-Wolf algorithm), ease of peptide synthesis (e,g., avoidance of prolines); and high surface probability (e.g., as predicted by the Emini algorithm; FIG. 8 and FIG. 9).

A CARD-3, CARD-4, CARD-5, or CARD-6 immunogen typically is used to prepare antibodies by immunizing a suitable subject, (e.g., rabbit, goat, mouse or other mammal) with the immunogen. An appropriate immunogenic preparation can contain, for example, recombinantly expressed CARD-3, CARD-4, CARD-5, or CARD-6 protein or a chemically synthesized CARD-3, CARD-4, CARD-5, or CARD-6 polypeptide. The preparation can further include an adjuvant, such as Freund's complete or incomplete adjuvant, or similar immunostimulatory agent. Immunization of a suitable subject with an immunogenic CARD-3, CARD-4, CARD-5, or CARD-6 preparation induces a polyclonal anti-CARD-3, CARD-4, CARD-5, or CARD-6 antibody response. For example, polypeptides including amino acids 128-139 or 287-298 of human CARD-4L were conjugated to KLH and the resulting conjugates were used to immunize rabbits and polyclonal antibodies that specifically recognize the two immunogen peptides were generated.

Accordingly, another aspect of the invention pertains to anti-CARD-3, CARD-4, CARD-5, or CARD-6 antibodies. The term "antibody" as used herein refers to immunoglobulin molecules and immunologically active portions of immunoglobulin molecules, i.e., molecules that contain an antigen binding site which specifically binds an antigen, such as CARD-3, CARD-4, CARD-5, or CARD-6. A molecule which specifically binds to CARD-3, CARD-4, CARD-5, or CARD-6 is a molecule which binds CARD-3, CARD-4, CARD-5, or CARD-6, but does not substantially bind other molecules in a sample, e.g., a biological sample, which naturally contains CARD-3, CARD-4, CARD-5, or CARD-6. Examples of immunologically active portions of immunoglobulin molecules include F(ab) and F(ab')2 fragments which can be generated by treating the antibody with an enzyme such as pepsin. The invention provides polyclonal and monoclonal antibodies that bind CARD-3, CARD-4, CARD-5, or CARD-6. The term "monoclonal antibody" or "monoclonal antibody composition", as used herein, refers to a population of antibody molecules that contain only one species of an antigen binding site capable of immunoreacting with a particular epitope of CARD-3, CARD-4, CARD-5, or CARD-6. A monoclonal antibody composition thus typically displays a single binding affinity for a particular CARD-3, CARD-4, CARD-5, or CARD-6 protein with which it immunoreacts.

Polyclonal anti-CARD-3, CARD-4, CARD-5, or CARD-6 antibodies can be prepared as described above by immunizing a suitable subject with a CARD-3, CARD-4, CARD-5, or CARD-6 immunogen. The anti-CARD-3, CARD-4, CARD-5, or CARD-6 antibody titer in the immunized subject can be monitored over time by standard techniques, such as with an enzyme linked immunosorbent assay (ELISA) using immobilized CARD-3, CARD-4, CARD-5, or CARD-6. If desired, the antibody molecules directed against CARD-3, CARD-4, CARD-5, or CARD-6 can be isolated from the mammal (e.g., from the blood) and further purified by well-known techniques, such as protein A chromatography to obtain the IgG fraction. At an appropriate time after immunization, e.g., when the anti-CARD-3, CARD-4, CARD-5, or CARD-6 antibody titers are highest, antibody-producing cells can be obtained from the subject and used to prepare monoclonal antibodies by standard techniques, such as the hybridoma technique originally described by Kohler and Milstein (1975) Nature 256:495–497, the human B cell hybridoma technique (Kozbor et al. (1983) Immunol Today 4:72), the EBV-hybridoma technique (Cole et al. (1985), Monoclonal Antibodies and Cancer Therapy, Alan R. Liss, Inc., pp. 77–96) or trioma techniques. The technology for producing various antibodies monoclonal antibody hybridomas is well known (see generally Current Protocols in Immunology (1994)

Coligan et al. (eds.) John Wiley & Sons, Inc., New York, N.Y.). Briefly, an immortal cell line (typically a myeloma) is fused to lymphocytes (typically splenocytes) from a mammal immunized with a CARD-3, CARD-4, CARD-5, or CARD-6 immunogen as described above, and the culture supernatants of the resulting hybridoma cells are screened to identify a hybridoma producing a monoclonal antibody that binds CARD-3, CARD-4, CARD-5, or CARD-6.

Any of the many well known protocols used for fusing lymphocytes and immortalized cell lines can be applied for the purpose of generating an anti-CARD-3, CARD-4, CARD-5, or CARD-6 monoclonal antibody (see, e.g., Current Protocols in Immunology, supra; Galfre et al. (1977) Nature 266:55052; R. H. Kenneth, in Monoclonal Antibodies: A New Dimension In Biological Analyses, Plenum Publishing Corp., New York, N.Y. (1980); and Lerner (1981) Yale J. Biol. Med., 54:387–402). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line, e.g., a myeloma cell line that is sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind CARD-3, CARD-4, CARD-5, or CARD-6, e.g., using a standard ELISA assay.

Alternative to preparing monoclonal antibody-secreting hybridomas, a monoclonal anti-CARD-3, CARD-4, CARD-5, or CARD-6 antibody can be identified and isolated by screening a recombinant combinatorial immunoglobulin library (e.g., an antibody phage display library) with CARD-3, CARD-4, CARD-5, or CARD-6 to thereby isolate immunoglobulin library members that bind CARD-3, CARD-4, CARD-5, or CARD-6. Kits for generating and screening phage display libraries are commercially available (e.g., the Pharmacia Recombinant Phage Antibody System, Catalog No. 27-9400-01; and the Stratagene SurfZAP Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) Bio/Technology 9:1370–1372; Hay et al. (1992) Hum. Antibod. Hybridomas 3:81–85; Huse et al. (1989) Science 246:1275–1281; Griffiths et al. (1993) EMBO J. 12:725–734.

Additionally, recombinant anti-CARD-3, CARD-4, CARD-5, or CARD-6 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) Science 240:1041–1043; Liu et al. (1987) Proc. Natl. Acad. Sci. USA 84:3439–3443; Liu et al. (1987) J. Immunol. 139:3521–3526; Sun et al. (1987) Proc. Natl. Acad. Sci. USA 84:214–218; Nishimura et al. (1987) Canc. Res. 47:999–1005; Wood et al. (1985) Nature 314:446–449; and Shaw et al. (1988) J. Natl. Cancer Inst. 80:1553–1559); Morrison, (1985) Science 229:1202–1207; Oi et al. (1986) Bio/Techniques 4:214; U.S. Pat. No. 5,225,539; Jones et al. (1986) Nature 321:552–525; Verhoeyan et al. (1988) Science 239:1534; and Beidler et al. (1988) J. Immunol. 141:4053–4060.

An anti-CARD-3, CARD-4, CARD-5, or CARD-6 antibody (e.g., monoclonal antibody) can be used to isolate CARD-3, CARD-4, CARD-5, or CARD-6 by standard techniques, such as affinity chromatography or immunoprecipitation. An anti-CARD-3, CARD-4, CARD-5, or CARD-6 antibody can facilitate the purification of natural CARD-3, CARD-4, CARD-5, or CARD-6 from cells and of recombinantly produced CARD-3, CARD-4, CARD-5, or CARD-6 expressed in host cells. Moreover, an anti-CARD-3, CARD-4, CARD-5, or CARD-6 antibody can be used to detect CARD-3, CARD-4, CARD-5, or CARD-6 protein (e.g., in a cellular lysate or cell supernatant) in order to evaluate the abundance and pattern of expression of the CARD-3, CARD-4, CARD-5, or CARD-6 protein. Anti-CARD-3, CARD-4, CARD-5, or CARD-6 antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^3H$.

III. Recombinant Expression Vectors and Host Cells

Another aspect of the invention pertains to vectors, preferably expression vectors, containing a nucleic acid encoding CARD-3, CARD-4, CARD-5, or CARD-6 (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operatively linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., CARD-3, CARD-4, CARD-5, or CARD-6 proteins, mutant forms of CARD-3, CARD-4, CARD-5, or CARD-6, fusion proteins, etc.).

The recombinant expression vectors of the invention can be designed for expression of CARD-3, CARD-4, CARD-5, or CARD-6 in prokaryotic or eukaryotic cells, e.g., bacterial cells such as *E. coli*, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) Gene 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., (1988) Gene 69:301–315) and pET 11d (Studier et al., Gene Expression Technology: Methods in Enzymology 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gn1 gene under the transcriptional control of the lacUV5 promoter.

One strategy to maximize recombinant protein expression in *E. coli* is to express the protein in a host bacteria with an impaired capacity to proteolytically cleave the recombinant protein (Gottesman, Gene Expression Technology: Methods in Enzymology 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. (1992) Nucleic Acids Res. 20:2111–2118). Such alteration of nucleic acid sequences of the invention can be carried out by standard DNA synthesis techniques.

In another embodiment, the CARD-3, CARD-4, CARD-5, or CARD-6 expression vector is a yeast expression vector. Examples of vectors for expression in yeast *S. cerivisae* include pYepSec1 (Baldari et al. (1987) EMBO J. 6:229–234), pMFa (Kurjan and Herskowitz, (1982) Cell 30:933–943), pJRY88 (Schultz et al. (1987) Gene 54:113–123), pYES2 (Invitrogen Corporation, San Diego, Calif.), pGBT9 (Clontech, Palo Alto, Calif.), pGAD10 (Clontech, Palo Alto, Calif.), pYADE4 and pYGAE2 and pYPGE2 (Brunelli and Pall, (1993) Yeast 9:1299–1308), pYPGE15 (Brunelli and Pall, (1993) Yeast 9:1309–1318), pACTII (Dr. S. E. Elledge, Baylor College of Medicine), and picZ (In Vitrogen Corp, San Diego, Calif.). For example, in Example 7 the expression of a fusion protein comprising amino acids 1–145 of human CARD-4L fused to the DNA-binding domain of *S. cerevisiae* transcription factor GAL4 from the yeast expression vector pGBT9 is described. In another example, Example 8 describes the expression of a fusion protein comprising amino acids 406–953 of human CARD-4L fused to the DNA-binding domain of *S. cerevisiae* transcription factor GAL4 from the yeast expression vector pGBT9. In yet another example, Example 7 describes the expression of a fusion protein comprising CARD-3 fused to the transcriptional activation domain of *S. cerevisiae* transcription factor GAL4 from the yeast expression vector pACTII.

Alternatively, CARD-3, CARD-4, CARD-5, or CARD-6 can be expressed in insect cells using baculovirus expression vectors. Baculovirus vectors available for expression of proteins in cultured insect cells (e.g., Sf 9 cells) include the pAc series (Smith et al. (1983) Mol. Cell Biol. 3:2156–2165) and the pVL series (Lucklow and Summers (1989) Virology 170:31–39).

In yet another embodiment, a nucleic acid of the invention is expressed in mammalian cells using a mammalian expression vector. Examples of mammalian expression vectors include pCDM8 (Seed (1987) Nature 329:840), pCI (Promega), and pMT2PC (Kaufman et al. (1987) EMBO J. 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al. (supra). For example, Example 9, Example 10, and Example 12 describe the expression of human CARD-4 or fragments thereof, CARD-3, or both from the mammalian expression vector pCI.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268–277), lymphoid-specific promoters (Calame and Eaton (1988) Adv. Immunol. 43:235–275), in particular promoters of T cell receptors (Winoto and Baltimore (1989) EMBO J. 8:729–733) and immunoglobulins (Banerji et al. (1983) Cell 33:729–740; Queen and Baltimore (1983) Cell 33:741–748), neuron-specific promoters (e.g., the neurofilament promoter; Byrne and Ruddle (1989) Proc. Natl. Acad. Sci. USA 86:5473–5477), pancreas-specific promoters (Edlund et al. (1985) Science 230:912–916), and mammary gland-specific promoters (e.g., milk whey promoter; U.S. Pat. No. 4,873, 316 and European Application Publication No. 264,166). Developmentally-regulated promoters are also encompassed, for example the murine hox promoters (Kessel and Gruss (1990) Science 249:374–379) and the α-fetoprotein promoter (Campes and Tilghman (1989) Genes Dev. 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to CARD-3, CARD-4, CARD-5, or CARD-6 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (Reviews—Trends in Genetics, Vol. 1(1) 1986).

Another aspect of the invention pertains to host cells into which a recombinant expression vector of the invention or isolated nucleic acid molecule of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, CARD-3, CARD-4, CARD-5, or CARD-6 protein can be expressed in bacterial cells such as *E. coli,* insect cells, yeast or mammalian cells (such as Chinese hamster ovary cells (CHO) or COS cells). Other suitable host cells are known to those skilled in the art. For example, in Example 7 a *Saccharomyces cerevisiae* host cell for recombinant CARD-4 and CARD-3 expression is described, and in Examples 9, 10, 12, 17, and 18, a 293T host cell for expression of CARD-4 or CARD-5 or fragments thereof or CARD-3 are described.

Vector DNA or an isolated nucleic acid molecule of the invention can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In some cases vector DNA is retained by the host cell. In other cases the host cell does not retain vector DNA and retains only an isolated nucleic acid molecule of the invention carried by the vector. In some cases, and isolated nucleic acid molecule of the invention is used to transform a cell without the use of a vector.

In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding CARD-3, CARD-4, CARD-5, or CARD-6 or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a CARD-3, CARD-4, CARD-5, or CARD-6 protein. Accordingly, the invention further provides methods for producing CARD-3, CARD-4, CARD-5, or CARD-6 protein using the host cells of the invention. In one embodiment, the method comprises culturing the host cell of the invention (into which a recombinant expression vector or isolated nucleic acid molecule encoding CARD-3, CARD-4, CARD-5, or CARD-6 has been introduced) in a suitable medium such that CARD-3, CARD-4, CARD-5, or CARD-6 protein is produced. In another embodiment, the method further comprises isolating CARD-3, CARD-4, CARD-5, or CARD-6 from the medium or the host cell.

The host cells of the invention can also be used to produce nonhuman transgenic animals. For example, in one embodiment, a host cell of the invention is a fertilized oocyte or an embryonic stem cell into which CARD-3, CARD-4, CARD-5, or CARD-6-coding sequences have been introduced. Such host cells can then be used to create non-human transgenic animals in which exogenous CARD-3, CARD-4, CARD-5, or CARD-6 sequences have been introduced into their genome or homologous recombinant animals in which endogenous CARD-3, CARD-4, CARD-5, or CARD-6 sequences have been altered. Such animals are useful for studying the function and/or activity of CARD-3, CARD-4, CARD-5, or CARD-6 and for identifying and/or evaluating modulators of CARD-3, CARD-4, CARD-5, or CARD-6 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous CARD-3, CARD-4, CARD-5, or CARD-6 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing CARD-3, CARD-4, CARD-5, or CARD-6-encoding nucleic acid into the male pronuclei of a fertilized oocyte, e.g., by microinjection, retroviral infection, and allowing the oocyte to develop in a pseudopregnant female foster animal. The CARD-3, CARD-4, CARD-5, or CARD-6 cDNA sequence, e.g., that of SEQ ID NO:1, SEQ ID NO:3, SEQ ID NO:7, SEQ ID NO:9, SEQ ID:25, SEQ ID NO:27, SEQ ID NO:38, SEQ ID NO:40, SEQ ID NO:42, SEQ ID NO:48, SEQ ID NO:50, SEQ ID NO:51, SEQ ID NO:53, SEQ ID NO:54, SEQ ID NO:56, SEQ ID NO:60, SEQ ID NO:62, or the cDNA of ATCC 203037, or the cDNA of ATCC 203035, or the cDNA of ATCC 203036, or the cDNA of ATCC PTA-211, the cDNA of ATCC PTA-212, or the cDNA of ATCC PTA-213) can be introduced as a transgene into the genome of a non-human animal. Alternatively, a nonhuman homolog or ortholog of the human CARD-3, CARD-4, CARD-5, or CARD-6 gene, such as a mouse CARD-3, CARD-4, CARD-5, or CARD-6 gene, can be isolated based on hybridization to the human CARD-3, CARD-4, CARD-5, or CARD-6 cDNA and used as a transgene. For example, the mouse ortholog of CARD-4, FIG. 15 and SEQ ID NO:42 can be used to make a transgenic animal using standard methods. Intronic sequences and polyadenylation signals can also be included in the transgene to increase the efficiency of expression of the transgene. A tissue-specific regulatory sequence(s) can be operably linked to the CARD-3, CARD-4, CARD-5, or CARD-6 transgene to direct expression of CARD-3, CARD-4, CARD-5, or CARD-6 protein to particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of the CARD-3, CARD-4, CARD-5, or CARD-6 transgene in its genome and/or expression of CARD-3, CARD-4, CARD-5, or CARD-6 mRNA in tissues or cells of the animals. A transgenic founder animal can then be used to breed additional animals carrying the transgene. Moreover, transgenic animals carrying a transgene encoding CARD-3, CARD-4, CARD-5, or CARD-6 can further be bred to other transgenic animals carrying other transgenes.

To create an homologous recombinant animal, a vector is prepared which contains at least a portion of a CARD-3, CARD-4, CARD-5, or CARD-6 gene (e.g., a human or a non-human homolog of the CARD-3, CARD-4, CARD-5, or CARD-6 gene, e.g., a murine CARD-3, CARD-4, CARD-5, or CARD-6 gene) into which a deletion, addition or substitution has been introduced to thereby alter, e.g., functionally disrupt, the CARD-3, CARD-4, CARD-5, or CARD-6 gene. In an embodiment, the vector is designed such that, upon homologous recombination, the endogenous CARD-3, CARD-4, CARD-5, or CARD-6 gene is functionally disrupted (i.e., no longer encodes a functional protein; also referred to as a "knock out" vector). Alternatively, the vector can be designed such that, upon homologous recombination, the endogenous CARD-3, CARD-4, CARD-5, or CARD-6 gene is mutated or otherwise altered but still encodes functional protein (e.g., the upstream regulatory region can be altered to thereby alter the expression of the endogenous CARD-3, CARD-4, CARD-5, or CARD-6 protein). In the homologous recombination vector, the altered portion of the CARD-3, CARD-4, CARD-5, or CARD-6 gene is flanked at its 5' and 3' ends by additional nucleic acid of the CARD-3, CARD-4, CARD-5, or CARD-6 gene to allow for homologous recombination to occur between the exogenous CARD-3, CARD-4, CARD-5, or CARD-6 gene carried by the vector and an endogenous CARD-3, CARD-4, CARD-5, or CARD-6 gene in an embryonic stem cell. The additional flanking CARD-3, CARD-4, CARD-5, or CARD-6 nucleic acid is of sufficient length for successful homologous recombination with the endogenous gene. Typically, several kilobases of flanking DNA (both at the 5' and 3' ends) are included in the vector (see, e.g., Thomas and Capecchi (1987) Cell 51:503 for a description of homologous recombination vectors). The vector is introduced into an embryonic stem cell line (e.g., by electroporation) and cells in which the introduced CARD-3, CARD-4, CARD-5, or CARD-6 gene has homologously recombined with the endogenous CARD-3, CARD-4, CARD-5, or CARD-6 gene are selected (see, e.g., Li et al. (1992) Cell 69:915). The selected cells are then injected into a blastocyst of an animal (e.g., a mouse) to form aggregation chimeras (see, e.g., Bradley in Teratocarcinomas and Embryonic Stem Cells: A Practical Approach, Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) Current Opinion in Bio/Technology 2:823–829 and in PCT Publication Nos. WO 90/11354, WO 91/01140, WO 92/0968, and WO 93/04169.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) Proc. Natl. Acad. Sci. USA 89:6232–6236. Another example of a recombinase system is the FLP recombinase system of *Saccharomyces cerevisiae* (O'Gorman et al. (1991) Science 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) Nature 385:810–813 and PCT Publication Nos. WO 97/07668 and WO 97/07669. In brief, a cell, e.g., a somatic cell, from the transgenic animal can be isolated and induced to exit the growth cycle and enter Go phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The CARD-3, CARD-4, CARD-5, or CARD-6 nucleic acid molecules, CARD-3, CARD-4, CARD-5, or CARD-6 proteins, and anti-CARD-3, CARD-4, CARD-5, or CARD-6 antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a polypeptide or nucleic acid of the invention. Such methods comprise formulating a pharmaceutically acceptable carrier with an agent which modulates expression or activity of a polypeptide or nucleic acid of the invention. Such compositions can further include additional active agents. Thus, the invention further includes methods for preparing a pharmaceutical composition by formulating a pharmaceutically acceptable carrier with an agent which modulates expression or activity of a polypeptide or nucleic acid of the invention and one or more addtional active compounds.

The agent which modulates expressioon or activity may, for example, be a small molecule. For example, such small molecules include peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight les than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to modulated. Such appropriate doses may be determined using the assays described herein. When one or more of these small molecules is to be administerd to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL?

(BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a CARD-3, CARD-4, CARD-5, or CARD-6 protein or anti-CARD-3, CARD-4, CARD-5, or CARD-6 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see, e.g., Chen et al. (1994) Proc. Natl. Acad. Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) detection assays (e.g., chromosomal mapping, tissue typing, forensic biology), c) predictive medicine (e.g., diagnostic assays, prognostic assays, monitoring clinical trials, and pharmacogenomics); and d) methods of treatment (e.g., therapeutic and prophylactic). A CARD-3, CARD-4, CARD-5, or CARD-6 protein interacts with other cellular proteins and can thus be used for (i) regulation of cellular proliferation; (ii) regulation of cellular differentiation; and (iii) regulation of cell survival. The isolated nucleic acid molecules of the invention can be used to express CARD-3, CARD-4, CARD-5, or CARD-6 protein (e.g., via a recombinant expression vector in a host cell in gene therapy applications), to detect CARD-3, CARD-4, CARD-5, or CARD-6 mRNA (e.g., in a biological sample) or a genetic lesion in a CARD-3, CARD-4, CARD-5, or CARD-6 gene, and to modulate CARD-3, CARD-4, CARD-5, or CARD-6 activity. In addition, the CARD-3, CARD-4, CARD-5, or CARD-6 proteins can be used to screen drugs or compounds which modulate the CARD-3, CARD-4, CARD-5, or CARD-6 activity or expression as well as to treat disorders characterized by insufficient or excessive production of CARD-3, CARD-4, CARD-5, or CARD-6 protein or production of CARD-3, CARD-4, CARD-5, or CARD-6 protein forms which have decreased or aberrant activity compared to CARD-3, CARD-4, CARD-5, or CARD-6 wild type protein. In addition, the anti-CARD-3, CARD-4, CARD-5, or CARD-6 antibodies of the invention can be used to detect and isolate CARD-3, CARD-4, CARD-5, or CARD-6 proteins and modulate CARD-3, CARD-4, CARD-5, or CARD-6 activity.

This invention further pertains to novel agents identified by the above-described screening assays and uses thereof for treatments as described herein.

A. Screening Assays

The invention provides a method (also referred to herein as a "screening assay") for identifying modulators, i.e., candidate or test compounds or agents (e.g., peptides, peptidomimetics, small molecules or other drugs) which bind to CARD-3, CARD-4, CARD-5, or CARD-6 proteins or biologically active portions thereof or have a stimulatory or inhibitory effect on, for example, CARD-3, CARD-4, CARD-5, or CARD-6 expression or CARD-3, CARD-4, CARD-5, or CARD-6 activity. An example of a biologically active portion of human CARD-4 is amino acids 1–145 encoding the CARD domain which is sufficient to exhibit CARD-3-binding activity as described in Example 7. Amino acids 406–953 of human CARD-4L comprising the leucine rich repeat domain represent a biologically active portion of CARD-4L because they possess hNUDC-binding activity as described in Example 8. An example of a biologically active portion of human CARD-5 is amino acids 111–881 (SEQ ID NO:58) encoding the CARD domain.

Among the screening assays provided by the invention are screening to identify molecules that prevent the dimerization of a CARD-containing polypeptide of the invention, screening to identify molecules which block the binding of a CARD containing polypeptide to a CARD-containing polypeptide of the invention (e.g., CARD-4), screening to identify a competitive inhibitor of the binding of a nucleotide to the nucleotide binding site of a CARD-containing polypeptide of the invention, e.g., human CARD-4L, screening to identify compounds which block the interaction between the leucine-rich repeat of a CARD-containing polypeptide of the invention and a ligand which binds to the leucine-rich repeat.

For CARD-6, screening assays can be used to identify molecules which modulate a CARD-6 mediated increase in transcription of genes having an AP-1 or NF-κB binding site. For example, expression of a reporter under the control of NF-κB (or AP-1) is measured in the presence and absence of a candidate molecule and in the presence and absence of CARD-6 to identify those molecules which alter expression of the reporter in a CARD-6 dependent manner. In addition, screening assays can be used to identify molecules which modulate a CARD-6 mediated increase in CHOP phosphorylation. For example, the expression of a reporter gene under the control of CHOP is measured in the presence and absence of a candidate small molecule and in the presence and absence of CARD-6 to identify those molecules which alter expression of the reporter in a CARD-6 dependent manner. A screening assay can be carried out to identify molecules which modulate the CARD-6 mediated increase in CHOP phosphorylation. For example, CHOP phosphorylation is measured in the presence and absence of a candidate molecule and in the presence and absence of CARD-6. Phosphorylation of CHOP can be measured using an antibody which binds to phosphorylated CHOP, but not to non-phosphorylated CHOP.

For nucleotide binding site-containing polypeptides of the invention, e.g., human CARD-4L, screening assays can be used to identify molecules that modulate the activity of the nucleotide binding site. For example, molecules can be tested for their ability to modulate, e.g., antagonize, the hydrolysis of ATP by the nucleotide binding site of a polypeptide of the invention. Methods of detecting the hydrolysis of ATP by a nucleotide binding site are described in, for example, Gadsby et al., Physiol. Rev. 79:S77–S107, 1999.

For CARD-5, screening assays can be used to identify molecules that interfere with the interaction between the CARD domain of CARD-5 and a CARD-5 ligand, e.g., caspase-1, CARD-7, or CARD-5. Additionally, screening assays can be used to identify molecules that modulate a CARD-5-mediated increase in transcription of genes having an NF-κB binding site.

In one embodiment, the invention provides assays for screening candidate or test compounds which bind to or modulate the activity of a CARD-3, CARD-4, CARD-5, or CARD-6 proteins or polypeptides or biologically active portions thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) Anticancer Drug Des. 12:145). Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Libraries of compounds may be presented in solution (e.g., Houghten (1992) Bio/Techniques 13:412–421), or on beads (Lam (1991) Nature 354:82–84), chips (Fodor (1993) Nature 364:555–556), bacteria (U.S. Pat. No. 5,223,409), spores (U.S. Pat. Nos. 5,571,698; 5,403,484; and 5,223,409), plasmids (Cull et al. (1992) Proc. Natl. Acad. Sci. USA 89:1865–1869) or on phage (Scott and Smith (1990) Science 249:386–390; Devlin (1990) Science 249:404–406; Cwirla et al. (1990) Proc. Natl. Acad. Sci. 87:6378–6382; and Felici (1991) J. Mol. Biol. 222:301–310).

Determining the ability of the test compound to modulate the activity of CARD-3, CARD-4, CARD-5, or CARD-6 or a biologically active portion thereof can be accomplished, for example, by determining the ability of the CARD-3, CARD-4, CARD-5, or CARD-6 protein to bind to or interact with a CARD-3, CARD-4, CARD-5, or CARD-6 target molecule. As used herein, a "target molecule" is a molecule with which a CARD-3, CARD-4, CARD-5, or CARD-6 protein binds or interacts in nature, for example, a molecule associated with the internal surface of a cell membrane or a cytoplasmic molecule. A CARD-3, CARD-4, CARD-5, or CARD-6 target molecule can be a non-CARD-3, CARD-4, CARD-5, or CARD-6 molecule or a CARD-3, CARD-4, CARD-5, or CARD-6 protein or polypeptide of the present invention. In one embodiment, a CARD-3, CARD-4, CARD-5, or CARD-6 target molecule is a component of an apoptotic signal transduction pathway, e.g., CARD-3 and CARD-4. The target, for example, can be a second intracellular protein which has catalytic activity or a protein which facilitates the association of downstream signaling molecules with CARD-3, CARD-4, CARD-5, or CARD-6. In another embodiment, CARD-3, CARD-4, CARD-5, or CARD-6 target molecules include CARD-3 because CARD-3 was found to bind to CARD-4 (Examples 7 and 12), hNUDC because hNUDC was found to bind to CARD-4 (Example 8), and caspase-1, CARD-7, and CARD-5 because these were each found to bind to CARD-5 (Example 17).

Determining the ability of the test compound to modulate the activity of CARD-3, CARD-4, CARD-5, or CARD-6 or a biologically active portion thereof can be accomplished, for example, by determining the ability of the CARD-3, CARD-4, CARD-5, or CARD-6 protein to bind to or interact with any of the specific proteins listed in the previous paragraph as CARD-3, CARD-4, CARD-5, or CARD-6 target molecules. In another embodiment, CARD-3, CARD-4, CARD-5, or CARD-6 target molecules include all proteins that bind to a CARD-3, CARD-4, CARD-5, or CARD-6 protein or a fragment thereof in a two-hybrid system binding assay which can be used without undue experimentation to isolate such proteins from cDNA or genomic two-hybrid system libraries. For example, Example 7 describes the use of the CARD-4 CARD domain region to identify CARD-3 in a two-hybrid screen, Example 8 describes the use of the CARD-4 leucine rich repeat domain region to identify hNUDC in a two-hybrid screen, and Example 17 describes the use of the CARD-5 CARD domain region to identify caspase-1, CARD-7, and CARD-5 in a two-hybrid screen. The binding assays described in this section can be cell-based or cell free (described subsequently).

Determining the ability of the CARD-3, CARD-4, CARD-5, or CARD-6 protein to bind to or interact with a CARD-3, CARD-4, CARD-5, or CARD-6 target molecule can be accomplished by one of the methods described above for determining direct binding. In an embodiment, determining the ability of the CARD-3, CARD-4, CARD-5, or CARD-6 protein to bind to or interact with a CARD-3, CARD-4, CARD-5, or CARD-6 target molecule can be accomplished by determining the activity of the target molecule. For example, the activity of the target molecule can be determined by detecting induction of a cellular second messenger of the target (e.g., intracellular Ca2+, diacylglycerol, IP3, etc.), detecting catalytic/enzymatic activity of the target on an appropriate substrate, detecting the induction of a reporter gene (e.g., a CARD-3, CARD-4, CARD-5, or CARD-6-responsive regulatory element operatively linked to a nucleic acid encoding a detectable marker, e.g. luciferase), or detecting a cellular response, for example, cell survival, cellular differentiation, or cell proliferation. For example, in Example 12 CARD-4 is shown to bind to CARD-3 and in Example 10, by monitoring a cellular response, CARD-4 is shown to enhance caspase 9 activity, cell death or apoptosis. Because CARD-3 and CARD-4 enhance caspase 9 activity, activity can be monitored by assaying the caspase 9-mediated apoptosis cellular response or caspase 9 enzymatic activity. In addition, and in another embodiment, genes induced by CARD-3, CARD-4, CARD-5, or CARD-6 expression can be identified by expressing CARD-3, CARD-4, CARD-5, or CARD-6 in a cell line and conducting a transcriptional profiling experiment wherein the mRNA expression patterns of the cell line transformed with an empty expression vector and the cell line transformed with a CARD-3, CARD-4, CARD-5, or CARD-6 expression vector are compared. The promoters of genes induced by CARD-3, CARD-4, CARD-5, or CARD-6 expression can be operatively linked to reporter genes suitable for screening such as luciferase, secreted alkaline phosphatase, or beta-galactosidase and the resulting constructs could be introduced into appropriate expression vectors. A recombinant cell line containing CARD-3, CARD-4, CARD-5, or CARD-6 and transfected with an expression vector containing a CARD-3, CARD-4, CARD-5, or CARD-6 responsive promoter operatively linked to a reporter gene can be used to identify test compounds that modulate CARD-3, CARD-4, CARD-5, or CARD-6 activity by assaying the expression of the reporter gene in response to contacting the recombinant cell line with test compounds. CARD-3, CARD-4, CARD-5, or CARD-6 agonists can be identified as increasing the expression of the reporter gene and CARD-3, CARD-4, CARD-5, or CARD-6 antagonists can be identified as decreasing the expression of the reporter gene.

In another embodiment of the invention, the ability of a test compound to modulate the activity of CARD-3, CARD-4, CARD-5, CARD-6 or biologically active portions thereof can be determined by assaying the ability of the test compound to modulate CARD-3, CARD-4, CARD-5, or CARD-6-dependent pathways or processes where the CARD-3, CARD-4, CARD-5, or CARD-6 target proteins that mediate the CARD-3, CARD-4, CARD-5, or CARD-6 effect are known or unknown. Potential CARD-3, CARD-4, CARD-5, or CARD-6-dependent pathways or processes include, but are not limited to, the modulation of cellular signal transduction pathways and their related second messenger molecules (e.g., intracellular $Ca^{2+}$, diacylglycerol, IP3, cAMP etc.), cellular enzymatic activities, cellular responses (e.g., cell survival, cellular differentiation, or cell proliferation), or the induction or repression of cellular or heterologous mRNAs or proteins. CARD-3, CARD-4, CARD-5, or CARD-6-dependent pathways or processes could be assayed by standard cell-based or cell free assays appropriate for the specific pathway or process under study. For example, Examples 9 and 18 describe how expression of CARD-4S, CARD-4L, or CARD-5 in 293T cells induces the NF-κB pathway as determined by the measurement of a cotransfected NF-κB pathway luciferase reporter gene. In another embodiment, cells cotransfected with CARD-4 or CARD-5 and the NF-κB luciferase reporter gene could be contacted with a test compound and test compounds that block CARD-4 or CARD-5 activity could be identified by their reduction of CARD-4 or CARD-5-dependent NF-κB pathway luciferase reporter gene expression. Test compounds that agonize CARD-4 or CARD-5 would be expected to increase reporter gene expression. In another embodiment, CARD-4 or CARD-5 could be expressed in a cell line and the recombinant CARD-4 or CARD-5-expressing cell line could be contacted with a test compound. Test compounds that inhibit CARD-4 or CARD-5 activity could be identified by their reduction of CARD-4 or CARD-5-dependent NF-κB pathway stimulation as measured by the assay of a NF-κB pathway reporter gene, NF-κB nuclear localization, IκB phosphorylation or proteolysis, or other standard assays for NF-κB pathway activation known to those skilled in the art.

In yet another embodiment, an assay of the present invention is a cell-free assay comprising contacting a CARD-3, CARD-4, CARD-5, or CARD-6 protein or biologically active portion thereof with a test compound and determining the ability of the test compound to bind to the CARD-3, CARD-4, CARD-5, or CARD-6 protein or biologically active portion thereof. Binding of the test compound to the CARD-3, CARD-4, CARD-5, or CARD-6 protein can be determined either directly or indirectly as described above. In one embodiment, a competitive binding assay includes contacting the CARD-3, CARD-4, CARD-5, or CARD-6 protein or biologically active portion thereof with a compound known to bind CARD-3, CARD-4, CARD-5, or CARD-6 to form an assay mixture, contacting the assay mixture with a test compound, and determining the ability of the test compound to interact with a CARD-3, CARD-4, CARD-5, or CARD-6 protein, wherein determining the ability of the test compound to interact with a CARD-3, CARD-4, CARD-5, or CARD-6 protein comprises determining the ability of the test compound to preferentially bind to CARD-3, CARD-4, CARD-5, or CARD-6 or biologically active portion thereof as compared to the known binding compound.

In another embodiment, an assay is a cell-free assay comprising contacting CARD-3, CARD-4, CARD-5, or CARD-6 protein or biologically active portion thereof with a test compound and determining the ability of the test compound to modulate (e.g., stimulate or inhibit) the activity of the CARD-3, CARD-4, CARD-5, or CARD-6 protein or biologically active portion thereof. Determining the ability of the test compound to modulate the activity of CARD-3, CARD-4, CARD-5, or CARD-6 can be accomplished, for example, by determining the ability of the CARD-3, CARD-4, CARD-5, or CARD-6 protein to bind to a CARD-3, CARD-4, CARD-5, or CARD-6 target molecule by one of the methods described above for determining direct binding. In an alternative embodiment, determining the ability of the test compound to modulate the activity of CARD-3, CARD-4, CARD-5, or CARD-6 can be accomplished by determining the ability of the CARD-3, CARD-4, CARD-5, or CARD-6 protein to further modulate a CARD-3, CARD-4, CARD-5, or CARD-6 target molecule. For example, the catalytic/enzymatic activity of the target molecule on an appropriate substrate can be determined as previously described.

In yet another embodiment, the cell-free assay comprises contacting the CARD-3, CARD-4, CARD-5, or CARD-6 protein or biologically active portion thereof with a known compound which binds CARD-3, CARD-4, CARD-5, or CARD-6 to form an assay mixture, contacting the assay mixture with a test compound, and determining the ability of the test compound to interact with a CARD-3, CARD-4, CARD-5, or CARD-6 protein, wherein determining the ability of the test compound to interact with a CARD-3, CARD-4, CARD-5, or CARD-6 protein comprises determining the ability of the CARD-3,CARD-4, CARD-5, or CARD-6 protein to preferentially bind to or modulate the activity of a CARD-3, CARD-4, CARD-5, or CARD-6 target molecule. The cell-free assays of the present invention are amenable to use of both the soluble form or the membrane-associated form of CARD-3, CARD-4, CARD-5, or CARD-6. A membrane-associated form of CARD-3, CARD-4, CARD-5, or CARD-6 refers to CARD-3, CARD-4, CARD-5, or CARD-6 that interacts with a membrane-bound target molecule In the case of cell-free assays comprising the membrane-associated form of CARD-3, CARD-4, CARD-5, or CARD-6, it may be desirable to utilize a solubilizing agent such that the membrane-associated form of CARD-3, CARD-4, CARD-5, or CARD-6 is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, 3-[(3-cholamidopropyl)dimethylamminio]-1-propane sulfonate (CHAPS), 3-[(3-cholamidopropyl) dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either CARD-3, CARD-4, CARD-5, or CARD-6 or its target molecule to facilitate separation of complexed from uncomplexed forms of one or both of the proteins, as well as to accommodate automation of the assay. Binding of a test compound to CARD-3, CARD-4, CARD-5, or CARD-6, or interaction of CARD-3, CARD-4, CARD-5, or CARD-6 with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase/CARD-3, CARD-4, CARD-5, or CARD-6 fusion proteins or glutathione-S-transferase/target fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or CARD-3, CARD-4, CARD-5, or CARD-6 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of CARD-3, CARD-4, CARD-5, or CARD-6 binding or activity determined using standard techniques. In an alternative embodiment, MYC or HA epitope tag CARD-3 or CARD-4 fusion proteins or MYC or HA epitope tag target fusion proteins can be adsorbed onto anti-MYC or anti-HA antibody coated microbeads or onto anti-MYC or anti-HA antibody coated microtitre plates, which are then combined with the test compound or the test compound and either the non-adsorbed target protein or CARD-3 or CARD-4 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of CARD-3 or CARD-4 binding or activity determined using standard techniques. Example 12 describes an HA epitope tagged CARD-4 protein that physically interacts in a coimmunoprecipitation assay with MYC epitope tagged CARD-3. In an embodiment of the invention, HA epitope tagged CARD-4 could be used in combination with MYC epitope CARD-3 in the sort of protein-protein interaction assay described earlier in this paragraph.

Other techniques for immobilizing proteins on matrices can also be used in the screening assays of the invention. For example, CARD-3, CARD-4, CARD-5, or CARD-6 or its target molecule can be immobilized utilizing conjugation of biotin and streptavidin. Biotinylated CARD-3 or CARD-4 or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with CARD-3, CARD-4, CARD-5, CARD-6 or target molecules but which do not interfere with binding of the protein to its target molecule can be derivatized to the wells of the plate, and unbound target or protein trapped in the wells by antibody conjugation. Methods for detecting such complexes, in addition to those described above for the GST-immobilized complexes and epitope tag immobilized complexes, include immunodetection of complexes using antibodies reactive with the CARD-3, CARD-4, CARD-5, or CARD-6 or target molecule, as well as enzyme-linked assays which rely on detecting an enzymatic activity associated with the CARD-3, CARD-4, CARD-5, CARD-6 or target molecule.

In another embodiment, modulators of CARD-3, CARD-4, CARD-5, or CARD-6 expression are identified in a method in which a cell is contacted with a candidate compound and the expression of the CARD-3, CARD-4, CARD-5, or CARD-6 promoter, mRNA or protein in the cell is determined. The level of expression of CARD-3, CARD-4, CARD-5, or CARD-6 mRNA or protein in the presence of the candidate compound is compared to the level of expression of CARD-3, CARD-4, CARD-5, or CARD-6 mRNA or protein in the absence of the candidate compound. The candidate compound can then be identified as a modulator of CARD-3, CARD-4, CARD-5, or CARD-6 expression based on this comparison. For example, when expression of CARD-3, CARD-4, CARD-5, or CARD-6 mRNA or protein is greater (statistically significantly greater) in the presence of the candidate compound than in its absence, the candidate compound is identified as a stimulator of CARD-3, CARD-4, CARD-5, or CARD-6 mRNA or protein expression. Alternatively, when expression of CARD-3, CARD-4, CARD-5, or CARD-6 mRNA or protein is less (statistically significantly less) in the presence of the candidate compound than in its absence, the candidate compound is identified as an inhibitor of CARD-3, CARD-4, CARD-5, or CARD-6 mRNA or protein expression. The level of CARD-3, CARD-4, CARD-5, or CARD-6 mRNA or protein expression in the cells can be determined by methods described herein for detecting CARD-3, CARD-4, CARD-5, or CARD-6 mRNA or protein. The activity of the CARD-3, CARD-4, CARD-5, or CARD-6 promoter can be assayed by linking the CARD-3, CARD-4, CARD-5, or CARD-6 promoter to a reporter gene such as luciferase, secreted alkaline phosphatase, or beta-galactosidase and introducing the resulting construct into an appropriate vector, transfecting a host cell line, and measuring the activity of the reporter gene in response to test compounds. For example, two CARD-4-specific mRNAs were detected in a Northern blotting experiment, one of 4.6 kilobases and the other of 6.5–7.0 kilobases (Example 11). In Example 11, CARD-4-specific mRNA species were found to be widely distributed in the tissues and cell lines studied.

In yet another aspect of the invention, the CARD-3, CARD-4, CARD-5, or CARD-6 proteins can be used as "bait proteins" in a two hybrid assay or three hybrid assay (see, e.g., U.S. Pat. No. 5,283,317; Zervos et al. (1993) Cell 72:223-232; Madura et al. (1993) J. Biol. Chem. 268:12046–12054; Bartel et al. (1993) Bio/Techniques 14:920–924; Iwabuchi et al. (1993) Oncogene 8:1693–1696; and PCT Publication No. WO 94/10300), to identify other proteins, which bind to or interact with CARD-3, CARD-4, CARD-5, or CARD-6 ("CARD-3, CARD-4, CARD-5, or CARD-6-binding proteins" or "CARD-3, CARD-4, CARD-5, or CARD-6-bp") and modulate CARD-3, CARD-4, CARD-5, or CARD-6 activity. Such CARD-3, CARD-4, CARD-5, or CARD-6-binding proteins are also likely to be involved in the propagation of signals by the CARD-3, CARD-4, CARD-5, or CARD-6 proteins as, for example, upstream or downstream elements of the CARD-3, CARD-4, CARD-5, or CARD-6 pathway. For example, Example 7 describes the construction of a two-hybrid screening bait construct including human CARD-4L amino acids 1–145 comprising the CARD domain and the use of this bait construct to screen human mammary gland and prostate gland two-hybrid libraries resulting in the identification of human CARD-3 as a CARD-4 interacting protein. In another example, Example 8 describes the construction of a two-hybrid screening bait construct including human CARD-4 amino acids 406–953 comprising the LRR domain and the use of this bait construct to screen a human mammary gland two-hybrid libraries resulting in the identification of hNUDC as a CARD-4 interacting protein. In another example, Example 17 describes the construction of a two-hybrid screening bait construct including human CARD-5 CARD domain and the use of this bait construct to screen a panel of 26 CARD domains, resulting in the identification of caspase-1, CARD-7, and CARD-5 as CARD-5 interacting proteins.

The two-hybrid system is based on the modular nature of most transcription factors, which consist of separable DNA-binding and activation domains. Briefly, the assay utilizes two different DNA constructs. In one construct, the gene that codes for CARD-3, CARD-4, CARD-5, or CARD-6 is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an CARD-3, CARD-4, CARD-5, or CARD-6-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with CARD-3, CARD-4, CARD-5, or CARD-6.

In an embodiment of the invention, the ability of a test compound to modulate the activity of CARD-3, CARD-4, CARD-5, or CARD-6, or a biologically active portion thereof can be determined by assaying the ability of the test compound to block the binding of CARD-3, CARD-4, CARD-5, or CARD-6 to its target proteins in a two-hybrid system assay. Example 7 describes a two-hybrid system assay for the interaction between CARD-3 and CARD-4, Example 8 describes a two-hybrid system assay for the interaction between CARD-4 and its target protein hNUDC, and Example 17 describes a two-hybrid system assay for the interaction between CARD-5 and its target proteins caspase-1, CARD-7, and CARD-5. To screen for test compounds that block the interaction between CARD-3, CARD-4, CARD-5 and their target proteins, which include but are not limited to CARD-3, CARD-4, hNUDC, caspase-1, CARD-7, and CARD-5, a yeast two-hybrid screening strain coexpressing the interacting bait and prey constructs, for example, a CARD-4 bait construct and a CARD-3 prey construct as described in Example 7, is contacted with the test compound and the activity of the two-hybrid system reporter gene, usually HIS3, lacZ, or URA3 is assayed. If the strain remains viable but exhibits a significant decrease in reporter gene activity, this would indicate that the test compound has inhibited the interaction between the bait and prey proteins. This assay could be automated for high throughput drug screening purposes. In another embodiment of the invention, CARD-3, CARD-4, CARD-5, or CARD-6 and their target proteins could be configured in the reverse two-hybrid system (Vidal et al. (1996) Proc. Natl. Acad. Sci. USA 93:10321–6 and Vidal et al. (1996) Proc. Natl. Acad. Sci. USA 93:10315–20) designed specifically for efficient drug screening. In the reverse two-hybrid system, inhibition of a CARD-3 or CARD-4 physical interaction with a target protein would result in induction of a reporter gene in contrast to the normal two-hybrid system where inhibition of CARD-3, CARD-4, CARD-5, or CARD-6 physical interaction with a target protein would lead to reporter gene repression. The reverse two-hybrid system is preferred for drug screening because reporter gene induction is more easily assayed than report gene repression.

Alternative embodiments of the invention are proteins found to physically interact with proteins that bind to CARD-3, CARD-4, CARD-5, or CARD-6. CARD-3, CARD-4, CARD-5, or CARD-6 interactors, including but not limited to hNUDC and CARD-3, could be configured into two-hybrid system baits and used in two-hybrid screens to identify additional members of the CARD-3, CARD-4, CARD-5, or CARD-6 pathway. The interactors of CARD-3, CARD-4, CARD-5, or CARD-6 interactors identified in this way could be useful targets for therapeutic intervention in CARD-3, CARD-4, CARD-5, or CARD-6 related diseases and pathologies and an assay of their enzymatic or binding activity could be useful for the identification of test compounds that modulate CARD-3, CARD-4, CARD-5, or CARD-6 activity.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. Accordingly, CARD-3, CARD-4, CARD-5, or CARD-6 nucleic acid molecules described herein or fragments thereof, can be used to map the location of CARD-3, CARD-4, CARD-5, or CARD-6 genes on a chromosome. The mapping of the CARD-3, CARD-4, CARD-5, or CARD-6 sequences to chromosomes is an important first step in correlating these sequences with genes associated with disease.

Briefly, CARD-3, CARD-4, CARD-5, or CARD-6 genes can be mapped to chromosomes by preparing PCR primers (preferably 15–25 bp in length) from the CARD-3, CARD-4, CARD-5, or CARD-6 sequences. Computer analysis of CARD-3, CARD-4, CARD-5, or CARD-6 sequences can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the CARD-3, CARD-4, CARD-5, or CARD-6 sequences will yield an amplified fragment. For example, in Example 6, human CARD-4-specific PCR primers were used to screen DNAs from a somatic cell hybrid panel showing that human CARD-4 maps to chromosome 7 close to the SHGC-31928 genetic marker.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio et al. (1983) Science 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the CARD-3, CARD-4, CARD-5, or CARD-6 sequences to design oligonucleotide primers, sublocalization can be achieved with panels of fragments from specific chromosomes. Other mapping strategies which can similarly be used to map a CARD-3, CARD-4, CARD-5, or CARD-6 sequence to its chromosome include in situ hybridization (described in Fan et al. (1990) Proc. Natl. Acad. Sci. USA 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical like colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., (Human Chromosomes: A Manual of Basic Techniques (Pergamon Press, New York, 1988)).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) Nature, 325:783–787.

Moreover, differences in the DNA sequences between individuals affected and unaffected with a disease associated with the CARD-3, CARD-4, CARD-5, or CARD-6 gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The CARD-3, CARD-4, CARD-5, or CARD-6 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the CARD-3, CARD-4, CARD-5, or CARD-6 sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The CARD-3, CARD-4, CARD-5, or CARD-6 sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1, SEQ ID NO:7, SEQ ID NO:25, SEQ ID NO:38, SEQ ID NO:40, SEQ ID NO:42, SEQ ID NO:48, SEQ ID NO:51, SEQ ID NO:54, and SEQ ID NO:60 can comfortably provide positive individual identification with a panel of perhaps 10 to 1,000 primers which each yield a noncoding amplified sequence of 100 bases. If predicted coding sequences, such as those in SEQ ID NO:3, SEQ ID NO:9, SEQ ID NO:27, SEQ ID NO:50, SEQ ID NO:53, SEQ ID NO:56, and SEQ ID NO:62 are used, a more appropriate number of primers for positive individual identification would be 500–2,000.

If a panel of reagents from CARD-3, CARD-4, CARD-5, or CARD-6 sequences described herein is used to generate a unique identification database for an individual, those same reagents can later be used to identify tissue from that individual. Using the unique identification database, positive identification of the individual, living or dead, can be made from extremely small tissue samples.

3. Use of Partial Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1, SEQ ID NO:7, SEQ ID NO:25, SEQ ID NO:38, SEQ ID NO:40, SEQ ID NO:42, SEQ ID NO:48, SEQ ID NO:51, SEQ ID NO:54, and SEQ ID NO:60 are particularly appropriate for this use as greater numbers of polymorphisms occur in the noncoding regions, making it easier to differentiate individuals using this technique. Examples of polynucleotide reagents include the CARD-3, CARD-4, CARD-5, or CARD-6 sequences or portions thereof, e.g., fragments derived from the noncoding regions of SEQ ID NO:1, SEQ ID NO:7, SEQ ID NO:25, SEQ ID NO:38, SEQ ID NO:40, SEQ ID NO:42, SEQ ID NO:48, SEQ ID NO:51, SEQ ID NO:54, and SEQ ID NO:60 which have a length of at least 20 or 30 bases.

The sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such CARD-3, CARD-4, CARD-5, or CARD-6 probes can be used to identify tissue by species and/or by organ type.

In a similar fashion, these reagents, e.g., CARD-3, CARD-4, CARD-5, or CARD-6 primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining CARD-3, CARD-4, CARD-5, or CARD-6 protein and/or nucleic acid expression as well as CARD-3, CARD-4, CARD-5, or CARD-6 activity, in the context of a biological sample (e.g., blood, serum, cells, tissue) to thereby determine whether an individual is afflicted with a disease or disorder, or is at risk of developing a disorder, associated with aberrant CARD-3, CARD-4, CARD-5, or CARD-6 expression or activity. The invention also provides for prognostic (or predictive) assays for determining whether an individual is at risk of developing a disorder associated with CARD-3, CARD-4, CARD-5, or CARD-6 protein, nucleic acid expression or activity. For example, mutations in a CARD-3, CARD-4, CARD-5, or CARD-6 gene can be assayed in a biological sample. Such assays can be used for prognostic or predictive purpose to thereby prophylactically treat an individual prior to the onset of a disorder characterized by or associated with CARD-3, CARD-4, CARD-5, or CARD-6 protein, nucleic acid expression or activity.

Another aspect of the invention provides methods for determining CARD-3, CARD-4, CARD-5, or CARD-6 protein, nucleic acid expression or CARD-3, CARD-4, CARD-5, or CARD-6 activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs or other compounds) on the expression or activity of CARD-3, CARD-4, CARD-5, or CARD-6 in clinical trials.

These and other agents are described in further detail in the following sections.

1. Diagnostic Assays

An exemplary method for detecting the presence or absence of CARD-3, CARD-4, CARD-5, or CARD-6 in a biological sample involves obtaining a biological sample from a test subject and contacting the biological sample with a compound or an agent capable of detecting CARD-3, CARD-4, CARD-5, or CARD-6 protein or nucleic acid (e.g., mRNA, genomic DNA) that encodes CARD-3, CARD-4, CARD-5, or CARD-6 protein such that the presence of CARD-3, CARD-4, CARD-5, or CARD-6 is detected in the biological sample. An agent for detecting CARD-3, CARD-4, CARD-5, or CARD-6 mRNA or genomic DNA is a labeled nucleic acid probe capable of hybridizing to CARD-3, CARD-4, CARD-5, or CARD-6 mRNA or genomic DNA. The nucleic acid probe can be, for example, a full-length CARD-3, CARD-4, CARD-5, or CARD-6 nucleic acid, such as the nucleic acid of SEQ ID NO:1 or 3, SEQ ID NO:7 or 9, SEQ ID NO:25 or 27, SEQ ID NO:38, SEQ ID NO:40, SEQ ID NO:42, SEQ ID NO:48 or 50, SEQ ID NO:51 or SEQ ID NO:53 or SEQ ID NO:54 or SEQ ID NO:56, SEQ ID NO:60 or 62, or a portion thereof, such as an oligonucleotide of at least 15, 30, 50, 100, 250 or 500 nucleotides in length and sufficient to specifically hybridize under stringent conditions to mRNA or genomic DNA, or a human CARD-4 splice variant such as the nucleic acid of SEQ ID NO:38 or SEQ ID NO:40. Other suitable probes for use in the diagnostic assays of the invention are described herein. For example, Example 11 describes the use of a nucleic acid probe to detect CARD-4 mRNAs in human tissues and cell lines and the probe used in this experiment could be used for a diagnostic assay.

An agent for detecting CARD-3, CARD-4, CARD-5, or CARD-6 protein can be an antibody capable of binding to CARD-3, CARD-4, CARD-5, or CARD-6 protein, preferably an antibody with a detectable label. Antibodies can be polyclonal, or more preferably, monoclonal. For example, polypeptides corresponding to amino acids 128–139 and 287–298 of human CARD-4L were used to immunize rabbits and produce polyclonal antibodies that specifically recognize human CARD-4L. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect CARD-3, CARD-4, CARD-5, or CARD-6 mRNA, protein, or genomic DNA in a biological sample in vitro as well as in vivo, For example, in vitro techniques for detection of CARD-3, CARD-4, CARD-5, or CARD-6 mRNA include Northern hybridizations and in situ hybridizations. For example, Example 11 contains the use of a human CARD-4L nucleic acid probe for a Northern blotting analysis of mRNA species encoded by human CARD-4L detected in RNA samples from human tissues and cell lines. In vitro techniques for detection of CARD-3 or CARD-4 protein include enzyme linked immunosorbent assays (ELISAs), Western blots, immunoprecipitations and immunofluorescence. In vitro techniques for detection of CARD- 3, CARD-4, CARD-5, or CARD-6 genomic DNA include Southern hybridizations. Furthermore, in vivo techniques for detection of CARD-3, CARD-4, CARD-5, or CARD-6 protein include introducing into a subject a labeled anti-CARD-3, CARD-4, CARD-5, or CARD-6 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. An biological sample is a peripheral blood leukocyte sample isolated by conventional means from a subject.

In another embodiment, the methods further involve obtaining a control biological sample from a control subject, contacting the control sample with a compound or agent capable of detecting CARD-3, CARD-4, CARD-5, or CARD-6 protein, mRNA, or genomic DNA, such that the presence of CARD-3, CARD-4, CARD-5, or CARD-6 protein, mRNA or genomic DNA is detected in the biological sample, and comparing the presence of CARD-3, CARD-4, CARD-5, or CARD-6 protein, mRNA or genomic DNA in the control sample with the presence of CARD-3, CARD-4, CARD-5, or CARD-6 protein, mRNA or genomic DNA in the test sample.

The invention also encompasses kits for detecting the presence of CARD-3, CARD-4, CARD-5, or CARD-6 in a biological sample (a test sample). Such kits can be used to determine if a subject is suffering from or is at increased risk of developing a disorder associated with aberrant expression of CARD-3, CARD-4, CARD-5, or CARD-6 (e.g., an immunological disorder). For example, the kit can comprise a labeled compound or agent capable of detecting CARD-3, CARD-4, CARD-5, or CARD-6 protein or mRNA in a biological sample and means for determining the amount of CARD-3, CARD-4, CARD-5, or CARD-6 in the sample (e.g., an anti-CARD-3, CARD-4, CARD-5, or CARD-6 antibody or an oligonucleotide probe which binds to DNA encoding CARD-3, CARD-4, CARD-5, or CARD-6, e.g., SEQ ID NO:1, SEQ ID NO:3, SEQ ID NO:7, SEQ ID NO:9, SEQ ID NO:25, SEQ ID NO:27, SEQ ID NO:38, SEQ ID NO:40, SEQ ID NO:42, SEQ IS NO:48, SEQ ID NO:50, SEQ ID NO:51, SEQ ID NO:53, SEQ ID NO:54, SEQ ID NO:56, SEQ ID NO:60, or SEQ ID NO:62). Kits may also include instruction for observing that the tested subject is suffering from or is at risk of developing a disorder associated with aberrant expression of CARD-3, CARD-4, CARD-5, or CARD-6 if the amount of CARD-3, CARD-4, CARD-5, or CARD-6 protein or mRNA is above or below a normal level.

For antibody-based kits, the kit may comprise, for example: (1) a first antibody (e.g., attached to a solid support) which binds to CARD-3, CARD-4, CARD-5, or CARD-6 protein; and, optionally, (2) a second, different antibody which binds to CARD-3, CARD-4, CARD-5, or CARD-6 protein or the first antibody and is conjugated to a detectable agent.

For oligonucleotide-based kits, the kit may comprise, for example: (1) a oligonucleotide, e.g., a detectably labelled oligonucleotide, which hybridizes to a CARD-3, CARD-4, CARD-5, or CARD-6 nucleic acid sequence or (2) a pair of primers useful for amplifying a CARD-3, CARD-4, CARD-5, or CARD-6 nucleic acid molecule.

The kit may also comprise, e.g., a buffering agent, a preservative, or a protein stabilizing agent. The kit may also comprise components necessary for detecting the detectable agent (e.g., an enzyme or a substrate). The kit may also contain a control sample or a series of control samples which can be assayed and compared to the test sample contained, Each component of the kit is usually enclosed within an individual container and all of the various containers are within a single package along with instructions for observing whether the tested subject is suffering from or is at risk of developing a disorder associated with aberrant expression of CARD-3, CARD-4, CARD-5, or CARD-6.

2. Prognostic Assays

The methods described herein can furthermore be utilized as diagnostic or prognostic assays to identify subjects having or at risk of developing a disease or disorder associated with aberrant CARD-3, CARD-4, CARD-5, or CARD-6 expression or activity. For example, the assays described herein, such as the preceding diagnostic assays or the following assays, can be utilized to identify a subject having or at risk of developing a disorder associated with CARD-3, CARD-4, CARD-5, or CARD-6 protein, nucleic acid expression or activity. Alternatively, the prognostic assays can be utilized to identify a subject having or at risk for developing such a disease or disorder. Thus, the present invention provides a method in which a test sample is obtained from a subject and CARD-3, CARD-4, CARD-5, or CARD-6 protein or nucleic acid (e.g., mRNA, genomic DNA) is detected, wherein the presence of CARD-3, CARD-4, CARD-5, or CARD-6 protein or nucleic acid is diagnostic for a subject having or at risk of developing a disease or disorder associated with aberrant CARD-3, CARD-4, CARD-5, or CARD-6 expression or activity, As used herein, a "test sample" refers to a biological sample obtained from a subject of interest. For example, a test sample can be a biological fluid (e.g., serum), cell sample, or tissue. Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant CARD-3, CARD-4, CARD-5, or CARD-6 expression or activity. For example, such methods can be used to determine whether a subject can be effectively treated with a specific agent or class of agents (e.g., agents of a type which decrease CARD-3, CARD-4, CARD-5, or CARD-6 activity). Thus, the present invention provides methods for determining whether a subject can be effectively treated with an agent for a disorder associated with aberrant CARD-3, CARD-4, CARD-5, or CARD-6 expression or activity in which a test sample is obtained and CARD-3, CARD-4, CARD-5, or CARD-6 protein or nucleic acid is detected (e.g., wherein the presence of CARD-3, CARD-4, CARD-5, or CARD-6 protein or nucleic acid is diagnostic for a subject that can be administered the agent to treat a disorder associated with aberrant CARD-3, CARD-4, CARD-5, or CARD-6 expression or activity).

The methods of the invention can also be used to detect genetic lesions or mutations in a CARD-3, CARD-4, CARD-5, or CARD-6 gene, thereby determining if a subject with the lesioned gene is at risk for a disorder characterized by aberrant cell proliferation and/or differentiation. In preferred embodiments, the methods include detecting, in a sample of cells from the subject, the presence or absence of a genetic lesion characterized by at least one of an alteration affecting the integrity of a gene encoding a CARD-3, CARD-4, CARD-5, or CARD-6-protein, or the mis-expression of the CARD-3, CARD-4, CARD-5, or CARD-6 gene. For example, such genetic lesions can be detected by ascertaining the existence of at least one of 1) a deletion of one or more nucleotides from a CARD-3, CARD-4, CARD-5, or CARD-6 gene; 2) an addition of one or more nucleotides to a CARD-3, CARD-4, CARD-5, or CARD-6 gene; 3) a substitution of one or more nucleotides of a CARD-3, CARD-4, CARD-5, or CARD-6 gene; 4) a chromosomal rearrangement of a CARD-3, CARD-4, CARD-5, or CARD-6 gene; 5) an alteration in the level of a messenger RNA transcript of a CARD-3, CARD-4, CARD-5, or CARD-6 gene; 6) aberrant modification of a CARD-3, CARD-4, CARD-5, or CARD-6 gene, such as of the methylation pattern of the genomic DNA; 7) the presence of a non-wild type splicing pattern of a messenger RNA transcript of a CARD-3, CARD-4, CARD-5, or CARD-6 gene (e.g, caused by a mutation in a splice donor or splice acceptor site); 8) a non-wild type level of a CARD-3, CARD-4, CARD-5, or CARD-6-protein; 9) allelic loss of a CARD-3, CARD-4, CARD-5, or CARD-6 gene; and 10) inappropriate post-translational modification of a CARD-3, CARD-4, CARD-5, or CARD-6-protein. As described herein, there are a large number of assay techniques known in the art which can be used for detecting lesions in a CARD-3, CARD-4, CARD-5, or CARD-6 gene. A biological sample is a peripheral blood leukocyte sample isolated by conventional means from a subject.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077–1080; and Nakazawa et al. (1994) Proc. Natl. Acad. Sci. USA 91:360–364), the latter of which can be particularly useful for detecting point mutations in the CARD-3 or CARD-4-gene (see, e.g., Abravaya et al. (1995) Nucleic Acids Res. 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a CARD-3, CARD-4, CARD-5, or CARD-6 gene under conditions such that hybridization and amplification of the CARD-3, CARD-4, CARD-5, or CARD-6-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) Proc. Natl. Acad. Sci. USA 87:1874–1878), transcriptional amplification system (Kwoh, et al. (1989) Proc. Natl. Acad. Sci. USA 86:1173–1177), Q-Beta Replicase (Lizardi et al. (1988) Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a CARD-3, CARD-4, CARD-5, or CARD-6 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498, 531) can be used to score for the presence of specific mutations by development or loss of a ribozyme cleavage site.

In other embodiments, genetic mutations in CARD-3, CARD-4, CARD-5, or CARD-6 can be identified by hybridizing a sample and control nucleic acids, e.g., DNA or RNA, to high density arrays containing hundreds or thousands of oligonucleotides probes (Cronin et al. (1996) Human Mutation 7:244–255; Kozal et al. (1996) Nature Medicine 2:753–759). For example, genetic mutations in CARD-3 or CARD-4 can be identified in two-dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the CARD-3, CARD-4, CARD-5, or CARD-6 gene and detect mutations by comparing the sequence of the sample CARD-3, CARD-4, CARD-5, or CARD-6 with the corresponding wild-type (control) sequence. Examples of sequencing reactions include those based on techniques developed by Maxam and Gilbert ((1977) Proc. Natl. Acad. Sci. USA 74:560) or Sanger ((1977) Proc. Natl. Acad. Sci. USA 74:5463). It is also contemplated that any of a variety of automated sequencing procedures can be utilized when performing the diagnostic assays ((1995) Bio/Techniques 19:448), including sequencing by mass spectrometry (see, e.g., PCT Publication No. WO 94/16101; Cohen et al. (1996) Adv. Chromatogr. 36:127–162; and Griffin et al. (1993) Appl. Biochem. Biotechnol. 38:147–159).

Other methods for detecting mutations in the CARD-3 or CARD-4 gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes of formed by hybridizing (labeled) RNA or DNA containing the wild-type CARD-3, CARD-4, CARD-5, or CARD-6 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton et al (1988) Proc. Natl Acad Sci USA 85:4397; Saleeba et al (1992) Methods Enzymol. 217:286–295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in CARD-3, CARD-4, CARD-5, or CARD-6 cDNAs obtained from samples of cells. For example, the mutY enzyme of E. coli cleaves A at G/A mismatches and the thymidine DNA glycosylase from HeLa cells cleaves T at G/T mismatches (Hsu et al. (1994) Carcinogenesis 15:1657–1662). According to an exemplary embodiment, a probe based on a CARD-3, CARD-4, CARD-5, or CARD-6 sequence, e.g., a wild-type CARD-3, CARD-4, CARD-5, or CARD-6 sequence, is hybridized to a cDNA or other DNA product from a test cell(s). The duplex is treated with a DNA mismatch repair enzyme, and the cleavage products, if any, can be detected from electrophoresis protocols or the like See, e.g., U.S. Pat. No. 5,459,039.

In other embodiments, alterations in electrophoretic mobility will be used to identify mutations in CARD-3, CARD-4, CARD-5, or CARD-6 genes. For example, single strand conformation polymorphism (SSCP) may be used to detect differences in electrophoretic mobility between mutant and wild type nucleic acids (Orita et al. (1989) Proc Natl. Acad. Sci USA: 86:2766, see also Cotton (1993) Mutat. Res. 285:125–144; and Hayashi (1992) Genet Anal Tech Appl 9:73–79). Single-stranded DNA fragments of sample and control CARD-3 or CARD-4 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In an embodiment, the subject method utilizes heteroduplex analysis to separate double stranded heteroduplex molecules on the basis of changes in electrophoretic mobility (Keen et al. (1991) Trends Genet 7:5).

In yet another embodiment, the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al. (1989) Proc. Natl Acad. Sci USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437–2448) or at the extreme 3' end of one primer where, under appropriate conditions, mismatch can prevent, or reduce polymerase extension (Prossner (1993) Tibtech 11:238). In addition, it may be desirable to introduce a novel restriction site in the region of the mutation to create cleavage-based detection (Gasparini et al. (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a CARD-3, CARD-4, CARD-5, or CARD-6 gene.

Furthermore, any cell type or tissue, preferably peripheral blood leukocytes, in which CARD-3 or CARD-4 is expressed may be utilized in the prognostic assays described herein.

3. Pharmacogenomics

Agents, or modulators which have a stimulatory or inhibitory effect on CARD-3, CARD-4, CARD-5, or CARD-6 activity (e.g.,CARD-3, CARD-4, CARD-5, or CARD-6 gene expression) as identified by a screening assay described herein can be administered to individuals to treat (prophylactically or therapeutically) disorders (e.g., an immunological disorder) associated with aberrant CARD-3, CARD-4, CARD-5, or CARD-6 activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of CARD-3, CARD-4, CARD-5, or CARD-6 protein, expression of CARD-3, CARD-4, CARD-5, or CARD-6 nucleic acid, or mutation content of CARD-3, CARD-4, CARD-5, or CARD-6 genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) Clin. Chem. 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of CARD-3, CARD-4, CARD-5, or CARD-6 protein, expression of CARD-3 or CARD-4 nucleic acid, or mutation content of CARD-3, CARD-4, CARD-5, or CARD-6 genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a CARD-3, CARD-4, CARD-5, or CARD-6 modulator, such as a modulator identified by one of the exemplary screening assays described herein.

4. Monitoring of Effects During Clinical Trials

Monitoring the influence of agents (e.g., drugs, compounds) on the expression or activity of CARD-3, CARD-4, CARD-5, or CARD-6 (e.g., the ability to modulate aberrant cell proliferation and/or differentiation) can be applied not only in basic drug screening, but also in clinical trials. For example, the effectiveness of an agent determined by a screening assay as described herein to increase CARD-3, CARD-4, CARD-5, or CARD-6 gene expression, protein levels, or upregulate CARD-3, CARD-4, CARD-5, or CARD-6 activity, can be monitored in clinical trails of subjects exhibiting decreased CARD-3, CARD-4, CARD-5, or CARD-6 gene expression, protein levels, or downregulated CARD-3, CARD-4, CARD-5, or CARD-6 activity. Alternatively, the effectiveness of an agent determined by a screening assay to decrease CARD-3, CARD-4, CARD-5, or CARD-6 gene expression, protein levels, or downregulated CARD-3, CARD-4, CARD-5, or CARD-6 activity, can be monitored in clinical trials of subjects exhibiting increased CARD-3, CARD-4, CARD-5, or CARD-6 gene expression, protein levels, or upregulated CARD-3, CARD-4, CARD-5, or CARD-6 activity. In such clinical trials, the expression or activity of CARD-3, CARD-4, CARD-5, or CARD-6 and, preferably, other genes that have been implicated in, for example, a cellular proliferation disorder can be used as a "read out" or markers of the immune responsiveness of a particular cell.

For example, and not by way of limitation, genes, including CARD-3, CARD-4, CARD-5, or CARD-6, that are modulated in cells by treatment with an agent (e.g., compound, drug or small molecule) which modulates CARD-3, CARD-4, CARD-5, or CARD-6 activity (e.g., identified in a screening assay as described herein) can be identified. Thus, to study the effect of agents on cellular proliferation disorders, for example, in a clinical trial, cells can be isolated and RNA prepared and analyzed for the levels of expression of CARD-3, CARD-4, CARD-5, or CARD-6 and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of CARD-3, CARD-4, CARD-5, or CARD-6 or other genes. In this way, the gene expression pattern can serve as a marker, indicative of the physiological response of the cells to the agent. Accordingly, this response state may be determined before, and at various points during, treatment of the individual with the agent.

In an embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a CARD-3, CARD-4, CARD-5, or CARD-6 protein, mRNA, or genomic DNA in the preadministration sample; (iii) obtaining one or more post-administration samples from the subject; (iv) detecting the level of expression or activity of the CARD-3, CARD-4, CARD-5, or CARD-6 protein, mRNA, or genomic DNA in the post-administration samples; (v) comparing the level of expression or activity of the CARD-3, CARD-4, CARD-5, or CARD-6 protein, mRNA, or genomic DNA in the pre-administration sample with the CARD-3, CARD-4, CARD-5, or CARD-6 protein, mRNA, or genomic DNA in the post administration sample or samples; and (vi) altering the administration of the agent to the subject accordingly. For example, increased administration of the agent may be desirable to increase the expression or activity of CARD-3, CARD-4, CARD-5, or CARD-6 to higher levels than detected, i.e., to increase the effectiveness of the agent. Alternatively, decreased administration of the agent may be desirable to decrease expression or activity of CARD-3, CARD-4, CARD-5, or CARD-6 to lower levels than detected, i.e., to decrease the effectiveness of the agent.

5. Transcriptional Profiling

The CARD-3, CARD-4, CARD-5, and CARD-6 nucleic acid molecules described herein, including small oligonucleotides, can be used in transcriptionally profiling. For example, these nucleic acids can be used to examine the expression of CARD-3, CARD-4, CARD-5, and CARD-6 in normal tissue or cells and in tissue or cells subject to a disease state, e.g., tissue or cells derived from a patient having a disease of interest or cultured cells which model or reflect a disease state of interest, e.g., cells of a cultured tumor cell line. By measuring expression of CARD-3, CARD-4, CARD-5, and CARD-6, together or individually, a profile of expression in normal and disease states can be developed. This profile can be used diagnostically and to examine the effectiveness of a therapeutic regime.

C. Methods of Treatment

The present invention provides for both prophylactic and therapeutic methods of treating a subject at risk of (or susceptible to) a disorder or having a disorder associated with aberrant CARD-3, CARD-4, CARD-5, or CARD-6 expression or activity, examples of which are provided herein.

1. Prophylactic Methods

In one aspect, the invention provides a method for preventing in a subject, a disease or condition associated with an aberrant CARD-3, CARD-4, CARD-5, or CARD-6 expression or activity, by administering to the subject an agent which modulates CARD-3, CARD-4, CARD-5, or CARD-6 expression or at least one CARD-3, CARD-4, CARD-5, or CARD-6 activity. Subjects at risk for a disease which is caused or contributed to by aberrant CARD-3, CARD-4, CARD-5, or CARD-6 expression or activity can be identified by, for example, any or a combination of diagnostic or prognostic assays as described herein. Administration of a prophylactic agent can occur prior to the manifestation of symptoms characteristic of the CARD-3, CARD-4, CARD-5, or CARD-6 aberrancy, such that a disease or disorder is prevented or, alternatively, delayed in its progression. Depending on the type of CARD-3, CARD-4, CARD-5, or CARD-6 aberrancy, for example, a CARD-3, CARD-4, CARD-5, or CARD-6 agonist or CARD-3, CARD-4, CARD-5, or CARD-6 antagonist agent can be used for treating the subject. The appropriate agent can be determined based on screening assays described herein. Activities of CARD-3, CARD-4, CARD-5, or CARD-6 that could be modulated for prophylactic purposes include, but are not limited to: 1) CARD-3, CARD-4, CARD-5, or CARD-6 gene or protein expression, for example, see Example 11 for a description of the mRNA expression pattern of human CARD-4; 2)CARD-3, CARD-4, CARD-5, or CARD-6 binding to a target protein, for example, see Examples 7, 8, 12, and 17 for a description of proteins known to bind to CARD-3, CARD-4, or CARD-5; 3) CARD-4 and CARD-5 regulation of NF-κB as described in Example 9 and 18; and 4) CARD-3 and CARD-4 enhancement of caspase 9 activity as described in Example 10.

2. Therapeutic Methods

Another aspect of the invention pertains to methods of modulating CARD-3, CARD-4, CARD-5, or CARD-6 expression or activity for therapeutic purposes. The modulatory method of the invention involves contacting a cell with an agent that modulates one or more of the activities of CARD-3, CARD-4, CARD-5, or CARD-6 protein activity associated with the cell. An agent that modulates CARD-3, CARD-4, CARD-5, or CARD-6 protein activity can be an agent as described herein, such as a nucleic acid or a protein, a naturally-occurring cognate ligand of a CARD-3, CARD-4, CARD-5, or CARD-6 protein, a peptide, a CARD-3, CARD-4, CARD-5, or CARD-6 peptidomimetic, or other small molecule. In one embodiment, the agent stimulates one or more of the biological activities of CARD-3, CARD-4, CARD-5, or CARD-6 protein. Examples of such stimulatory agents include active CARD-3, CARD-4, CARD-5, or CARD-6 protein and a nucleic acid molecule encoding CARD-3, CARD-4, CARD-5, or CARD-6 that has been introduced into the cell. In another embodiment, the agent inhibits one or more of the biological activities of CARD-3, CARD-4, CARD-5, or CARD-6 protein. Examples of such inhibitory agents include antisense CARD-3, CARD-4, CARD-5, or CARD-6 nucleic acid molecules and anti-CARD-3, CARD-4, CARD-5, or CARD-6 antibodies. These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant expression or activity of a CARD-3, CARD-4, CARD-5, or CARD-6 protein or nucleic acid molecule or a disorder related to CARD-3, CARD-4, CARD-5 or CARD-6 expression or activity. In one embodiment, the method involves administering an agent (e.g., an agent identified by a screening assay described herein), or combination of agents that modulates (e.g., upregulates or downregulates) CARD-3, CARD-4, CARD-5, or CARD-6 expression or activity. In another embodiment, the method involves administering a CARD-3, CARD-4, CARD-5, or CARD-6 protein or nucleic acid molecule as therapy to compensate for reduced or aberrant CARD-3, CARD-4, CARD-5, or CARD-6 expression or activity. Activities of CARD-3, CARD-4, CARD-5, or CARD-6 that could be modulated for therapeutic purposes include, but are not limited to, 1) CARD-3, CARD-4, CARD-5, or CARD-6 gene or protein expression, for example, see Example 11 for a description of the mRNA expression pattern of human CARD-4; 2)CARD-3, CARD-4, CARD-5, or CARD-6 binding to a target protein, for example, see Examples 7, 8, 12, and 17 for a description of proteins known to bind to CARD-3, CARD-4, or CARD-5; 3) CARD-4 or CARD-5 regulation of NF-κB as described in Examples 9 and 18; and 4) CARD-4 enhancement of caspase 9 activity as described in Example 10.

Stimulation of CARD-3, CARD-4, CARD-5, or CARD-6 activity is desirable in situations in which CARD-3, CARD-4, CARD-5, or CARD-6 is abnormally downregulated and/or in which increased CARD-3, CARD-4, CARD-5, or CARD-6 activity is likely to have a beneficial effect. Conversely, inhibition of CARD-3, CARD-4, CARD-5, or CARD-6 activity is desirable in situations in which CARD-3, CARD-4, CARD-5, or CARD-6 is abnormally upregulated, e.g., in myocardial infarction, and/or in which decreased CARD-3, CARD-4, CARD-5, or CARD-6 activity is likely to have a beneficial effect. Since CARD-4 and CARD-5 may be involved in the processing of cytokines, inhibiting the activity or expression CARD-4 or CARD-5 may be beneficial in patients that have aberrant inflammation.

This invention is further illustrated by the following examples which should not be construed as limiting. The contents of all references, patents and published patent applications cited throughout this application are hereby incorporated by reference.

EXAMPLES

Example 1

Isolation and Characterization of Full-length Human CARD-3 and CARD-4L/S cDNAs

A profile of known CARD domains was used to search databases of cDNA sequences and partial cDNA sequences using TBLASTN (Washington University; version 2.0, BLOSUM62 search matix). This search led to the identification of CARD-3. Using CARD-3 to search databases of cDNA sequences and partial cDNA sequences, another potential CARD cDNA was found. This cDNA sequence was used screen a human umbilical vein endothelial library (HUVE) and a clone containing the partial CARD-4S was identified. The human umbilical vein endothelial library was then rescreened using a probe designed against the partial CARD-4S sequence and a clone containing the CARD-4L sequence was identified.

Example 2
Characterization of CARD-3 AND CARD-4L/S Proteins

In this example, the predicted amino acid sequences of human CARD-3 and CARD-4L/S proteins were compared to amino acid sequences of known proteins and various motifs were identified. For example, the CARD domains of CARD-3 and CARD-4 were aligned (FIG. 7) with the CARD domains of ARC-CARD (SEQ ID NO:31), cIAP1-CARD (SEQ ID NO:32) and cIAP2-CARD (SEQ ID NO:33). In addition, the molecular weight of the human CARD-3 and CARD-4L/S proteins were predicted.

The human CARD-3 cDNA was isolated as described above (FIG. 1; SEQ ID NO:1) and encodes a 540 amino acid protein (FIG. 2: SEQ ID NO:2). CARD-3 also includes one predicted kinase domain (amino acid 1 to amino acid 300 of SEQ ID NO:2; SEQ ID NO:4), which is followed by a predicted linker domain (amino acid 301 to amino acid 431 of SEQ ID NO:2; SEQ ID NO:5) and a predicted CARD domain (amino acid 432 to amino acid 540 of SEQ ID NO:2; SEQ ID NO:6).

The human CARD-4L cDNA was isolated as described above (FIG. 3; SEQ ID NO:7) and has a 2859 nucleotide open reading frame (nucleotides 245–3103 of SEQ ID NO:7; SEQ ID NO:9) which encodes a 953 amino acid protein (FIG. 4; SEQ ID NO:8). CARD-4L protein has a predicted CARD domain (amino acids 15–114; SEQ ID NO:10). CARD-4L is also predicted to have a nucleotide binding domain which extends from about amino acid 198 to about amino acid 397 of SEQ ID NO:8; SEQ ID NO:11, a predicted Walker Box "A", which extends from about amino acid 202 to about amino acid 209 of SEQ ID NO:8; SEQ ID NO:12, a predicted Walker Box "B", which extends from about amino acid 280 to about amino acid 284, of SEQ ID NO:8; SEQ ID NO:13, a predicted kinase 1a (P-loop) domain, which extends from about amino acid 197 to about amino acid 212 of SEQ ID NO:8; SEQ ID NO:46, a predicted kinase 2 domain, which extends from about amino acid 273 to about amino acid 288 of SEQ ID NO:8; SEQ ID NO:47, a predicted kinase 3a subdomain, which extends from about amino acid 327 to about amino acid 338 of SEQ ID NO:8; SEQ ID NO:14, ten predicted Leucine-rich repeats which extend from about amino acid 674 to about amino acid 950 of SEQ ID NO:8. The first Leucine-rich repeat is predicted to extend from about amino acid 674 to about amino acid 701 of SEQ ID NO:8; SEQ ID NO:15. The second Leucine-rich repeat is predicted to extend from about amino acid 702 to about amino acid 727 of SEQ ID NO:8; SEQ ID NO:16. The third Leucine-rich repeat is predicted to extend from about amino acid 728 to about amino acid 754 of SEQ ID NO:8; SEQ ID NO:17. The fourth Leucine-rich repeat is predicted to extend from about amino acid 755 to about amino acid 782 of SEQ ID NO:8; SEQ ID NO:18. The fifth Leucine-rich repeat is predicted to extend from about amino acid 783 to about amino acid 810 of SEQ ID NO:8; SEQ ID NO:19. The sixth Leucine-rich repeat is predicted to extend from about amino acid 811 to about amino acid 838 of SEQ ID NO:8; SEQ ID NO:20. The seventh Leucine-rich repeat is predicted to extend from about amino acid 839 to about amino acid 866 of SEQ ID NO:8; SEQ ID NO:21. The eighth Leucine-rich repeat is predicted to extend from about amino acid 867 to about amino acid 894 of SEQ ID NO:8; SEQ ID NO:22. The ninth Leucine-rich repeat is predicted to extend from about amino acid 895 to about amino acid 922 of SEQ ID NO:8; SEQ ID NO:23 and the tenth leucine-rich repeat is predicted to extend from about amino acid 923 to about amino acid 950 of SEQ ID NO:8; SEQ ID NO:24.

The human partial CARD-4S cDNA isolated as described above (FIG. 5; SEQ ID NO:25) encodes a 490 amino acid protein (FIG. 6; SEQ ID NO:26). CARD-4S includes one predicted partial CARD domain (amino acids 1–74 of SEQ ID NO:26). CARD-4S is also predicted to have a P-Loop which extends from about amino acid 163 to about amino acid 170 of SEQ ID NO:26; SEQ ID NO:29, and a predicted Walker Box "B" which extends form about amino acid 241 to about amino acid 245 of SEQ ID NO:26; SEQ ID NO:30.

A plot showing the predicted structural features of CARD-4L is presented in FIG. 8. This figure shows the predicted alpha regions (Garnier-Robinson and Chou-Fasman), the predicted beta regions (Garnier-Robinson and Chou-Fasman), the predicted turn regions (Garnier-Robinson and Chou-Fasman) and the predicted coil regions (Garnier-Robinson and Chou-Fasman). Also included in the figure is a hydrophilicity plot (Kyte-Doolittle), the predicted alpha and beta-amphatic regions (Eisenberg), the predicted flexible regions (Karplus-Schulz), the predicted antigenic index (Jameson-Wolf) and the predicted surface probability plot (Emini).

A plot showing the predicted sturctural features of CARD-4S is also presented in FIG. 9. This figure shows the predicted alpha regions (Garnier-Robinson and Chou-Fasman), the predicted beta regions (Garnier-Robinson and Chou-Fasman), the predicted turn regions (Garnier-Robinson and Chou-Fasman) and the predicted coil regions (Garnier-Robinson and Chou-Fasman). Also included in the figure is a hydrophilicity plot (Kyte-Doolittle), the predicted alpha and beta-amphatic regions (Eisenberg), the predicted flexible regions (Karplus-Schulz), the predicted antigenic index (Jameson-Wolf) and the predicted surface probability plot (Emini).

The predicted MW of CARD-3 is approximately 61 kDa. The predicted MW of CARD-4L is approximately 108 kDa.

Example 3

Preparation of CARD-3 and CARD-4 Proteins

Recombinant CARD-3 and CARD-4 can be produced in a variety of expression systems. For example, the CARD-3 and CARD-4 peptides can be expressed as a recombinant glutathione-S-transferase (GST) fusion protein in *E. coli* and the fusion protein can be isolated and characterized. Specifically, as described above, CARD-3 or CARD-4 can be fused to GST and the fusion protein can be expressed in *E. coli* strain PEB199. Expression of the GST-CARD-3 or GST-CARD-4 fusion protein in PEB199 can be induced with IPTG. The recombinant fusion protein can be purified from crude bacterial lysates of the induced PEB199 strain by affinity chromatography on glutathione beads.

Example 4

Identification of Splice Variants of CARD-4

The 5' untranslated sequence from CARD-4L was used to search databases of cDNA sequences and partial cDNA sequences using BLASTN (Washington University; version 2.0, BLOSUM62 search matrix) for additional CARD-4 cDNA clones. This search led to the identification of two cDNA clones, clone Z from a human lymph node library and the Y clone from a human brain cDNA library. Both clones were sequenced and found to represent probable splice variants of CARD-4 that encode truncated CARD-4 proteins, Y encoding a 249 amino acid protein and Z encoding a 164 amino acid protein. FIG. 10 shows the nucleotide (SEQ ID NO:38) and FIG. 11 the predicted amino acid (SEQ ID NO:39) sequences of human CARD-4Y; FIG. 12 shows the nucleotide (SEQ ID NO:40) and FIG. 13 the amino acid (SEQ ID NO:41) sequences of human CARD-4Z; and FIG. 14 shows an alignment of the CARD-4L, CARD-4Y, and CARD-4Z amino acid sequences generated by the Clustal program using a PAM250 residue weight table.

Example 5

Identification of Murine CARD-4

The CARD-4 polypeptide sequence was used to search databases of cDNA sequences and partial cDNA sequences using the TBLASTN program (version 1.4, BLOSUM62 search matrix, and a word length of 3) for murine CARD-4 cDNA clones. This search led to the identification of a partial murine CARD-4 clone designated murine CARD-4L. The rapid identification of cDNA ends procedure (RACE) was applied to the 5' end of the murine CARD-4L clone to elucidate the 5' end of the murine CARD-4L cDNA. FIG. 15 shows the murine CARD-4L nucleotide sequence(SEQ ID NO:42), FIG. 16 shows the murine CARD-4L amino acid sequence (SEQ ID NO:43), and FIG. 17 shows an alignment of the murine CARD-4L and human CARD-4L amino acid sequences generated by the Clustal program using a PAM250 residue weight table.

Example 6

Identification of the Chromosomal Location of Human CARD-4

To determine the chromosomal location of the human CARD-4 gene, the polymerase chain reaction carried out with human CARD-4-specific primers card4t, with the 5' to 3' sequence agaaggtctggtcggcaaa (SEQ ID NO:44), and card4k, with the 5' to 3' sequence aagccctgagtggaagca (SEQ ID NO:45), was used to screen DNAs from a commercially available somatic cell hybrid panel. This analysis showed that human CARD-4 maps to chromosome 7 close to the SHGC-31928 genetic marker.

Example 7

Identification of CARD-3 in a Yeast Two-hybrid Screen for Proteins that Physically Interact with the CARD Domain of Human CARD-4

DNA encoding amino acids 1–145 of human CARD-4 comprising the CARD domain was cloned into a yeast two-hybrid screening vector to create a CARD-4, 1–145-GAL4 DNA-binding domain fusion for two-hybrid screening. The CARD-4, 1–145-GAL4 DNA-binding domain fusion was used to screen human mammary gland and human prostate two-hybrid libraries for gene products that could physically associate with CARD-4, 1–145. Twelve library plasmids expressing CARD4, 1–145 interacting proteins were found to contain the CARD-domain containing protein CARD-3 thus establishing a direct or indirect physical interaction between CARD-4 and CARD-3.

In addition, DNA encoding amino acids 435–540 of CARD-3 comprising the CARD domain of CARD-3 (SEQ ID NO:6) was cloned into a yeast two-hybrid GAL4 transcriptional activation domain fusion vector to create a CARD-3, 435–540-GAL4 transcriptional activation domain fusion. To test whether the CARD domain of CARD-3 binds CARD-4, 1–145, the CARD-3, 435–540-GAL4 transcriptional activation domain fusion expression vector and the CARD-4, 1–145-GAL4 DNA-binding domain fusion vector were cotransformed into a two-hybrid screening *Saccharomyces cerevisiae* (yeast) strain. The resulting cotransformed yeast strain expressed the two reporter genes that indicate a physical interaction between the two hybrid proteins in the experiment, in this case, the CARD-3, 435–540-GAL4 transcriptional activation domain fusion protein and the CARD-4, 1–145-GAL4 DNA-binding domain fusion protein. This experiment established a physical interaction between the CARD domain of CARD-3 and the CARD domain of CARD-4.

Example 8

Identification of hNUDC in a Yeast Two-hybrid Screen for Proteins that Physically Interact with the LRR Domain of Human CARD-4

DNA encoding amino acids 406–953 of human CARD-4L comprising the LRR domain was cloned into a yeast two-hybrid screening vector to create a CARD-4, 406–953-GAL4 DNA-binding domain fusion for two-hybrid screening. The CARD-4, 406–953-GAL4 DNA-binding domain fusion was used to screen a human mammary gland two-hybrid library for gene products that could physically associate with CARD-4, 406–953. One library plasmid expressing a CARD-4, 406–953 interacting protein was found to contain the hNUDC protein, the human ortholog of the rat NUDC protein that has been implicated in nuclear movement (Morris et al., Curr. Biol. 8:603 [1998], Morris et al., Exp. Cell Res. 238:23 [1998]), thus establishing a physical interaction between CARD-4 and hNUDC.

Example 9

Discovery of Regulation by CARD-4 of NF-κB

The first group of experiments described in this Example were carried out to determine if CARD-4 can activate the NF-κB pathway. CARD-4 regulation of the NF-κB pathway is of interest because the NF-κB pathway is involved in many diseases described in (New England Journal of Medicine 336:1066 [1997]) and (American Journal of Cardiology 76:18C [1995]) and other references known to those skilled in the art. Participation of CARD-4 in the NF-κB pathway would make CARD-4 an attractive target for drugs that modulate the NF-κB pathway for treatment of NF-κB pathway-dependent diseases, conditions, and biological processes.

The first group of experiments showed specific CARD-4-mediated NF-κB pathway induction.

The second group of experiments described in this Example were carried out to determine if CARD-3, the NIK serine/threonine protein kinase (Su et al., EMBO J. 16:1279 [1997]), or the signal transduction protein TRAF6 (Cao et al., Nature 383:443[1996]), proteins known to participate in the induction of NF-κB (McCarthy et al., J. Biol. Chem. 273:16968 [1998]), are involved in transducing the CARD-4-dependent NF-κB pathway induction signal. It was found that CARD-3, NIK, and TRAF6 are all involved in transducing the CARD-4-mediated NF-κB pathway induction signal.

In nine transfection experiments, 293T cells coexpressing an NF-κB reporter plasmid and either pCI, pCI-CARD-4L (expressing CARD-4L), pCI-CARD-4S (expressing CARD-4S), pCI-APAFL (expressing Apaf-1), pCI-APAFS (expressing an Apaf-1 variant lacking WD repeats), pCI-CARD-4LnoCARD (expressing CARD-4L without a CARD domain), pCI-CARD4LnoLRR (expressing CARD-4L without a LRR), pCI-CARD4LCARDonly (expressing CARD-4L CARD domain only), or pCI-CARD4NBSonly (expressing CARD-4L nucleotide binding sequence only) were created. 293T cells cells were plated in 6 well plates (35 mm wells) and transfected 2 days later (90% confluency) with 1 μg of NF-κB luciferase reporter plasmid (pNF-κB-Luc, Stratagene), 200 ng of pCMV β-gal, 600 ng of pCI vector and 200 ng of indicated expression plasmids using SuperFect transfection reagent (Qiagen). For dominant-negative experiments, 2 ng of CARD4 expressing plasmid and 800 ng of dominant-negative plasmid were used. Cells were harvested 48 h after transfection and luciferase activity in 1000-fold diluted cell extracts was determined using the Luciferase Assay System (Promega). In addition, β-galactosidase activities were determined and used to normalize transfection efficiency.

Relative luciferase activity was determined at the end of the experiment to assess NF-κB pathway activation by the gene expressed by the pCI-based plasmid in each transfected cell line. The cell lines containing pCI, pCI-APAFS, pCI-APAFL, pCI-CARD-4LnoCARD, and pCI-CARD4NBSonly had similar baseline levels of luciferase expression but the cell lines containing pCI-CARD-4L, pCI-CARD4LnoLRR, and pCI-CARD4LCARDonly had luciferase expression about nine fold elevated relative to baseline and the cell line containing pCI-CARD4S had luciferase expression sixteen fold elevated relative to baseline. This result demonstrates induction by CARD-4S and CARD-4L of the NF-κB pathway. This CARD-4 mediated NF-κB pathway induction is dependent on the CARD-4 CARD domain because the pCI-CARD-4noCARD construct expressing CARD-4 lacking its CARD domain did not induce the luciferase reporter gene and pCI-CARD4LCARDonly expressing the CARD-4 CARD domain did induce the luciferase reporter gene. Also, the CARD-4 LRR domains are not required for NF-κB pathway activation because pCI-CARD4LnoLRR expressing a CARD-4 mutant protein lacking LRR domains is able to induce the luciferase reporter gene. In addition, the CARD-4 NBS domain is not sufficient for NF-κB pathway activation because pCI-CARD4NBSonly expressing CARD-4 NBS domain is not able to induce the luciferase reporter gene. In addition, the induction of the NF-κB pathway by CARD-4 is specific, as neither Apaf-expressing construct in this experiment induced luciferase activation.

In five transfection experiments, 293T cells coexpressing an NF-κB reporter plasmid (NF-κB-luciferase, Stratagene) and pCI-CARD-4L and either, no vector, pCI-TRAF6-DN (expressing a dominant negative version of TRAF-6), pCI-NIK-DN (expressing a dominant negative version of NIK kinase), pCI-CARD3CARDonly (expressing the CARD domain of CARD-3, which acts as a dominant negative version of CARD-3), or pCI-Bcl-XL (expressing the anti-apoptotic protein Bcl-XL) were created. TRAF6-DN, NIK-DN, and CARD3-CARDonly are dominant negative alleles of the TRAF6, NIK, and CARD3 genes, respectively. After 48 hours, cells were lysed and the relative luciferase activity was determined (Promega Kit) to assess NF-κB pathway activation by the genes expressed by the one or two pCI-based plasmids in each transfected cell line. The cell lines containing pCI-CARD-4L only or pCI-CARD-4L and pCI-Bcl-XL had relative luciferase reporter gene expression of about 18 units. The cell lines containing pCI-CARD-4L and pCI-TRAF6-DN, pCI-CARD-4L and pCI-NIK-DN, or pCI-CARD-4L and pCI-CARD3CARDonly had relative luciferase reporter gene expression of about 4 units. Inhibition of CARD-4L-mediated NF-κB pathway induction by TRAF6-DN, NIK-DN, and CARD-3CARDonly is specific as Bcl-XL did not inhibit CARD-4L-mediated NF-κB pathway induction.

These results demonstrate that dominant negative alleles of TRAF6, NIK and CARD-3 expressed, respectively, from pCI-TRAF6-DN, pCI-NIK-DN, and pCI-CARD3CARDonly block induction of the NF-κB reporter gene by CARD-4L expression (pCI-CARD-4L) and suggest that TRAF6, NIK, and CARD-3 act downstream of CARD-4L to transduce the CARD-4L NF-κB pathway induction stimulus.

In an additional experiment, coexpression of CARD-4 and the CARD domain of CARD-3 revealed that the CARD domain of CARD-3 functions as a dominant negative mutant suggesting that CARD-3 is a downstream mediator of CARD-4 function.

Example 10

Discovery of CARD-4 Enhancement of Caspase-9 Activity

In ten transfection experiments, 293T cells coexpressing a beta galactosidase-expressing plasmid (pCMV β-gal from Stratagene) as a marker for viable cells and either pCI, pCI-CARD-3, pCI-APAF, pCI-CARD-4L, pCI-CARD-4S, pCI-CARD4LnoLRR, pCI-CARD4NBSonly, pCI-CARD4LCARDonly, pCI-CARD-4LnoCARD or pCI-casp9 (expressing caspase-9) were created. Transfections included 400 ng of pCMV β-gal, 800 ng of expression plasmid, and Superfect transfection reagent from Qiagen and were carried out according to the manufacturer's directions. After 40–48 hours, cells were fixed and stained for beta-galactosidase expression and cell viability was determined by counting the number of beta galactosidase positive cells. Expression of pCI, pCI-CARD-3, pCI-APAF, pCI-CARD-4L, pCI-CARD-4S, pCI-CARD4LnoLRR, pCI-CARD4NBSonly, pCI-CARD4LCARDonly, and pCI-CARD-4LnoCARD did not result in loss of cell viability. As expected, expression of pCI-casp9 in 293T cells resulted in a loss of viability of about 75% of the cells in the experiment.

It was next tested whether pCI, pCI-CARD-3, pCI-APAF, pCI-CARD-4L, pCI-CARD-4S, pCI-CARD4LnoLRR, pCI-CARD4NBSonly, pCI-CARD4LCARDonly, or pCI-CARD-4LnoCARD would regulate caspase 9-mediated apoptosis. In nine transfection experiments, 293T cells coexpressing a beta galactosidase-expressing plasmid as a marker for viable cells, pCI-casp9, and either pCI, pCI-CARD-3, pCI-APAF, pCI-CARD-4L, pCI-CARD-4S, pCI-CARD4LnoLRR, pCI-CARD4NBSonly, pCI-CARD4LCARDonly, and pCI-CARD-4LnoCARD were created. After 40–48 hours, cells were fixed and stained for beta-galactosidase expression and cell viability was determined by counting the number of beta galactosidase positive cells. Expression of pCI, pCI-CARD-4LnoCARD, and pCI-CARD4NBSonly in the caspase 9-expressing 293T cells had no effect on the caspase 9-induced apoptosis. However, pCI-CARD-3, pCI-CARD-4L, pCI-CARD-4S, pCI-CARD4LnoLRR, pCI-CARD4LCARDonly and, as expected, pCI-APAF enhanced the level of caspase 9-induced apoptosis to 20 or less beta galactosidase positive cells per experiment from about 100 beta glactosidase positive cells per experiment.

This experiment demonstrated that CARD-4 can enhance caspase 9-mediated apoptosis because coexpression of CARD-4L or CARD-4S with caspase-9 dramatically increases caspase-9 mediated apoptosis. Furthermore, the CARD-4 CARD domain (SEQ ID NO:10) is necessary and sufficient for CARD-4-mediated enhancement of caspase-9-potentiated apoptosis because CARD-4L lacking its CARD domain (pCI-CARD-4LnoCARD) does not enhance caspase-9-mediated apoptosis while the CARD-4 CARD domain expressed alone (pCI-CARD4LCARDonly) does induce caspase-9 mediated apoptosis. In addition, the LRR present in CARD-4 is not required for CARD-4 enhancement of caspase-9-mediated apoptosis because expression of a CARD-4 protein lacking the LRR (pCI-CARD4LnoLRR) still enhances caspase-9-mediated apoptosis. The CARD-4 NBS is not sufficient for CARD-4 enhancement of caspase-9-mediated apoptosis because expression of the CARD-4 NBS only (pCI-CARD4NBSonly) does not enhance caspase-9 mediated apoptosis. This experiment also demonstrates that CARD-3 can enhance caspase-9-mediated apoptosis.

As detailed below in Example 12, CARD-4 does not appear to interact directly with caspase-9, suggesting that potentiation of caspase-9 activity by CARD-4 is mediated by activation of downstream pathways.

Example 11
Identification and Tissue Distribution of mRNA Species Expressed by the Human CARD-4 Gene Northern analysis of mRNAs extracted from adult human tissues revealed a 4.6 kilobase mRNA band that was expressed in most tissues examined. Highest expression was observed heart, spleen, placenta and lung. CARD-4 was also observed to be expressed in fetal brain, lung, liver and kidney. Cancer cell lines expressing the 4.6 kilobase CARD-4 mRNA include HeLa, K562, Molt4, SW480, A549 and melanoma. A larger 6.5 to 7.0 kilobase CARD-4 mRNA was expressed in heart, spleen, lung, fetal lung, fetal liver, and in the Molt4 and SW480 cell lines.

Example 12
Physical Association of CARD-4 with CARD-3

CARD-4-specific PCR primers with the 3' primer encoding the HA epitope tag were used to amplify the CARD-4L gene epitope tagged with HA and this PCR product was cloned into the mammalian expression vector pCI. CARD-3-specific PCR primers with the 5' primer encoding the MYC epitope tag were used to amplify the CARD-3 gene epitope tagged with MYC and this PCR product was cloned into the mammalian expression vector pCI. CARD-3-specific PCR primers with the 5' primer encoding the MYC epitope tag were used to amplify the CARD-3 gene lacking the CARD domain (SEQ ID NO:6) epitope tagged with MYC and this PCR product was cloned into the mammalian expression vector pCI. Caspase 9-specific PCR primers with the 3' primer encoding the MYC epitope tag were used to amplify the caspase 9 gene epitope tagged with MYC and this PCR product was cloned into the mammalian expression vector pCI. In three transfection experiments, 293T cells coexpressing pCI-CARD-4LcHA and either pCI-CARD3nMYC, pCI-CARD3noCARDnMYC, or pCI-casp9cMYC were created. Cells from each transfected line were lysed and an immunoprecipitation procedure was carried out on each lysate with an anti-MYC epitope tag antibody to precipitate the CARD-4LcHA expressed by each cell line and any physically associated proteins. Immunoprecipitated proteins were separated by electrophoresis on denaturing polyacrylamide gels, transferred to nylon filters, and probed with an anti-HA epitope tag antibody in a Western blotting experiment to determine whether the MYC-tagged protein that was coexpressed with the CARD-4LcHA protein had coimmunoprecipitated with the CARD-4LcHA protein. In this experiment, CARD-3 was found to coimmunoprecipitate with CARD-4 while CARD-3 lacking its CARD domain and caspase-9 did not coimmunoprecipitate with CARD-4. This experiment demonstrates that CARD-4 and CARD-3 physically associate and that CARD-3 requires its CARD domain to associate with CARD-4. In addition, CARD-4 appears to not associate with caspase-9.

Example 13
CARD-4 Genomic Sequence

FIG. 18 is depicts the 32042 nucleotide genomic sequence of CARD-4 (SEQ ID NO:63). This sequence is based the CARD-4 cDNA sequence described above and a BAC sequence (DBEST Accession No. AC006027). The CARD-4 cDNA sequence described above was used to correct three errors in the BAC sequence, including one error resulting in a frameshift. The CARD-4 genomic sequence of FIG. 18 includes the following introns and exons: exon 1: nucleotides 364–685, encoding amino acids 1–67 (start codon at nucleotides 485–487); intron 1: nucleotides 686–2094; exon 2: nucleotides 2095–2269, encoding amino acids 67–126; intron 2: nucleotides 2270–4365; exon 3: nucleotides 366–6190, encoding amino acids 126–734; intron 3: nucleotides 6191–9024; exon 4: nucleotides 9025–9108, encoding amino acids 734–762; intron 4: nucleotides 9109–10355; exon 5: nucleotides 10356–10439, encoding amino acids 762–790; intron 5: nucleotides 10440–11181; exon 6: nucleotides 1182–11265, encoding amino acids 790–818; intron 6: nucleotides 11266–19749; exon 7: nucleotides 19750–19833, encoding amino acids 818–846; intron 7: nucleotides 19834–21324; exon 8: nucleotides 21325–21408, encoding amino acids 846–874; intron 8: nucleotides 21409–24226; exon 9: nucleotides 24227–24310, amino acids 874–903; intron 9: nucleotides 24311–27948; exon 10: nucleotides 27949–28032, amino acids 903–930; intron 10: nucleotides 28033–31695; exon 11: nucleotides 31696–32024, encoding amino acids 930–953 (stop codon at nucleotides 31766–31768).

The introns in the CARD-4 genomic sequence contain consensus splice donor and acceptor sites (Molecular Cell Biology, Darnell et al., eds.,1996). The CARD-4 genomic sequence is usful for genetic identification and mapping and identifying mutations, e.g., mutations is splice donor or splice acceptor sites.

Example 14
Isolation and Characterization of Full-length Murine CARD-5 and Human CARD-5

The amino acid sequence of the CARD domain of RAIDD (amino acids 1 to 94) was used to search a proprietary murine cDNA sequence database using the BLASTX program with the BLOSUM62 matrix and a protein word length of three. This search led to the identification of a murine clone, jtmaa010ht2, present in a coronary artery smooth muscle cell library. This clone encodes a protein designated CARD-5. The 761 nucleotide murine CARD-5 cDNA of SEQ ID NO:60 has a 579 nucleotide open reading frame (SEQ ID NO:62) encoding a 193 amino acid protein (SEQ ID NO:61). The cDNA and protein sequences of murine CARD-5 are shown in FIG. 19.

Murine CARD-5 is predicted to be an intracellular protein having a molecular weight of 21.4 kDa prior to post-translational modification.

Figure 20:
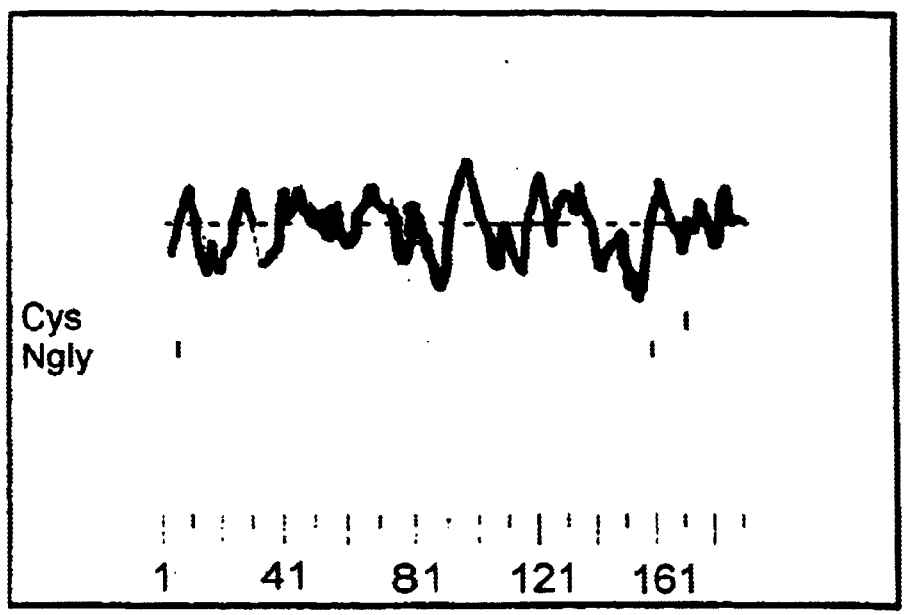
FIG. 20 depicts a hydropathy plot of murine CARD-5. Relatively hydrophobic residues are above the dashed horizontal line, and relatively hydrophilic residues are below the dashed horizontal line. The cysteine residues (cys) and potential N-glycosylation sites (Ngly) are indicated by short vertical lines just below the hydropathy trace.

FIG. 20 depicts a hydropathy plot of murine CARD-5. Relatively hydrophobic residues are above the dashed horizontal line, and relatively hydrophilic residues are below the dashed horizontal line. The cysteine residues (cys) and potential N-glycosylation sites (Ngly) are indicated by short vertical lines just below the hydropathy trace.

The murine CARD-5 nucleotide sequence was used to search a proprietary database of human cDNA sequences. This search led to the identification of a human CARD-5 cDNA clone, jthza027g11t1, present in a testes library.

The 740 nucleotide murine CARD-5 cDNA of SEQ ID NO:48 has a 585 nucleotide open reading frame (SEQ ID NO:50) encoding a 195 amino acid protein (SEQ ID NO:49). The cDNA and protein sequences of human CARD-5 are shown in FIG. 21.

Human CARD-5 is predicted to be an intracellular protein having a molecular weight of 21.6 kDa prior to post-translational modification.

Figure 22:
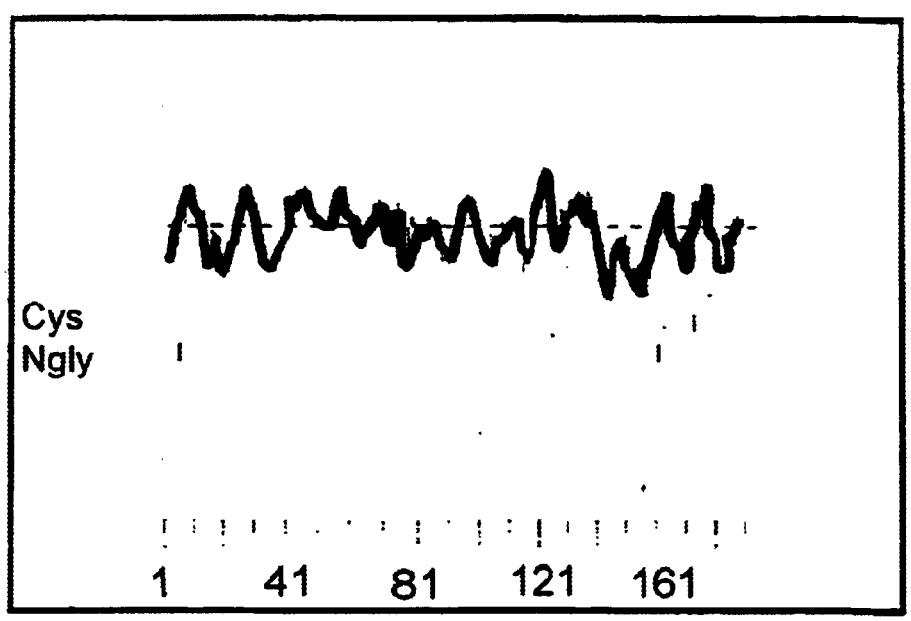
FIG. 22 depicts a hydropathy plot of human CARD-5. Relatively hydrophobic residues are above the dashed horizontal line, and relatively hydrophilic residues are below the dashed horizontal line. The cysteine residues (cys) and potential N-glycosylation sites (Ngly) are indicated by short vertical lines just below the hydropathy trace.

FIG. 22 depicts a hydropathy plot of human CARD-5. Relatively hydrophobic residues are above the dashed horizontal line, and relatively hydrophilic residues are below the dashed horizontal line. The cysteine residues (cys) and potential N-glycosylation sites (Ngly) are indicated by short vertical lines just below the hydropathy trace.

FIG. 23 depicts an alignment of the cDNA sequences of murine (SEQ ID NO:60) and human (SEQ ID NO:48) CARD-5. In this alignment the sequences are 68.2% identical. FIG. 24 depicts an alignment of the amino acid sequences of murine (SEQ ID NO:61) and human (SEQ ID NO:49) CARD-5. In this alignment the sequences are 71.8% identical.

Both murine and human CARD-5 include a CARD domain. The CARD domain of murine CARD-5 extends from amino acid 110 to 179 of SEQ ID NO:61 (SEQ ID NO:57). The CARD domain of human CARD-5 extends from amino acid 111 to 181 of SEQ ID NO:49 (SEQ ID NO:58). FIG. 27 depicts an alignment of the CARD domains of murine CARD-5 (SEQ ID NO:57), human CARD-5 (SEQ ID NO:58), and RAIDD (SEQ ID NO:70).

Example 15

Isolation and Characterization of Full-length Rat CARD-6 and Human CARD-6

A generalized CARD domain model was used to search a proprietary rat cDNA sequence database. This search led to the identification of a rat cDNA clone present in a sciatic nerve cDNA library. This clone encodes a protein desigated CARD-6. The 5252 nucleotide rat CARD-6 cDNA of SEQ ID NO:51 has a 2715 nucleotide open reading frame (SEQ ID NO:53) encoding a 905 amino acid protein (SEQ ID NO:52). The cDNA and protein sequences of rat CARD-6 are shown in FIG. 25. Rat CARD-6 is predicted to be an intracellular protein having a molecular weight of 100.2 kDa prior to post-translational modification.

Figure 26:
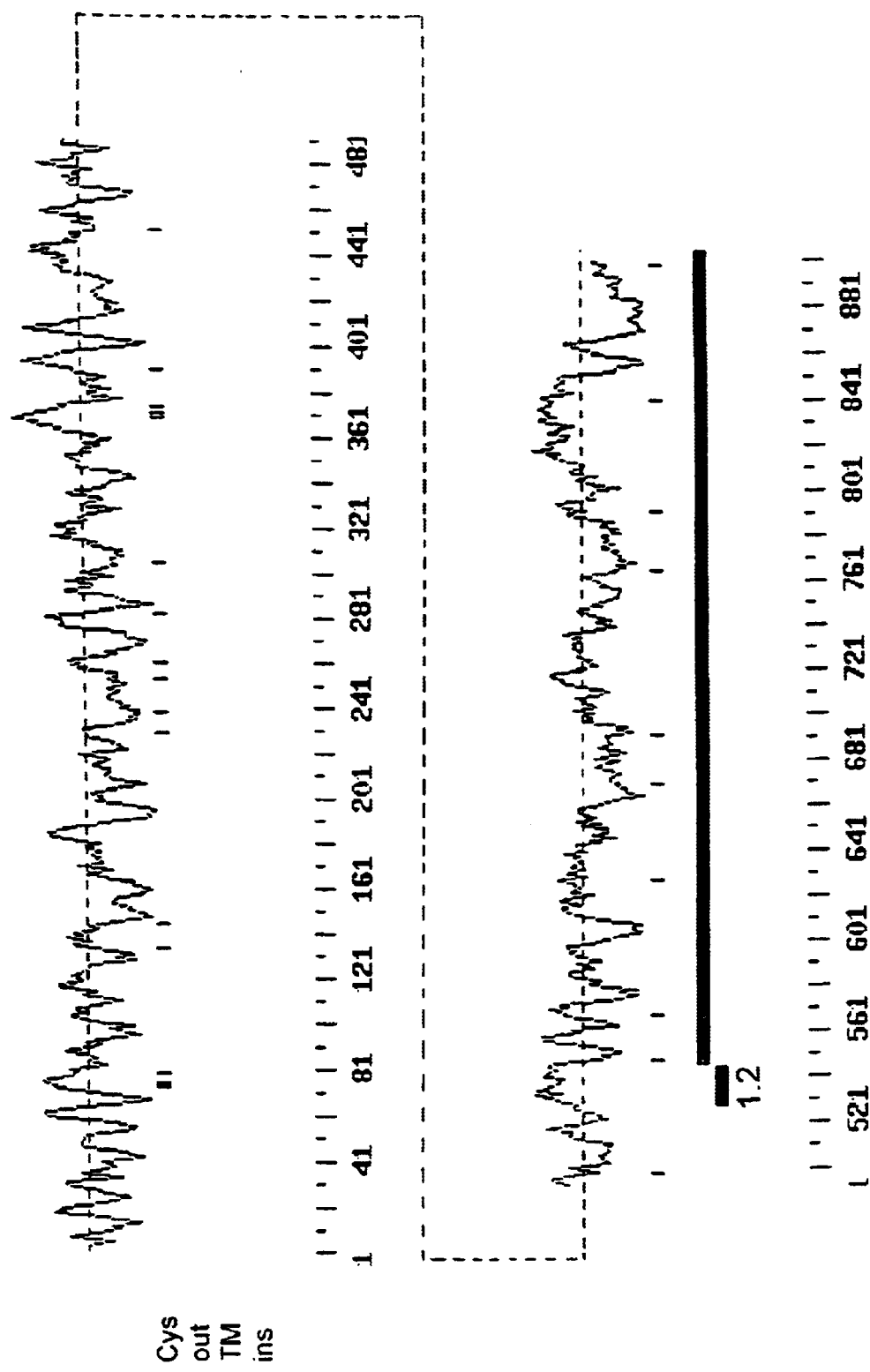
FIG. 26 depicts a hydropathy plot of rat CARD-6. Relatively hydrophobic residues are above the dashed horizontal line, and relatively hydrophilic residues are below the dashed horizontal line. The cysteine residues (cys) and potential N-glycosylation sites (Ngly) are indicated by short vertical lines just below the hydropathy trace.

FIG. 26 depicts a hydropathy plot of rat CARD-6. Relatively hydrophobic residues are above the dashed horizontal line, and relatively hydrophilic residues are below the dashed horizontal line. The cysteine residues (cys) and potential N-glycosylation sites (Ngly) are indicated by short vertical lines just below the hydropathy trace.

Rat CARD-6 contains a CARD domain which extends from amino acid 1 to amino acid 108 of SEQ ID NO:52 (SEQ ID NO:59). Rat CARD-6 also has a proline-rich c-terminus which extends from amino acid 698 to amino acid 905 of SEQ ID NO:52 (SEQ ID NO:65). This proline-rich domain includes five putative SH3 binding sites. These binding sites have the sequence PXXP and are located at amino acids 710 to 713 (PAHP), 806 to 809 (PLRP), 819 to 822 (PIPP), 857 to 860 (PPHP), and 881 to 884 (PSQP) of SEQ ID NO:52.

The rat CARD-6 cDNA sequence described above was used to search a proprietary sequence database. This search led to the identification of a clone from a human muscle cell library encoding a carboxy-terminal portion of human CARD-6. A probe designed based on the sequence of this clone was used to screen a human adrenal gland library. This screening led to the identification of a clone encoding an amino-terminal portion of human CARD-6. The clone encoding an amino terminal portion of human CARD-6 contains a region encoding a CARD domain. This CARD domain-encoding sequence was used to screen a proprietary database. This screening led to the identification of a clone, jthAb086d02, present in an adrenal gland library, which encodes full length human CARD-6.

The 4244 nucleotide human CARD-6 cDNA of SEQ ID NO:54 has a 3111 nucleotide open reading frame (SEQ ID NO:56) encoding a 1037 amino acid protein (SEQ ID NO:55). The cDNA and protein sequences of human CARD-6 are shown in FIG. 28.

N-glycosylation sites are present at amino acids 49–52, 415–418, and 812–815 of SEQ ID NO:55. Human CARD-6 contains cAMP and cGMP-dependent protein kinase phosphorylation sites at amino acids 151–154 and 429–432 of SEQ ID NO:55. Protein kinase C phosphorylation sites are present at amino acids 34–36, 57–59, 135–137, 154–156, 161–163, 298–300, 339–341, 346–348, 443–445, 664–666, 693–695, 746–748, 882–884, 905–907 and 951–953 of SEQ ID NO:55. Casein kinase II phosphorylation sites are present at amino acids 6–9, 28–31, 40–43, 112–115, 135–138, 154–157, 278–281, 321 324, 339–342, 354–357, 642–645, 670–673, and 707–710 of SEQ ID NO:55. Tyrosine kinase phosphorylation sites are present at amino acids 37–34 and 163–169 of SEQ ID NO:55. An ATP/GTP-binding site motif A (P-loop) site is present at amino acids 775–782 of SEQ ID NO:55.

Figure 29:
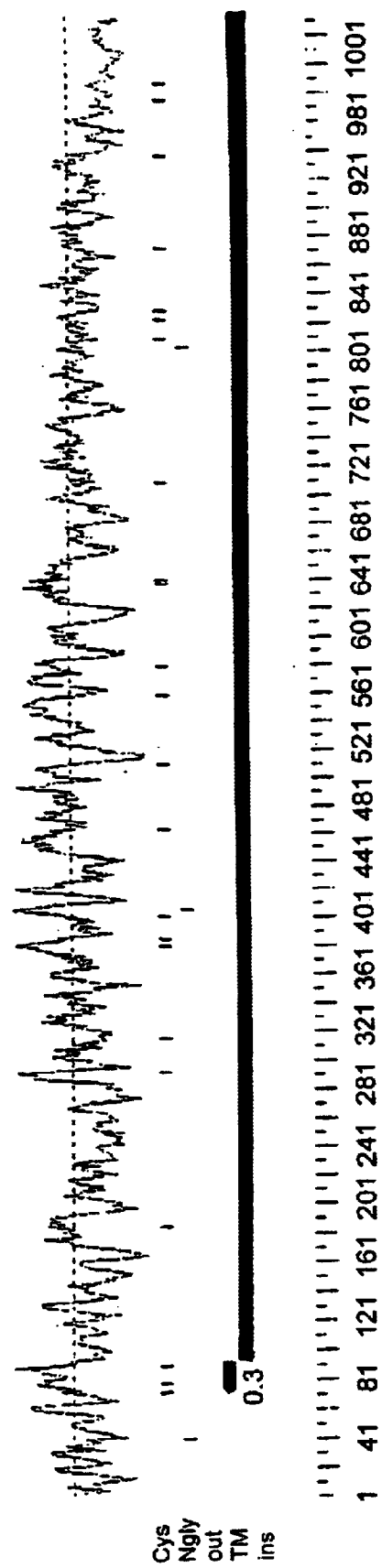
FIG. 29 depicts a hydropathy plot of human CARD-6. Relatively hydrophobic residues are above the dashed horizontal line, and relatively hydrophilic residues are below the dashed horizontal line.
Figure 31:
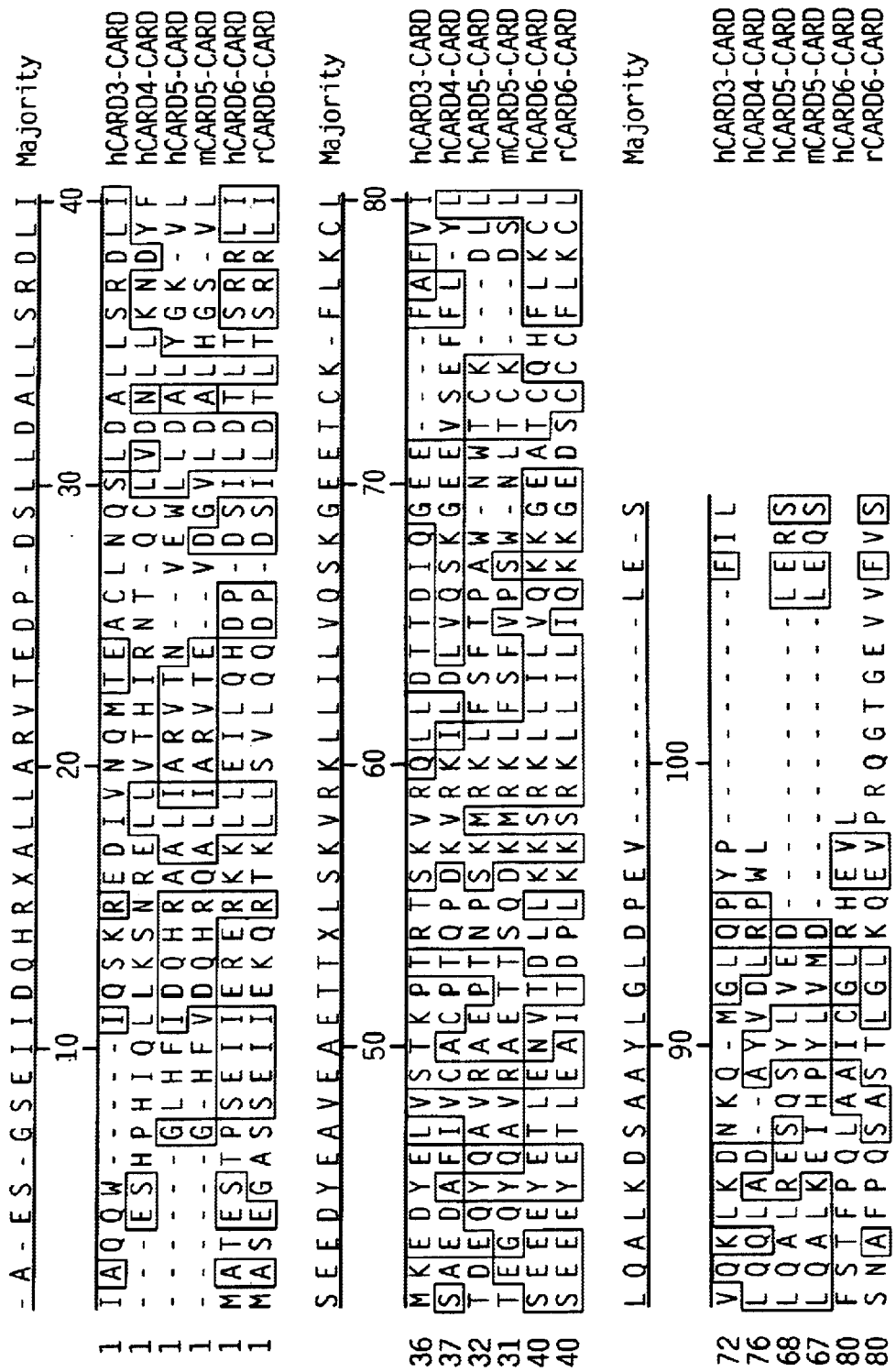
FIG. 31 depicts an alignment of the CARD domains of human CARD-3, human CARD-4, human CARD-5, murine CARD-5, human CARD-6, and rat CARD-6. This alignment was created using the Clustal method with PAM250 residue weight table. A consensus sequence is also depicted (SEQ ID NO:71).

FIG. 29 depicts a hydropathy plot of human CARD-6. Relatively hydrophobic regions are above the horizontal line, and relatively hydrophilic regions are below the horizontal line. Cysteine residues are indicated by short vertical lines just below the hydropathy trace.

Human CARD-6 is predicted to have a molecular weight of 116.5 kD before post-translational modification.

Human CARD-6 includes a CARD domain at amino acids 5–92 of SEQ ID NO:55 (SEQ ID NO:64). FIG. 30 depicts an alignment of the CARD domain domain of human CARD-6 and a consensus CARD domain derived from a hidden Markov model (SEQ ID NO:67).

Northern blot analysis of rat CARD-6 expression revealed that CARD-6 is expressed at a high level in the heart (6.5 kb transcript and a 7 kb transcript). This analysis also revealed that human CARD-6 is expressed in the brain, spleen, lung, liver, muscle, and kidney.

Example 16

CARD-6 Increases Intracellular Signaling

The studies described in this Example demonstrate that CARD-6 expression can increase intracellular signalling.

In a first study, a vector which expresses rat CARD-6 under the control of a CMV promoter was transiently transfected into 293 cells along with pNFκβ-Luc (Stratagene Inc., LaJolla, Calif.). The pNFκβ-Luc vector is a reporter plasmid in which a luciferase gene is under the control of a promoter which includes a TATA box and five NFκβ binding elements. Cotransfection of the rat CARD-6 expression vector increased luciferase expression by pNFκβ-Luc 18-fold over that observed in the absence of the rat CARD-6 expression vector. This result indicates that CARD-6 stimulates a signalling pathway involving NF-κβ.

In a second study, a vector expressing CARD-6 under the control of the CMV promoter was transiently transfected into 293 cells along with pAP-1-Luc (Strategene, Inc.). The pAP-1-Luc vector is a reported plasmid in which a luciferase gene is under the control of a promoter which includes a TATA box and seven AP-1 binding sites. Co-transfection of the rat CARD-6 expression vector increased luciferase expression by pAP-1-Luc 4-fold over that observed in the absence of the rat CARD-6 expression vector. This result indicates that CARD-6 stimulates a signaling pathway involving AP-1.

Additional studies suggest that CARD-6 can stimulate phosphorylation of CHOP (GADD153), possibly by activating the stress activated kinase, JNK/p38.

Example 17

Identification of Interactions Between CARD-5 and Proteins with CARD Domains

A mammalian two-hybrid screening assay revealed that CARD-5 interacts with the CARD domain of several CARD domain-containing proteins.

The Stratagene® Mammalian Two-Hybrid Assay Kit (Stratagene, Inc; La Jolla, Calif.) was used to prepare a vector expressing a protein (Ga14-BD/CARD-5) consisting of the DNA binding domain of yeast Ga14 (amino acids 1–147) fused to the CARD domain of human CARD-5 (amino acids 92 to 195 of SEQ ID NO:49). For a description of the Stratagene® Mammalian Two-Hybrid Assay Kit, see, e.g., Hosfield and Chang (1999) *Strategies Newsletter* 2(2) :62–65. In addition, a library of DNA sequences encoding 26 CARD domains was used to create a library of expression vectors encoding the murine NF-κB transcriptional activation domain (amino acids 364–550) fused to a CARD domain (NF-κB-AD/CARD). The Ga14-BD /CARD-5 vector, the NF-κB-AD/CARD domain vector library, and a luciferase reporter construct with an upstream Ga14 binding site were introduced into human 293T embryonic kidney cells. If a given CARD domain expressed fused to the NF-κB transcriptional activation domain interacts with the CARD domain of CARD-5, the NF-κB transcriptional activation domain will be brought into proximity with the promoter controlling luciferase expression, activating luciferase expression and permitting detection of the interaction. This analysis revealed that the CARD domain of CARD-5 interacts with the CARD domain of caspase-1, CARD-7, and CARD-5 itself.

CARD-7 contains a C-terminal CARD domain as well as an N-terminal pyrin domain, a nucleotide binding site, and a leucine rich repeat region. Detailed information concerning CARD-7 can be found in U.S. application Ser. No. 09/428,252, filed Oct. 27, 1999, the content of which is incorporated herein by reference.

Caspase-1 promotes inflammation by processing an inactive cytokine precursor, e.g., the IL-1β precursor, into an active proinflammatory cytokine. Caspase-1 also plays a role in the activation of apoptosis. The caspase-1 polypeptide is initially synthesized in an inactive form that becomes activated following an oligomerization event mediated through its N-terminal CARD domain. An upstream activator of caspase-1 may possess a CARD domain that interacts with the CARD domain of caspase-1 thereby leading to its oligomerization. Furthermore, a decoy molecule that attenuates caspase-1 activation may also interact with caspase-1 via a CARD-CARD interaction.

The finding that the C-terminal CARD domain of CARD-5 binds to the CARD domain of caspase-1 suggests that CARD-5 may be a modulator of caspase-1 activity. For example, CARD-5 may function as an upstream activator adaptor of caspase-1. Alternatively, CARD-5 binding to caspase-1 may attenuate the caspase-1 activation mediated by other upstream adaptors.

CARD-5 also possess an N-terminal pyrin domain. An upstream pyrin domain containing protein may thus bind to CARD-5, functioning as a regulator of CARD-5 in the context of a caspase-1 regulation pathway. For example, the upstream pyrin domain containing protein may engage the CARD-5/caspase-1 complex, e.g., via the pyrin domain of CARD-5, and thereby activate caspase-1 via its oligomerization. Examples of pyrin domain containing proteins, and possible upstream regulators of CARD-5, include NBS-1 and Pyrin-1. Detailed information concerning NBS-1 and Pyrin-1 can be found in U.S. application Ser. No. 09/506,067, filed Feb. 17, 2000, and U.S. application Ser. No. 09/653,901, filed Sep. 1, 2000. The entire content each of these applications is incorporated herein by reference.

Example 18

NF-kB Activation by CARD-5

The binding of CARD-5 to caspase-1 described above suggests that CARD-5-caspase-1 interactions may be part of a signaling pathway involved in inflammation, apoptosis, and/or NF-κB activation. Consistent with this signal transduction model, CARD-5 was shown to be an inducer of NF-κB activation. Expression of CARD-5 in 293T cells resulted in a 20–30 fold increase in NF-κB activity.

The NF-κB activity assay was performed as described in Example 9. An NF-κB reporter plasmid was co-transfected with a construct encoding CARD-5. In the reporter plasmid, the luciferase gene was placed under the control of the NF-κB promoter. Relative luciferase activity was determined at the end of the experiment to assess NF-κB pathway activation by CARD-5.

Example 19

Deposit of Clones

A plasmid containing a cDNA encoding human CARD-3 (pXE17A) was deposited with the American Type Culture Collection (ATCC), Manasass, Va. on May 14, 1998, and assigned Accession Number 203037.

A plasmid containing a cDNA encoding human CARD-4L (pC4L1) was deposited with the American Type Culture Collection (ATCC), Manasass, Va. on Jul. 7, 1998, and assigned Accession Number 203035.

A plasmid containing a cDNA encoding human CARD-4S (pDB33E) was deposited with the American Type Culture Collection (ATCC), Manasass, Va. on May 14, 1998, and assigned Accession Number 203036.

A plasmid containing a cDNA encoding murine CARD-5 (EpMC5) was deposited with the American Type Culture Collection (ATCC), Manasass, Va. on Jun. 11, 1999, and assigned Accession Number PTA-212.

A plasmid containing a cDNA encoding rat CARD-6 (EpRC6) was deposited with the American Type Culture Collection (ATCC), Manassas, Va. on Jun. 11, 1999, and assigned Accession Number PTA-211.

A clone (EpHC5) containing a cDNA molecule encoding human CARD-5, a clone (EpCH6e) containing a cDNA molecule encoding an amino terminal portion of human CARD-6, a clone (EpHC6c) containing a cDNA molecule encoding a carboxy terminal portion of human CARD-6, and a clone (EpHC6) containing a cDNA molecule encoding human CARD-6 were deposited with the American Type Culture Collection (ATCC) Manassas, Va. on Jun. 11, 1999, as a composite deposit and assigned Accession Number PTA-213. To distinguish the strains and isolate a strain harboring a particular cDNA clone, one can first streak out an aliquot of the mixture to single colonies on nutrient medium (e.g., LB plates) supplemented with 100 µg/ml ampicillin, grow single colonies, and then extract the plasmid DNA from a selected colony using a standard minipreparation procedure. Next, one can digest a sample of the DNA minipreparation with a combination of the restriction enzymes Sal I and Not I and resolve the resultant products on a 0.8% agarose gel using standard DNA electrophoresis conditions. The digestion will liberate DNA fragments as follows:

| | |
|---|---|
| Human CARD-5 (EpHC5) | 0.6 kb and 3.0 kb |
| Human CARD-6 amino-terminal portion (EpHC6e) (amino acids 1–279) | 1.0 kb and 4.3 kb |
| Human CARD-6 carboxy terminal portion (EpHC6c) (amino acid 93–1037) | 3.8 kb and 3.0 kb |
| Human CARD-6 (EpHC6) (amino acids 1–1037) | 4.2 kb and 3.0 kb |

Equivalents

Those skilled in the art will recognize, or be able to ascertain using no more than routine experimentation, many equivalents to the specific embodiments of the invention described herein. Such equivalents are intended to be encompassed by the following claims.

SEQUENCE LISTING

```
<160> NUMBER OF SEQ ID NOS: 71

<210> SEQ ID NO 1
<211> LENGTH: 1931
<212> TYPE: DNA
<213> ORGANISM: Homo sapiens
<220> FEATURE:
<221> NAME/KEY: CDS
<222> LOCATION: (214)...(1833)

<400> SEQUENCE: 1
ccacgcgtcc ggtcagctct ggttcggaga agcagcggct ggcgtgggcc atccggggaa        60
tgggcgccct cgtgacctag tgttgcgggg caaaaagggt cttgccggcc tcgctcgtgc       120 agggcgtat  ctgggcgcct gagcgcggcg tgggagcctt gggagccgcc gcagcaggg        180 gcacaccgg aaccggcctg agcgcccggg acc atg aac ggg gag gcc atc tgc         234
                                  Met Asn Gly Glu Ala Ile Cys
                                   1               5 agc gcc ctg ccc acc att ccc tac cac aaa ctc gcc gac ctg cgc tac         282
Ser Ala Leu Pro Thr Ile Pro Tyr His Lys Leu Ala Asp Leu Arg Tyr
        10                  15                  20 ctg agc cgc ggc gcc tct ggc act gtg tcg tcc gcc cgc cac gca gac         330
Leu Ser Arg Gly Ala Ser Gly Thr Val Ser Ser Ala Arg His Ala Asp
 25                  30                  35 tgg cgc gtc cag gtg gcc gtg aag cac ctg cac atc cac act ccg ctg         378
Trp Arg Val Gln Val Ala Val Lys His Leu His Ile His Thr Pro Leu
40                  45                  50                  55 ctc gac agt gaa aga aag gat gtc tta aga gaa gct gaa att tta cac         426
Leu Asp Ser Glu Arg Lys Asp Val Leu Arg Glu Ala Glu Ile Leu His
                60                  65                  70 aaa gct aga ttt agt tac att ctt cca att ttg gga att tgc aat gag         474
Lys Ala Arg Phe Ser Tyr Ile Leu Pro Ile Leu Gly Ile Cys Asn Glu
            75                  80                  85 cct gaa ttt ttg gga ata gtt act gaa tac atg cca aat gga tca tta         522
Pro Glu Phe Leu Gly Ile Val Thr Glu Tyr Met Pro Asn Gly Ser Leu
        90                  95                 100 aat gaa ctc cta cat agg aaa act gaa tat cct gat gtt gct tgg cca         570
Asn Glu Leu Leu His Arg Lys Thr Glu Tyr Pro Asp Val Ala Trp Pro
    105                 110                 115
```

-continued

| | | |
|---|---|---|
| ttg aga ttt cgc atc ctg cat gaa att gcc ctt ggt gta aat tac ctg<br>Leu Arg Phe Arg Ile Leu His Glu Ile Ala Leu Gly Val Asn Tyr Leu<br>120                     125                  130                    135 | 618 |
| cac aat atg act cct cct tta ctt cat cat gac ttg aag act cag aat<br>His Asn Met Thr Pro Pro Leu Leu His His Asp Leu Lys Thr Gln Asn<br>                    140                    145                    150 | 666 |
| atc tta ttg gac aat gaa ttt cat gtt aag att gca gat ttt ggt tta<br>Ile Leu Leu Asp Asn Glu Phe His Val Lys Ile Ala Asp Phe Gly Leu<br>                155                    160                    165 | 714 |
| tca aag tgg cgc atg atg tcc ctc tca cag tca cga agt agc aaa tct<br>Ser Lys Trp Arg Met Met Ser Leu Ser Gln Ser Arg Ser Ser Lys Ser<br>        170                    175                    180 | 762 |
| gca cca gaa gga ggg aca att atc tat atg cca cct gaa aac tat gaa<br>Ala Pro Glu Gly Gly Thr Ile Ile Tyr Met Pro Pro Glu Asn Tyr Glu<br>185                     190                  195 | 810 |
| cct gga caa aaa tca agg gcc agt atc aag cac gat ata tat agc tat<br>Pro Gly Gln Lys Ser Arg Ala Ser Ile Lys His Asp Ile Tyr Ser Tyr<br>200                     205                  210                    215 | 858 |
| gca gtt atc aca tgg gaa gtg tta tcc aga aaa cag cct ttt gaa gat<br>Ala Val Ile Thr Trp Glu Val Leu Ser Arg Lys Gln Pro Phe Glu Asp<br>                    220                    225                    230 | 906 |
| gtc acc aat cct ttg cag ata atg tat agt gtg tca caa gga cat cga<br>Val Thr Asn Pro Leu Gln Ile Met Tyr Ser Val Ser Gln Gly His Arg<br>                235                    240                    245 | 954 |
| cct gtt att aat gaa gaa agt ttg cca tat gat ata cct cac cga gca<br>Pro Val Ile Asn Glu Glu Ser Leu Pro Tyr Asp Ile Pro His Arg Ala<br>250                     255                  260 | 1002 |
| cgt atg atc tct cta ata gaa agt gga tgg gca caa aat cca gat gaa<br>Arg Met Ile Ser Leu Ile Glu Ser Gly Trp Ala Gln Asn Pro Asp Glu<br>265                     270                  275 | 1050 |
| aga cca tct ttc tta aaa tgt tta ata gaa ctt gaa cca gtt ttg aga<br>Arg Pro Ser Phe Leu Lys Cys Leu Ile Glu Leu Glu Pro Val Leu Arg<br>280                     285                  290                  295 | 1098 |
| aca ttt gaa gag ata act ttt ctt gaa gct gtt att cag cta aag aaa<br>Thr Phe Glu Glu Ile Thr Phe Leu Glu Ala Val Ile Gln Leu Lys Lys<br>                    300                    305                    310 | 1146 |
| aca aag tta cag agt gtt tca agt gcc att cac cta tgt gac aag aag<br>Thr Lys Leu Gln Ser Val Ser Ser Ala Ile His Leu Cys Asp Lys Lys<br>                315                    320                    325 | 1194 |
| aaa atg gaa tta tct ctg aac ata cct gta aat cat ggt cca caa gag<br>Lys Met Glu Leu Ser Leu Asn Ile Pro Val Asn His Gly Pro Gln Glu<br>                    330                    335                    340 | 1242 |
| gaa tca tgt gga tcc tct cag ctc cat gaa aat agt ggt tct cct gaa<br>Glu Ser Cys Gly Ser Ser Gln Leu His Glu Asn Ser Gly Ser Pro Glu<br>345                     350                  355 | 1290 |
| act tca agg tcc ctg cca gct cct caa gac aat gat ttt tta tct aga<br>Thr Ser Arg Ser Leu Pro Ala Pro Gln Asp Asn Asp Phe Leu Ser Arg<br>360                     365                  370                    375 | 1338 |
| aaa gct caa gac tgt tat ttt atg aag ctg cat cac tgt cct gga aat<br>Lys Ala Gln Asp Cys Tyr Phe Met Lys Leu His His Cys Pro Gly Asn<br>                    380                    385                    390 | 1386 |
| cac agt tgg gat agc acc att tct gga tct caa agg gct gca ttc tgt<br>His Ser Trp Asp Ser Thr Ile Ser Gly Ser Gln Arg Ala Ala Phe Cys<br>                395                    400                    405 | 1434 |
| gat cac aag acc att cca tgc tct tca gca ata ata aat cca ctc tca<br>Asp His Lys Thr Ile Pro Cys Ser Ser Ala Ile Ile Asn Pro Leu Ser<br>                    410                    415                    420 | 1482 |
| act gca gga aac tca gaa cgt ctg cag cct ggt ata gcc cag cag tgg<br>Thr Ala Gly Asn Ser Glu Arg Leu Gln Pro Gly Ile Ala Gln Gln Trp<br>425                     430                  435 | 1530 |

```
atc cag agc aaa agg gaa gac att gtg aac caa atg aca gaa gcc tgc    1578
Ile Gln Ser Lys Arg Glu Asp Ile Val Asn Gln Met Thr Glu Ala Cys
440             445                 450                 455 ctt aac cag tcg cta gat gcc ctt ctg tcc agg gac ttg atc atg aaa    1626
Leu Asn Gln Ser Leu Asp Ala Leu Leu Ser Arg Asp Leu Ile Met Lys
            460                 465                 470 gag gac tat gaa ctt gtt agt acc aag cct aca agg acc tca aaa gtc    1674
Glu Asp Tyr Glu Leu Val Ser Thr Lys Pro Thr Arg Thr Ser Lys Val
                475                 480                 485 aga caa tta cta gac act act gac atc caa gga gaa gaa ttt gcc aaa    1722
Arg Gln Leu Leu Asp Thr Thr Asp Ile Gln Gly Glu Glu Phe Ala Lys
        490                 495                 500 gtt ata gta caa aaa ttg aaa gat aac aaa caa atg ggt ctt cag cct    1770
Val Ile Val Gln Lys Leu Lys Asp Asn Lys Gln Met Gly Leu Gln Pro
            505                 510                 515 tac ccg gaa ata ctt gtg gtt tct aga tca cca tct tta aat tta ctt    1818
Tyr Pro Glu Ile Leu Val Val Ser Arg Ser Pro Ser Leu Asn Leu Leu
520                 525                 530                 535 caa aat aaa agc atg taagtgactg tttttcaaga agaaatgtgt ttcataaaag    1873
Gln Asn Lys Ser Met
                540 gatatttata aaaaaaaaaa aaaaaaaaaa aaaaaaaaaa aaaaaaaaaa aaaaaaa     1931

<210> SEQ ID NO 2
<211> LENGTH: 540
<212> TYPE: PRT
<213> ORGANISM: Homo sapiens

<400> SEQUENCE: 2

Met Asn Gly Glu Ala Ile Cys Ser Ala Leu Pro Thr Ile Pro Tyr His
1               5                   10                  15

Lys Leu Ala Asp Leu Arg Tyr Leu Ser Arg Gly Ala Ser Gly Thr Val
            20                  25                  30

Ser Ser Ala Arg His Ala Asp Trp Arg Val Gln Val Ala Val Lys His
        35                  40                  45

Leu His Ile His Thr Pro Leu Leu Asp Ser Glu Arg Lys Asp Val Leu
    50                  55                  60

Arg Glu Ala Glu Ile Leu His Lys Ala Arg Phe Ser Tyr Ile Leu Pro
65                  70                  75                  80

Ile Leu Gly Ile Cys Asn Glu Pro Glu Phe Leu Gly Ile Val Thr Glu
                85                  90                  95

Tyr Met Pro Asn Gly Ser Leu Asn Glu Leu Leu His Arg Lys Thr Glu
            100                 105                 110

Tyr Pro Asp Val Ala Trp Pro Leu Arg Phe Arg Ile Leu His Glu Ile
        115                 120                 125

Ala Leu Gly Val Asn Tyr Leu His Asn Met Thr Pro Pro Leu Leu His
    130                 135                 140

His Asp Leu Lys Thr Gln Asn Ile Leu Leu Asp Asn Glu Phe His Val
145                 150                 155                 160

Lys Ile Ala Asp Phe Gly Leu Ser Lys Trp Arg Met Met Ser Leu Ser
                165                 170                 175

Gln Ser Arg Ser Ser Lys Ser Ala Pro Glu Gly Gly Thr Ile Ile Tyr
            180                 185                 190

Met Pro Pro Glu Asn Tyr Glu Pro Gly Gln Lys Ser Arg Ala Ser Ile
        195                 200                 205

Lys His Asp Ile Tyr Ser Tyr Ala Val Ile Thr Trp Glu Val Leu Ser
```

```
              210                 215                 220
Arg Lys Gln Pro Phe Glu Asp Val Thr Asn Pro Leu Gln Ile Met Tyr
225                 230                 235                 240

Ser Val Ser Gln Gly His Arg Pro Val Ile Asn Glu Glu Ser Leu Pro
                245                 250                 255

Tyr Asp Ile Pro His Arg Ala Arg Met Ile Ser Leu Ile Glu Ser Gly
                260                 265                 270

Trp Ala Gln Asn Pro Asp Glu Arg Pro Ser Phe Leu Lys Cys Leu Ile
                275                 280                 285

Glu Leu Glu Pro Val Leu Arg Thr Phe Glu Ile Thr Phe Leu Glu
                290                 295                 300

Ala Val Ile Gln Leu Lys Lys Thr Lys Leu Gln Ser Val Ser Ser Ala
305                 310                 315                 320

Ile His Leu Cys Asp Lys Lys Met Glu Leu Ser Leu Asn Ile Pro
                325                 330                 335

Val Asn His Gly Pro Gln Glu Glu Ser Cys Gly Ser Ser Gln Leu His
                340                 345                 350

Glu Asn Ser Gly Ser Pro Glu Thr Ser Arg Ser Leu Pro Ala Pro Gln
                355                 360                 365

Asp Asn Asp Phe Leu Ser Arg Lys Ala Gln Asp Cys Tyr Phe Met Lys
                370                 375                 380

Leu His His Cys Pro Gly Asn His Ser Trp Asp Ser Thr Ile Ser Gly
385                 390                 395                 400

Ser Gln Arg Ala Ala Phe Cys Asp His Lys Thr Ile Pro Cys Ser Ser
                405                 410                 415

Ala Ile Ile Asn Pro Leu Ser Thr Ala Gly Asn Ser Glu Arg Leu Gln
                420                 425                 430

Pro Gly Ile Ala Gln Gln Trp Ile Gln Ser Lys Arg Glu Asp Ile Val
                435                 440                 445

Asn Gln Met Thr Glu Ala Cys Leu Asn Gln Ser Leu Asp Ala Leu Leu
                450                 455                 460

Ser Arg Asp Leu Ile Met Lys Glu Asp Tyr Glu Leu Val Ser Thr Lys
465                 470                 475                 480

Pro Thr Arg Thr Ser Lys Val Arg Gln Leu Leu Asp Thr Thr Asp Ile
                485                 490                 495

Gln Gly Glu Glu Phe Ala Lys Val Ile Val Gln Lys Leu Lys Asp Asn
                500                 505                 510

Lys Gln Met Gly Leu Gln Pro Tyr Pro Glu Ile Leu Val Val Ser Arg
                515                 520                 525

Ser Pro Ser Leu Asn Leu Leu Gln Asn Lys Ser Met
530                 535                 540

<210> SEQ ID NO 3
<211> LENGTH: 1620
<212> TYPE: DNA
<213> ORGANISM: Homo sapiens

<400> SEQUENCE: 3
atgaacgggg aggccatctg cagcgccctg cccaccattc cctaccacaa actcgccgac    60
ctgcgctacc tgagccgcgg cgcctctggc actgtgtcgt ccgcccgcca cgcagactgg   120
cgcgtccagg tggccgtgaa gcacctgcac atccacactc cgctgctcga cagtgaaaga   180
aaggatgtct taagagaagc tgaaattta cacaaagcta gatttagtta cattcttcca   240
atttttggga a tttgcaatga gcctgaattt ttgggaatag ttactgaata catgccaaat   300
```

-continued

```
ggatcattaa atgaactcct acataggaaa actgaatatc ctgatgttgc ttggccattg      360
agatttcgca tcctgcatga aattgccctt ggtgtaaatt acctgcacaa tatgactcct      420
cctttacttc atcatgactt gaagactcag aatatcttat tggacaatga atttcatgtt      480
aagattgcag attttggttt atcaaagtgg cgcatgatgt ccctctcaca gtcacgaagt      540
agcaaatctg caccagaagg agggacaatt atctatatgc cacctgaaaa ctatgaacct      600
ggacaaaaat caagggccag tatcaagcac gatatatata gctatgcagt tatcacatgg      660
gaagtgttat ccagaaaaca gccttttgaa gatgtcacca atcctttgca gataatgtat      720
agtgtgtcac aaggacatcg acctgttatt aatgaagaaa gtttgccata tgatatacct      780
caccgagcac gtatgatctc tctaatagaa agtggatggg cacaaaatcc agatgaaaga      840
ccatctttct taaaatgttt aatagaactt gaaccagttt tgagaacatt tgaagagata      900
acttttcttg aagctgttat tcagctaaag aaaacaaagt tacagagtgt ttcaagtgcc      960
attcacctat gtgacaagaa gaaaatggaa ttatctctga acatacctgt aaatcatggt     1020
ccacaagagg aatcatgtgg atcctctcag ctccatgaaa atagtggttc tcctgaaact     1080
tcaaggtccc tgccagctcc tcaagacaat gattttttat ctagaaaagc tcaagactgt     1140
tattttatga agctgcatca ctgtcctgga aatcacagtt gggatagcac catttctgga     1200
tctcaaaggg ctgcattctg tgatcacaag accattccat gctcttcagc aataataaat     1260
ccactctcaa ctgcaggaaa ctcagaacgt ctgcagcctg gtatagccca gcagtggatc     1320
cagagcaaaa gggaagacat tgtgaaccaa atgacagaag cctgccttaa ccagtcgcta     1380
gatgcccttc tgtccaggga cttgatcatg aaagaggact atgaacttgt tagtaccaag     1440
cctacaagga cctcaaaagt cagacaatta ctagacacta ctgacatcca aggagaagaa     1500
tttgccaaag ttatagtaca aaaattgaaa gataacaaac aaatgggtct tcagccttac     1560
ccggaaatac ttgtggtttc tagatcacca tctttaaatt tacttcaaaa taaaagcatg     1620
```

<210> SEQ ID NO 4
<211> LENGTH: 300
<212> TYPE: PRT
<213> ORGANISM: Homo sapiens

<400> SEQUENCE: 4

```
Met Asn Gly Glu Ala Ile Cys Ser Ala Leu Pro Thr Ile Pro Tyr His
  1               5                  10                  15

Lys Leu Ala Asp Leu Arg Tyr Leu Ser Arg Gly Ala Ser Gly Thr Val
             20                  25                  30

Ser Ser Ala Arg His Ala Asp Trp Arg Val Gln Val Ala Val Lys His
         35                  40                  45

Leu His Ile His Thr Pro Leu Leu Asp Ser Glu Arg Lys Asp Val Leu
     50                  55                  60

Arg Glu Ala Glu Ile Leu His Lys Ala Arg Phe Ser Tyr Ile Leu Pro
 65                  70                  75                  80

Ile Leu Gly Ile Cys Asn Glu Pro Glu Phe Leu Gly Ile Val Thr Glu
                 85                  90                  95

Tyr Met Pro Asn Gly Ser Leu Asn Glu Leu Leu His Arg Lys Thr Glu
            100                 105                 110

Tyr Pro Asp Val Ala Trp Pro Leu Arg Phe Arg Ile Leu His Glu Ile
        115                 120                 125

Ala Leu Gly Val Asn Tyr Leu His Asn Met Thr Pro Pro Leu Leu His
    130                 135                 140
```

-continued

His Asp Leu Lys Thr Gln Asn Ile Leu Leu Asp Asn Glu Phe His Val
145                 150                 155                 160

Lys Ile Ala Asp Phe Gly Leu Ser Lys Trp Arg Met Met Ser Leu Ser
                165                 170                 175

Gln Ser Arg Ser Ser Lys Ser Ala Pro Glu Gly Gly Thr Ile Ile Tyr
            180                 185                 190

Met Pro Pro Glu Asn Tyr Glu Pro Gly Gln Lys Ser Arg Ala Ser Ile
        195                 200                 205

Lys His Asp Ile Tyr Ser Tyr Ala Val Ile Thr Trp Glu Val Leu Ser
    210                 215                 220

Arg Lys Gln Pro Phe Glu Asp Val Thr Asn Pro Leu Gln Ile Met Tyr
225                 230                 235                 240

Ser Val Ser Gln Gly His Arg Pro Val Ile Asn Glu Glu Ser Leu Pro
                245                 250                 255

Tyr Asp Ile Pro His Arg Ala Arg Met Ile Ser Leu Ile Glu Ser Gly
            260                 265                 270

Trp Ala Gln Asn Pro Asp Glu Arg Pro Ser Phe Leu Lys Cys Leu Ile
        275                 280                 285

Glu Leu Glu Pro Val Leu Arg Thr Phe Glu Glu Ile
290                 295                 300

<210> SEQ ID NO 5
<211> LENGTH: 131
<212> TYPE: PRT
<213> ORGANISM: Homo sapiens

<400> SEQUENCE: 5

Thr Phe Leu Glu Ala Val Ile Gln Leu Lys Lys Thr Lys Leu Gln Ser
1               5                   10                  15

Val Ser Ser Ala Ile His Leu Cys Asp Lys Lys Met Glu Leu Ser
            20                  25                  30

Leu Asn Ile Pro Val Asn His Gly Pro Gln Glu Glu Ser Cys Gly Ser
        35                  40                  45

Ser Gln Leu His Glu Asn Ser Gly Ser Pro Glu Thr Ser Arg Ser Leu
    50                  55                  60

Pro Ala Pro Gln Asp Asn Asp Phe Leu Ser Arg Lys Ala Gln Asp Cys
65                  70                  75                  80

Tyr Phe Met Lys Leu His His Cys Pro Gly Asn His Ser Trp Asp Ser
                85                  90                  95

Thr Ile Ser Gly Ser Gln Arg Ala Ala Phe Cys Asp His Lys Thr Ile
            100                 105                 110

Pro Cys Ser Ser Ala Ile Ile Asn Pro Leu Ser Thr Ala Gly Asn Ser
        115                 120                 125

Glu Arg Leu
    130

<210> SEQ ID NO 6
<211> LENGTH: 109
<212> TYPE: PRT
<213> ORGANISM: Homo sapiens

<400> SEQUENCE: 6

Gln Pro Gly Ile Ala Gln Gln Trp Ile Gln Ser Lys Arg Glu Asp Ile
1               5                   10                  15

Val Asn Gln Met Thr Glu Ala Cys Leu Asn Gln Ser Leu Asp Ala Leu
            20                  25                  30

```
Leu Ser Arg Asp Leu Ile Met Lys Glu Asp Tyr Glu Leu Val Ser Thr
         35                  40                  45

Lys Pro Thr Arg Thr Ser Lys Val Arg Gln Leu Leu Asp Thr Thr Asp
     50                  55                  60

Ile Gln Gly Glu Glu Phe Ala Lys Val Ile Val Gln Lys Leu Lys Asp
 65                  70                  75                  80

Asn Lys Gln Met Gly Leu Gln Pro Tyr Pro Glu Ile Leu Val Val Ser
                 85                  90                  95

Arg Ser Pro Ser Leu Asn Leu Leu Gln Asn Lys Ser Met
                100                 105

<210> SEQ ID NO 7
<211> LENGTH: 3382
<212> TYPE: DNA
<213> ORGANISM: Homo sapiens
<220> FEATURE:
<221> NAME/KEY: CDS
<222> LOCATION: (245)...(3104)

<400> SEQUENCE: 7
tttttatggg aatcgcagct tggaagagac agarcaattc cagaawtaaa ttgraattga      60
agatttaacc aatgttgttt taaaatattc taacttcaaa gaatgatgcc agaacttwaa     120
aagggrctgc gcagagtagc aggggccctg gagggcgcgg cctgaatcct gattgccctt     180
ctgctgagag gacacacgca gctgaagatg aatttgggaa aagtagccgc ttgctacttt     240 aact atg gaa gag cag ggc cac agt gag atg gaa ata atc cca tca gag      289
     Met Glu Glu Gln Gly His Ser Glu Met Glu Ile Ile Pro Ser Glu
      1               5                  10                  15 tct cac ccc cac att caa tta ctg aaa agc aat cgg gaa ctt ctg gtc      337
Ser His Pro His Ile Gln Leu Leu Lys Ser Asn Arg Glu Leu Leu Val
                 20                  25                  30 act cac atc cgc aat act cag tgt ctg gtg gac aac ttg ctg aag aat      385
Thr His Ile Arg Asn Thr Gln Cys Leu Val Asp Asn Leu Leu Lys Asn
             35                  40                  45 gac tac ttc tcg gcc gaa gat gcg gag att gtg tgt gcc tgc ccc acc      433
Asp Tyr Phe Ser Ala Glu Asp Ala Glu Ile Val Cys Ala Cys Pro Thr
         50                  55                  60 cag cct gac aag gtc cgc aaa att ctg gac ctg gta cag agc aag ggc      481
Gln Pro Asp Lys Val Arg Lys Ile Leu Asp Leu Val Gln Ser Lys Gly
 65                  70                  75 gag gag gtg tcc gag ttc ttc ctc tac ttg ctc cag caa ctc gca gat      529
Glu Glu Val Ser Glu Phe Phe Leu Tyr Leu Leu Gln Gln Leu Ala Asp
 80                  85                  90                  95 gcc tac gtg gac ctc agg cct tgg ctg ctg gag atc ggc ttc tcc cct      577
Ala Tyr Val Asp Leu Arg Pro Trp Leu Leu Glu Ile Gly Phe Ser Pro
                100                 105                 110 tcc ctg ctc act cag agc aaa gtc gtg gtc aac act gac cca gtg agc      625
Ser Leu Leu Thr Gln Ser Lys Val Val Val Asn Thr Asp Pro Val Ser
             115                 120                 125 agg tat acc cag cag ctg cga cac cat ctg ggc cgt gac tcc aag ttc      673
Arg Tyr Thr Gln Gln Leu Arg His His Leu Gly Arg Asp Ser Lys Phe
         130                 135                 140 gtg ctg tgc tat gcc cag aag gag gag ctg ctg ctg gag gag atc tac      721
Val Leu Cys Tyr Ala Gln Lys Glu Glu Leu Leu Leu Glu Glu Ile Tyr
145                 150                 155 atg gac acc atc atg gag ctg gtt ggc ttc agc aat gag agc ctg ggc      769
Met Asp Thr Ile Met Glu Leu Val Gly Phe Ser Asn Glu Ser Leu Gly
160                 165                 170                 175
```

-continued

```
agc ctg aac agc ctg gcc tgc ctc ctg gac cac acc acc ggc atc ctc      817
Ser Leu Asn Ser Leu Ala Cys Leu Leu Asp His Thr Thr Gly Ile Leu
            180                 185                 190 aat gag cag ggt gag acc atc ttc atc ctg ggt gat gct ggg gtg ggc      865
Asn Glu Gln Gly Glu Thr Ile Phe Ile Leu Gly Asp Ala Gly Val Gly
        195                 200                 205 aag tcc atg ctg cta cag cgg ctg cag agc ctc tgg gcc acg ggc cgg      913
Lys Ser Met Leu Leu Gln Arg Leu Gln Ser Leu Trp Ala Thr Gly Arg
    210                 215                 220 cta gac gca ggg gtc aaa ttc ttc ttc cac ttt cgc tgc cgc atg ttc      961
Leu Asp Ala Gly Val Lys Phe Phe Phe His Phe Arg Cys Arg Met Phe
225                 230                 235 agc tgc ttc aag gaa agt gac agg ctg tgt ctg cag gac ctg ctc ttc     1009
Ser Cys Phe Lys Glu Ser Asp Arg Leu Cys Leu Gln Asp Leu Leu Phe
240                 245                 250                 255 aag cac tac tgc tac cca gag cgg gac ccc gag gag gtg ttt gcc ttc     1057
Lys His Tyr Cys Tyr Pro Glu Arg Asp Pro Glu Glu Val Phe Ala Phe
                260                 265                 270 ctg ctg cgc ttc ccc cac gtg gcc ctc ttc acc ttc gat ggc ctg gac     1105
Leu Leu Arg Phe Pro His Val Ala Leu Phe Thr Phe Asp Gly Leu Asp
            275                 280                 285 gag ctg cac tcg gac ttg gac ctg agc cgc gtg cct gac agc tcc tgc     1153
Glu Leu His Ser Asp Leu Asp Leu Ser Arg Val Pro Asp Ser Ser Cys
        290                 295                 300 ccc tgg gag cct gcc cac ccc ctg gtc ttg ctg gcc aac ctg ctc agt     1201
Pro Trp Glu Pro Ala His Pro Leu Val Leu Leu Ala Asn Leu Leu Ser
    305                 310                 315 ggg aag ctg ctc aag ggg gct agc aag ctg ctc aca gcc cgc aca ggc     1249
Gly Lys Leu Leu Lys Gly Ala Ser Lys Leu Leu Thr Ala Arg Thr Gly
320                 325                 330                 335 atc gag gtc ccg cgc cag ttc ctg cgg aag aag gtg ctt ctc cgg ggc     1297
Ile Glu Val Pro Arg Gln Phe Leu Arg Lys Lys Val Leu Leu Arg Gly
                340                 345                 350 ttc tcc ccc agc cac ctg cgc gcc tat gcc agg agg atg ttc ccc gag     1345
Phe Ser Pro Ser His Leu Arg Ala Tyr Ala Arg Arg Met Phe Pro Glu
            355                 360                 365 cgg gcc ctg cag gac cgc ctg ctg agc cag ctg gag gcc aac ccc aac     1393
Arg Ala Leu Gln Asp Arg Leu Leu Ser Gln Leu Glu Ala Asn Pro Asn
        370                 375                 380 ctc tgc agc ctg tgc tct gtg ccc ctc ttc tgc tgg atc atc ttc cgg     1441
Leu Cys Ser Leu Cys Ser Val Pro Leu Phe Cys Trp Ile Ile Phe Arg
    385                 390                 395 tgc ttc cag cac ttc cgt gct gcc ttt gaa ggc tca cca cag ctg ccc     1489
Cys Phe Gln His Phe Arg Ala Ala Phe Glu Gly Ser Pro Gln Leu Pro
400                 405                 410                 415 gac tgc acg atg acc ctg aca gat gtc ttc ctc ctg gtc act gag gtc     1537
Asp Cys Thr Met Thr Leu Thr Asp Val Phe Leu Leu Val Thr Glu Val
                420                 425                 430 cat ctg aac agg atg cag ccc agc agc ctg gtg cag cgg aac aca cgc     1585
His Leu Asn Arg Met Gln Pro Ser Ser Leu Val Gln Arg Asn Thr Arg
            435                 440                 445 agc cca gtg gag acc ctc cac gcc ggc cgg gac act ctg tgc tcg ctg     1633
Ser Pro Val Glu Thr Leu His Ala Gly Arg Asp Thr Leu Cys Ser Leu
        450                 455                 460 ggg cag gtg gcc cac cgg ggc atg gag aag agc ctc ttt gtc ttc acc     1681
Gly Gln Val Ala His Arg Gly Met Glu Lys Ser Leu Phe Val Phe Thr
    465                 470                 475 cag gag gag gtg cag gcc tcc ggg ctg cag gag aga gac atg cag ctg     1729
Gln Glu Glu Val Gln Ala Ser Gly Leu Gln Glu Arg Asp Met Gln Leu
480                 485                 490                 495
```

```
ggc ttc ctg cgg gct ttg ccg gag ctg ggc ccc ggg ggt gac cag cag      1777
Gly Phe Leu Arg Ala Leu Pro Glu Leu Gly Pro Gly Gly Asp Gln Gln
            500                 505                 510 tcc tat gag ttt ttc cac ctc acc ctc cag gcc ttc ttt aca gcc ttc      1825
Ser Tyr Glu Phe Phe His Leu Thr Leu Gln Ala Phe Phe Thr Ala Phe
            515                 520                 525 ttc ctc gtg ctg gac gac agg gtg ggc act cag gag ctg ctc agg ttc      1873
Phe Leu Val Leu Asp Asp Arg Val Gly Thr Gln Glu Leu Leu Arg Phe
            530                 535                 540 ttc cag gag tgg atg ccc cct gcg ggg gca gcg acc acg tcc tgc tat      1921
Phe Gln Glu Trp Met Pro Pro Ala Gly Ala Ala Thr Thr Ser Cys Tyr
    545                 550                 555 cct ccc ttc ctc ccg ttc cag tgc ctg cag ggc agt ggt ccg gcg cgg      1969
Pro Pro Phe Leu Pro Phe Gln Cys Leu Gln Gly Ser Gly Pro Ala Arg
560                 565                 570                 575 gaa gac ctc ttc aag aac aag gat cac ttc cag ttc acc aac ctc ttc      2017
Glu Asp Leu Phe Lys Asn Lys Asp His Phe Gln Phe Thr Asn Leu Phe
                580                 585                 590 ctg tgc ggg ctg ttg tcc aaa gcc aaa cag aaa ctc ctg cgg cat ctg      2065
Leu Cys Gly Leu Leu Ser Lys Ala Lys Gln Lys Leu Leu Arg His Leu
                595                 600                 605 gtg ccc gcg gca gcc ctg agg aga aag cgc aag gcc ctg tgg gca cac      2113
Val Pro Ala Ala Ala Leu Arg Arg Lys Arg Lys Ala Leu Trp Ala His
            610                 615                 620 ctg ttt tcc agc ctg cgg ggc tac ctg aag agc ctg ccc cgc gtt cag      2161
Leu Phe Ser Ser Leu Arg Gly Tyr Leu Lys Ser Leu Pro Arg Val Gln
    625                 630                 635 gtc gaa agc ttc aac cag gtg cag gcc atg ccc acg ttc atc tgg atg      2209
Val Glu Ser Phe Asn Gln Val Gln Ala Met Pro Thr Phe Ile Trp Met
640                 645                 650                 655 ctg cgc tgc atc tac gag aca cag agc cag aag gtg ggg cag ctg gcg      2257
Leu Arg Cys Ile Tyr Glu Thr Gln Ser Gln Lys Val Gly Gln Leu Ala
                660                 665                 670 gcc agg ggc atc tgc gcc aac tac ctc aag ctg acc tac tgc aac gcc      2305
Ala Arg Gly Ile Cys Ala Asn Tyr Leu Lys Leu Thr Tyr Cys Asn Ala
                675                 680                 685 tgc tcg gcc gac tgc agc gcc ctc tcc ttc gtc ctg cat cac ttc ccc      2353
Cys Ser Ala Asp Cys Ser Ala Leu Ser Phe Val Leu His His Phe Pro
            690                 695                 700 aag cgg ctg gcc cta gac cta gac aac aac aat ctc aac gac tac ggc      2401
Lys Arg Leu Ala Leu Asp Leu Asp Asn Asn Asn Leu Asn Asp Tyr Gly
    705                 710                 715 gtg cgg gag ctg cag ccc tgc ttc agc cgc ctc act gtt ctc aga ctc      2449
Val Arg Glu Leu Gln Pro Cys Phe Ser Arg Leu Thr Val Leu Arg Leu
720                 725                 730                 735 agc gta aac cag atc act gac ggt ggg gta aag gtg cta agc gaa gag      2497
Ser Val Asn Gln Ile Thr Asp Gly Gly Val Lys Val Leu Ser Glu Glu
                740                 745                 750 ctg acc aaa tac aaa att gtg acc tat ttg ggt tta tac aac aac cag      2545
Leu Thr Lys Tyr Lys Ile Val Thr Tyr Leu Gly Leu Tyr Asn Asn Gln
            755                 760                 765 atc acc gat gtc gga gcc agg tac gtc acc aaa atc ctg gat gaa tgc      2593
Ile Thr Asp Val Gly Ala Arg Tyr Val Thr Lys Ile Leu Asp Glu Cys
            770                 775                 780 aaa ggc ctc acg cat ctt aaa ctg gga aaa aac aaa ata aca agt gaa      2641
Lys Gly Leu Thr His Leu Lys Leu Gly Lys Asn Lys Ile Thr Ser Glu
785                 790                 795 gga ggg aag tat ctc gcc ctg gct gtg aag aac agc aaa tca atc tct      2689
Gly Gly Lys Tyr Leu Ala Leu Ala Val Lys Asn Ser Lys Ser Ile Ser
```

```
                                                                       -continued
           800             805             810             815
gag gtt ggg atg tgg ggc aat caa gtt ggg gat gaa gga gca aaa gcc         2737
Glu Val Gly Met Trp Gly Asn Gln Val Gly Asp Glu Gly Ala Lys Ala
                    820             825             830 ttc gca gag gct ctg cgg aac cac ccc agc ttg acc acc ctg agt ctt         2785
Phe Ala Glu Ala Leu Arg Asn His Pro Ser Leu Thr Thr Leu Ser Leu
                835             840             845 gcg tcc aac ggc atc tcc aca gaa gga gga aag agc ctt gcg agg gcc         2833
Ala Ser Asn Gly Ile Ser Thr Glu Gly Gly Lys Ser Leu Ala Arg Ala
            850             855             860 ctg cag cag aac acg tct cta gaa ata ctg tgg ctg acc caa aat gaa         2881
Leu Gln Gln Asn Thr Ser Leu Glu Ile Leu Trp Leu Thr Gln Asn Glu
        865             870             875 ctc aac gat gaa gtg gca gag agt ttg gca gaa atg ttg aaa gtc aac         2929
Leu Asn Asp Glu Val Ala Glu Ser Leu Ala Glu Met Leu Lys Val Asn
880             885             890             895 cag acg tta aag cat tta tgg ctt atc cag aat cag atc aca gct aag         2977
Gln Thr Leu Lys His Leu Trp Leu Ile Gln Asn Gln Ile Thr Ala Lys
                900             905             910 ggg act gcc cag ctg gca gat gcg tta cag agc aac act ggc ata aca         3025
Gly Thr Ala Gln Leu Ala Asp Ala Leu Gln Ser Asn Thr Gly Ile Thr
            915             920             925 gag att tgc cta aat gga aac ctg ata aaa cca gag gag gcc aaa gtc         3073
Glu Ile Cys Leu Asn Gly Asn Leu Ile Lys Pro Glu Glu Ala Lys Val
        930             935             940 tat gaa gat gag aag cgg att atc tgt ttc t gagaggatgc tttcctgttc        3124
Tyr Glu Asp Glu Lys Arg Ile Ile Cys Phe
945             950 atggggtttt tgccctggag cctcagcagc aaatgccact ctgggcagtc ttttgtgtca       3184
gtgtcttaaa ggggcctgcg caggcgggac tatcaggagt ccactgccty catgatgcaa       3244
gccagcttcc tgtgcagaag gtctggtcgg caaactccct aagtaccgc tacaattctg        3304 cagaaaaaga atgtgtcttg cgagctgttt tagttacagt aaatacactg tgaagagaaa       3364
aaaaaaacgg acgcgtgg                                                     3382

<210> SEQ ID NO 8
<211> LENGTH: 953
<212> TYPE: PRT
<213> ORGANISM: Homo sapiens

<400> SEQUENCE: 8

Met Glu Glu Gln Gly His Ser Glu Met Glu Ile Ile Pro Ser Glu Ser
 1               5                   10                  15

His Pro His Ile Gln Leu Leu Lys Ser Asn Arg Glu Leu Leu Val Thr
            20                  25                  30

His Ile Arg Asn Thr Gln Cys Leu Val Asp Asn Leu Leu Lys Asn Asp
        35                  40                  45

Tyr Phe Ser Ala Glu Asp Ala Glu Ile Val Cys Ala Cys Pro Thr Gln
    50                  55                  60

Pro Asp Lys Val Arg Lys Ile Leu Asp Leu Val Gln Ser Lys Gly Glu
65                  70                  75                  80

Glu Val Ser Glu Phe Phe Leu Tyr Leu Leu Gln Gln Leu Ala Asp Ala
                85                  90                  95

Tyr Val Asp Leu Arg Pro Trp Leu Leu Glu Ile Gly Phe Ser Pro Ser
            100                 105                 110

Leu Leu Thr Gln Ser Lys Val Val Asn Thr Asp Pro Val Ser Arg
        115                 120                 125
```

```
Tyr Thr Gln Gln Leu Arg His His Leu Gly Arg Asp Ser Lys Phe Val
    130                 135                 140

Leu Cys Tyr Ala Gln Lys Glu Glu Leu Leu Glu Glu Ile Tyr Met
145                 150                 155                 160

Asp Thr Ile Met Glu Leu Val Gly Phe Ser Asn Glu Ser Leu Gly Ser
                165                 170                 175

Leu Asn Ser Leu Ala Cys Leu Leu Asp His Thr Thr Gly Ile Leu Asn
            180                 185                 190

Glu Gln Gly Glu Thr Ile Phe Ile Leu Gly Asp Ala Gly Val Gly Lys
        195                 200                 205

Ser Met Leu Leu Gln Arg Leu Gln Ser Leu Trp Ala Thr Gly Arg Leu
    210                 215                 220

Asp Ala Gly Val Lys Phe Phe His Phe Arg Cys Arg Met Phe Ser
225                 230                 235                 240

Cys Phe Lys Glu Ser Asp Arg Leu Cys Leu Gln Asp Leu Leu Phe Lys
                245                 250                 255

His Tyr Cys Tyr Pro Glu Arg Asp Pro Glu Val Phe Ala Phe Leu
            260                 265                 270

Leu Arg Phe Pro His Val Ala Leu Phe Thr Phe Asp Gly Leu Asp Glu
        275                 280                 285

Leu His Ser Asp Leu Asp Leu Ser Arg Val Pro Asp Ser Ser Cys Pro
    290                 295                 300

Trp Glu Pro Ala His Pro Leu Val Leu Leu Ala Asn Leu Leu Ser Gly
305                 310                 315                 320

Lys Leu Leu Lys Gly Ala Ser Lys Leu Leu Thr Ala Arg Thr Gly Ile
                325                 330                 335

Glu Val Pro Arg Gln Phe Leu Arg Lys Val Leu Leu Arg Gly Phe
            340                 345                 350

Ser Pro Ser His Leu Arg Ala Tyr Ala Arg Arg Met Phe Pro Glu Arg
        355                 360                 365

Ala Leu Gln Asp Arg Leu Leu Ser Gln Leu Glu Ala Asn Pro Asn Leu
    370                 375                 380

Cys Ser Leu Cys Ser Val Pro Leu Phe Cys Trp Ile Ile Phe Arg Cys
385                 390                 395                 400

Phe Gln His Phe Arg Ala Ala Phe Glu Gly Ser Pro Gln Leu Pro Asp
                405                 410                 415

Cys Thr Met Thr Leu Thr Asp Val Phe Leu Leu Val Thr Glu Val His
            420                 425                 430

Leu Asn Arg Met Gln Pro Ser Ser Leu Val Gln Arg Asn Thr Arg Ser
        435                 440                 445

Pro Val Glu Thr Leu His Ala Gly Arg Asp Thr Leu Cys Ser Leu Gly
    450                 455                 460

Gln Val Ala His Arg Gly Met Glu Lys Ser Leu Phe Val Phe Thr Gln
465                 470                 475                 480

Glu Glu Val Gln Ala Ser Gly Leu Gln Glu Arg Asp Met Gln Leu Gly
                485                 490                 495

Phe Leu Arg Ala Leu Pro Glu Leu Gly Pro Gly Asp Gln Gln Ser
            500                 505                 510

Tyr Glu Phe Phe His Leu Thr Leu Gln Ala Phe Thr Ala Phe Phe
        515                 520                 525

Leu Val Leu Asp Asp Arg Val Gly Thr Gln Glu Leu Leu Arg Phe Phe
530                 535                 540
```

```
Gln Glu Trp Met Pro Pro Ala Gly Ala Ala Thr Thr Ser Cys Tyr Pro
545                 550                 555                 560

Pro Phe Leu Pro Phe Gln Cys Leu Gln Gly Ser Gly Pro Ala Arg Glu
                565                 570                 575

Asp Leu Phe Lys Asn Lys Asp His Phe Gln Phe Thr Asn Leu Phe Leu
            580                 585                 590

Cys Gly Leu Leu Ser Lys Ala Lys Gln Lys Leu Leu Arg His Leu Val
        595                 600                 605

Pro Ala Ala Ala Leu Arg Arg Lys Arg Lys Ala Leu Trp Ala His Leu
    610                 615                 620

Phe Ser Ser Leu Arg Gly Tyr Leu Lys Ser Leu Pro Arg Val Gln Val
625                 630                 635                 640

Glu Ser Phe Asn Gln Val Gln Ala Met Pro Thr Phe Ile Trp Met Leu
                645                 650                 655

Arg Cys Ile Tyr Glu Thr Gln Ser Gln Lys Val Gly Gln Leu Ala Ala
            660                 665                 670

Arg Gly Ile Cys Ala Asn Tyr Leu Lys Leu Thr Tyr Cys Asn Ala Cys
        675                 680                 685

Ser Ala Asp Cys Ser Ala Leu Ser Phe Val Leu His His Phe Pro Lys
    690                 695                 700

Arg Leu Ala Leu Asp Leu Asp Asn Asn Asn Leu Asn Asp Tyr Gly Val
705                 710                 715                 720

Arg Glu Leu Gln Pro Cys Phe Ser Arg Leu Thr Val Leu Arg Leu Ser
                725                 730                 735

Val Asn Gln Ile Thr Asp Gly Gly Val Lys Val Leu Ser Glu Glu Leu
            740                 745                 750

Thr Lys Tyr Lys Ile Val Thr Tyr Leu Gly Leu Tyr Asn Asn Gln Ile
        755                 760                 765

Thr Asp Val Gly Ala Arg Tyr Val Thr Lys Ile Leu Asp Glu Cys Lys
    770                 775                 780

Gly Leu Thr His Leu Lys Leu Gly Lys Asn Lys Ile Thr Ser Glu Gly
785                 790                 795                 800

Gly Lys Tyr Leu Ala Leu Ala Val Lys Asn Ser Lys Ser Ile Ser Glu
                805                 810                 815

Val Gly Met Trp Gly Asn Gln Val Gly Asp Glu Gly Ala Lys Ala Phe
            820                 825                 830

Ala Glu Ala Leu Arg Asn His Pro Ser Leu Thr Thr Leu Ser Leu Ala
        835                 840                 845

Ser Asn Gly Ile Ser Thr Glu Gly Gly Lys Ser Leu Ala Arg Ala Leu
    850                 855                 860

Gln Gln Asn Thr Ser Leu Glu Ile Leu Trp Leu Thr Gln Asn Glu Leu
865                 870                 875                 880

Asn Asp Glu Val Ala Glu Ser Leu Ala Glu Met Leu Lys Val Asn Gln
                885                 890                 895

Thr Leu Lys His Leu Trp Leu Ile Gln Asn Gln Ile Thr Ala Lys Gly
            900                 905                 910

Thr Ala Gln Leu Ala Asp Ala Leu Gln Ser Asn Thr Gly Ile Thr Glu
        915                 920                 925

Ile Cys Leu Asn Gly Asn Leu Ile Lys Pro Glu Glu Ala Lys Val Tyr
    930                 935                 940

Glu Asp Glu Lys Arg Ile Ile Cys Phe
945                 950
```

-continued

<210> SEQ ID NO 9
<211> LENGTH: 2859
<212> TYPE: DNA
<213> ORGANISM: Homo sapiens

<400> SEQUENCE: 9

| | | | | | |
|---|---|---|---|---|---|
| atggaagagc | agggccacag | tgagatggaa | ataatcccat | cagagtctca | cccccacatt | 60 |
| caattactga | aaagcaatcg | ggaacttctg | gtcactcaca | tccgcaatac | tcagtgtctg | 120 |
| gtggacaact | tgctgaagaa | tgactacttc | tcggccgaag | atgcggagat | tgtgtgtgcc | 180 |
| tgccccaccc | agcctgacaa | ggtccgcaaa | attctggacc | tggtacagag | caagggcgag | 240 |
| gaggtgtccg | agttcttcct | ctacttgctc | cagcaactcg | cagatgccta | cgtggacctc | 300 |
| aggccttggc | tgctggagat | cggcttctcc | ccttccctgc | tcactcagag | caaagtcgtg | 360 |
| gtcaacactg | acccagtgag | caggtatacc | cagcagctg | acaccatct | gggccgtgac | 420 |
| tccaagttcg | tgctgtgcta | tgcccagaag | gaggagctgc | tgctggagga | gatctacatg | 480 |
| gacaccatca | tggagctggt | tggcttcagc | aatgagagcc | tgggcagcct | gaacagcctg | 540 |
| gcctgcctcc | tggaccacac | caccggcatc | ctcaatgagc | agggtgagac | catcttcatc | 600 |
| ctgggtgatg | ctggggtggg | caagtccatg | ctgctacagc | ggctgcagag | cctctgggcc | 660 |
| acgggccggc | tagacgcagg | ggtcaaattc | ttcttccact | ttcgctgccg | catgttcagc | 720 |
| tgcttcaagg | aaagtgacag | gctgtgtctg | caggacctgc | tcttcaagca | ctactgctac | 780 |
| ccagagcggg | accccgagga | ggtgtttgcc | ttcctgctgc | gcttccccca | cgtggccctc | 840 |
| ttcaccttcg | atggcctgga | cgagctgcac | tcggacttgg | acctgagccg | cgtgcctgac | 900 |
| agctcctgcc | cctgggagcc | tgcccacccc | ctggtcttgc | tggccaacct | gctcagtggg | 960 |
| aagctgctca | aggggctag | caagctgctc | acagcccgca | caggcatcga | ggtcccgcgc | 1020 |
| cagttcctgc | ggaagaaggt | gcttctccgg | ggcttctccc | ccagccacct | gcgcgcctat | 1080 |
| gccaggagga | tgttccccga | gcgggccctg | caggaccgcc | tgctgagcca | gctggaggcc | 1140 |
| aaccccaacc | tctgcagcct | gtgctctgtg | cccctcttct | gctggatcat | cttccggtgc | 1200 |
| ttccagcact | ccgtgctgc | ctttgaaggc | tcaccacagc | tgcccgactg | cacgatgacc | 1260 |
| ctgacagatg | tcttcctcct | ggtcactgag | gtccatctga | acaggatgca | gcccagcagc | 1320 |
| ctggtgcagc | ggaacacacg | cagcccagtg | gagaccctcc | acgccggccg | ggacactctg | 1380 |
| tgctcgctgg | ggcaggtggc | ccaccggggc | atggagaaga | gcctctttgt | cttcacccag | 1440 |
| gaggaggtgc | aggcctccgg | gctgcaggag | agagacatgc | agctgggctt | cctgcgggct | 1500 |
| ttgccggagc | tgggccccgg | gggtgaccag | cagtcctatg | agttttttcca | cctcaccctc | 1560 |
| caggccttct | ttacagcctt | cttcctcgtg | ctggacgaca | gggtgggcac | tcaggagctg | 1620 |
| ctcaggttct | tccaggagtg | gatgcccct | gcggggcag | cgaccacgtc | tgctatcct | 1680 |
| cccttcctcc | cgttccagtg | cctgcaggc | agtggtccgg | cgcgggaaga | cctcttcaag | 1740 |
| aacaaggatc | acttccagtt | caccaacctc | ttcctgtgcg | ggctgttgtc | caaagccaaa | 1800 |
| cagaaactcc | tgcggcatct | ggtgcccgcg | gcagccctga | ggagaaagcg | caaggccctg | 1860 |
| tgggcacacc | tgttttccag | cctgcggggc | tacctgaaga | gcctgccccg | cgttcaggtc | 1920 |
| gaaagcttca | ccaggtgca | ggccatgccc | acgttcatct | ggatgctgcg | ctgcatctac | 1980 |
| gagacacaga | gccagaaggt | ggggcagctg | gcggccaggg | gcatctgcgc | caactacctc | 2040 |
| aagctgaccct | actgcaacgc | ctgctcggcc | gactgcagcg | ccctctcctt | cgtcctgcat | 2100 |
| cacttcccca | agcggctggc | cctagaccta | gacaacaaca | atctcaacga | ctacggcgtg | 2160 |

-continued

```
cgggagctgc agccctgctt cagccgcctc actgttctca gactcagcgt aaaccagatc    2220
actgacggtg gggtaaaggt gctaagcgaa gagctgacca aatacaaaat tgtgacctat    2280 ttgggttat  acaacaacca gatcaccgat gtcggagcca ggtacgtcac caaaatcctg    2340
gatgaatgca aaggcctcac gcatcttaaa ctgggaaaaa acaaaataac aagtgaagga    2400
gggaagtatc tcgccctggc tgtgaagaac agcaaatcaa tctctgaggt tgggatgtgg    2460
ggcaatcaag ttggggatga aggagcaaaa gccttcgcag aggctctgcg gaaccacccc    2520
agcttgacca ccctgagtct tgcgtccaac ggcatctcca cagaaggagg aaagagcctt    2580
gcgagggccc tgcagcagaa cacgtctcta gaaatactgt ggctgaccca aaatgaactc    2640
aacgatgaag tggcagagag tttggcagaa atgttgaaag tcaaccagac gttaaagcat    2700
ttatggctta tccagaatca gatcacagct aaggggactg cccagctggc agatgcgtta    2760
cagagcaaca ctggcataac agagatttgc ctaaatggaa acctgataaa accagaggag    2820
gccaaagtct atgaagatga gaagcggatt atctgtttc                          2859
```

<210> SEQ ID NO 10
<211> LENGTH: 100
<212> TYPE: PRT
<213> ORGANISM: Homo sapiens

<400> SEQUENCE: 10

```
Glu Ser His Pro His Ile Gln Leu Leu Lys Ser Asn Arg Glu Leu Leu
 1               5                  10                  15

Val Thr His Ile Arg Asn Thr Gln Cys Leu Val Asp Asn Leu Leu Lys
            20                  25                  30

Asn Asp Tyr Phe Ser Ala Glu Asp Ala Glu Ile Val Cys Ala Cys Pro
        35                  40                  45

Thr Gln Pro Asp Lys Val Arg Lys Ile Leu Asp Leu Val Gln Ser Lys
    50                  55                  60

Gly Glu Glu Val Ser Glu Phe Phe Leu Tyr Leu Gln Gln Leu Ala
65                  70                  75                  80

Asp Ala Tyr Val Asp Leu Arg Pro Trp Leu Leu Glu Ile Gly Phe Ser
                85                  90                  95

Pro Ser Leu Leu
            100
```

<210> SEQ ID NO 11
<211> LENGTH: 200
<212> TYPE: PRT
<213> ORGANISM: Homo sapiens

<400> SEQUENCE: 11

```
Ile Phe Ile Leu Gly Asp Ala Gly Val Gly Lys Ser Met Leu Leu Gln
 1               5                  10                  15

Arg Leu Gln Ser Leu Trp Ala Thr Gly Arg Leu Asp Ala Gly Val Lys
            20                  25                  30

Phe Phe Phe His Phe Arg Cys Arg Met Phe Ser Cys Phe Lys Glu Ser
        35                  40                  45

Asp Arg Leu Cys Leu Gln Asp Leu Leu Phe Lys His Tyr Cys Tyr Pro
    50                  55                  60

Glu Arg Asp Pro Glu Glu Val Phe Ala Phe Leu Leu Arg Phe Pro His
65                  70                  75                  80

Val Ala Leu Phe Thr Phe Asp Gly Leu Asp Glu Leu His Ser Asp Leu
                85                  90                  95
```

```
Asp Leu Ser Arg Val Pro Asp Ser Ser Cys Pro Trp Glu Pro Ala His
            100                 105                 110

Pro Leu Val Leu Leu Ala Asn Leu Leu Ser Gly Lys Leu Leu Lys Gly
        115                 120                 125

Ala Ser Lys Leu Leu Thr Ala Arg Thr Gly Ile Glu Val Pro Arg Gln
    130                 135                 140

Phe Leu Arg Lys Lys Val Leu Leu Arg Gly Phe Ser Pro Ser His Leu
145                 150                 155                 160

Arg Ala Tyr Ala Arg Arg Met Phe Pro Glu Arg Ala Leu Gln Asp Arg
                165                 170                 175

Leu Leu Ser Gln Leu Glu Ala Asn Pro Asn Leu Cys Ser Leu Cys Ser
            180                 185                 190

Val Pro Leu Phe Cys Trp Ile Ile
            195                 200

<210> SEQ ID NO 12
<211> LENGTH: 8
<212> TYPE: PRT
<213> ORGANISM: Homo sapiens

<400> SEQUENCE: 12

Gly Asp Ala Gly Val Gly Lys Ser
1               5

<210> SEQ ID NO 13
<211> LENGTH: 5
<212> TYPE: PRT
<213> ORGANISM: Homo sapiens

<400> SEQUENCE: 13

Leu Phe Thr Phe Asp
1               5

<210> SEQ ID NO 14
<211> LENGTH: 13
<212> TYPE: PRT
<213> ORGANISM: Homo sapiens

<400> SEQUENCE: 14

Ala Ser Lys Leu Leu Thr Ala Arg Thr Gly Ile Glu Val
1               5                   10

<210> SEQ ID NO 15
<211> LENGTH: 28
<212> TYPE: PRT
<213> ORGANISM: Homo sapiens

<400> SEQUENCE: 15

Gly Ile Cys Ala Asn Tyr Leu Lys Leu Thr Tyr Cys Asn Ala Cys Ser
1               5                   10                  15

Ala Asp Cys Ser Ala Leu Ser Phe Val Leu His His
            20                  25

<210> SEQ ID NO 16
<211> LENGTH: 26
<212> TYPE: PRT
<213> ORGANISM: Homo sapiens

<400> SEQUENCE: 16

Phe Pro Lys Arg Leu Ala Leu Asp Leu Asp Asn Asn Asn Leu Asn Asp
1               5                   10                  15
```

Tyr Gly Val Arg Glu Leu Gln Pro Cys Phe
            20                  25

<210> SEQ ID NO 17
<211> LENGTH: 27
<212> TYPE: PRT
<213> ORGANISM: Homo sapiens

<400> SEQUENCE: 17

Ser Arg Leu Thr Val Leu Arg Leu Ser Val Asn Gln Ile Thr Asp Gly
 1               5                  10                  15

Gly Val Lys Val Leu Ser Glu Glu Leu Thr Lys
            20                  25

<210> SEQ ID NO 18
<211> LENGTH: 28
<212> TYPE: PRT
<213> ORGANISM: Homo sapiens

<400> SEQUENCE: 18

Tyr Lys Ile Val Thr Tyr Leu Gly Leu Tyr Asn Asn Gln Ile Thr Asp
 1               5                  10                  15

Val Gly Ala Arg Tyr Val Thr Lys Ile Leu Asp Glu
            20                  25

<210> SEQ ID NO 19
<211> LENGTH: 28
<212> TYPE: PRT
<213> ORGANISM: Homo sapiens

<400> SEQUENCE: 19

Cys Lys Gly Leu Thr His Leu Lys Leu Gly Lys Asn Lys Ile Thr Ser
 1               5                  10                  15

Glu Gly Gly Lys Tyr Leu Ala Leu Ala Val Lys Asn
            20                  25

<210> SEQ ID NO 20
<211> LENGTH: 28
<212> TYPE: PRT
<213> ORGANISM: Homo sapiens

<400> SEQUENCE: 20

Ser Lys Ser Ile Ser Glu Val Gly Met Trp Gly Asn Gln Val Gly Asp
 1               5                  10                  15

Glu Gly Ala Lys Ala Phe Ala Glu Ala Leu Arg Asn
            20                  25

<210> SEQ ID NO 21
<211> LENGTH: 28
<212> TYPE: PRT
<213> ORGANISM: Homo sapiens

<400> SEQUENCE: 21

His Pro Ser Leu Thr Thr Leu Ser Leu Ala Ser Asn Gly Ile Ser Thr
 1               5                  10                  15

Glu Gly Gly Lys Ser Leu Ala Arg Ala Leu Gln Gln
            20                  25

<210> SEQ ID NO 22
<211> LENGTH: 28
<212> TYPE: PRT
<213> ORGANISM: Homo sapiens

```
<400> SEQUENCE: 22

Asn Thr Ser Leu Glu Ile Leu Trp Leu Thr Gln Asn Glu Leu Asn Asp
 1               5                  10                  15

Glu Val Ala Glu Ser Leu Ala Glu Met Leu Lys Val
             20                  25

<210> SEQ ID NO 23
<211> LENGTH: 28
<212> TYPE: PRT
<213> ORGANISM: Homo sapiens

<400> SEQUENCE: 23

Asn Gln Thr Leu Lys His Leu Trp Leu Ile Gln Asn Gln Ile Thr Ala
 1               5                  10                  15

Lys Gly Thr Ala Gln Leu Ala Asp Ala Leu Gln Ser
             20                  25

<210> SEQ ID NO 24
<211> LENGTH: 28
<212> TYPE: PRT
<213> ORGANISM: Homo sapiens

<400> SEQUENCE: 24

Asn Thr Gly Ile Thr Glu Ile Cys Leu Asn Gly Asn Leu Ile Lys Pro
 1               5                  10                  15

Glu Glu Ala Lys Val Tyr Glu Asp Glu Lys Arg Ile
             20                  25

<210> SEQ ID NO 25
<211> LENGTH: 3080
<212> TYPE: DNA
<213> ORGANISM: Homo sapiens
<220> FEATURE:
<221> NAME/KEY: CDS
<222> LOCATION: (1)...(1470)

<400> SEQUENCE: 25 cac gcg tcc gac ttg ctg aag aat gac tac ttc tcg gcc gaa gat gcg      48
His Ala Ser Asp Leu Leu Lys Asn Asp Tyr Phe Ser Ala Glu Asp Ala
 1               5                  10                  15 gag att gtg tgt gcc tgc ccc acc cag cct gac aag gtc cgc aaa att      96
Glu Ile Val Cys Ala Cys Pro Thr Gln Pro Asp Lys Val Arg Lys Ile
             20                  25                  30 ctg gac ctg gta cag agc aag ggc gag gag gtg tcc gag ttc ttc ctc     144
Leu Asp Leu Val Gln Ser Lys Gly Glu Glu Val Ser Glu Phe Phe Leu
         35                  40                  45 tac ttg ctc cag caa ctc gca gat gcc tac gtg gac ctc agg cct tgg     192
Tyr Leu Leu Gln Gln Leu Ala Asp Ala Tyr Val Asp Leu Arg Pro Trp
     50                  55                  60 ctg ctg gag atc ggc ttc tcc cct tcc ctg ctc act cag agc aaa gtc     240
Leu Leu Glu Ile Gly Phe Ser Pro Ser Leu Leu Thr Gln Ser Lys Val
 65                  70                  75                  80 gtg gtc aac act gac cca gtg agc agg tat acc cag cag ctg cga cac     288
Val Val Asn Thr Asp Pro Val Ser Arg Tyr Thr Gln Gln Leu Arg His
                 85                  90                  95 cat ctg ggc cgt gac tcc aag ttc gtg ctg tgc tat gcc cag aag gag     336
His Leu Gly Arg Asp Ser Lys Phe Val Leu Cys Tyr Ala Gln Lys Glu
            100                 105                 110 gag ctg ctg ctg gag gag atc tac atg gac acc atc atg gag ctg gtt     384
Glu Leu Leu Leu Glu Glu Ile Tyr Met Asp Thr Ile Met Glu Leu Val
        115                 120                 125
```

-continued

```
ggc ttc agc aat gag agc ctg ggc agc ctg aac agc ctg gcc tgc ctc        432
Gly Phe Ser Asn Glu Ser Leu Gly Ser Leu Asn Ser Leu Ala Cys Leu
        130             135             140 ctg gac cac acc acc ggc atc ctc aat gag cag ggt gag acc atc ttc        480
Leu Asp His Thr Thr Gly Ile Leu Asn Glu Gln Gly Glu Thr Ile Phe
145             150             155             160 atc ctg ggt gat gct ggg gtg ggc aag tcc atg ctg cta cag cgg ctg        528
Ile Leu Gly Asp Ala Gly Val Gly Lys Ser Met Leu Leu Gln Arg Leu
                165             170             175 cag agc ctc tgg gcc acg ggc cgg cta gac gca ggg gtc aaa ttc ttc        576
Gln Ser Leu Trp Ala Thr Gly Arg Leu Asp Ala Gly Val Lys Phe Phe
            180             185             190 ttc cac ttt cgc tgc cgc atg ttc agc tgc ttc aag gaa agt gac agg        624
Phe His Phe Arg Cys Arg Met Phe Ser Cys Phe Lys Glu Ser Asp Arg
        195             200             205 ctg tgt ctg cag gac ctg ctc ttc aag cac tac tgc tac cca gag cgg        672
Leu Cys Leu Gln Asp Leu Leu Phe Lys His Tyr Cys Tyr Pro Glu Arg
    210             215             220 gac ccc gag gag gtg ttt gcc ttc ctg ctg cgc ttc ccc cac gtg gcc        720
Asp Pro Glu Glu Val Phe Ala Phe Leu Leu Arg Phe Pro His Val Ala
225             230             235             240 ctc ttc acc ttc gat ggc ctg gac gag ctg cac tcg gac ttg gac ctg        768
Leu Phe Thr Phe Asp Gly Leu Asp Glu Leu His Ser Asp Leu Asp Leu
                245             250             255 agc cgc gtg cct gac agc tcc tgc ccc tgg gag cct gcc cac ccc ctg        816
Ser Arg Val Pro Asp Ser Ser Cys Pro Trp Glu Pro Ala His Pro Leu
            260             265             270 gtc ttg ctg gcc aac ctg ctc agt ggg aag ctg ctc aag ggg gct agc        864
Val Leu Leu Ala Asn Leu Leu Ser Gly Lys Leu Leu Lys Gly Ala Ser
        275             280             285 aag ctg ctc aca gcc cgc aca ggc atc gag gtc ccg cgc cag ttc ctg        912
Lys Leu Leu Thr Ala Arg Thr Gly Ile Glu Val Pro Arg Gln Phe Leu
    290             295             300 cgg aag aag gtg ctt ctc cgg ggc ttc tcc ccc agc cac ctg cgc gcc        960
Arg Lys Lys Val Leu Leu Arg Gly Phe Ser Pro Ser His Leu Arg Ala
305             310             315             320 tat gcc agg agg atg ttc ccc gag cgg gcc ctg cag gac cgc ctg ctg       1008
Tyr Ala Arg Arg Met Phe Pro Glu Arg Ala Leu Gln Asp Arg Leu Leu
                325             330             335 agc cag ctg gag gcc aac ccc aac ctc tgc agc ctg tgc tct gtg ccc       1056
Ser Gln Leu Glu Ala Asn Pro Asn Leu Cys Ser Leu Cys Ser Val Pro
            340             345             350 ctc ttc tgc tgg atc atc ttc cgg tgc ttc cag cac ttc cgt gct gcc       1104
Leu Phe Cys Trp Ile Ile Phe Arg Cys Phe Gln His Phe Arg Ala Ala
        355             360             365 ttt gaa ggc tca cca cag ctg ccc gac tgc acg atg acc ctg aca gat       1152
Phe Glu Gly Ser Pro Gln Leu Pro Asp Cys Thr Met Thr Leu Thr Asp
    370             375             380 gtc ttc ctc ctg gtc act gag gtc cat ctg aac agg atg cag ccc agc       1200
Val Phe Leu Leu Val Thr Glu Val His Leu Asn Arg Met Gln Pro Ser
385             390             395             400 agc ctg gtg cag cgg aac aca cgc agc cca gtg gag acc ctc cac gcc       1248
Ser Leu Val Gln Arg Asn Thr Arg Ser Pro Val Glu Thr Leu His Ala
                405             410             415 ggc cgg gac act ctg tgc tcg ctg ggg cag gtg gcc cac cgg ggc atg       1296
Gly Arg Asp Thr Leu Cys Ser Leu Gly Gln Val Ala His Arg Gly Met
            420             425             430 gag aag agc ctc ttt gtc ttc acc cag gag gag gtg cag gcc tcc ggg       1344
Glu Lys Ser Leu Phe Val Phe Thr Gln Glu Glu Val Gln Ala Ser Gly
        435             440             445
```

```
ctg cag gag aga gac atg cag ctg ggc ttc ctg cgg gct ttg ccg gag    1392
Leu Gln Glu Arg Asp Met Gln Leu Gly Phe Leu Arg Ala Leu Pro Glu
        450                 455                 460 ctg ggc ccc ggg ggt gac cag cag tcc tat gag ttt ttc cac ctc agc    1440
Leu Gly Pro Gly Gly Asp Gln Gln Ser Tyr Glu Phe Phe His Leu Ser
465                 470                 475                 480 ctc ctc acc tgt aaa act ggg atc cca gta tagactttgg aaatcagtag      1490
Leu Leu Thr Cys Lys Thr Gly Ile Pro Val
                485                 490 acaccatatg cttcaaaaaa cagggctat taaaatgaca tcaggagcca gaaagtctca   1550
tggctgtgct ttctcttgaa gtttatacaa caaccagatc accgatgtcg gagccagact   1610
gggaaaaaac aaaataacaa gtgaaggagg aagtatctc gccctggctg tgaagaacag    1670
caaatcaatc tctgaggttg ggatgtgggg caatcaagtt ggggatgaag gagcaaaagc   1730
cttcgcagag gctctgcgga accaccccag cttgaccacc ctgagtcttg cgtccaacgg   1790
catctccaca gaaggaggaa agagccttgc gagggccctg cagcagaaca cgtctctaga   1850
aatactgtgg ctgacccaaa atgaactcaa cgatgaagtg gcagagagtt tggcagaaat   1910
gttgaaagtc aaccagacgt taaagcattt atggcttatc cagaatcaga tcacagtctt   1970
ttgtgtcagt gtcttaaagg ggcctgcgca ggcgggacta tcaggagtcc actgcctcca   2030
tgatgcaagc cagcttcctg tgcagaaggt ctggtcggca aactccctaa gtacccgcta   2090
caattctgca gaaaagaat gtgtcttgcg agctgttgta gttacagtaa atacactgtg    2150
aagagacttt attgcctatt ataattattt ttatctgaag ctagaggaat aaagctgtga   2210
gcaaacagag gaggccagcc tcacctcatt ccaacacctg ccatagggac caacgggagc   2270
gagttggtca ccgctctttt cattgaagag ttgaggatgt ggcacaaagt tggtgccaag   2330
cttcttgaat aaaacgtgtt tgatggatta gtattatacc tgaaatattt tcttccttct   2390
cagcactttc ccatgtattg atactggtcc cacttcacag ctggagacac cggagtatgt   2450
gcagtgtggg atttgactcc tccaaggttt tgtggaaagt taatgtcaag gaaaggatgc   2510
accacgggct tttaattta atcctggagt ctcactgtct gctggcaaag atagagaatg     2570
ccctcagctc ttagctggtc taagaatgac gatgccttca aaatgctgct tccactcagg   2630
gcttctcctc tgctaggcta ccctcctcta gaaggctgag taccatgggc tacagtgtct   2690
ggccttggga agaagtgatt ctgtccctcc aaagaaatag ggcatggctt gcccctgtgg   2750
ccctggcatc caaatggctg cttttgtctc ccttacctcg tgaagagggg aagtctcttc   2810
ctgcctccca gcagctgaa gggtgactaa acgggcgcca agactcaggg gatcggctgg   2870
gaactgggcc agcagagcat gttggacacc ccccaccatg gtgggcttgt ggtggctgct   2930
ccatgagggt gggggtgata ctactagatc acttgtcctc ttgccagctc atttgttaat   2990
aaaatactga aaacacaaaa aaaaaaaaaa aaaaaaaaaa aaaaaaaaaa aaaaaaaaa    3050 aaaaaaaaaa aaaaaaaaa aaaaaaaaa                                      3080
```

<210> SEQ ID NO 26
<211> LENGTH: 490
<212> TYPE: PRT
<213> ORGANISM: Homo sapiens

<400> SEQUENCE: 26

```
His Ala Ser Asp Leu Leu Lys Asn Asp Tyr Phe Ser Ala Glu Asp Ala
 1               5                  10                  15

Glu Ile Val Cys Ala Cys Pro Thr Gln Pro Asp Lys Val Arg Lys Ile
```

```
                      20                  25                  30
Leu Asp Leu Val Gln Ser Lys Gly Glu Val Ser Glu Phe Phe Leu
             35                  40                  45
Tyr Leu Leu Gln Gln Leu Ala Asp Ala Tyr Val Asp Leu Arg Pro Trp
         50                  55                  60
Leu Leu Glu Ile Gly Phe Ser Pro Ser Leu Leu Thr Gln Ser Lys Val
 65                  70                  75                  80
Val Val Asn Thr Asp Pro Val Ser Arg Tyr Thr Gln Gln Leu Arg His
                 85                  90                  95
His Leu Gly Arg Asp Ser Lys Phe Val Leu Cys Tyr Ala Gln Lys Glu
                100                 105                 110
Glu Leu Leu Leu Glu Glu Ile Tyr Met Asp Thr Ile Met Glu Leu Val
             115                 120                 125
Gly Phe Ser Asn Glu Ser Leu Gly Ser Leu Asn Ser Leu Ala Cys Leu
         130                 135                 140
Leu Asp His Thr Thr Gly Ile Leu Asn Glu Gln Gly Glu Thr Ile Phe
145                 150                 155                 160
Ile Leu Gly Asp Ala Gly Val Gly Lys Ser Met Leu Leu Gln Arg Leu
                165                 170                 175
Gln Ser Leu Trp Ala Thr Gly Arg Leu Asp Ala Gly Val Lys Phe Phe
             180                 185                 190
Phe His Phe Arg Cys Arg Met Phe Ser Cys Phe Lys Glu Ser Asp Arg
         195                 200                 205
Leu Cys Leu Gln Asp Leu Leu Phe Lys His Tyr Cys Tyr Pro Glu Arg
 210                 215                 220
Asp Pro Glu Glu Val Phe Ala Phe Leu Leu Arg Phe Pro His Val Ala
225                 230                 235                 240
Leu Phe Thr Phe Asp Gly Leu Asp Glu Leu His Ser Asp Leu Asp Leu
                245                 250                 255
Ser Arg Val Pro Asp Ser Ser Cys Pro Trp Glu Pro Ala His Pro Leu
             260                 265                 270
Val Leu Leu Ala Asn Leu Leu Ser Gly Lys Leu Leu Lys Gly Ala Ser
         275                 280                 285
Lys Leu Leu Thr Ala Arg Thr Gly Ile Glu Val Pro Arg Gln Phe Leu
 290                 295                 300
Arg Lys Lys Val Leu Leu Arg Gly Phe Ser Pro Ser His Leu Arg Ala
305                 310                 315                 320
Tyr Ala Arg Arg Met Phe Pro Glu Arg Ala Leu Gln Asp Arg Leu Leu
                325                 330                 335
Ser Gln Leu Glu Ala Asn Pro Asn Leu Cys Ser Leu Cys Ser Val Pro
             340                 345                 350
Leu Phe Cys Trp Ile Ile Phe Arg Cys Phe Gln His Phe Arg Ala Ala
         355                 360                 365
Phe Glu Gly Ser Pro Gln Leu Pro Asp Cys Thr Met Thr Leu Thr Asp
 370                 375                 380
Val Phe Leu Leu Val Thr Glu Val His Leu Asn Arg Met Gln Pro Ser
385                 390                 395                 400
Ser Leu Val Gln Arg Asn Thr Arg Ser Pro Val Glu Thr Leu His Ala
                405                 410                 415
Gly Arg Asp Thr Leu Cys Ser Leu Gly Gln Val Ala His Arg Gly Met
             420                 425                 430
Glu Lys Ser Leu Phe Val Phe Thr Gln Glu Glu Val Gln Ala Ser Gly
         435                 440                 445
```

Leu Gln Glu Arg Asp Met Gln Leu Gly Phe Leu Arg Ala Leu Pro Glu
    450                 455                 460

Leu Gly Pro Gly Gly Asp Gln Gln Ser Tyr Glu Phe Phe His Leu Ser
465                 470                 475                 480

Leu Leu Thr Cys Lys Thr Gly Ile Pro Val
                485                 490

<210> SEQ ID NO 27
<211> LENGTH: 1470
<212> TYPE: DNA
<213> ORGANISM: Homo sapiens

<400> SEQUENCE: 27

| | | | | | |
|---|---|---|---|---|---|
| cacgcgtccg | acttgctgaa | gaatgactac | ttctcggccg | aagatgcgga | gattgtgtgt | 60 |
| gcctgcccca | cccagcctga | caaggtccgc | aaaattctgg | acctggtaca | gagcaagggc | 120 |
| gaggaggtgt | ccgagttctt | cctctacttg | ctccagcaac | tcgcagatgc | ctacgtggac | 180 |
| ctcaggcctt | ggctgctgga | gatcggcttc | tcccttccc | tgctcactca | gagcaaagtc | 240 |
| gtggtcaaca | ctgacccagt | gagcaggtat | acccagcagc | tgcgacacca | tctgggccgt | 300 |
| gactccaagt | tcgtgctgtg | ctatgcccag | aaggaggagc | tgctgctgga | ggagatctac | 360 |
| atggacacca | tcatggagct | ggttggcttc | agcaatgaga | cctgggcag | cctgaacagc | 420 |
| ctggcctgcc | tcctggacca | caccaccggc | atcctcaatg | agcagggtga | gaccatcttc | 480 |
| atcctgggtg | atgctgggt | gggcaagtcc | atgctgctac | agcggctgca | gagcctctgg | 540 |
| gccacgggcc | ggctagacgc | aggggtcaaa | ttcttcttcc | actttcgctg | ccgcatgttc | 600 |
| agctgcttca | aggaaagtga | caggctgtgt | ctgcaggacc | tgctcttcaa | gcactactgc | 660 |
| tacccagagc | gggaccccga | ggaggtgttt | gccttcctgc | tgcgcttccc | ccacgtggcc | 720 |
| ctcttcacct | tcgatggcct | ggacgagctg | cactcggact | tggacctgag | ccgcgtgcct | 780 |
| gacagctcct | gccctggga | gcctgcccac | cccctggtct | tgctggccaa | cctgctcagt | 840 |
| gggaagctgc | tcaaggggc | tagcaagctg | ctcacagccc | gcacaggcat | cgaggtcccg | 900 |
| cgccagttcc | tgcggaagaa | ggtgcttctc | cggggcttct | cccccagcca | cctgcgcgcc | 960 |
| tatgccagga | ggatgttccc | cgagcgggcc | ctgcaggacc | gcctgctgag | ccagctggag | 1020 |
| gccaacccca | acctctgcag | cctgtgctct | gtgccctct | tctgctggat | catcttccgg | 1080 |
| tgcttccagc | acttccgtgc | tgcctttgaa | ggctcaccac | agctgcccga | ctgcacgatg | 1140 |
| accctgacag | atgtcttcct | cctggtcact | gaggtccatc | tgaacaggat | gcagcccagc | 1200 |
| agcctggtgc | agcggaacac | acgcagccca | gtggagaccc | tccacgccgg | ccgggacact | 1260 |
| ctgtgctcgc | tggggcaggt | ggcccaccgg | ggcatggaga | gagcctctt | tgtcttcacc | 1320 |
| caggaggagg | tgcaggcctc | cgggctgcag | gagagagaca | tgcagctggg | cttcctgcgg | 1380 |
| gctttgccgg | agctgggccc | cggggtgac | cagcagtcct | atgagttttt | ccacctcagc | 1440 |
| ctcctcacct | gtaaaactgg | gatcccagta | | | | 1470 |

<210> SEQ ID NO 28
<211> LENGTH: 74
<212> TYPE: PRT
<213> ORGANISM: Homo sapiens

<400> SEQUENCE: 28

His Ala Ser Asp Leu Leu Lys Asn Asp Tyr Phe Ser Ala Glu Asp Ala
  1               5                  10                  15

-continued

```
Glu Ile Val Cys Ala Cys Pro Thr Gln Pro Asp Lys Val Arg Lys Ile
                20                  25                  30

Leu Asp Leu Val Gln Ser Lys Gly Glu Val Ser Glu Phe Phe Leu
            35                  40                  45

Tyr Leu Leu Gln Gln Leu Ala Asp Ala Tyr Val Asp Leu Arg Pro Trp
    50                  55                  60

Leu Leu Glu Ile Gly Phe Ser Pro Ser Leu
 65                  70
```

<210> SEQ ID NO 29
<211> LENGTH: 8
<212> TYPE: PRT
<213> ORGANISM: Homo sapiens

<400> SEQUENCE: 29

```
Gly Asp Ala Gly Val Gly Lys Ser
 1               5
```

<210> SEQ ID NO 30
<211> LENGTH: 5
<212> TYPE: PRT
<213> ORGANISM: Homo sapiens

<400> SEQUENCE: 30

```
Leu Phe Thr Phe Asp
 1               5
```

<210> SEQ ID NO 31
<211> LENGTH: 94
<212> TYPE: PRT
<213> ORGANISM: Homo sapiens

<400> SEQUENCE: 31

```
Ala Gln Glu Arg Pro Ser Glu Thr Thr Asp Arg Glu Arg Lys Arg Leu
 1               5                  10                  15

Val Glu Thr Leu Gln Ala Asp Ser Gly Leu Leu Leu Asp Ala Leu Leu
                20                  25                  30

Ala Arg Gly Val Leu Thr Gly Pro Glu Tyr Glu Ala Leu Asp Ala Leu
            35                  40                  45

Pro Asp Ala Glu Arg Arg Val Arg Arg Leu Leu Leu Leu Val Gln Gly
    50                  55                  60

Lys Gly Glu Ala Ala Cys Gln Glu Leu Leu Arg Cys Ala Gln Arg Thr
 65                  70                  75                  80

Ala Gly Ala Pro Asp Pro Ala Trp Asp Trp Gln His Val Gly
                85                  90
```

<210> SEQ ID NO 32
<211> LENGTH: 89
<212> TYPE: PRT
<213> ORGANISM: Homo sapiens

<400> SEQUENCE: 32

```
Met Ala Ser Asp Asp Leu Ser Leu Ile Arg Lys Asn Arg Met Ala Leu
 1               5                  10                  15

Phe Gln Gln Leu Thr Cys Val Leu Pro Ile Leu Asp Asn Leu Leu Lys
                20                  25                  30

Ala Asn Val Thr Asn Lys Gln Glu His Asp Ile Ile Lys Gln Lys Thr
            35                  40                  45

Gln Ile Pro Leu Gln Ala Arg Glu Leu Ile Asp Thr Ile Trp Val Lys
    50                  55                  60
```

```
Gly Asn Ala Ala Ala Asn Ile Phe Lys Asn Cys Leu Lys Glu Ile Asp
 65                  70                  75                  80

Ser Thr Leu Tyr Lys Asn Leu Phe Val
                 85
```

<210> SEQ ID NO 33
<211> LENGTH: 89
<212> TYPE: PRT
<213> ORGANISM: Homo sapiens

<400> SEQUENCE: 33

```
Lys Glu Ser Asn Asp Leu Leu Leu Ile Arg Lys Asn Arg Met Ala Leu
  1               5                  10                  15

Phe Gln His Leu Thr Cys Val Ile Pro Ile Leu Asp Ser Leu Leu Thr
                 20                  25                  30

Ala Gly Ile Ile Asn Glu Gln Glu His Asp Val Ile Lys Gln Lys Thr
             35                  40                  45

Gln Thr Ser Leu Gln Ala Arg Glu Leu Ile Asp Thr Ile Leu Val Lys
         50                  55                  60

Gly Asn Ile Ala Ala Thr Val Phe Arg Asn Ser Leu Gln Glu Ala Glu
 65                  70                  75                  80

Ala Val Leu Tyr Glu His Leu Phe Val
                 85
```

<210> SEQ ID NO 34
<211> LENGTH: 24
<212> TYPE: DNA
<213> ORGANISM: Homo sapiens

<400> SEQUENCE: 34
ccctggtact tgcccctccg gtag                                          24

<210> SEQ ID NO 35
<211> LENGTH: 18
<212> TYPE: DNA
<213> ORGANISM: Homo sapiens

<400> SEQUENCE: 35
cctggtactt gcccctcc                                                 18

<210> SEQ ID NO 36
<211> LENGTH: 23
<212> TYPE: DNA
<213> ORGANISM: Homo sapiens

<400> SEQUENCE: 36
tcgttaagcc cttgaagaca gtg                                           23

<210> SEQ ID NO 37
<211> LENGTH: 30
<212> TYPE: DNA
<213> ORGANISM: Homo sapiens

<400> SEQUENCE: 37
tcgttagccc ttgaagacca gtgagtgtag                                    30

<210> SEQ ID NO 38
<211> LENGTH: 4302
<212> TYPE: DNA
<213> ORGANISM: Homo sapiens
<220> FEATURE:

-continued

```
<221> NAME/KEY: CDS
<222> LOCATION: (438)...(1184)
<221> NAME/KEY: misc_feature
<222> LOCATION: (1)...(4302)
<223> OTHER INFORMATION: n = A,T,C or G

<400> SEQUENCE: 38
cccgcgtccg cgtccccgga ccatggcgct ctccgggctc ttctctagct ctcagcggct      60
gcgaagtctg tnaacctggt ggccaagtga ttgtaagtca ggagactttc cttcggtttc     120
tgcctttgat ggcaagaggt ggagattgtg gcggcgatta cagaaaacat ctgggaagac     180
aagttgctgt tttatggga atcgcaggct tggaagagac agaagcaatt ccagaaataa      240
attggaaatt gaagatttaa acaatgttgt tttaaaatat tctaacttca agaatgatg     300 ccagaaactt aaaagggc tgcgcagagt agcaggggcc ctggagggcg cggcctgaat       360
cctgattgcc cttctgctga aggacacac gcagctgaag atgaatttgg gaaaagtagc      420
cgcttgctac tttaact atg gaa gag cag ggc cac agt gag atg gaa ata       470
                   Met Glu Glu Gln Gly His Ser Glu Met Glu Ile
                    1               5                  10 atc cca tca gag tct cac ccc cac att caa tta ctg aaa agc aat cgg      518
Ile Pro Ser Glu Ser His Pro His Ile Gln Leu Leu Lys Ser Asn Arg
            15                  20                  25 gaa ctt ctg gtc act cac atc cgc aat act cag tgt ctg gtg gac aac      566
Glu Leu Leu Val Thr His Ile Arg Asn Thr Gln Cys Leu Val Asp Asn
        30                  35                  40 ttg ctg aag aat gac tac ttc tcg gcc gaa gat gcg gag att gtg tgt      614
Leu Leu Lys Asn Asp Tyr Phe Ser Ala Glu Asp Ala Glu Ile Val Cys
    45                  50                  55 gcc tgc ccc acc cag cct gac aag gtc cgc aaa att ctg gac ctg gta      662
Ala Cys Pro Thr Gln Pro Asp Lys Val Arg Lys Ile Leu Asp Leu Val
60                  65                  70                  75 cag agc aag ggc gag gag gtg tcc gag ttc ttc ctc tac ttg ctc cag      710
Gln Ser Lys Gly Glu Glu Val Ser Glu Phe Phe Leu Tyr Leu Leu Gln
                80                  85                  90 caa ctc gca gat gcc tac gtg gac ctc agg cct tgg ctg ctg gag atc      758
Gln Leu Ala Asp Ala Tyr Val Asp Leu Arg Pro Trp Leu Leu Glu Ile
            95                  100                 105 ggc ttc tcc cct tcc ctg ctc act cag agc aaa gtc gtg gtc aac act      806
Gly Phe Ser Pro Ser Leu Leu Thr Gln Ser Lys Val Val Val Asn Thr
        110                 115                 120 gac cca gtg agc agg tat acc cag cag ctg cga cac cat ctg ggc cgt      854
Asp Pro Val Ser Arg Tyr Thr Gln Gln Leu Arg His His Leu Gly Arg
    125                 130                 135 gac tcc aag ttc gtg ctg tgc tat gcc cag aag gag gag ctg ctg ctg      902
Asp Ser Lys Phe Val Leu Cys Tyr Ala Gln Lys Glu Glu Leu Leu Leu
140                 145                 150                 155 gag gag atc tac atg gac acc atc atg gag ctg gtt ggc ttc agc aat      950
Glu Glu Ile Tyr Met Asp Thr Ile Met Glu Leu Val Gly Phe Ser Asn
                160                 165                 170 gag agc ctg ggc agc ctg aac agc ctg gcc tgc ctc ctg gac cac acc      998
Glu Ser Leu Gly Ser Leu Asn Ser Leu Ala Cys Leu Leu Asp His Thr
            175                 180                 185 acc ggc atc ctc aat gag cag gct gct tca agg aaa gtg aca ggc tgt     1046
Thr Gly Ile Leu Asn Glu Gln Ala Ala Ser Arg Lys Val Thr Gly Cys
        190                 195                 200 gtc tgc agg acc tgc tct tca agc act act gct acc cag agc ggg acc     1094
Val Cys Arg Thr Cys Ser Ser Ser Thr Thr Ala Thr Gln Ser Gly Thr
    205                 210                 215 ccg agg agg tgt ttg cct tcc tgc tgc gct tcc ccc acg tgg ccc tct     1142
```

| | | |
|---|---|---|
| Pro Arg Arg Cys Leu Pro Ser Cys Cys Ala Ser Pro Thr Trp Pro Ser<br>220                   225                   230                   235 | | |
| tca cct tcg atg gcc tgg acg agc tgc act cgg act tgg acc<br>Ser Pro Ser Met Ala Trp Thr Ser Cys Thr Arg Thr Trp Thr<br>                240                   245 | | 1184 |
| tgagccgcgt gcctgacagc tcctgcccct gggagcctgc ccaccccctg gtcttgctgg | | 1244 |
| ccaacctgct cagtgggaag ctgctcaagg gggctagcaa gctgctcaca gcccgcacag | | 1304 |
| gcatcgaggt cccgcgccag ttcctgcgga agaaggtgct tctccggggc ttctccccca | | 1364 |
| gccacctgcg cgcctatgcc aggaggatgt tccccgagcg ggccctgcag gaccgcctgc | | 1424 |
| tgagccagct ggaggccaac cccaacctct gcagcctgtg ctctgtgccc ctcttctgct | | 1484 |
| ggatcatctt ccggtgcttc cagcacttcc gtgctgcctt tgaaggctca ccacagctgc | | 1544 |
| ccgactgcac gatgaccctg acagatgtct tcctcctggt cactgaggtc catctgaaca | | 1604 |
| ggatgcagcc cagcagcctg gtgcagcgga acacacgcag cccagtggag accctccacg | | 1664 |
| ccggccggga cactctgtgc tcgctgggc aggtggccca ccggggcatg gagaagagcc | | 1724 |
| tctttgtctt cacccaggag gaggtgcagg cctccgggct gcaggagaga gacatgcagc | | 1784 |
| tgggcttcct gcgggctttg ccggagctgg gccccggggg tgaccagcag tcctatgagt | | 1844 |
| ttttccacct caccctccag gccttcttta cagccttctt cctcgtgctg gacgacaggg | | 1904 |
| tgggcactca ggagctgctc aggttcttcc aggagtggat gccccctgcg ggggcagcga | | 1964 |
| ccacgtcctg ctatcctccc ttcctcccgt ccagtgcct gcagggcagt ggtccggcgc | | 2024 |
| gggaagacct cttcaagaac aaggatcact tccagttcac caacctcttc ctgtgcgggc | | 2084 |
| tgttgkccaa agccaaacag aaactcctgc ggcatctggt gcccgcggca gccctgagga | | 2144 |
| gaaagcgcaa ggccctgtgg gcacacctgt tttccagcct gcggggctac ctgaagagcc | | 2204 |
| tgccccgcgt tcaggtcgaa agcttcaacc aggtgcaggc catgcccacg ttcatctgga | | 2264 |
| tgctgcgctg catctacgag acacagagcc agaaggtggg gcagctggcg gccagggggca | | 2324 |
| tctgcgccaa ctacctcaag ctgacctact gcaacgcctg ctcggccgac tgcagcgccc | | 2384 |
| tctccttcgt cctgcatcac ttccccaagc ggctggccct agacctagac aacaacaatc | | 2444 |
| tcaacgacta cggcgtgcgg gagctgcagc cctgcttcag ccgcctcact gttctcagac | | 2504 |
| tcagcgtaaa ccagatcact gacggtgggg taaaggtgct aagcgaagag ctgaccaaat | | 2564 |
| acaaaattgt gacctatttg ggtttataca acaaccagat caccgatgtc ggagccaggt | | 2624 |
| acgtcaccaa aatcctggat gaatgcaaag gcctcacgca tcttaaactg gaaaaaaaca | | 2684 |
| aaataacaag tgaaggaggg aagtatctcg ccctggctgt gaagaacagc aaatcaatct | | 2744 |
| ctgaggttgg gatgtgggc aatcaagttg gggatgaagg agcaaaagcc ttcgcagagg | | 2804 |
| ctctgcggaa ccacccagc ttgaccaccc tgagtcttgc gtccaacggc atctccacag | | 2864 |
| aaggaggaaa gagccttgcg agggccctgc agcagaacac gtctctagaa atactgtggc | | 2924 |
| tgacccaaaa tgaactcaac gatgaagtgg cagagagttt ggcagaaatg ttgaaagtca | | 2984 |
| accagacgtt aaagcattta tggcttatcc agaatcasat cacagctwar gggactgccc | | 3044 |
| agctggcaga tgcgttacag agcaacactg gcataacaga gatttgccta aatggaaacc | | 3104 |
| tgataaaacc agaggaggcc aaagtctatg aagatgagaa gcggattatc tgtttctgag | | 3164 |
| aggatgcttt cctgttcatg gggtttttgc cctggagcct cagcagcaaa tgccactytg | | 3224 |
| ggcagtcttt tgtgtcagtg tcttaaaggg gcctgcgcag gcgggactat caggagtcca | | 3284 |
| ctgcctccat gatgcaagcc agcttcctgt gcagaaggtc tggtcggcaa actccctaag | | 3344 |

```
tacccgctac aattctgcag aaaaagaatg tgtcttgcga gctgttgtag ttacagtaaa    3404
tacactgtga agagacttta ttgcctatta taattatttt tatctgaagc tagaggaata    3464
aagctgtgag caaacagagg aggccagcct cacctcattc caacacctgc catagggacc    3524
aacgggagcg agttggtcac cgctcttttc attgaagagt tgaggatgtg cacaaagtt    3584 ggtgccaagc ttcttgaata aaacgtgttt gatggattag tattatacct gaaatatttt    3644
cttccttctc agcactttcc catgtattga tactggtccc acttcacagc tggagacacc    3704
ggagtatgtg cagtgtggga tttgactcct ccaaggtttt gtggaaagtt aatgtcaagg    3764
aaaggatgca ccacgggctt ttaattttaa tcctggagtc tcactgtctg ctggcaaaga    3824
tagagaatgc cctcagctct tagctggtct aagaatgacg atgccttcaa aatgctgctt    3884
ccactcaggg cttctcctct gctaggctac cctcctctag aaggctgagt accatgggct    3944
acagtgtctg gccttgggaa gaagtgattc tgtccctcca agaaataggg catggcttg    4004 cccctgtggc cctggcatcc aaatggctgc ttttgtctcc cttacctcgt gaagagggga    4064
agtctcttcc tgcctcccaa gcagctgaag ggtgactaaa cgggcgccaa gactcagggg    4124
atcggctggg aactgggcca gcagagcatg ttggacaccc cccaccatgg tgggcttgtg    4184
gtggctgctc catgagggtg ggggtgatac tactagatca cttgtcctct tgccagctca    4244
tttgttaata aaatactgaa aacccaaaaa aaaaaaaaaa aaaaaaaaaa aagggcgg     4302
```

<210> SEQ ID NO 39
<211> LENGTH: 249
<212> TYPE: PRT
<213> ORGANISM: Homo sapiens

<400> SEQUENCE: 39

```
Met Glu Glu Gln Gly His Ser Glu Met Glu Ile Ile Pro Ser Glu Ser
 1               5                  10                  15

His Pro His Ile Gln Leu Leu Lys Ser Asn Arg Glu Leu Leu Val Thr
            20                  25                  30

His Ile Arg Asn Thr Gln Cys Leu Val Asp Asn Leu Leu Lys Asn Asp
        35                  40                  45

Tyr Phe Ser Ala Glu Asp Ala Glu Ile Val Cys Ala Cys Pro Thr Gln
    50                  55                  60

Pro Asp Lys Val Arg Lys Ile Leu Asp Leu Val Gln Ser Lys Gly Glu
65                  70                  75                  80

Glu Val Ser Glu Phe Phe Leu Tyr Leu Leu Gln Gln Leu Ala Asp Ala
                85                  90                  95

Tyr Val Asp Leu Arg Pro Trp Leu Leu Glu Ile Gly Phe Ser Pro Ser
            100                 105                 110

Leu Leu Thr Gln Ser Lys Val Val Asn Thr Asp Pro Val Ser Arg
        115                 120                 125

Tyr Thr Gln Gln Leu Arg His His Leu Gly Arg Asp Ser Lys Phe Val
    130                 135                 140

Leu Cys Tyr Ala Gln Lys Glu Glu Leu Leu Glu Glu Ile Tyr Met
145                 150                 155                 160

Asp Thr Ile Met Glu Leu Val Gly Phe Ser Asn Glu Ser Leu Gly Ser
                165                 170                 175

Leu Asn Ser Leu Ala Cys Leu Leu Asp His Thr Thr Gly Ile Leu Asn
            180                 185                 190

Glu Gln Ala Ala Ser Arg Lys Val Thr Gly Cys Val Cys Arg Thr Cys
        195                 200                 205
```

```
Ser Ser Ser Thr Thr Ala Thr Gln Ser Gly Thr Pro Arg Arg Cys Leu
    210                 215                 220
Pro Ser Cys Cys Ala Ser Pro Thr Trp Pro Ser Ser Pro Ser Met Ala
225                 230                 235                 240
Trp Thr Ser Cys Thr Arg Thr Trp Thr
                245

<210> SEQ ID NO 40
<211> LENGTH: 1400
<212> TYPE: DNA
<213> ORGANISM: Homo sapiens
<220> FEATURE:
<221> NAME/KEY: CDS
<222> LOCATION: (489)...(980)
<221> NAME/KEY: misc_feature
<222> LOCATION: (1)...(1400)
<223> OTHER INFORMATION: n = A,T,C or G

<400> SEQUENCE: 40
cacgcgtccg cgctactgcg ggagcagcgt cctcccgggc cacggcgctt cccggccccg      60
gcgtccccgg accatggcgc tctccgggct cttctctagc tctcagcggc tgcgaagtct     120
gtaaacctgg tggccaagtg attgtaagtc aggagacttt ccttcggttt ctgcctttga     180 tgcaagagg tggagattgt ggcggcgatt acagaaaaca tctgggaaga caagttgctg      240
tttttatggg aatcgcaggc ttggaagaga cagaagcaat tccagaaata aattggaaat     300
tgaagattta acaatgttg ttttaaaata ttctaacttc aaagaatgat gccagaaact      360 taaaagggg ctgcgcagag tagcagggc cctggagggc gcggcctgaa tcctgattgc      420
ccttctgctg agaggacaca cgcagctgaa gatgaatttg ggaaaagtag ccgcttgcta     480 ctttaact atg gaa gag cag ggc cac agt gag atg gaa ata atc cca tca     530
         Met Glu Glu Gln Gly His Ser Glu Met Glu Ile Ile Pro Ser
           1               5                  10 gag tct cac ccc cac att caa tta ctg aaa agc aat cgg gaa ctt ctg     578
Glu Ser His Pro His Ile Gln Leu Leu Lys Ser Asn Arg Glu Leu Leu
 15                  20                  25                  30 gtc act cac atc cgc aat act cag tgt ctg gtg gac aac ttg ctg aag     626
Val Thr His Ile Arg Asn Thr Gln Cys Leu Val Asp Asn Leu Leu Lys
                 35                  40                  45 aat gac tac ttc tcg gcc gaa gat gcg gag att gtg tgt gcc tgc ccc     674
Asn Asp Tyr Phe Ser Ala Glu Asp Ala Glu Ile Val Cys Ala Cys Pro
             50                  55                  60 acc cag cct gac aag gtc cgc aaa att ctg gac ctg gta cag agc aag     722
Thr Gln Pro Asp Lys Val Arg Lys Ile Leu Asp Leu Val Gln Ser Lys
         65                  70                  75 ggc gag gag gtg tcc gag ttc ttc ctc tac ttg ctc cag caa ctc gca     770
Gly Glu Glu Val Ser Glu Phe Phe Leu Tyr Leu Leu Gln Gln Leu Ala
     80                  85                  90 gat gcc tac gtg gac ctc agg cct tgg ctg ctg gag atc ggc ttc tcc     818
Asp Ala Tyr Val Asp Leu Arg Pro Trp Leu Leu Glu Ile Gly Phe Ser
 95                 100                 105                 110 cct tcc ctg ctc act cag agc aaa gtc gtg gtc aac act gac cca ggt     866
Pro Ser Leu Leu Thr Gln Ser Lys Val Val Val Asn Thr Asp Pro Gly
                115                 120                 125 agt agt cag ccc cag caa gac cgc agg cac cag tgc aag cag ggc cct     914
Arg Ser Gln Pro Gln Gln Asp Arg Arg His Gln Cys Lys Gln Gly Pro
            130                 135                 140 ggg ggg ttt ggt aat ggc tgg gcc agc cct gag tgc cac ctc agg aag     962
Gly Gly Phe Gly Asn Gly Trp Ala Ser Pro Glu Cys His Leu Arg Lys
        145                 150                 155
```

-continued

```
cag gcc cag gtg cta ttt tgattttaga aaggaacagc tgaatcctgt         1010
Gln Ala Gln Val Leu Phe
    160 ctcccaagtg cagcccaggt ggctgcgatt gaactgccca cacctcgatg gtctggttta  1070 tagagggcc tttggaagta tgggaatggc ctgtgttctg accccttgct ttcttcctat   1130 tctgacatat gtagacattt taatggttgc acaaattcaa ggttgtattt ttttttcttt  1190 aaaaaaatct ttagctggac atggtagcac acacctgtag ttccagctac tcaggaggct  1250 gaggcaagag gactgcttga gccccagagt ctaaggctgc agcgagctat gattgtgccc  1310 ctacactcca cagcctgggt tttagagtga gaccctgtct ctaaaaaaaa aaaaaaaaa   1370 aaaaaaaaaa aaaaaaaaaa aaangggcgg                                  1400
```

<210> SEQ ID NO 41
<211> LENGTH: 164
<212> TYPE: PRT
<213> ORGANISM: Homo sapiens

<400> SEQUENCE: 41

```
Met Glu Glu Gln Gly His Ser Glu Met Glu Ile Ile Pro Ser Glu Ser
  1               5                  10                  15

His Pro His Ile Gln Leu Leu Lys Ser Asn Arg Glu Leu Leu Val Thr
             20                  25                  30

His Ile Arg Asn Thr Gln Cys Leu Val Asp Asn Leu Leu Lys Asn Asp
         35                  40                  45

Tyr Phe Ser Ala Glu Asp Ala Glu Ile Val Cys Ala Cys Pro Thr Gln
     50                  55                  60

Pro Asp Lys Val Arg Lys Ile Leu Asp Leu Val Gln Ser Lys Gly Glu
 65                  70                  75                  80

Glu Val Ser Glu Phe Phe Leu Tyr Leu Leu Gln Gln Leu Ala Asp Ala
                 85                  90                  95

Tyr Val Asp Leu Arg Pro Trp Leu Leu Glu Ile Gly Phe Ser Pro Ser
            100                 105                 110

Leu Leu Thr Gln Ser Lys Val Val Val Asn Thr Asp Pro Gly Arg Ser
        115                 120                 125

Gln Pro Gln Gln Asp Arg Arg His Gln Cys Lys Gln Gly Pro Gly Gly
    130                 135                 140

Phe Gly Asn Gly Trp Ala Ser Pro Glu Cys His Leu Arg Lys Gln Ala
145                 150                 155                 160

Gln Val Leu Phe
```

<210> SEQ ID NO 42
<211> LENGTH: 4141
<212> TYPE: DNA
<213> ORGANISM: Mus musculus
<220> FEATURE:
<221> NAME/KEY: CDS
<222> LOCATION: (261)...(3119)

<400> SEQUENCE: 42

```
ccacgcgtcc gcggaccgcg agcggtagcg ccctccctcc cagctgttgt cccgcccgat    60
ccgcgaccct agtccccgga tccccttgct gagagtcacc gtactccagg gccaactgag   120
ccaaagtcct gccaacttgg gtcagcaatg aaaggcagga tcctgggtgg tggccctgaa   180
tcctgatttg tctgccctgc cagcgagaca catgtggtca agatgaatt tgagaaaagt    240 agctgctggc tacttgaaca atg gag gaa cac ggc cat cat gag atg gaa ggc   293
                       Met Glu Glu His Gly His His Glu Met Glu Gly
```

-continued

|     |     |     |     |     | 1   |     |     |     |     | 5   |     |     |     |     | 10  |     |      |
|-----|-----|-----|-----|-----|-----|-----|-----|-----|-----|-----|-----|-----|-----|-----|-----|-----|------|
| acc | cca | ttg | ggt | tgt | cac | tcc | cac | att | aaa | ctg | ctg | aag | atc | aac | agg |     | 341  |
| Thr | Pro | Leu | Gly | Cys | His | Ser | His | Ile | Lys | Leu | Leu | Lys | Ile | Asn | Arg |     |      |
|     |     |     | 15  |     |     |     |     | 20  |     |     |     |     | 25  |     |     |     |      |
| gaa | cat | ctg | gtc | acc | aac | att | cgg | aac | act | cag | tgt | ctg | gtg | gac | aac |     | 389  |
| Glu | His | Leu | Val | Thr | Asn | Ile | Arg | Asn | Thr | Gln | Cys | Leu | Val | Asp | Asn |     |      |
|     |     | 30  |     |     |     |     | 35  |     |     |     |     | 40  |     |     |     |     |      |
| ttg | ctg | gag | aat | ggc | tac | ttc | tca | gcc | gaa | gat | gca | gag | att | gtg | tgt |     | 437  |
| Leu | Leu | Glu | Asn | Gly | Tyr | Phe | Ser | Ala | Glu | Asp | Ala | Glu | Ile | Val | Cys |     |      |
|     | 45  |     |     |     |     | 50  |     |     |     |     | 55  |     |     |     |     |     |      |
| gcc | tgt | ccc | acc | aag | cct | gac | aag | gtc | cga | aag | atc | ctt | gac | ctg | gtg |     | 485  |
| Ala | Cys | Pro | Thr | Lys | Pro | Asp | Lys | Val | Arg | Lys | Ile | Leu | Asp | Leu | Val |     |      |
| 60  |     |     |     |     | 65  |     |     |     |     | 70  |     |     |     |     | 75  |     |      |
| cag | agc | aaa | ggc | gag | gag | gtg | tct | gag | ttc | ttc | ctc | tac | gtg | ctg | cag |     | 533  |
| Gln | Ser | Lys | Gly | Glu | Glu | Val | Ser | Glu | Phe | Phe | Leu | Tyr | Val | Leu | Gln |     |      |
|     |     |     |     | 80  |     |     |     |     | 85  |     |     |     |     | 90  |     |     |      |
| cag | ctg | gag | gat | gct | tac | gtg | gac | ctc | agg | ctg | tgg | ctc | tca | gaa | att |     | 581  |
| Gln | Leu | Glu | Asp | Ala | Tyr | Val | Asp | Leu | Arg | Leu | Trp | Leu | Ser | Glu | Ile |     |      |
|     |     |     | 95  |     |     |     |     | 100 |     |     |     |     | 105 |     |     |     |      |
| ggc | ttc | tcc | cct | tcc | cag | ctc | att | cgg | acc | aaa | act | atc | gtc | aat | act |     | 629  |
| Gly | Phe | Ser | Pro | Ser | Gln | Leu | Ile | Arg | Thr | Lys | Thr | Ile | Val | Asn | Thr |     |      |
|     |     | 110 |     |     |     |     | 115 |     |     |     |     | 120 |     |     |     |     |      |
| gac | cca | gta | agc | agg | tat | acc | caa | cag | ctg | cga | cac | caa | ctg | ggc | cgc |     | 677  |
| Asp | Pro | Val | Ser | Arg | Tyr | Thr | Gln | Gln | Leu | Arg | His | Gln | Leu | Gly | Arg |     |      |
|     | 125 |     |     |     |     | 130 |     |     |     |     | 135 |     |     |     |     |     |      |
| gac | tcc | aag | ttc | atg | ctg | tgc | tac | gcc | cag | aag | gag | gac | ctg | ctg | ctg |     | 725  |
| Asp | Ser | Lys | Phe | Met | Leu | Cys | Tyr | Ala | Gln | Lys | Glu | Asp | Leu | Leu | Leu |     |      |
| 140 |     |     |     |     | 145 |     |     |     |     | 150 |     |     |     |     | 155 |     |      |
| gag | gag | acc | tat | atg | gac | aca | ctc | atg | ggg | ctg | gta | ggc | ttc | aac | aat |     | 773  |
| Glu | Glu | Thr | Tyr | Met | Asp | Thr | Leu | Met | Gly | Leu | Val | Gly | Phe | Asn | Asn |     |      |
|     |     |     |     | 160 |     |     |     |     | 165 |     |     |     |     | 170 |     |     |      |
| gaa | aac | ctg | ggc | agc | cta | gga | ggc | ctg | gat | tgc | ctg | ctg | gac | cac | agt |     | 821  |
| Glu | Asn | Leu | Gly | Ser | Leu | Gly | Gly | Leu | Asp | Cys | Leu | Leu | Asp | His | Ser |     |      |
|     |     |     | 175 |     |     |     |     | 180 |     |     |     |     | 185 |     |     |     |      |
| acg | ggc | gtc | ctc | aac | gag | cat | ggc | gag | act | gtc | ttc | gtg | ttc | ggg | gac |     | 869  |
| Thr | Gly | Val | Leu | Asn | Glu | His | Gly | Glu | Thr | Val | Phe | Val | Phe | Gly | Asp |     |      |
|     | 190 |     |     |     |     | 195 |     |     |     |     | 200 |     |     |     |     |     |      |
| gcg | gga | gtg | ggc | aag | tcc | atg | ctg | ctg | cag | agg | ttg | cag | agc | ctc | tgg |     | 917  |
| Ala | Gly | Val | Gly | Lys | Ser | Met | Leu | Leu | Gln | Arg | Leu | Gln | Ser | Leu | Trp |     |      |
| 205 |     |     |     |     | 210 |     |     |     |     | 215 |     |     |     |     |     |     |      |
| gcg | tca | ggc | agg | ttg | acc | tcc | aca | gcc | aaa | ttc | ttc | ttc | cac | ttc | cgc |     | 965  |
| Ala | Ser | Gly | Arg | Leu | Thr | Ser | Thr | Ala | Lys | Phe | Phe | Phe | His | Phe | Arg |     |      |
| 220 |     |     |     | 225 |     |     |     |     | 230 |     |     |     |     | 235 |     |     |      |
| tgc | cgc | atg | ttc | agc | tgc | ttc | aag | gag | agc | gac | atg | ctg | agt | ctg | cag |     | 1013 |
| Cys | Arg | Met | Phe | Ser | Cys | Phe | Lys | Glu | Ser | Asp | Met | Leu | Ser | Leu | Gln |     |      |
|     |     |     | 240 |     |     |     |     | 245 |     |     |     |     | 250 |     |     |     |      |
| gac | ctg | ctc | ttc | aag | cat | ttc | tgc | tac | ccg | gag | cag | gac | ccc | gag | gag |     | 1061 |
| Asp | Leu | Leu | Phe | Lys | His | Phe | Cys | Tyr | Pro | Glu | Gln | Asp | Pro | Glu | Glu |     |      |
|     |     | 255 |     |     |     |     | 260 |     |     |     |     | 265 |     |     |     |     |      |
| gtg | ttc | tcc | ttc | ttg | ctg | cgc | ttt | ccc | cac | aca | gcg | ctc | ttc | act | ttt |     | 1109 |
| Val | Phe | Ser | Phe | Leu | Leu | Arg | Phe | Pro | His | Thr | Ala | Leu | Phe | Thr | Phe |     |      |
|     | 270 |     |     |     |     | 275 |     |     |     |     | 280 |     |     |     |     |     |      |
| gac | ggc | ctg | gat | gag | ctg | cac | tca | gac | ttc | gac | ctg | agc | cgc | gtg | ccg |     | 1157 |
| Asp | Gly | Leu | Asp | Glu | Leu | His | Ser | Asp | Phe | Asp | Leu | Ser | Arg | Val | Pro |     |      |
| 285 |     |     |     |     | 290 |     |     |     |     | 295 |     |     |     |     |     |     |      |
| gat | agc | tgc | tgc | ccc | tgg | gag | ccg | gct | cac | cct | ctg | gtc | ctg | ctg | gct |     | 1205 |
| Asp | Ser | Cys | Cys | Pro | Trp | Glu | Pro | Ala | His | Pro | Leu | Val | Leu | Leu | Ala |     |      |
| 300 |     |     |     |     | 305 |     |     |     |     | 310 |     |     |     |     | 315 |     |      |
| aac | ctc | cta | agt | ggg | agg | ctg | ctc | aag | ggt | gcc | ggc | aaa | ttg | ctc | act |     | 1253 |

```
                                                                  -continued Asn Leu Leu Ser Gly Arg Leu Leu Lys Gly Ala Gly Lys Leu Leu Thr
            320                 325                 330 gct cgc aca ggc gtg gag gtc ccc cgc cag ctc ctg cgc aaa aag gtg      1301
Ala Arg Thr Gly Val Glu Val Pro Arg Gln Leu Leu Arg Lys Lys Val
            335                 340                 345 ctg ctc cgg ggc ttc tcc cca agt cac ctg cgc gcc tat gcc cgc cgg      1349
Leu Leu Arg Gly Phe Ser Pro Ser His Leu Arg Ala Tyr Ala Arg Arg
            350                 355                 360 atg ttc ccc gag cgc aca gcg cag gag cat ctg ctg cag cag ctg gat      1397
Met Phe Pro Glu Arg Thr Ala Gln Glu His Leu Leu Gln Gln Leu Asp
            365                 370                 375 gcc aac ccc aac ctc tgc agc ctg tgc ggg gtg ccg ctc ttc tgt tgg      1445
Ala Asn Pro Asn Leu Cys Ser Leu Cys Gly Val Pro Leu Phe Cys Trp
380                 385                 390                 395 atc atc ttc cgt tgt ttc cag cac ttc cag acg gtc ttc gag ggc tcc      1493
Ile Ile Phe Arg Cys Phe Gln His Phe Gln Thr Val Phe Glu Gly Ser
                400                 405                 410 tct tca cag ttg ccg gac tgt gct gtg acc ctg acc gat gtc ttt ctg      1541
Ser Ser Gln Leu Pro Asp Cys Ala Val Thr Leu Thr Asp Val Phe Leu
                415                 420                 425 ctg gtc act gag gtg cat ctg aac agg ccg cag ccc agc agc ctg gtg      1589
Leu Val Thr Glu Val His Leu Asn Arg Pro Gln Pro Ser Ser Leu Val
            430                 435                 440 cag cgc aac acg cgc agc ccg gcg gaa acc cta cgt gca ggc tgg cgc      1637
Gln Arg Asn Thr Arg Ser Pro Ala Glu Thr Leu Arg Ala Gly Trp Arg
            445                 450                 455 acg ctg cat gcg ctg gga gag gtg gct cac cga ggc acc gac aag agc      1685
Thr Leu His Ala Leu Gly Glu Val Ala His Arg Gly Thr Asp Lys Ser
460                 465                 470                 475 ctc ttt gtg ttt ggc cag gag gag gtg cag gcg tcg aag ctg cag gaa      1733
Leu Phe Val Phe Gly Gln Glu Glu Val Gln Ala Ser Lys Leu Gln Glu
                480                 485                 490 gga gat ctg cag ctg ggc ttc ctg cgg gct ttg ccc gat gtg ggc cct      1781
Gly Asp Leu Gln Leu Gly Phe Leu Arg Ala Leu Pro Asp Val Gly Pro
                495                 500                 505 gag cag ggc cag tct tac gaa ttt ttc cac ctt acg ctc cag gcc ttc      1829
Glu Gln Gly Gln Ser Tyr Glu Phe Phe His Leu Thr Leu Gln Ala Phe
            510                 515                 520 ttc acc gcc ttc ttc ctg gta gca gat gac aaa gtg agc acc cgg gag      1877
Phe Thr Ala Phe Phe Leu Val Ala Asp Asp Lys Val Ser Thr Arg Glu
            525                 530                 535 ttg ctg agg ttc ttt cga gaa tgg acg tct cct gga gag gca aca agc      1925
Leu Leu Arg Phe Phe Arg Glu Trp Thr Ser Pro Gly Glu Ala Thr Ser
540                 545                 550                 555 tcg tcc tgc cat tct tcc ttc ttc tcc ttc cag tgc ctg ggc ggc aga      1973
Ser Ser Cys His Ser Ser Phe Phe Ser Phe Gln Cys Leu Gly Gly Arg
                560                 565                 570 agc cgg ttg ggc cct gat cct ttc agg aac aaa gat cac ttc cag ttc      2021
Ser Arg Leu Gly Pro Asp Pro Phe Arg Asn Lys Asp His Phe Gln Phe
            575                 580                 585 acc aac ctc ttc gtg tgc ggg cta ctg gcc aaa gcc cga cag aaa ctc      2069
Thr Asn Leu Phe Val Cys Gly Leu Leu Ala Lys Ala Arg Gln Lys Leu
            590                 595                 600 ctt cgg cag ctg gtg ccc aag gct atc ctg agg agg aag cgc aag gcc      2117
Leu Arg Gln Leu Val Pro Lys Ala Ile Leu Arg Arg Lys Arg Lys Ala
            605                 610                 615 ctg tgg gct cac ctg ttt gct agc ctg cgc tcc tac ttg aag agc cta      2165
Leu Trp Ala His Leu Phe Ala Ser Leu Arg Ser Tyr Leu Lys Ser Leu
620                 625                 630                 635
```

```
cct cgg gtc cag tct gga ggc ttt aac cag gtg cat gcc atg ccc aca    2213
Pro Arg Val Gln Ser Gly Gly Phe Asn Gln Val His Ala Met Pro Thr
            640                 645                 650 ttc ctg tgg atg ctg cgc tgc atc tat gag acg cag agc cag aag gtg    2261
Phe Leu Trp Met Leu Arg Cys Ile Tyr Glu Thr Gln Ser Gln Lys Val
    655                 660                 665 ggg cgc ctc gcc gcc agg ggc atc agt gcg gac tac ctc aag ctg gcc    2309
Gly Arg Leu Ala Ala Arg Gly Ile Ser Ala Asp Tyr Leu Lys Leu Ala
        670                 675                 680 ttt tgc aac gct tgc tct gcg gac tgc agc gcc ctg tcc ttc gtc ctg    2357
Phe Cys Asn Ala Cys Ser Ala Asp Cys Ser Ala Leu Ser Phe Val Leu
685                 690                 695 cat cac ttc cac agg cag ctg gcc cta gac ctg gac aac aac aac ctc    2405
His His Phe His Arg Gln Leu Ala Leu Asp Leu Asp Asn Asn Asn Leu
700                 705                 710                 715 aat gac tat ggc gtg cag gag ctg cag cct tgc ttt agc cgt ctc acg    2453
Asn Asp Tyr Gly Val Gln Glu Leu Gln Pro Cys Phe Ser Arg Leu Thr
            720                 725                 730 gtt atc aga ctc agc gtc aac cag atc acc gac acg ggg gtg aag gtg    2501
Val Ile Arg Leu Ser Val Asn Gln Ile Thr Asp Thr Gly Val Lys Val
    735                 740                 745 cta tgt gag gaa ctg acc aag tat aag atc gtg acg ttc ctg ggt tta    2549
Leu Cys Glu Glu Leu Thr Lys Tyr Lys Ile Val Thr Phe Leu Gly Leu
        750                 755                 760 tac aac aac cag ata act gat atc gga gcc agg tat gtg gcc caa atc    2597
Tyr Asn Asn Gln Ile Thr Asp Ile Gly Ala Arg Tyr Val Ala Gln Ile
765                 770                 775 ctg gat gaa tgc aga ggc ctc aag cac ctt aaa cta ggg aaa aac aga    2645
Leu Asp Glu Cys Arg Gly Leu Lys His Leu Lys Leu Gly Lys Asn Arg
780                 785                 790                 795 ata aca agt gag ggc ggg aag tgt gtg gct ttg gct gtg aag aac agc    2693
Ile Thr Ser Glu Gly Gly Lys Cys Val Ala Leu Ala Val Lys Asn Ser
            800                 805                 810 acc tcc atc gtt gat gtt ggg atg tgg ggt aat cag att gga gac gaa    2741
Thr Ser Ile Val Asp Val Gly Met Trp Gly Asn Gln Ile Gly Asp Glu
    815                 820                 825 ggg gca aag gcc ttc gca gag gca ttg aag gac cac ccc agc ctg acc    2789
Gly Ala Lys Ala Phe Ala Glu Ala Leu Lys Asp His Pro Ser Leu Thr
        830                 835                 840 act ctc agt ctt gca ttc aat ggc atc tct ccg gag gga ggg aag agc    2837
Thr Leu Ser Leu Ala Phe Asn Gly Ile Ser Pro Glu Gly Gly Lys Ser
845                 850                 855 ctt gcg cag gcc ctg aag cag aac acc aca ctg aca gta atc tgg ctg    2885
Leu Ala Gln Ala Leu Lys Gln Asn Thr Thr Leu Thr Val Ile Trp Leu
860                 865                 870                 875 acc aaa aat gaa ctt aat gat gag tct gca gag tgc ttc gct gag atg    2933
Thr Lys Asn Glu Leu Asn Asp Glu Ser Ala Glu Cys Phe Ala Glu Met
            880                 885                 890 ctg aga gtg aac cag acg cta cgg cat tta tgg ctg atc cag aat cgc    2981
Leu Arg Val Asn Gln Thr Leu Arg His Leu Trp Leu Ile Gln Asn Arg
    895                 900                 905 atc aca gcc aag ggg aca gcg cag ctg gcg agg gca ctg cag aag aac    3029
Ile Thr Ala Lys Gly Thr Ala Gln Leu Ala Arg Ala Leu Gln Lys Asn
        910                 915                 920 aca gcc ata aca gag att tgt ctc aat gga aac ttg att aag ccc gag    3077
Thr Ala Ile Thr Glu Ile Cys Leu Asn Gly Asn Leu Ile Lys Pro Glu
925                 930                 935 gag gcc aaa gtc ttc gag aat gag aag aga atc atc tgc ttc                3119
Glu Ala Lys Val Phe Glu Asn Glu Lys Arg Ile Ile Cys Phe
940                 945                 950
```

-continued

```
tgacggacgc tcctgggcag gatctttgtc ctaggttgct cctcagtcac agacagcact    3179
gtgcagtcag cagggtagca ggatgctgtg cagcgcctgc agcaaggtgc ctgtcaggag    3239
cccacacctc cacagtgcac accgatgtcc cctgctcatg cttggactgg tagcacccgc    3299
gccgcggctg agaccctgca gacgcaggga gtcttaggaa ccatcgtcac cactcaaagc    3359
cagcagggca tcttctgtac aaagatctcc ctgcatatcc actagacgga agctgaagga    3419
acgcaacagc agaggaggcc aacagacgcc tggctgaagg ctccgtggga ccaacggtgt    3479
caccttcaga aaagagctgg gaacttgagc agagccgatg gtaacttctt ggggaaagaa    3539
ggcacccagt gactgcatgg ttattctgag tcctccttcc tctgcttagt ccctctcact    3599
gtacaggtct gtttcttcct cgcagctgtg gctgctgaag taggtccact gtggggagag    3659
ctcatcacag actttggttc ggttctggat tctcagtggt ggcaaccgag agtcagacga    3719
taccctctag gtcagtctca gaggatctct atgctgtgag agggttgagg gcccacccag    3779
aattttttttt ttttaccagt ttttactgtg cctgccccag gagggagaat tacttcccag    3839
cctccacagc agcaggcatg gcttgcctca atggtcctga gatcccaaca aaactctctc    3899
ccttgcctgt gagcagaaag tatcttcatg tcctcagaag ttggagggtg actggacaca    3959
gttaagactc agagagccag ctgatagctc aaagcaaagc atggcacata cccaccacca    4019
taccatggtg cgcatgggat gggacagttg gaatgttgca gataacgtgt tcttttgcca    4079
gttcatttgt taataaaata tttaaaacgt taaaaaaaaa aaaaaaaaaa aaaaagggc    4139
gg                                                                  4141
```

<210> SEQ ID NO 43
<211> LENGTH: 953
<212> TYPE: PRT
<213> ORGANISM: Mus musculus

<400> SEQUENCE: 43

```
Met Glu Glu His Gly His His Glu Met Glu Gly Thr Pro Leu Gly Cys
  1               5                  10                  15

His Ser His Ile Lys Leu Leu Lys Ile Asn Arg Glu His Leu Val Thr
             20                  25                  30

Asn Ile Arg Asn Thr Gln Cys Leu Val Asp Asn Leu Leu Glu Asn Gly
         35                  40                  45

Tyr Phe Ser Ala Glu Asp Ala Glu Ile Val Cys Ala Cys Pro Thr Lys
     50                  55                  60

Pro Asp Lys Val Arg Lys Ile Leu Asp Leu Val Gln Ser Lys Gly Glu
 65                  70                  75                  80

Glu Val Ser Glu Phe Phe Leu Tyr Val Leu Gln Gln Leu Glu Asp Ala
                 85                  90                  95

Tyr Val Asp Leu Arg Leu Trp Leu Ser Glu Ile Gly Phe Ser Pro Ser
            100                 105                 110

Gln Leu Ile Arg Thr Lys Thr Ile Val Asn Thr Asp Pro Val Ser Arg
        115                 120                 125

Tyr Thr Gln Gln Leu Arg His Gln Leu Gly Arg Asp Ser Lys Phe Met
    130                 135                 140

Leu Cys Tyr Ala Gln Lys Glu Asp Leu Leu Glu Glu Thr Tyr Met
145                 150                 155                 160

Asp Thr Leu Met Gly Leu Val Gly Phe Asn Asn Glu Asn Leu Gly Ser
                165                 170                 175

Leu Gly Gly Leu Asp Cys Leu Leu Asp His Ser Thr Gly Val Leu Asn
```

```
                    180                 185                 190
Glu His Gly Glu Thr Val Phe Val Phe Gly Asp Ala Gly Val Gly Lys
            195                 200                 205
Ser Met Leu Leu Gln Arg Leu Gln Ser Leu Trp Ala Ser Gly Arg Leu
            210                 215                 220
Thr Ser Thr Ala Lys Phe Phe His Phe Arg Cys Arg Met Phe Ser
225                 230                 235                 240
Cys Phe Lys Glu Ser Asp Met Leu Ser Leu Gln Asp Leu Leu Phe Lys
                245                 250                 255
His Phe Cys Tyr Pro Glu Gln Asp Pro Glu Val Phe Ser Phe Leu
            260                 265                 270
Leu Arg Phe Pro His Thr Ala Leu Phe Thr Phe Asp Gly Leu Asp Glu
            275                 280                 285
Leu His Ser Asp Phe Asp Leu Ser Arg Val Pro Asp Ser Cys Cys Pro
            290                 295                 300
Trp Glu Pro Ala His Pro Leu Val Leu Ala Asn Leu Leu Ser Gly
305                 310                 315                 320
Arg Leu Leu Lys Gly Ala Gly Lys Leu Leu Thr Ala Arg Thr Gly Val
                325                 330                 335
Glu Val Pro Arg Gln Leu Leu Arg Lys Val Leu Leu Arg Gly Phe
            340                 345                 350
Ser Pro Ser His Leu Arg Ala Tyr Ala Arg Arg Met Phe Pro Glu Arg
            355                 360                 365
Thr Ala Gln Glu His Leu Leu Gln Gln Leu Asp Ala Asn Pro Asn Leu
            370                 375                 380
Cys Ser Leu Cys Gly Val Pro Leu Phe Cys Trp Ile Ile Phe Arg Cys
385                 390                 395                 400
Phe Gln His Phe Gln Thr Val Phe Glu Gly Ser Ser Gln Leu Pro
                405                 410                 415
Asp Cys Ala Val Thr Leu Thr Asp Val Phe Leu Leu Val Thr Glu Val
                420                 425                 430
His Leu Asn Arg Pro Gln Pro Ser Ser Leu Val Gln Arg Asn Thr Arg
            435                 440                 445
Ser Pro Ala Glu Thr Leu Arg Ala Gly Trp Arg Thr Leu His Ala Leu
450                 455                 460
Gly Glu Val Ala His Arg Gly Thr Asp Lys Ser Leu Phe Val Phe Gly
465                 470                 475                 480
Gln Glu Glu Val Gln Ala Ser Lys Leu Gln Glu Gly Asp Leu Gln Leu
                485                 490                 495
Gly Phe Leu Arg Ala Leu Pro Asp Val Gly Pro Glu Gln Gly Gln Ser
                500                 505                 510
Tyr Glu Phe Phe His Leu Thr Leu Gln Ala Phe Phe Thr Ala Phe Phe
            515                 520                 525
Leu Val Ala Asp Asp Lys Val Ser Thr Arg Glu Leu Leu Arg Phe Phe
            530                 535                 540
Arg Glu Trp Thr Ser Pro Gly Glu Ala Thr Ser Ser Cys His Ser
545                 550                 555                 560
Ser Phe Phe Ser Phe Gln Cys Leu Gly Gly Arg Ser Arg Leu Gly Pro
                565                 570                 575
Asp Pro Phe Arg Asn Lys Asp His Phe Gln Phe Thr Asn Leu Phe Val
            580                 585                 590
Cys Gly Leu Leu Ala Lys Ala Arg Gln Lys Leu Leu Arg Gln Leu Val
            595                 600                 605
```

```
Pro Lys Ala Ile Leu Arg Arg Lys Arg Lys Ala Leu Trp Ala His Leu
    610                 615                 620

Phe Ala Ser Leu Arg Ser Tyr Leu Lys Ser Leu Pro Arg Val Gln Ser
625                 630                 635                 640

Gly Gly Phe Asn Gln Val His Ala Met Pro Thr Phe Leu Trp Met Leu
                645                 650                 655

Arg Cys Ile Tyr Glu Thr Gln Ser Gln Lys Val Gly Arg Leu Ala Ala
            660                 665                 670

Arg Gly Ile Ser Ala Asp Tyr Leu Lys Leu Ala Phe Cys Asn Ala Cys
        675                 680                 685

Ser Ala Asp Cys Ser Ala Leu Ser Phe Val Leu His His Phe His Arg
690                 695                 700

Gln Leu Ala Leu Asp Leu Asp Asn Asn Asn Leu Asn Asp Tyr Gly Val
705                 710                 715                 720

Gln Glu Leu Gln Pro Cys Phe Ser Arg Leu Thr Val Ile Arg Leu Ser
                725                 730                 735

Val Asn Gln Ile Thr Asp Thr Gly Val Lys Val Leu Cys Glu Glu Leu
            740                 745                 750

Thr Lys Tyr Lys Ile Val Thr Phe Leu Gly Leu Tyr Asn Asn Gln Ile
        755                 760                 765

Thr Asp Ile Gly Ala Arg Tyr Val Ala Gln Ile Leu Asp Glu Cys Arg
770                 775                 780

Gly Leu Lys His Leu Lys Leu Gly Lys Asn Arg Ile Thr Ser Glu Gly
785                 790                 795                 800

Gly Lys Cys Val Ala Leu Ala Val Lys Asn Ser Thr Ser Ile Val Asp
                805                 810                 815

Val Gly Met Trp Gly Asn Gln Ile Gly Asp Glu Gly Ala Lys Ala Phe
            820                 825                 830

Ala Glu Ala Leu Lys Asp His Pro Ser Leu Thr Thr Leu Ser Leu Ala
        835                 840                 845

Phe Asn Gly Ile Ser Pro Glu Gly Gly Lys Ser Leu Ala Gln Ala Leu
850                 855                 860

Lys Gln Asn Thr Thr Leu Thr Val Ile Trp Leu Thr Lys Asn Glu Leu
865                 870                 875                 880

Asn Asp Glu Ser Ala Glu Cys Phe Ala Glu Met Leu Arg Val Asn Gln
                885                 890                 895

Thr Leu Arg His Leu Trp Leu Ile Gln Asn Arg Ile Thr Ala Lys Gly
            900                 905                 910

Thr Ala Gln Leu Ala Arg Ala Leu Gln Lys Asn Thr Ala Ile Thr Glu
        915                 920                 925

Ile Cys Leu Asn Gly Asn Leu Ile Lys Pro Glu Glu Ala Lys Val Phe
930                 935                 940

Glu Asn Glu Lys Arg Ile Ile Cys Phe
945                 950

<210> SEQ ID NO 44
<211> LENGTH: 19
<212> TYPE: DNA
<213> ORGANISM: Homo sapiens

<400> SEQUENCE: 44
agaaggtctg gtcggcaaa                                              19

<210> SEQ ID NO 45
```

-continued

```
<211> LENGTH: 18
<212> TYPE: DNA
<213> ORGANISM: Homo sapiens

<400> SEQUENCE: 45
aagccctgag tggaagca                                              18

<210> SEQ ID NO 46
<211> LENGTH: 86
<212> TYPE: PRT
<213> ORGANISM: Homo sapiens

<400> SEQUENCE: 46

Ser Arg Tyr Thr Gln Gln Leu Arg His His Leu Gly Arg Asp Ser Lys
 1               5                  10                  15

Phe Val Leu Cys Tyr Ala Gln Lys Glu Leu Leu Glu Glu Ile
            20                  25                  30

Tyr Met Asp Thr Ile Met Glu Leu Val Gly Phe Ser Asn Glu Ser Leu
        35                  40                  45

Gly Ser Leu Asn Ser Leu Ala Cys Leu Leu Asp His Thr Thr Gly Ile
    50                  55                  60

Leu Asn Glu Gln Gly Glu Thr Ile Phe Ile Leu Gly Asp Ala Gly Val
65                  70                  75                  80

Gly Lys Ser Met Leu Leu
                85

<210> SEQ ID NO 47
<211> LENGTH: 16
<212> TYPE: PRT
<213> ORGANISM: Homo sapiens

<400> SEQUENCE: 47

Tyr Cys Tyr Pro Glu Arg Asp Pro Glu Glu Val Phe Ala Phe Leu Leu
 1               5                  10                  15

<210> SEQ ID NO 48
<211> LENGTH: 740
<212> TYPE: DNA
<213> ORGANISM: Homo sapiens
<220> FEATURE:
<221> NAME/KEY: CDS
<222> LOCATION: (54)...(638)

<400> SEQUENCE: 48
cgcgtccggc tgcagcgggg tgagcggcgg cagcggccgg ggatcctgga gcc atg      56
                                                          Met
                                                           1 ggg cgc gcg cgc gac gcc atc ctg gat gcg ctg gag aac ctg acc gcc   104
Gly Arg Ala Arg Asp Ala Ile Leu Asp Ala Leu Glu Asn Leu Thr Ala
        5                  10                  15 gag gag ctc aag aag ttc aag ctg aag ctg ctg tcg gtg ccg ctg cgc   152
Glu Glu Leu Lys Lys Phe Lys Leu Lys Leu Leu Ser Val Pro Leu Arg
            20                  25                  30 gag ggc tac ggg cgc atc ccg cgg ggc gcg ctg ctg tcc atg gac gcc   200
Glu Gly Tyr Gly Arg Ile Pro Arg Gly Ala Leu Leu Ser Met Asp Ala
        35                  40                  45 ttg gac ctc acc gac aag ctg gtc agc ttc tac ctg gag acc tac ggc   248
Leu Asp Leu Thr Asp Lys Leu Val Ser Phe Tyr Leu Glu Thr Tyr Gly
    50                  55                  60                  65 gcc gag ctc acc gct aac gtg ctg cgc gac atg ggc ctg cag gag atg   296
Ala Glu Leu Thr Ala Asn Val Leu Arg Asp Met Gly Leu Gln Glu Met
                70                  75                  80
```

```
gcc ggg cag ctg cag gcg gcc acg cac cag ggc tct gga gcc gcg cca      344
Ala Gly Gln Leu Gln Ala Ala Thr His Gln Gly Ser Gly Ala Ala Pro
         85                  90                  95 gct ggg atc cag gcc cct cct cag tcg gca gcc aag cca ggc ctg cac      392
Ala Gly Ile Gln Ala Pro Pro Gln Ser Ala Ala Lys Pro Gly Leu His
        100                 105                 110 ttt ata gac cag cac cgg gct gcg ctt atc gcg agg gtc aca aac gtt      440
Phe Ile Asp Gln His Arg Ala Ala Leu Ile Ala Arg Val Thr Asn Val
    115                 120                 125 gag tgg ctg ctg gat gct ctg tac ggg aag gtc ctg acg gat gag cag      488
Glu Trp Leu Leu Asp Ala Leu Tyr Gly Lys Val Leu Thr Asp Glu Gln
130                 135                 140                 145 tac cag gca gtg cgg gcc gag ccc acc aac cca agc aag atg cgg aag      536
Tyr Gln Ala Val Arg Ala Glu Pro Thr Asn Pro Ser Lys Met Arg Lys
                150                 155                 160 ctc ttc agt ttc aca cca gcc tgg aac tgg acc tgc aag gac ttg ctc      584
Leu Phe Ser Phe Thr Pro Ala Trp Asn Trp Thr Cys Lys Asp Leu Leu
                165                 170                 175 ctc cag gcc cta agg gag tcc cag tcc tac ctg gtg gag gac ctg gag      632
Leu Gln Ala Leu Arg Glu Ser Gln Ser Tyr Leu Val Glu Asp Leu Glu
            180                 185                 190 cgg agc tgaggctcct tcccagcaac actccggtca gcccctggca atcccaccaa       688
Arg Ser
    195 atcatcctga atctgatctt tttatacaca atatacgaaa agccagcttg aa            740

<210> SEQ ID NO 49
<211> LENGTH: 195
<212> TYPE: PRT
<213> ORGANISM: Homo sapiens

<400> SEQUENCE: 49

Met Gly Arg Ala Arg Asp Ala Ile Leu Asp Ala Leu Glu Asn Leu Thr
  1               5                  10                  15

Ala Glu Glu Leu Lys Lys Phe Lys Leu Lys Leu Leu Ser Val Pro Leu
                 20                  25                  30

Arg Glu Gly Tyr Gly Arg Ile Pro Arg Gly Ala Leu Leu Ser Met Asp
             35                  40                  45

Ala Leu Asp Leu Thr Asp Lys Leu Val Ser Phe Tyr Leu Glu Thr Tyr
         50                  55                  60

Gly Ala Glu Leu Thr Ala Asn Val Leu Arg Asp Met Gly Leu Gln Glu
 65                  70                  75                  80

Met Ala Gly Gln Leu Gln Ala Ala Thr His Gln Gly Ser Gly Ala Ala
                 85                  90                  95

Pro Ala Gly Ile Gln Ala Pro Pro Gln Ser Ala Ala Lys Pro Gly Leu
            100                 105                 110

His Phe Ile Asp Gln His Arg Ala Ala Leu Ile Ala Arg Val Thr Asn
        115                 120                 125

Val Glu Trp Leu Leu Asp Ala Leu Tyr Gly Lys Val Leu Thr Asp Glu
    130                 135                 140

Gln Tyr Gln Ala Val Arg Ala Glu Pro Thr Asn Pro Ser Lys Met Arg
145                 150                 155                 160

Lys Leu Phe Ser Phe Thr Pro Ala Trp Asn Trp Thr Cys Lys Asp Leu
                165                 170                 175

Leu Leu Gln Ala Leu Arg Glu Ser Gln Ser Tyr Leu Val Glu Asp Leu
            180                 185                 190
```

-continued

```
Glu Arg Ser
        195

<210> SEQ ID NO 50
<211> LENGTH: 585
<212> TYPE: DNA
<213> ORGANISM: Homo sapiens

<400> SEQUENCE: 50
atggggcgcg cgcgcgacgc catcctggat gcgctggaga acctgaccgc cgaggagctc    60
aagaagttca agctgaagct gctgtcggtg ccgctgcgcg agggctacgg gcgcatcccg   120
cggggcgcgc tgctgtccat ggacgccttg gacctcaccg acaagctggt cagcttctac   180
ctggagacct acggcgccga gctcaccgct aacgtgctgc gcgacatggg cctgcaggag   240
atggccgggc agctgcaggc ggccacgcac cagggctctg gagccgcgcc agctgggatc   300
caggcccctc ctcagtcggc agccaagcca ggcctgcact ttatagacca gcaccgggct   360
gcgcttatcg cgagggtcac aaacgttgag tggctgctga tgctctgta cgggaaggtc   420 ctgacggatg agcagtacca ggcagtgcgg gccgagccca ccaacccaag caagatgcgg   480
aagctcttca gtttcacacc agcctggaac tggacctgca aggacttgct cctccaggcc   540
ctaagggagt cccagtccta cctggtggag gacctggagc ggagc                  585

<210> SEQ ID NO 51
<211> LENGTH: 5252
<212> TYPE: DNA
<213> ORGANISM: Rattus rattus
<220> FEATURE:
<221> NAME/KEY: CDS
<222> LOCATION: (169)...(2883)

<400> SEQUENCE: 51
cccgcgtccg gacttcccctt ccagtgtttg ttcctctctg ctctctccaa cagaaggtat    60
ttttggcatg tttatctttt gctaagtagg atttctgtct ttctttgtta acacagattt   120
ctttctgtgc cagaatgacc tgatccattt cctggtttgt agaaagcc atg gct tca    177
                                                    Met Ala Ser
                                                      1 gag ggt gct tcc tca gaa atc ata gaa aaa cag cga aca aag ttg ctc    225
Glu Gly Ala Ser Ser Glu Ile Ile Glu Lys Gln Arg Thr Lys Leu Leu
   5                  10                  15 agt gtc ctc caa caa gat ccc gac tct atc ttg gac acg tta acc tct    273
Ser Val Leu Gln Gln Asp Pro Asp Ser Ile Leu Asp Thr Leu Thr Ser
20                  25                  30                  35 cgg aga ctg att tct gag gag gag tat gag act cta gag gca att aca    321
Arg Arg Leu Ile Ser Glu Glu Glu Tyr Glu Thr Leu Glu Ala Ile Thr
                40                  45                  50 gat cct ctg aag aaa agc cgg aag ctg tta att ttg atc cag aag aag    369
Asp Pro Leu Lys Lys Ser Arg Lys Leu Leu Ile Leu Ile Gln Lys Lys
            55                  60                  65 gga gag gac agc tgt tgt tgt ttc ctc aag tgt ctg tct aat gcc ttt    417
Gly Glu Asp Ser Cys Cys Cys Phe Leu Lys Cys Leu Ser Asn Ala Phe
        70                  75                  80 cca cag tca gct tcc acc ttg ggt tta aag cag gaa gtt cca cgg cag    465
Pro Gln Ser Ala Ser Thr Leu Gly Leu Lys Gln Glu Val Pro Arg Gln
    85                  90                  95 ggg act gga gag gtt gtc gag gtg agc agg ggt ttg gaa gat ccc ttt    513
Gly Thr Gly Glu Val Val Glu Val Ser Arg Gly Leu Glu Asp Pro Phe
100                 105                 110                 115 tct ctt ggg acc ata acc cca gaa ata gca gag ctc tca gaa gag aaa    561
```

```
                                                                                       -continued Ser Leu Gly Thr Ile Thr Pro Glu Ile Ala Glu Leu Ser Glu Glu Lys
            120                 125                 130 gaa tgc ccg ggt ctg gga gct ccg gag ttc ttc acc tgc aag gaa agc          609
Glu Cys Pro Gly Leu Gly Ala Pro Glu Phe Phe Thr Cys Lys Glu Ser
            135                 140                 145 agc cac agg gaa ccg gaa gta cct tct tgg gag aat cag gaa ggg cgt          657
Ser His Arg Glu Pro Glu Val Pro Ser Trp Glu Asn Gln Glu Gly Arg
        150                 155                 160 ggt gca cag caa gtc acc gct ccg cgt tca gtc aaa gga gtt gag tat          705
Gly Ala Gln Gln Val Thr Ala Pro Arg Ser Val Lys Gly Val Glu Tyr
    165                 170                 175 gaa gtt cca gca agt atc tcc ctc tta agc gac ggg cag aga tac gag          753
Glu Val Pro Ala Ser Ile Ser Leu Leu Ser Asp Gly Gln Arg Tyr Glu
180                 185                 190                 195 gag cca gat gat tcg ctg tac tta gaa gaa ggg gaa ggt gaa gag tct          801
Glu Pro Asp Asp Ser Leu Tyr Leu Glu Glu Gly Glu Gly Glu Glu Ser
                200                 205                 210 ctt ggg tac cct gaa gat gtt ttg gag gaa ggg gcc ggc gat gac cca          849
Leu Gly Tyr Pro Glu Asp Val Leu Glu Glu Gly Ala Gly Asp Asp Pro
            215                 220                 225 cag tgc ttt gta tat gat agt gag gag gaa tgc gag tat gag gaa aac          897
Gln Cys Phe Val Tyr Asp Ser Glu Glu Glu Cys Glu Tyr Glu Glu Asn
        230                 235                 240 atg ggc tcc tcc ggt gaa gac agt agc tgc gac gac act tca gag acc          945
Met Gly Ser Ser Gly Glu Asp Ser Ser Cys Asp Asp Thr Ser Glu Thr
    245                 250                 255 tgc gtt cca ttg gaa ggg gag aaa agc gct gaa gaa aga aaa aga gtg          993
Cys Val Pro Leu Glu Gly Glu Lys Ser Ala Glu Glu Arg Lys Arg Val
260                 265                 270                 275 ttt caa cac gtc ctg tcc tgt ttg aac atg gat aga aac aga aag ctt         1041
Phe Gln His Val Leu Ser Cys Leu Asn Met Asp Arg Asn Arg Lys Leu
                280                 285                 290 ctc cca gag ttc gtg agg cag ttt tcc ata gac cga gga tgt gag tgg         1089
Leu Pro Glu Phe Val Arg Gln Phe Ser Ile Asp Arg Gly Cys Glu Trp
            295                 300                 305 aca ccc aag acc cca gga gac tta gct tgg aat ttc ttg atg aaa gtt         1137
Thr Pro Lys Thr Pro Gly Asp Leu Ala Trp Asn Phe Leu Met Lys Val
        310                 315                 320 cag gct tta gac tcg aca gcc aga gat tct atc ctg agg ccc gag gtg         1185
Gln Ala Leu Asp Ser Thr Ala Arg Asp Ser Ile Leu Arg Pro Glu Val
    325                 330                 335 gcg ggt gaa gag aat gaa gaa ttg ccg gct gga ata gag aag tta ggc         1233
Ala Gly Glu Glu Asn Glu Glu Leu Pro Ala Gly Ile Glu Lys Leu Gly
340                 345                 350                 355 att gga gac ccc caa acc atc cat ccc ctg gat gtc ctc tgc gcc tgc         1281
Ile Gly Asp Pro Gln Thr Ile His Pro Leu Asp Val Leu Cys Ala Cys
                360                 365                 370 atg ctt tgt gca gac agc tcc ttg cag cgt gaa gtc atg tca aac atg         1329
Met Leu Cys Ala Asp Ser Ser Leu Gln Arg Glu Val Met Ser Asn Met
            375                 380                 385 tac caa tgc cag ttt gct ctt ccc ctg cta ctg cca gat gct gag aac         1377
Tyr Gln Cys Gln Phe Ala Leu Pro Leu Leu Leu Pro Asp Ala Glu Asn
        390                 395                 400 aac aaa aac ctc tta atg gta ggg gcc atg aag gac tta aag cag ccc         1425
Asn Lys Asn Leu Leu Met Val Gly Ala Met Lys Asp Leu Lys Gln Pro
    405                 410                 415 tca gca cag tcc tca gga ggg ccc ctc agg gaa aca gac aca ttt ctg         1473
Ser Ala Gln Ser Ser Gly Gly Pro Leu Arg Glu Thr Asp Thr Phe Leu
420                 425                 430                 435
```

```
                                                      -continued ggt ctc aca aag atg cct gtc atc tct ttt gtg cga cta gga cgc tgc          1521
Gly Leu Thr Lys Met Pro Val Ile Ser Phe Val Arg Leu Gly Arg Cys
            440                 445                 450 agc ttc tcc aag tcc aga att gtt aac aca ctg ctc agc tcc tcc cag          1569
Ser Phe Ser Lys Ser Arg Ile Val Asn Thr Leu Leu Ser Ser Ser Gln
        455                 460                 465 cag aaa cca tac ccg att ttc ctc cat cag gat ctg tct gtc cct gtg          1617
Gln Lys Pro Tyr Pro Ile Phe Leu His Gln Asp Leu Ser Val Pro Val
    470                 475                 480 ctt cct cgg caa att tct gac ggc ctg gta gaa gta aca tgg tgc ttt          1665
Leu Pro Arg Gln Ile Ser Asp Gly Leu Val Glu Val Thr Trp Cys Phe
485                 490                 495 cct gac aag ttg ctg aag gaa agc ccg cat gct ttc cag aaa cct gtt          1713
Pro Asp Lys Leu Leu Lys Glu Ser Pro His Ala Phe Gln Lys Pro Val
500                 505                 510                 515 gct gtg gcc aac ctt cgt gga gat tta gaa agc ttt tgg ata caa ttt          1761
Ala Val Ala Asn Leu Arg Gly Asp Leu Glu Ser Phe Trp Ile Gln Phe
            520                 525                 530 ggt ttc ctg gta gaa gtt tcc tcc ggt ctt ttc ttt ttc aca gac tgc          1809
Gly Phe Leu Val Glu Val Ser Ser Gly Leu Phe Phe Phe Thr Asp Cys
        535                 540                 545 ctt ggt gag aag gaa tgg gac ttg cta atg ttt tta gga gag gac acc          1857
Leu Gly Glu Lys Glu Trp Asp Leu Leu Met Phe Leu Gly Glu Asp Thr
    550                 555                 560 att gaa cgg tgc tac ttt atc ctc agt ccc cag gct aag gag agt gaa          1905
Ile Glu Arg Cys Tyr Phe Ile Leu Ser Pro Gln Ala Lys Glu Ser Glu
565                 570                 575 gaa gcc cag att ttc caa agg atc cta aaa ctg aag cca tct cag cta          1953
Glu Ala Gln Ile Phe Gln Arg Ile Leu Lys Leu Lys Pro Ser Gln Leu
580                 585                 590                 595 ctg ttt tgg gaa gct gag gaa gct ggg gat aga agg aag act atg gag          2001
Leu Phe Trp Glu Ala Glu Glu Ala Gly Asp Arg Arg Lys Thr Met Glu
            600                 605                 610 gcc ctt caa gct gcc ctc cag gaa gta atg tcc tct cca ctc aga tgt          2049
Ala Leu Gln Ala Ala Leu Gln Glu Val Met Ser Ser Pro Leu Arg Cys
        615                 620                 625 gtg tcc ctt gaa gag atg gcc tct ctg gcc agg gag ctg ggc att cag          2097
Val Ser Leu Glu Glu Met Ala Ser Leu Ala Arg Glu Leu Gly Ile Gln
    630                 635                 640 gta gac caa gac ttt gaa gtt act caa gat att caa gtt tcc ccc aca          2145
Val Asp Gln Asp Phe Glu Val Thr Gln Asp Ile Gln Val Ser Pro Thr
645                 650                 655 aca gtt gaa ggt gaa aac caa caa cca tgt agt cag acc aaa agc ccg          2193
Thr Val Glu Gly Glu Asn Gln Gln Pro Cys Ser Gln Thr Lys Ser Pro
660                 665                 670                 675 gct gaa agc gga gct cag gag cca atc aga gag cca ggg gct caa tgt          2241
Ala Glu Ser Gly Ala Gln Glu Pro Ile Arg Glu Pro Gly Ala Gln Cys
            680                 685                 690 gac gac agt cag aat gct ccg gtt ttc cat cag act cca gta tac atg          2289
Asp Asp Ser Gln Asn Ala Pro Val Phe His Gln Thr Pro Val Tyr Met
        695                 700                 705 cct tat cca gca cac cca tgg gct ttg gcc atc aaa gct gga ggt aac          2337
Pro Tyr Pro Ala His Pro Trp Ala Leu Ala Ile Lys Ala Gly Gly Asn
    710                 715                 720 ttt tac cac gtt cct ttg aat gcc ccc tgg tta tgg gct ccc act ttg          2385
Phe Tyr His Val Pro Leu Asn Ala Pro Trp Leu Trp Ala Pro Thr Leu
725                 730                 735 gat cac agc aga ggg cta agt ggt tct ttc cat tcc cat gct aaa ccc          2433
Asp His Ser Arg Gly Leu Ser Gly Ser Phe His Ser His Ala Lys Pro
740                 745                 750                 755
```

```
act cac tct aag gcc ttc caa gct aac tgc cac cat ccc cat ccc tcc    2481
Thr His Ser Lys Ala Phe Gln Ala Asn Cys His His Pro His Pro Ser
            760                 765                 770 cat gct aaa ccc act cat gtg aat ccc tct cat gct aac ccc act cat    2529
His Ala Lys Pro Thr His Val Asn Pro Ser His Ala Asn Pro Thr His
            775                 780                 785 gtg cag cct tgc atg cta aac cca ctc act cta agg cct tcc aag cta    2577
Val Gln Pro Cys Met Leu Asn Pro Leu Thr Leu Arg Pro Ser Lys Leu
            790                 795                 800 aac cca ctc cct ctc aga cct ctt gga gcc aag cta act gca atc atg    2625
Asn Pro Leu Pro Leu Arg Pro Leu Gly Ala Lys Leu Thr Ala Ile Met
805                 810                 815 ccc atc cct ccc ttg cta aac cct ctc ata cga atc cct ctg atg cta    2673
Pro Ile Pro Pro Leu Leu Asn Pro Leu Ile Arg Ile Pro Leu Met Leu
820                 825                 830                 835 acc cca ctc atg tgc agc ctt ccc atg cta aac ccg ctc atc tac agt    2721
Thr Pro Leu Met Cys Ser Leu Pro Met Leu Asn Pro Leu Ile Tyr Ser
            840                 845                 850 ctt ccc aaa caa aac cct ccc cat ccc aat cta ctg cag ttc acg gca    2769
Leu Pro Lys Gln Asn Pro Pro His Pro Asn Leu Leu Gln Phe Thr Ala
            855                 860                 865 cac aaa cct cag cag tcc cag tct aag cct tct cag cag aga ccc agt    2817
His Lys Pro Gln Gln Ser Gln Ser Lys Pro Ser Gln Gln Arg Pro Ser
            870                 875                 880 cag cct aaa tca ttc cag acc aag cct tca cag gcc agg gcc tgc cac    2865
Gln Pro Lys Ser Phe Gln Thr Lys Pro Ser Gln Ala Arg Ala Cys His
            885                 890                 895 cca aga gca ggg aga cgt taaagaacat actctggaga tctgggaaat           2913
Pro Arg Ala Gly Arg Arg
900                 905 aaagtatggg ctttgcttaa gtattctttt tcatatagca agctgaagaa aagttttagt  2973
gaaagactga taaagtagc aaaacccaaa aaaggtatgc aaagtcttaa gtgcatagca   3033
aagtatccaa gtgtgggaaa tatggaagca gttaaaagta aatctggct gggcatggtg   3093
gcacacatct acaggttta gcatgggagg gctctgtcat cccaactcag agaagcaggc   3153
agatctctgt gtgtttgagg ccagtctggt ctacataaca acgacacaag caagtcctac  3213
atcagccata ctacaaaatg agaccccatc tggggacaaa agggttggat ctaacatcaa  3273
accaaagaaa tcagtcaagt attccagaag gcatcattaa ttacactcag tgggttacca  3333
caaccaaacc atactcgaca actaaccccc taaggagca agaaggagtt gggtgggtgt    3393
taggctgaac atgattgggg aagaactgaa gatagataag gtcattcgta atacaggtta  3453
tgggacttgt caaatccatt aaatgcaata ttaagaagca gtgggaatct taaggctaca  3513
ttaagctcca gtgagtcgca accctcccct attagatgat gtgagatttg aaccccagtg  3573
aatgggtgt gtctgatagc ccgtgtgtgt gacaaactgt gtaattataa agtgatgaaa   3633
acgtgggagt tcagcttatc tgtgttgaag aaaggctgct tcagaggtgc cttggttttg  3693
ggtttatgat cagccactga gcagatactc tgcaccattg gtacagttaa atcagcttgc  3753
ttctggtaat agccccaatc taccacattt atcccttaca ggcggaaata atgaatgatc  3813
agcaaaacat ccaattttac cttaaccttg gtactgattt gtatatgtat cattctttat  3873
ataatagcta agaaaattta gctcattagg ggttctgata tattagttta atggtttgaa  3933
gtcagaaatg tgttagtttt taatttaga gttaattgaa atattgaga tgaatttaca    3993
aaggctataa gtaatgtttg agagggttat aattttttgta gactctatact gttctgaaca 4053
```

-continued

```
tttggatagc ttctcgtagt tagcagtgtt atagaagaat atatttgatt caggtattta    4113
accagagctg ctcttagttt ttaagtgtca ccaagagtca ataaaaggct acattatctg    4173
aacatgtggg aacacaactg tgaccttaca cttaagagac tgaggaaggg aaatcaaggt    4233
tcaagccagc agcacatagt gagaccaggt ctcaagacac aaaaactatc caccttaagg    4293
aagattttaa aatttgcctc attaagaaat aaagtaagat ttataaattg gactaaatgt    4353
cacatctttg aacttatgac tgtttaattt tttgacttaa agtttaattt tattattgta    4413
tgcgtgtgtt gtatgtgtgt gcacatgtgt gccactgcat gtatgtggag gccatcagac    4473
aatgttgtag agtctgttct ttcctcttag ccctatgtgt tttacccact gagctaggcc    4533
acctactcct ataagtctaa ttttaaatag taaaatagtt ctaagaagtc aatcagggaa    4593
aaaaatggct gtcaaagtct caaagaaaaa tcgtattagc catggataga gactcacctc    4653
ttgaatcatt tgtgtctgag aatagcctaa tatcacaata atgtgtttgt acatgtgtta    4713
gttaatattg ttttcagagt atttaatctc tcatgattat tgtaaagatg aaaaaagaaa    4773
tagtgggcaa tgtatgtgag tatttaattt tgcctgacaa ttctgtcttt tagaatgata    4833
aatgtaagaa gtaaaataaa acggttcatt ctcagaacaa ctaagccagc tcacttaagt    4893
ctgggccctg ctggcattgg ctagtctagc taccccccacc caaacacaaa agtttagaga    4953
agaaaatgac tgagtcaagc ttgcctaatg acttttggac ataaagttta tggtcctaga    5013
aagccttaaa ataagtagga tataaaacat gtaaattaac ccacacatta tgtgggttga    5073
gaagcagaaa aatgtcagta gaacactcgg ccagtgcata agaaggaag agacctctgt    5133
tctgggttat aaaactgctc tttgtgctca atttgtcccc tgcttttgtt tgccagaatg    5193
tacaagatta taaataaac tcacttttac ttttaaaaaa aaaaaaaaa aaagggcgg     5252
```

<210> SEQ ID NO 52
<211> LENGTH: 905
<212> TYPE: PRT
<213> ORGANISM: Rattus rattus

<400> SEQUENCE: 52

```
Met Ala Ser Glu Gly Ala Ser Ser Glu Ile Ile Glu Lys Gln Arg Thr
  1               5                  10                  15

Lys Leu Leu Ser Val Leu Gln Gln Asp Pro Asp Ser Ile Leu Asp Thr
                 20                  25                  30

Leu Thr Ser Arg Arg Leu Ile Ser Glu Glu Tyr Glu Thr Leu Glu
             35                  40                  45

Ala Ile Thr Asp Pro Leu Lys Lys Ser Arg Lys Leu Leu Ile Leu Ile
         50                  55                  60

Gln Lys Lys Gly Glu Asp Ser Cys Cys Cys Phe Leu Lys Cys Leu Ser
 65                  70                  75                  80

Asn Ala Phe Pro Gln Ser Ala Ser Thr Leu Gly Leu Lys Gln Glu Val
                 85                  90                  95

Pro Arg Gln Gly Thr Gly Glu Val Val Glu Val Ser Arg Gly Leu Glu
                100                 105                 110

Asp Pro Phe Ser Leu Gly Thr Ile Thr Pro Glu Ile Ala Glu Leu Ser
            115                 120                 125

Glu Glu Lys Glu Cys Pro Gly Leu Gly Ala Pro Glu Phe Phe Thr Cys
        130                 135                 140

Lys Glu Ser Ser His Arg Glu Pro Glu Val Pro Ser Trp Glu Asn Gln
145                 150                 155                 160

Glu Gly Arg Gly Ala Gln Gln Val Thr Ala Pro Arg Ser Val Lys Gly
```

```
                165                 170                 175
Val Glu Tyr Glu Val Pro Ala Ser Ile Ser Leu Leu Ser Asp Gly Gln
            180                 185                 190

Arg Tyr Glu Glu Pro Asp Asp Ser Leu Tyr Leu Glu Glu Gly Glu Gly
            195                 200             205

Glu Glu Ser Leu Gly Tyr Pro Glu Asp Val Leu Glu Glu Gly Ala Gly
            210                 215             220

Asp Asp Pro Gln Cys Phe Val Tyr Asp Ser Glu Glu Cys Glu Tyr
225             230                 235                 240

Glu Glu Asn Met Gly Ser Ser Gly Glu Asp Ser Ser Cys Asp Asp Thr
            245                 250                 255

Ser Glu Thr Cys Val Pro Leu Glu Gly Glu Lys Ser Ala Glu Glu Arg
            260                 265                 270

Lys Arg Val Phe Gln His Val Leu Ser Cys Leu Asn Met Asp Arg Asn
            275                 280             285

Arg Lys Leu Leu Pro Glu Phe Val Arg Gln Phe Ser Ile Asp Arg Gly
            290                 295                 300

Cys Glu Trp Thr Pro Lys Thr Pro Gly Asp Leu Ala Trp Asn Phe Leu
305             310                 315                 320

Met Lys Val Gln Ala Leu Asp Ser Thr Ala Arg Asp Ser Ile Leu Arg
            325                 330                 335

Pro Glu Val Ala Gly Glu Asn Glu Glu Leu Pro Ala Gly Ile Glu
            340                 345                 350

Lys Leu Gly Ile Gly Asp Pro Gln Thr Ile His Pro Leu Asp Val Leu
            355                 360                 365

Cys Ala Cys Met Leu Cys Ala Asp Ser Ser Leu Gln Arg Glu Val Met
            370                 375             380

Ser Asn Met Tyr Gln Cys Gln Phe Ala Leu Pro Leu Leu Pro Asp
385             390                 395                 400

Ala Glu Asn Asn Lys Asn Leu Leu Met Val Gly Ala Met Lys Asp Leu
            405                 410                 415

Lys Gln Pro Ser Ala Gln Ser Ser Gly Gly Pro Leu Arg Glu Thr Asp
            420                 425                 430

Thr Phe Leu Gly Leu Thr Lys Met Pro Val Ile Ser Phe Val Arg Leu
            435                 440                 445

Gly Arg Cys Ser Phe Ser Lys Ser Arg Ile Val Asn Thr Leu Leu Ser
            450                 455             460

Ser Ser Gln Gln Lys Pro Tyr Pro Ile Phe Leu His Gln Asp Leu Ser
465             470                 475                 480

Val Pro Val Leu Pro Arg Gln Ile Ser Asp Gly Leu Val Glu Val Thr
            485                 490                 495

Trp Cys Phe Pro Asp Lys Leu Leu Lys Glu Ser Pro His Ala Phe Gln
            500                 505             510

Lys Pro Val Ala Val Ala Asn Leu Arg Gly Asp Leu Glu Ser Phe Trp
            515                 520             525

Ile Gln Phe Gly Phe Leu Val Glu Val Ser Ser Gly Leu Phe Phe Phe
            530                 535             540

Thr Asp Cys Leu Gly Glu Lys Glu Trp Asp Leu Leu Met Phe Leu Gly
545                 550                 555                 560

Glu Asp Thr Ile Glu Arg Cys Tyr Phe Ile Leu Ser Pro Gln Ala Lys
            565                 570                 575

Glu Ser Glu Glu Ala Gln Ile Phe Gln Arg Ile Leu Lys Leu Lys Pro
            580                 585                 590
```

```
Ser Gln Leu Leu Phe Trp Glu Ala Glu Ala Gly Asp Arg Arg Lys
        595                 600                 605

Thr Met Glu Ala Leu Gln Ala Ala Leu Gln Glu Val Met Ser Ser Pro
    610                 615                 620

Leu Arg Cys Val Ser Leu Glu Glu Met Ala Ser Leu Ala Arg Glu Leu
625                 630                 635                 640

Gly Ile Gln Val Asp Gln Asp Phe Glu Val Thr Gln Asp Ile Gln Val
                645                 650                 655

Ser Pro Thr Thr Val Glu Gly Glu Asn Gln Gln Pro Cys Ser Gln Thr
            660                 665                 670

Lys Ser Pro Ala Glu Ser Gly Ala Gln Glu Pro Ile Arg Glu Pro Gly
        675                 680                 685

Ala Gln Cys Asp Asp Ser Gln Asn Ala Pro Val Phe His Gln Thr Pro
    690                 695                 700

Val Tyr Met Pro Tyr Pro Ala His Pro Trp Ala Leu Ala Ile Lys Ala
705                 710                 715                 720

Gly Gly Asn Phe Tyr His Val Pro Leu Asn Ala Pro Trp Leu Trp Ala
                725                 730                 735

Pro Thr Leu Asp His Ser Arg Gly Leu Ser Gly Ser Phe His Ser His
            740                 745                 750

Ala Lys Pro Thr His Ser Lys Ala Phe Gln Ala Asn Cys His His Pro
        755                 760                 765

His Pro Ser His Ala Lys Pro Thr His Val Asn Pro Ser His Ala Asn
    770                 775                 780

Pro Thr His Val Gln Pro Cys Met Leu Asn Pro Leu Thr Leu Arg Pro
785                 790                 795                 800

Ser Lys Leu Asn Pro Leu Pro Leu Arg Pro Leu Gly Ala Lys Leu Thr
                805                 810                 815

Ala Ile Met Pro Ile Pro Pro Leu Leu Asn Pro Leu Ile Arg Ile Pro
            820                 825                 830

Leu Met Leu Thr Pro Leu Met Cys Ser Leu Pro Met Leu Asn Pro Leu
        835                 840                 845

Ile Tyr Ser Leu Pro Lys Gln Asn Pro Pro His Pro Asn Leu Leu Gln
850                 855                 860

Phe Thr Ala His Lys Pro Gln Gln Ser Gln Ser Lys Pro Ser Gln Gln
865                 870                 875                 880

Arg Pro Ser Gln Pro Lys Ser Phe Gln Thr Lys Pro Ser Gln Ala Arg
                885                 890                 895

Ala Cys His Pro Arg Ala Gly Arg Arg
            900                 905

<210> SEQ ID NO 53
<211> LENGTH: 2715
<212> TYPE: DNA
<213> ORGANISM: Rattus rattus

<400> SEQUENCE: 53
atggcttcag agggtgcttc ctcagaaatc atagaaaaac agcgaacaaa gttgctcagt      60
gtcctccaac aagatcccga ctctatcttg gacacgttaa cctctcggag actgattttct    120 gaggaggagt atgagactct agaggcaatt acagatcctc tgaagaaaag ccggaagctg     180
ttaattttga tccagaagaa gggagaggac agctgttgtt gtttcctcaa gtgtctgtct     240
aatgcctttc cacagtcagc ttccaccttg ggtttaaagc aggaagttcc acggcagggg     300
```

-continued

```
actggagagg ttgtcgaggt gagcagggt ttggaagatc cctttctct tgggaccata    360
acccagaaa tagcagagct ctcagaagag aaagaatgcc cgggtctggg agctccggag    420
ttcttcacct gcaaggaaag cagccacagg gaaccggaag taccttcttg ggagaatcag    480
gaagggcgtg gtgcacagca agtcaccgct ccgcgttcag tcaaaggagt tgagtatgaa    540
gttccagcaa gtatctccct cttaagcgac gggcagagat acgaggagcc agatgattcg    600
ctgtacttag aagaaggga aggtgaagag tctcttggt accctgaaga tgttttggag    660
gaagggccg gcgatgaccc acagtgcttt gtatatgata gtgaggagga atgcgagtat    720
gaggaaaaca tgggctcctc cggtgaagac agtagctgcg acgacacttc agagacctgc    780
gttccattgg aagggagaa agcgctgaa gaaagaaaaa gagtgtttca acacgtcctg    840
tcctgtttga acatggatag aaacagaaag cttctcccag agttcgtgag gcagttttcc    900
atagaccgag gatgtgagtg gacacccaag accccaggag acttagcttg gaatttcttg    960
atgaaagttc aggcttttaga ctcgacagcc agagattcta tcctgaggcc cgaggtggcg   1020
ggtgaagaga atgaagaatt gccggctgga atagagaagt taggcattgg agaccccaa   1080
accatccatc cctggatgt cctctgcgcc tgcatgcttt gtgcagacag ctccttgcag   1140
cgtgaagtca tgtcaaacat gtaccaatgc cagtttgctc ttcccctgct actgccagat   1200
gctgagaaca caaaaacct cttaatggta ggggccatga aggacttaaa gcagccctca   1260
gcacagtcct caggagggcc cctcagggaa acagacacat ttctgggtct cacaaagatg   1320
cctgtcatct ctttttgtgcg actaggacgc tgcagcttct ccaagtccag aattgttaac   1380
acactgctca gctcctccca gcagaaacca tacccgattt tcctccatca ggatctgtct   1440
gtccctgtgc ttcctcggca aatttctgac ggcctggtgg aagtgacatg gtgctttcct   1500
gacaagttgc tgaaggaaag cccgcatgct ttccagaaac ctgttgctgt ggccaaccrt   1560
cgtggagatt tagaaagctt ttggatacaa tttggtttcc tggtagaagt ttcctccggt   1620
cttttctttt tcacagactg ccttggtgag aaggaatggg acttgctaat gttttttagga   1680
gaggacacca ttgaacggtg ctactttatc ctcagtcccc aggctaagga gagtgaagaa   1740
gcccagattt tccaaaggat cctaaaactg aagccatctc agctactgtt ttgggaagct   1800
gaggaagctg gggatagaag gaagactatg gaggccttc aagctgccct ccaggaagta   1860
atgtcctctc cactcagatg tgtgtccctt gaagagatgg cctctctggc cagggagctg   1920
ggcattcagg tagaccaaga cttttgaagtt actcaagata ttcaagtttc ccccacaaca   1980
gttgaaggtg aaaaccaaca accatgtagt cagaccaaaa gcccggctga aagcggagct   2040
caggagccaa tcagagagcc aggggctcaa tgtgacgaca gtcagaatgc tccggttttc   2100
catcagactc cagtatacat gccttatcca gcacacccat gggctttggc catcaaagct   2160
ggaggtaact tttaccacgt tccttttgaat gcccctggt tatgggctcc cactttggat   2220
cacagcagag ggctaagtgg ttcttttccat tcccatgcta aacccactca ctctaaggcc   2280
ttccaagcta actgccacca tccccatccc tccatgcta aacccactca tgtgaatccc   2340
tctcatgcta accccactca tgtgcagcct tgcatgctaa accactcac tctaaggcct   2400
tccaagctaa acccactccc tctcagacct cttggagcca agctaactgc aatcatgccc   2460
atccctccct tgctaaaccc tctcatacga atccctctga tgctaaccc actcatgtgc   2520
agccttccca tgctaaaccc gctcatctac agtcttccca aacaaaaccc tccccatccc   2580
aatctactgc agttcacggc acacaaacct cagcagtccc agtctaagcc ttctcagcag   2640
agacccagtc agcctaaatc attccagacc aagccttcac aggccagggc ctgccaccca   2700
```

```
agagcaggga gacgt                                              2715

<210> SEQ ID NO 54
<211> LENGTH: 4244
<212> TYPE: DNA
<213> ORGANISM: Homo sapiens
<220> FEATURE:
<221> NAME/KEY: CDS
<222> LOCATION: (200)...(3310)

<400> SEQUENCE: 54
ccacgcgtcc gccggatcag agagtgctcc gagctgggtt gccccactgt gcttgtatct   60
gcactctcca acactaggca tcattgacat gttaaagctt agccaaatag aattgttctt   120
tgtcattctt ttttaacttt ttacttattc attaggatga tttcataata tatttcctgg   180
tttagaggaa acaggaaca atg gct acc gag agt act ccc tca gag atc ata    232
                      Met Ala Thr Glu Ser Thr Pro Ser Glu Ile Ile
                        1               5                   10 gaa aga gaa aga aaa aag ttg ctt gaa atc ctt caa cat gat cct gat    280
Glu Arg Glu Arg Lys Lys Leu Leu Glu Ile Leu Gln His Asp Pro Asp
         15                  20                  25 tct atc tta gac acg tta act tct cgg agg ctg att tct gag gaa gag    328
Ser Ile Leu Asp Thr Leu Thr Ser Arg Arg Leu Ile Ser Glu Glu Glu
 30                  35                  40 tat gag act ctg gag aat gtt aca gat ctc ctg aag aaa agt cgg aag    376
Tyr Glu Thr Leu Glu Asn Val Thr Asp Leu Leu Lys Lys Ser Arg Lys
     45                  50                  55 ctg tta att ttg gta cag aaa aag gga gag gcg acc tgt cag cat ttt    424
Leu Leu Ile Leu Val Gln Lys Lys Gly Glu Ala Thr Cys Gln His Phe
 60                  65                  70                  75 ctc aag tgt tta ttt agt act ttt cca cag tta gct gcc att tgc ggc    472
Leu Lys Cys Leu Phe Ser Thr Phe Pro Gln Leu Ala Ala Ile Cys Gly
             80                  85                  90 tta agg cat gaa gtt tta aaa cat gag aat aca gta cct cct caa tct    520
Leu Arg His Glu Val Leu Lys His Glu Asn Thr Val Pro Pro Gln Ser
         95                 100                 105 atg ggg gca agc agt aat tca gaa gat gct ttt tct cct gga ata aaa    568
Met Gly Ala Ser Ser Asn Ser Glu Asp Ala Phe Ser Pro Gly Ile Lys
    110                 115                 120 cag cct gaa gcc cct gag atc aca gtg ttc ttc agt gag aag gaa cac    616
Gln Pro Glu Ala Pro Glu Ile Thr Val Phe Phe Ser Glu Lys Glu His
125                 130                 135 ttg gat ttg gaa acc tct gag ttt ttc agg gac aag aaa act agt tat    664
Leu Asp Leu Glu Thr Ser Glu Phe Phe Arg Asp Lys Lys Thr Ser Tyr
140                 145                 150                 155 agg gaa aca gct ttg tct gcc agg aag aat gag aag gaa tat gac aca    712
Arg Glu Thr Ala Leu Ser Ala Arg Lys Asn Glu Lys Glu Tyr Asp Thr
             160                 165                 170 cca gaa gtc aca tta tca tat tca gtt gag aaa gtt gga tgt gaa gtt    760
Pro Glu Val Thr Leu Ser Tyr Ser Val Glu Lys Val Gly Cys Glu Val
         175                 180                 185 cca gca act att aca tat ata aaa gat gga cag aga tat gag gag cta    808
Pro Ala Thr Ile Thr Tyr Ile Lys Asp Gly Gln Arg Tyr Glu Glu Leu
    190                 195                 200 gat gat tct tta tac tta gga aaa gag gaa tat cta gga tct gtt gac    856
Asp Asp Ser Leu Tyr Leu Gly Lys Glu Glu Tyr Leu Gly Ser Val Asp
205                 210                 215 acc cct gaa gat gca gaa gcc act gtg gaa gag gag gtt tat gat gac    904
Thr Pro Glu Asp Ala Glu Ala Thr Val Glu Glu Glu Val Tyr Asp Asp
220                 225                 230                 235
```

-continued

| | |
|---|---|
| cca gag cac gtt gga tat gat ggt gaa gag gac ttc gag aat tca gaa<br>Pro Glu His Val Gly Tyr Asp Gly Glu Glu Asp Phe Glu Asn Ser Glu<br>240 245 250 | 952 |
| acc aca gag ttc tct ggt gaa gaa cca agt tat gag gga tca gaa acc<br>Thr Thr Glu Phe Ser Gly Glu Glu Pro Ser Tyr Glu Gly Ser Glu Thr<br>255 260 265 | 1000 |
| agc ctt tca ttg gag gag gaa cag gag aaa agt ata gaa gaa aga aaa<br>Ser Leu Ser Leu Glu Glu Glu Gln Glu Lys Ser Ile Glu Glu Arg Lys<br>270 275 280 | 1048 |
| aag gtg ttt aaa gat gtc ctg tta tgt ttg aac atg gat aga agc aga<br>Lys Val Phe Lys Asp Val Leu Leu Cys Leu Asn Met Asp Arg Ser Arg<br>285 290 295 | 1096 |
| aag gtt ctg cca gat ttt gtt aaa caa ttc tcc tta gat cga gga tgt<br>Lys Val Leu Pro Asp Phe Val Lys Gln Phe Ser Leu Asp Arg Gly Cys<br>300 305 310 315 | 1144 |
| aag tgg acc cct gag agt cca gga gac tta gcc tgg aat ttc ctg atg<br>Lys Trp Thr Pro Glu Ser Pro Gly Asp Leu Ala Trp Asn Phe Leu Met<br>320 325 330 | 1192 |
| aaa gtt caa gca cga gat gtg acg gct agg gat tca atc ctc agt cac<br>Lys Val Gln Ala Arg Asp Val Thr Ala Arg Asp Ser Ile Leu Ser His<br>335 340 345 | 1240 |
| aag gtt ctg gat gaa gat agc aag gag gat ttg ctg gct gga gtg gag<br>Lys Val Leu Asp Glu Asp Ser Lys Glu Asp Leu Leu Ala Gly Val Glu<br>350 355 360 | 1288 |
| aat ttg gaa att cga gac ata caa acc att aat ccc ctt gac gtg ctt<br>Asn Leu Glu Ile Arg Asp Ile Gln Thr Ile Asn Pro Leu Asp Val Leu<br>365 370 375 | 1336 |
| tgt gcc acc atg ctg tgt tca gat agc tct ttg caa cgc caa gtc atg<br>Cys Ala Thr Met Leu Cys Ser Asp Ser Ser Leu Gln Arg Gln Val Met<br>380 385 390 395 | 1384 |
| tca aac atg tat cag tgc cag ttt gct ctt ccc ctg cta ctg cca gat<br>Ser Asn Met Tyr Gln Cys Gln Phe Ala Leu Pro Leu Leu Leu Pro Asp<br>400 405 410 | 1432 |
| gca gaa aac aac aaa agc atc tta atg ctg ggg gcc atg aaa gac att<br>Ala Glu Asn Asn Lys Ser Ile Leu Met Leu Gly Ala Met Lys Asp Ile<br>415 420 425 | 1480 |
| gtg aag aag cag tca aca cag ttt tca ggg ggg cct aca gag gat aca<br>Val Lys Lys Gln Ser Thr Gln Phe Ser Gly Gly Pro Thr Glu Asp Thr<br>430 435 440 | 1528 |
| gaa aag ttt ctg act ctc atg aag atg cct gtc atc tct ttt gtg cgt<br>Glu Lys Phe Leu Thr Leu Met Lys Met Pro Val Ile Ser Phe Val Arg<br>445 450 455 | 1576 |
| cta gga tac tgt agc ttc tct aag tcc aga atc ctc aac aca ctt ctc<br>Leu Gly Tyr Cys Ser Phe Ser Lys Ser Arg Ile Leu Asn Thr Leu Leu<br>460 465 470 475 | 1624 |
| agc cct gcc cag ttg aaa tta cac aaa atc ttt ctt cat caa gat ttg<br>Ser Pro Ala Gln Leu Lys Leu His Lys Ile Phe Leu His Gln Asp Leu<br>480 485 490 | 1672 |
| cct ctt ttg gtg ctt ccc cgg caa atc tct gat ggc ctg gtt gag ata<br>Pro Leu Leu Val Leu Pro Arg Gln Ile Ser Asp Gly Leu Val Glu Ile<br>495 500 505 | 1720 |
| aca tgg tgt ttt cct gat agc gat gat aga aag gaa aac ccc ttt ttc<br>Thr Trp Cys Phe Pro Asp Ser Asp Asp Arg Lys Glu Asn Pro Phe Phe<br>510 515 520 | 1768 |
| caa aag cct gtt gct ctg gct aat ctc cgt gga aat cta gaa agt ttt<br>Gln Lys Pro Val Ala Leu Ala Asn Leu Arg Gly Asn Leu Glu Ser Phe<br>525 530 535 | 1816 |
| tgg act cag ttt ggt ttt ttg atg gaa gtt tct tca gct gtg ttt ttt<br>Trp Thr Gln Phe Gly Phe Leu Met Glu Val Ser Ser Ala Val Phe Phe | 1864 |

```
                                              -continued
540              545              550              555 ttc act gac tgt tta ggt gag aag gaa tgg gac ttg cta atg ttt tta     1912
Phe Thr Asp Cys Leu Gly Glu Lys Glu Trp Asp Leu Leu Met Phe Leu
            560              565              570 gga gag gct gcc att gaa aga tgc tac ttt gtt ctc agt tcc caa gcc     1960
Gly Glu Ala Ala Ile Glu Arg Cys Tyr Phe Val Leu Ser Ser Gln Ala
            575              580              585 agg gag agt gaa gag gct caa att ttt cag agg ata ctg aac ttg aag     2008
Arg Glu Ser Glu Glu Ala Gln Ile Phe Gln Arg Ile Leu Asn Leu Lys
            590              595              600 cca gca cag cta ctg ttt tgg gag agg gga gat gct ggg gat aga agg     2056
Pro Ala Gln Leu Leu Phe Trp Glu Arg Gly Asp Ala Gly Asp Arg Arg
            605              610              615 aag aac atg gag ggc ctt caa gct gcc ctc cag gaa gtg atg ttc tct     2104
Lys Asn Met Glu Gly Leu Gln Ala Ala Leu Gln Glu Val Met Phe Ser
620              625              630              635 tct tgc ctc aga tgt gtg tct gtg gag gat atg gcc gcc ctg gcc agg     2152
Ser Cys Leu Arg Cys Val Ser Val Glu Asp Met Ala Ala Leu Ala Arg
            640              645              650 gag ctg ggg att cag gta gat gaa gac ttt gaa aac act cag aga att     2200
Glu Leu Gly Ile Gln Val Asp Glu Asp Phe Glu Asn Thr Gln Arg Ile
            655              660              665 caa gtt tcc tct gga gaa aac atg gct ggg aca gct gaa ggt gag ggt     2248
Gln Val Ser Ser Gly Glu Asn Met Ala Gly Thr Ala Glu Gly Glu Gly
            670              675              680 cag caa aga cac agt cag cta aaa agc tca tct aaa agc cag gct cta     2296
Gln Gln Arg His Ser Gln Leu Lys Ser Ser Ser Lys Ser Gln Ala Leu
            685              690              695 atg cca att caa gag cct ggg act caa tgt gag ctc agc cag aat ctt     2344
Met Pro Ile Gln Glu Pro Gly Thr Gln Cys Glu Leu Ser Gln Asn Leu
700              705              710              715 cag aat ctc tat ggt acc cca gta ttc agg cct gtt cta gag aac tcc     2392
Gln Asn Leu Tyr Gly Thr Pro Val Phe Arg Pro Val Leu Glu Asn Ser
            720              725              730 tgg ctc ttt cca acc aga att gga ggt aac ttt aac cat gtt tcc ttg     2440
Trp Leu Phe Pro Thr Arg Ile Gly Gly Asn Phe Asn His Val Ser Leu
            735              740              745 aaa gcc tcc tgg gtt atg ggc cgc ccc ttt ggg tca gag cag agg cct     2488
Lys Ala Ser Trp Val Met Gly Arg Pro Phe Gly Ser Glu Gln Arg Pro
            750              755              760 aag tgg ttc cat cct ttg cct ttt cag aat gca ggg gcc cag ggc cga     2536
Lys Trp Phe His Pro Leu Pro Phe Gln Asn Ala Gly Ala Gln Gly Arg
765              770              775 ggt aaa agt ttt ggt att caa tcc ttc cat ccc cag ata ttt tat tca     2584
Gly Lys Ser Phe Gly Ile Gln Ser Phe His Pro Gln Ile Phe Tyr Ser
780              785              790              795 ggt gaa aga ttc atg aaa ttt tcc aga gtt gct cgg gga tgt cac tcg     2632
Gly Glu Arg Phe Met Lys Phe Ser Arg Val Ala Arg Gly Cys His Ser
            800              805              810 aat gga aca ttt ggg aga ctg cca aga ccc att tgt cag cat gta cag     2680
Asn Gly Thr Phe Gly Arg Leu Pro Arg Pro Ile Cys Gln His Val Gln
            815              820              825 gcc tgc cct gag aga cca caa atg atg gga act ctt gaa agg tct agg     2728
Ala Cys Pro Glu Arg Pro Gln Met Met Gly Thr Leu Glu Arg Ser Arg
            830              835              840 gca gta gcc tcc aag ata ggt cac tcc tat tcc ctg gat tca cag cca     2776
Ala Val Ala Ser Lys Ile Gly His Ser Tyr Ser Leu Asp Ser Gln Pro
845              850              855 gca aga gca gta ggg aag cca tgg cct cag caa gct tgc acc agg gta     2824
```

```
            Ala Arg Ala Val Gly Lys Pro Trp Pro Gln Gln Ala Cys Thr Arg Val
            860             865                 870                 875 aca gag tta act gaa gca act gga aaa ctg ata aga aca tcc cat att        2872
Thr Glu Leu Thr Glu Ala Thr Gly Lys Leu Ile Arg Thr Ser His Ile
                    880                 885                 890 gga aag cct cac cct cag tcc ttt caa cca gca gca gcc aca caa aaa        2920
Gly Lys Pro His Pro Gln Ser Phe Gln Pro Ala Ala Ala Thr Gln Lys
                895                 900                 905 cta aga cct gct tct cag caa gga gtc cag atg aag aca caa ggt ggg        2968
Leu Arg Pro Ala Ser Gln Gln Gly Val Gln Met Lys Thr Gln Gly Gly
        910                 915                 920 gct tca aat cca gct ctc caa ata ggg tcc cat ccc atg tgc aag agc        3016
Ala Ser Asn Pro Ala Leu Gln Ile Gly Ser His Pro Met Cys Lys Ser
    925                 930                 935 tct cag ttc aaa tcc gat cag tcc aac cca tcc aca gtc aaa cac tcc        3064
Ser Gln Phe Lys Ser Asp Gln Ser Asn Pro Ser Thr Val Lys His Ser
940                 945                 950                 955 cag cct aaa ccc ttc cat tct gtg ccc tct caa cct aaa tcc tct cag        3112
Gln Pro Lys Pro Phe His Ser Val Pro Ser Gln Pro Lys Ser Ser Gln
                960                 965                 970 aca aaa tcc tgt cag tcc cag ccc tcc caa act aaa cct tct cca tgc        3160
Thr Lys Ser Cys Gln Ser Gln Pro Ser Gln Thr Lys Pro Ser Pro Cys
                975                 980                 985 aaa tct act cag cct aag cca agc cag ccc tgg cct ccc cag tct aag        3208
Lys Ser Thr Gln Pro Lys Pro Ser Gln Pro Trp Pro Pro Gln Ser Lys
            990                 995                 1000 cct tct cag ccc aga ccc cct caa cct aag tca tcc tca acc aat cct        3256
Pro Ser Gln Pro Arg Pro Pro Gln Pro Lys Ser Ser Ser Thr Asn Pro
        1005                1010                1015 tca caa gct aag gca cac cac tca aaa gca ggg cag aag agg gga ggg        3304
Ser Gln Ala Lys Ala His His Ser Lys Ala Gly Gln Lys Arg Gly Gly
1020                1025                1030                1035 aag cat taaagagcta actccagaga tctataaagc atatcccttta cccaggccat       3360
Lys His tcctatcata tagtaagcag aagagttgcc atgaaagtaa aagactactg tcattagcat     3420
gtaaaacaaa gaaagatata catgaccgaa ttggatatct ttgtttgttt gtttgagaca     3480
gagtttcact cttgttgccc aggctggagt gcaatggcac gatctcggct caccgcaacc     3540
tctgcttcct ggcttaaagt gattctcctg cctcagcctc tcgagtagct gggattacag     3600
gcatgcacca ccacacccag ctaattttgt attttagta gaggcagggt ttctccatgt      3660
tggtcaggct ggtcttgaac tcccgacctc aggtgatccg cccacctagg cctctcaaag     3720
tgttgggatt acgtgtgtaa gccacagtgc ccagcccgaa ttggatatct ttaagatatc     3780
tgtaagtgtt atatccctaa ccaagaagaa aaatatgaaa ataattaaga ctagaatcaa     3840
gcagtagata attgaatcca atcttgggta ttattagata atgtataact tgcacccagg     3900 gaatggggt ctatgagaca accccacttg gagaagaatg gggttagggt ctctaattgc      3960
aaagtgactg tacaatagga cgaaagttgc ctctgtgtct gagaaagtat cttagttgtt     4020
ggctgctcca gaggtatctt tgtcaaaagc ttctggttca atatcagcca ctgagcagat     4080
aaccctgctt atttggtgtg gttaaatcaa ctagcttctg ctaatagccc caatttgctt     4140
gaatgggaaa actctctcat ttgacccctta taggtagaaa taatgaatta acaaccaata    4200
aaattaatca tttggcatta aaaaaaaaa aaaaaaaaa raaa                        4244

<210> SEQ ID NO 55
<211> LENGTH: 1037
```

```
<212> TYPE: PRT
<213> ORGANISM: Homo sapiens

<400> SEQUENCE: 55

Met Ala Thr Glu Ser Thr Pro Ser Glu Ile Ile Glu Arg Glu Arg Lys
  1               5                  10                  15

Lys Leu Leu Glu Ile Leu Gln His Asp Pro Asp Ser Ile Leu Asp Thr
             20                  25                  30

Leu Thr Ser Arg Arg Leu Ile Ser Glu Glu Glu Tyr Glu Thr Leu Glu
         35                  40                  45

Asn Val Thr Asp Leu Leu Lys Lys Ser Arg Lys Leu Leu Ile Leu Val
     50                  55                  60

Gln Lys Lys Gly Glu Ala Thr Cys Gln His Phe Leu Lys Cys Leu Phe
 65                  70                  75                  80

Ser Thr Phe Pro Gln Leu Ala Ala Ile Cys Gly Leu Arg His Glu Val
                 85                  90                  95

Leu Lys His Glu Asn Thr Val Pro Pro Gln Ser Met Gly Ala Ser Ser
            100                 105                 110

Asn Ser Glu Asp Ala Phe Ser Pro Gly Ile Lys Gln Pro Glu Ala Pro
        115                 120                 125

Glu Ile Thr Val Phe Phe Ser Glu Lys Glu His Leu Asp Leu Glu Thr
    130                 135                 140

Ser Glu Phe Phe Arg Asp Lys Lys Thr Ser Tyr Arg Glu Thr Ala Leu
145                 150                 155                 160

Ser Ala Arg Lys Asn Glu Lys Gly Tyr Asp Thr Pro Glu Val Thr Leu
                165                 170                 175

Ser Tyr Ser Val Glu Lys Val Gly Cys Glu Val Pro Ala Thr Ile Thr
            180                 185                 190

Tyr Ile Lys Asp Gly Gln Arg Tyr Glu Glu Leu Asp Asp Ser Leu Tyr
        195                 200                 205

Leu Gly Lys Glu Glu Tyr Leu Gly Ser Val Asp Thr Pro Glu Asp Ala
    210                 215                 220

Glu Ala Thr Val Glu Glu Val Tyr Asp Asp Pro Glu His Val Gly
225                 230                 235                 240

Tyr Asp Gly Glu Glu Asp Phe Glu Asn Ser Glu Thr Thr Glu Phe Ser
                245                 250                 255

Gly Glu Glu Pro Ser Tyr Glu Gly Ser Glu Thr Ser Leu Ser Leu Glu
            260                 265                 270

Glu Glu Gln Glu Lys Ser Ile Glu Glu Arg Lys Lys Val Phe Lys Asp
        275                 280                 285

Val Leu Leu Cys Leu Asn Met Asp Arg Ser Arg Lys Val Leu Pro Asp
    290                 295                 300

Phe Val Lys Gln Phe Ser Leu Asp Arg Gly Cys Lys Trp Thr Pro Glu
305                 310                 315                 320

Ser Pro Gly Asp Leu Ala Trp Asn Phe Leu Met Lys Val Gln Ala Arg
                325                 330                 335

Asp Val Thr Ala Arg Asp Ser Ile Leu Ser His Lys Val Leu Asp Glu
            340                 345                 350

Asp Ser Lys Glu Asp Leu Leu Ala Gly Val Glu Asn Leu Glu Ile Arg
        355                 360                 365

Asp Ile Gln Thr Ile Asn Pro Leu Asp Val Leu Cys Ala Thr Met Leu
    370                 375                 380

Cys Ser Asp Ser Ser Leu Gln Arg Gln Val Met Ser Asn Met Tyr Gln
385                 390                 395                 400
```

```
Cys Gln Phe Ala Leu Pro Leu Leu Pro Asp Ala Glu Asn Asn Lys
                405                 410                 415

Ser Ile Leu Met Leu Gly Ala Met Lys Asp Ile Val Lys Lys Gln Ser
            420                 425                 430

Thr Gln Phe Ser Gly Gly Pro Thr Glu Asp Thr Glu Lys Phe Leu Thr
        435                 440                 445

Leu Met Lys Met Pro Val Ile Ser Phe Val Arg Leu Gly Tyr Cys Ser
450                 455                 460

Phe Ser Lys Ser Arg Ile Leu Asn Thr Leu Leu Ser Pro Ala Gln Leu
465                 470                 475                 480

Lys Leu His Lys Ile Phe Leu His Gln Asp Leu Pro Leu Leu Val Leu
                485                 490                 495

Pro Arg Gln Ile Ser Asp Gly Leu Val Glu Ile Thr Trp Cys Phe Pro
            500                 505                 510

Asp Ser Asp Asp Arg Lys Glu Asn Pro Phe Phe Gln Lys Pro Val Ala
        515                 520                 525

Leu Ala Asn Leu Arg Gly Asn Leu Glu Ser Phe Trp Thr Gln Phe Gly
        530                 535                 540

Phe Leu Met Glu Val Ser Ser Ala Val Phe Phe Thr Asp Cys Leu
545                 550                 555                 560

Gly Glu Lys Glu Trp Asp Leu Leu Met Phe Leu Gly Glu Ala Ala Ile
                565                 570                 575

Glu Arg Cys Tyr Phe Val Leu Ser Ser Gln Ala Arg Glu Ser Glu Glu
            580                 585                 590

Ala Gln Ile Phe Gln Arg Ile Leu Asn Leu Lys Pro Ala Gln Leu Leu
        595                 600                 605

Phe Trp Glu Arg Gly Asp Ala Gly Asp Arg Arg Lys Asn Met Glu Gly
        610                 615                 620

Leu Gln Ala Ala Leu Gln Glu Val Met Phe Ser Ser Cys Leu Arg Cys
625                 630                 635                 640

Val Ser Val Glu Asp Met Ala Ala Leu Ala Arg Glu Leu Gly Ile Gln
                645                 650                 655

Val Asp Glu Asp Phe Glu Asn Thr Gln Arg Ile Gln Val Ser Ser Gly
            660                 665                 670

Glu Asn Met Ala Gly Thr Ala Glu Gly Glu Gly Gln Gln Arg His Ser
        675                 680                 685

Gln Leu Lys Ser Ser Ser Lys Ser Gln Ala Leu Met Pro Ile Gln Glu
        690                 695                 700

Pro Gly Thr Gln Cys Glu Leu Ser Gln Asn Leu Gln Asn Leu Tyr Gly
705                 710                 715                 720

Thr Pro Val Phe Arg Pro Val Leu Glu Asn Ser Trp Leu Phe Pro Thr
                725                 730                 735

Arg Ile Gly Gly Asn Phe Asn His Val Ser Leu Lys Ala Ser Trp Val
            740                 745                 750

Met Gly Arg Pro Phe Gly Ser Glu Gln Arg Pro Lys Trp Phe His Pro
        755                 760                 765

Leu Pro Phe Gln Asn Ala Gly Ala Gln Gly Arg Gly Lys Ser Phe Gly
        770                 775                 780

Ile Gln Ser Phe His Pro Gln Ile Phe Tyr Ser Gly Glu Arg Phe Met
785                 790                 795                 800

Lys Phe Ser Arg Val Ala Arg Gly Cys His Ser Asn Gly Thr Phe Gly
                805                 810                 815
```

```
Arg Leu Pro Arg Pro Ile Cys Gln His Val Gln Ala Cys Pro Glu Arg
            820                 825                 830

Pro Gln Met Met Gly Thr Leu Glu Arg Ser Arg Ala Val Ala Ser Lys
        835                 840                 845

Ile Gly His Ser Tyr Ser Leu Asp Ser Gln Pro Ala Arg Ala Val Gly
    850                 855                 860

Lys Pro Trp Pro Gln Gln Ala Cys Thr Arg Val Thr Glu Leu Thr Glu
865                 870                 875                 880

Ala Thr Gly Lys Leu Ile Arg Thr Ser His Ile Gly Lys Pro His Pro
                885                 890                 895

Gln Ser Phe Gln Pro Ala Ala Ala Thr Gln Lys Leu Arg Pro Ala Ser
            900                 905                 910

Gln Gln Gly Val Gln Met Lys Thr Gln Gly Gly Ala Ser Asn Pro Ala
        915                 920                 925

Leu Gln Ile Gly Ser His Pro Met Cys Lys Ser Ser Gln Phe Lys Ser
    930                 935                 940

Asp Gln Ser Asn Pro Ser Thr Val Lys His Ser Gln Pro Lys Pro Phe
945                 950                 955                 960

His Ser Val Pro Ser Gln Pro Lys Ser Ser Gln Thr Lys Ser Cys Gln
                965                 970                 975

Ser Gln Pro Ser Gln Thr Lys Pro Ser Pro Cys Lys Ser Thr Gln Pro
            980                 985                 990

Lys Pro Ser Gln Pro Trp Pro Gln Ser Lys Pro Ser Gln Pro Arg
        995                 1000                1005

Pro Pro Gln Pro Lys Ser Ser Ser Thr Asn Pro Ser Gln Ala Lys Ala
    1010                1015                1020

His His Ser Lys Ala Gly Gln Lys Arg Gly Gly Lys His
1025                1030                1035

<210> SEQ ID NO 56
<211> LENGTH: 3111
<212> TYPE: DNA
<213> ORGANISM: Homo sapiens

<400> SEQUENCE: 56
atggctaccg agagtactcc ctcagagatc atagaaagag aaagaaaaaa gttgcttgaa     60
atccttcaac atgatcctga ttctatctta gacacgttaa cttctcggag gctgatttct    120
gaggaagagt atgagactct ggagaatgtt acagatctcc tgaagaaaag tcggaagctg    180
ttaattttgg tacagaaaaa gggagaggcg acctgtcagc attttctcaa gtgtttattt    240 agtactttc cacagttagc tgccatttgc ggcttaaggc atgaagtttt aaaacatgag    300
aatacagtac ctcctcaatc tatgggggca agcagtaatt cagaagatgc tttttctcct    360
ggaataaaac agcctgaagc ccctgagatc acagtgttct tcagtgagaa ggaacacttg    420
gatttggaaa cctctgagtt tttcagggac aagaaaacta gttataggga acagctttg    480 tctgccagga gaatgagaa ggaatatgac acaccagaag tcacattatc atattcagtt    540
gagaaagttg atgtgaagt tccagcaact attacatata taaagatgg acagagatat    600 gaggagctag atgattcttt atacttagga aaagaggaat atctaggatc tgttgacacc    660
cctgaagatg cagaagccac tgtggaagag gaggtttatg atgacccaga gcacgttgga    720
tatgatggtg aagaggactt cgagaattca gaaaccacag agttctctgg tgaagaacca    780
agttatgagg gatcagaaac cagcctttca ttggaggagg aacaggagaa aagtatagaa    840
gaaagaaaaa aggtgtttaa agatgtcctg ttatgtttga catggatag aagcagaaag    900
```

```
gttctgccag attttgttaa acaattctcc ttagatcgag gatgtaagtg gaccccctgag    960
agtccaggag acttagcctg gaatttcctg atgaaagttc aagcacgaga tgtgacggct   1020
agggattcaa tcctcagtca caaggttctg gatgaagata gcaaggagga tttgctggct   1080
ggagtggaga atttggaaat tcgagacata caaaccatta atccccttga cgtgctttgt   1140
gccaccatgc tgtgttcaga tagctctttg caacgccaag tcatgtcaaa catgtatcag   1200
tgccagtttg ctcttcccct gctactgcca gatgcagaaa caacaaaag catcttaatg    1260
ctggggccca tgaaagacat tgtgaagaag cagtcaacac agtttcagg ggggcctaca    1320
gaggatacag aaaagtttct gactctcatg aagatgcctg tcatctcttt tgtgcgtcta   1380
ggatactgta gcttctctaa gtccagaatc ctcaacacac ttctcagccc tgcccagttg   1440
aaattacaca aaatctttct tcatcaagat ttgcctcttt tggtgcttcc ccggcaaatc   1500
tctgatggcc tggttgagat aacatggtgt tttcctgata gcgatgatag aaaggaaaac   1560
cccttttcc aaaagcctgt tgctctggct aatctccgtg gaaatctaga aagttttgg     1620
actcagtttg gttttttgat ggaagtttct tcagctgtgt ttttttttcac tgactgttta   1680
ggtgagaagg aatgggactt gctaatgttt ttaggagagg ctgccattga aagatgctac   1740
tttgttctca gttcccaagc cagggagagt gaagaggctc aaattttttca gaggatactg   1800
aacttgaagc cagcacagct actgttttgg gagagggag atgctgggga tagaaggaag    1860
aacatggagg gccttcaagc tgccctccag gaagtgatgt tctcttcttg cctcagatgt   1920
gtgtctgtgg aggatatggc cgccctggcc agggagctgg ggattcaggt agatgaagac   1980
tttgaaaaaca ctcagagaat tcaagtttcc tctggagaaa acatggctgg gacagctgaa  2040
ggtgagggtc agcaaagaca cagtcagcta aaaagctcat ctaaaagcca ggctctaatg   2100
ccaattcaag agcctgggac tcaatgtgag ctcagccaga atcttcagaa tctctatggt   2160
accccagtat tcaggcctgt tctagagaac tcctggctct ttccaaccag aattggaggt   2220
aactttaacc atgtttcctt gaaagcctcc tgggttatgg gccgccccctt tgggtcagag  2280
cagaggccta agtggttcca tcctttgcct tttcagaatg caggggccca gggccgaggt   2340
aaaagttttg gtattcaatc cttccatccc cagatatttt attcaggtga aagattcatg   2400
aaattttcca gagttgctcg gggatgtcac tcgaatggaa catttgggag actgccaaga   2460
cccatttgtc agcatgtaca ggcctgccct gagagaccac aaatgatggg aactcttgaa   2520
aggtctaggg cagtagcctc caagataggt cactcctatt ccctggattc acagccagca   2580
agagcagtag ggaagccatg gcctcagcaa gcttgcacca gggtaacaga gttaactgaa   2640
gcaactggaa aactgataag aacatcccat attggaaagc ctcaccctca gtccttcaa    2700
ccagcagcag ccacacaaaa actaagacct gcttctcagc aaggagtcca gatgaagaca   2760
caaggtgggg cttcaaatcc agctctccaa atagggtccc atcccatgtg caagagctct   2820
cagttcaaat ccgatcagtc caacccatcc acagtcaaac actcccagcc taaacccttc   2880
cattctgtgc cctctcaacc taaatcctct cagacaaaat cctgtcagtc ccagccctcc   2940
caaactaaac cttctccatg caaatctact cagcctaagc caagccagcc ctggcctccc   3000
cagtctaagc cttctcagcc cagacccct caacctaagt catcctcaac caatccttca    3060
caagctaagg cacaccactc aaaagcaggg cagaagaggg gagggaagca t             3111
```

<210> SEQ ID NO 57
<211> LENGTH: 70
<212> TYPE: PRT

-continued

<213> ORGANISM: Mus musculus

<400> SEQUENCE: 57

Gly His Phe Val Asp Gln His Arg Gln Ala Leu Ile Ala Arg Val Thr
 1               5                  10                  15

Glu Val Asp Gly Val Leu Asp Ala Leu His Gly Ser Val Leu Thr Glu
            20                  25                  30

Gly Gln Tyr Gln Ala Val Arg Ala Glu Thr Thr Ser Gln Asp Lys Met
        35                  40                  45

Arg Lys Leu Phe Ser Phe Val Pro Ser Trp Asn Leu Thr Cys Lys Asp
    50                  55                  60

Ser Leu Leu Gln Ala Leu
65                  70

<210> SEQ ID NO 58
<211> LENGTH: 71
<212> TYPE: PRT
<213> ORGANISM: Homo sapiens

<400> SEQUENCE: 58

Gly Leu His Phe Ile Asp Gln His Arg Ala Ala Leu Ile Ala Arg Val
 1               5                  10                  15

Thr Asn Val Glu Trp Leu Leu Asp Ala Leu Tyr Gly Lys Val Leu Thr
            20                  25                  30

Asp Glu Gln Tyr Gln Ala Val Arg Ala Glu Pro Thr Asn Pro Ser Lys
        35                  40                  45

Met Arg Lys Leu Phe Ser Phe Thr Pro Ala Trp Asn Trp Thr Cys Lys
    50                  55                  60

Asp Leu Leu Leu Gln Ala Leu
65                  70

<210> SEQ ID NO 59
<211> LENGTH: 107
<212> TYPE: PRT
<213> ORGANISM: Rattus rattus

<400> SEQUENCE: 59

Met Ala Ser Glu Gly Ala Ser Ser Glu Ile Ile Glu Lys Gln Arg Thr
 1               5                  10                  15

Lys Leu Leu Ser Val Leu Gln Gln Asp Pro Asp Ser Ile Leu Asp Thr
            20                  25                  30

Leu Thr Ser Arg Arg Leu Ile Ser Glu Glu Tyr Glu Thr Leu Glu
        35                  40                  45

Ala Ile Thr Asp Pro Leu Lys Lys Ser Arg Lys Leu Leu Ile Leu Ile
    50                  55                  60

Gln Lys Lys Gly Glu Asp Ser Cys Cys Cys Phe Leu Lys Cys Leu Ser
65                  70                  75                  80

Asn Ala Phe Pro Gln Ser Ala Ser Thr Leu Gly Leu Lys Gln Glu Val
                85                  90                  95

Pro Arg Gln Gly Thr Gly Glu Val Val Glu Val
            100                 105

<210> SEQ ID NO 60
<211> LENGTH: 777
<212> TYPE: DNA
<213> ORGANISM: Mus musculus
<220> FEATURE:
<221> NAME/KEY: CDS
<222> LOCATION: (89)...(667)

-continued

```
<400> SEQUENCE: 60
gtcgacccac gcgtccggca gcaggcaggc tgcagcaggc gagcagcagc aagagtaaaa        60
ggtgaccgcg gctgcccacc ccagagcc atg ggg cgg gca cga gat gcc atc          112
                                Met Gly Arg Ala Arg Asp Ala Ile
                                  1               5 ctg gac gct ctt gaa aac ttg tca ggg gat gaa ctc aaa aag ttc aag         160
Leu Asp Ala Leu Glu Asn Leu Ser Gly Asp Glu Leu Lys Lys Phe Lys
         10                  15                  20 atg aag ctg ctg aca gtg caa ctg cga gaa ggc tat ggg cgc atc cca         208
Met Lys Leu Leu Thr Val Gln Leu Arg Glu Gly Tyr Gly Arg Ile Pro
 25                  30                  35                  40 cgc ggg gcc ctg ctg cag atg gac gcc ata gat ctc act gac aaa ctt         256
Arg Gly Ala Leu Leu Gln Met Asp Ala Ile Asp Leu Thr Asp Lys Leu
                 45                  50                  55 gtc agc tac tat ctg gag tcg tat ggc ttg gag ctc aca atg act gtg         304
Val Ser Tyr Tyr Leu Glu Ser Tyr Gly Leu Glu Leu Thr Met Thr Val
             60                  65                  70 ctt aga gac atg ggc tta cag gag ctg gct gag cag ctg caa acg act         352
Leu Arg Asp Met Gly Leu Gln Glu Leu Ala Glu Gln Leu Gln Thr Thr
         75                  80                  85 aaa gaa gag tct gga gct gtg gca gct gca gcc agt gtc cct gct cag         400
Lys Glu Glu Ser Gly Ala Val Ala Ala Ala Ala Ser Val Pro Ala Gln
 90                  95                 100 agt aca gcc aga aca gga cac ttt gtg gac cag cac agg caa gca ctc         448
Ser Thr Ala Arg Thr Gly His Phe Val Asp Gln His Arg Gln Ala Leu
105                 110                 115                 120 att gcc agg gtc aca gaa gtg gac gga gtg ctg gat gct ttg cat ggc         496
Ile Ala Arg Val Thr Glu Val Asp Gly Val Leu Asp Ala Leu His Gly
                125                 130                 135 agt gtg ctg act gaa gga cag tac cag gca gtt cgt gca gag acc acc         544
Ser Val Leu Thr Glu Gly Gln Tyr Gln Ala Val Arg Ala Glu Thr Thr
            140                 145                 150 agc caa gac aag atg agg aag ctc ttc agc ttt gtt cca tcc tgg aac         592
Ser Gln Asp Lys Met Arg Lys Leu Phe Ser Phe Val Pro Ser Trp Asn
        155                 160                 165 ctg acc tgc aag gac tcc ctc ctc cag gcc ttg aag gaa ata cat ccc         640
Leu Thr Cys Lys Asp Ser Leu Leu Gln Ala Leu Lys Glu Ile His Pro
170                 175                 180 tac ttg gtg atg gac ctg gag cag agc tgaggtatct tttccagcta              687
Tyr Leu Val Met Asp Leu Glu Gln Ser
185                 190 cattatctag ctcctgactt tgtatacaca attttgaaa aaacaatttg tatttgtgtt        747
taaaaaaaaa aaaaaaaaaa gggcggccgc                                        777

<210> SEQ ID NO 61
<211> LENGTH: 193
<212> TYPE: PRT
<213> ORGANISM: Mus musculus

<400> SEQUENCE: 61

Met Gly Arg Ala Arg Asp Ala Ile Leu Asp Ala Leu Glu Asn Leu Ser
  1               5                  10                  15

Gly Asp Glu Leu Lys Lys Phe Lys Met Lys Leu Leu Thr Val Gln Leu
                 20                  25                  30

Arg Glu Gly Tyr Gly Arg Ile Pro Arg Gly Ala Leu Leu Gln Met Asp
             35                  40                  45

Ala Ile Asp Leu Thr Asp Lys Leu Val Ser Tyr Tyr Leu Glu Ser Tyr
```

```
            50                  55                  60
Gly Leu Glu Leu Thr Met Thr Val Leu Arg Asp Met Gly Leu Gln Glu
 65                  70                  75                  80

Leu Ala Glu Gln Leu Gln Thr Thr Lys Glu Glu Ser Gly Ala Val Ala
                 85                  90                  95

Ala Ala Ala Ser Val Pro Ala Gln Ser Thr Ala Arg Thr Gly His Phe
            100                 105                 110

Val Asp Gln His Arg Gln Ala Leu Ile Ala Arg Val Thr Glu Val Asp
            115                 120                 125

Gly Val Leu Asp Ala Leu His Gly Ser Val Leu Thr Glu Gly Gln Tyr
130                 135                 140

Gln Ala Val Arg Ala Glu Thr Thr Ser Gln Asp Lys Met Arg Lys Leu
145                 150                 155                 160

Phe Ser Phe Val Pro Ser Trp Asn Leu Thr Cys Lys Asp Ser Leu Leu
                165                 170                 175

Gln Ala Leu Lys Glu Ile His Pro Tyr Leu Val Met Asp Leu Glu Gln
            180                 185                 190

Ser

<210> SEQ ID NO 62
<211> LENGTH: 579
<212> TYPE: DNA
<213> ORGANISM: Mus musculus

<400> SEQUENCE: 62
atggggcggg cacgagatgc catcctggac gctcttgaaa acttgtcagg ggatgaactc      60
aaaaagttca agatgaagct gctgacagtg caactgcgag aaggctatgg gcgcatccca     120 cgcgggccc tgctgcagat ggacgccata gatctcactg acaaacttgt cagctactat     180
ctggagtcgt atggcttgga gctcacaatg actgtgctta gagacatggg cttacaggag     240
ctggctgagc agctgcaaac gactaaagaa gagtctggag ctgtggcagc tgcagccagt     300
gtccctgctc agagtacagc cagaacagga cactttgtgg accagcacag gcaagcactc     360
attgccaggg tcacagaagt ggacggagtg ctggatgctt tgcatggcag tgtgctgact     420
gaaggacagt accaggcagt tcgtgcagag accaccagcc aagacaagat gaggaagctc     480
ttcagctttg ttccatcctg gaacctgacc tgcaaggact ccctcctcca ggccttgaag     540
gaaatacatc cctacttggt gatggacctg gagcagagc                             579

<210> SEQ ID NO 63
<211> LENGTH: 32042
<212> TYPE: DNA
<213> ORGANISM: Homo sapiens

<400> SEQUENCE: 63
gatcatcgtt cactgcagcc ttgaactctt gtgctcatgt gatcctcctg ccttagcctc      60
cccaatagct gggactacag gtgcgccacc atgcctggct aattttttt attttttgtag     120 agatgggtgt ctcactatgt tgcacaggtt ggtctcaaac tactggcctt acttcaagct     180
atctacccat ctcagcctcc caaagcgctg ggattacagt catgagccaa cttgcctggc     240
cagataaagg tcttaagcat ggttccttcc tgctctaggt agagaaaccc acaaccagt      300 gggaggtggg gtgagctctt tctgtagctt ttgctttgct gatgatgtca ttgatctctt     360
caggggctgc gcagagtagc aggggccctg gaggcgcgg cctgaatcct gattgccctt      420
ctgctgagag gacacacgca gctgaagatg aatttgggaa agtagccgc ttgctacttt      480
```

-continued

| | |
|---|---|
| aactatggaa gagcagggcc acagtgagat ggaaataatc ccatcagagt ctcaccccca | 540 |
| cattcaatta ctgaaaagca atcgggaact tctggtcact cacatccgca atactcagtg | 600 |
| tctggtggac aacttgctga agaatgacta cttctcggcc gaagatgcgg agattgtgtg | 660 |
| tgcctgcccc acccagcctg acaaggtgcc ccggggacag ggacgggcat ggcattgtgt | 720 |
| ggacccoggg agctagaaga ggcctctccc tgctgatctg agtgaagagc gtgggagttt | 780 |
| agtccagcgg gcagggctgc attttggggt actaatagca cacaaatgcc tgggttagca | 840 |
| ggttgcacag tcaggtattt tacttctgtg tttgtgtctg gagcaaaccc tgacatctca | 900 |
| gttctcattg ctgtgtgtat tggttcccag acacttcatt tttagatccc ctttaaatta | 960 |
| ggagggaaaa agaacataag cataagagca tccccagcag cgatgttcat tcagtgcctc | 020 |
| tgaaggctgg agggctgctt gttgctgggt gagactcgga ggggaaccga ctcagggtca | 080 |
| ggaatgatga catcccacgg tgggtccaca gtgaagaatc ttccccgctc cactgtggga | 140 |
| cgccttaaca gcccttactt ccacttacgc tttgcgttat ctcctgaaaa ataaaatgga | 200 |
| gaccacaaat tccttcttgg ttagaggaat gacacaactc atttatgaca tgaccccgct | 260 |
| gggactcaga agagaccagg acggtttctg ggggaagcag tagcacactc gtgtgctttg | 320 |
| ttctcttctc ttgatttgtt ttcccacatt tttaacaaga aaaaaagccg tttttaatat | 380 |
| atggcctatc gccctcctac tgtgtggccc aggtgcctac ctcattatgc ccaagggtg | 440 |
| gttctcacct ctccactctc attcctgcac agcagttgtg tcaggttaag agggacaagg | 500 |
| agaaggctgg gcaccgtggc tcacgcctgt aatcccagca ctttgggagg ccgaggcagg | 560 |
| cagatcacct aaggtcagga gtttgagacc agcctggcca acatgggaa aacccgtctc | 620 |
| taataaaaac acaaaaatta gtcgggcatg gtggtgggtg cctgtaatcc cagccacttg | 680 |
| ggaggctgag gaaagagaat tccttgaacc tgggaggtgg aggttgcagt gagccaagat | 740 |
| tgtgccattg cactccagcc ctccagcctg ggtgacagac aagactctg tctcaaaaaa | 800 |
| gaaaaaaaaa aaaagaggt agagaagtcc atggctattt gtctgtcctt tttatttta | 860 |
| ggctcatgga agcctcctgg tttcttagag ctgagtggtt ttatttcttg ctcaggaggt | 920 |
| catttcacag attttcgggc tccaatatgt tgactgtcac agcagctggg gggatggcat | 980 |
| agctaccggc tgtactaaga actcagagcc ctgccctgag cctgcctgag ggtccttatg | 040 |
| gtaggaggat gcccctcatg ccagcccgtg ccctcatgct tgtgtcacct ccaggtccgc | 100 |
| aaaattctgg acctggtaca gagcaagggc gaggaggtgt ccgagttctt cctctacttg | 160 |
| ctccagcaac tcgcagatgc ctacgtggac ctcaggcctt ggctgctgga gatcggcttc | 220 |
| tccccttccc tgctcactca gagcaaagtc gtggtcaaca ctgacccagg taggagtcag | 280 |
| ccccagcaag accgcaggca ccagtgcaag cagggccctg gggggtttgg taatggctgg | 340 |
| gccagccctg agtgccacct caggaagcag gcccaggtgc tattttgatt ttagaaagga | 400 |
| acagctgaat cctgtctccc aagtgcagcc caggtggctg cgattgaact gcccacacct | 460 |
| cgatggtctg gtttatagag gggccttttgg aagtatggga atggcctgtg ttctgacccc | 520 |
| ttgctttctt cctattctga catatgtaga cattttaatg gttgcacaaa ttcaaggttg | 580 |
| tatttttttt tcttttaaaa aaatctttag ctggacatgg tagcacacac ctgtagttcc | 640 |
| agctactcag gaggctgagg caagaggact gcttgagccc cagagtctaa ggctgcagcg | 700 |
| agctatgatt gtgccctac actccagcct gggtgacaga gtgagaccct gtctctaaaa | 760 |
| aaggaaagaa aaaaattaaa aagccttgcc aggtttgatt ctaggcaaag tattctgtca | 820 |

-continued

```
ccgttgagtg ccagtccta  tttccaaact  aatggaagac  cccatcagtt  aactgattag   880
ttcaataagt atttttgct  gtatccacca  catgccaaga  ccctacactg  tgctggatgt   940
cagggagaca gtggtgagca gacacagaca  gggttcctgc  cctcagggag  cttcaagtca  3000
gctggaagag accaccagtc agcaatctca  aaaatgtgtc  aggacagcgg  cagtccaagg  3060
catgtgagaa catatcatta gggccaggat  ctgctctggg  gcaggagtct  tctttccctg  3120
cttttgaact ctccactttg agacagctgt  tggtaacata  ccagcaccaa  ggacctaagt  3180
cctgccttt  aaagaatcca atatgttgtt  ggaaacagaa  gcacaagaca  ggtgtgtgct  3240
taggggaaac aaggccagcc ggcagagtgt  cagtgctagg  ctccagcttc  cacagccct   3300
gcaggtgcct gccagccact gctagcttct  gactctgtct  gctccttcct  gtctcccctt  3360
gtttccttcc cccatgaaaa aaaaagaaag  tattcccatg  aggaatcatt  ctttcgaaag  3420
acttctctgt tggttccgtt agccagctac  tttactagct  tttacagtgt  aattcactct  3480
acaagcagtc tcacacaaaa gactacatat  tgtatgattc  tgtttatatg  aaatgtccag  3540
aaaaggtaaa tctatagaca aagcaaatca  gtagttgcct  acggcccagg  gattggctac  3600
aaataggctc cagaaaactc tgggaagatg  gtagagatgt  tctagacctg  gactgtggtg  3660
aggtttgcac aactttgtaa acttactaaa  aattactgac  aaatatataa  cactccctaa  3720
cactttggga ggccgaggtg ggcagatcgc  ttgaacccag  gaatttgaga  ccagcctggg  3780
caacatggcg agacccgtc  tctacaaaaa  acacaaaaa   ttagttgggc  ttggtggcat  3840
atgcctgtgt cccagctact tgggaggctg  aggtgggagg  attgcttgag  cctgggagtt  3900
tgagactgca tgattgggtc actgcaccct  agcctgagtg  acagagcagg  accctatctc  3960
taacaacaaa aaagcagtgt tggtggagga  gggccagcgt  ggccatctgg  cctggccctc  4020
gagtgcgagg ggcttcagtg tttagctgca  gttcagtgat  gacactgtgc  ggaggaataa  4080
gggtggcctg tctcagacac tgatcccagc  tgaagtttgt  caccttcttt  ctggcaaatc  4140
tgaggtcaag cagagagatc aaagcctggg  gccctcaggg  tcaggaatgc  tggctctgtg  4200
acgctcccca ggtcctgcat ctgaggagtg  gctgcgctgg  cctcagggcc  caggttgtga  4260
attttgtta  tgcactcgcc tctcctcttt  gagacctccc  tgtttgatgc  tgtttctgcc  4320
tctctcctca ccctgctgct gtgccctgcc  acccctccc   tccagtgagc  aggtatacc   4380
agcagctgcg acaccatctg ggccgtgact  ccaagttcgt  gctgtgctat  gcccagaagg  4440
aggagctgct gctggaggag atctacatgg  acaccatcat  ggagctggtt  ggcttcagca  4500
atgagagcct gggcagcctg aacagcctgg  cctgcctcct  ggaccacacc  accggcatcc  4560
tcaatgagca gggtgagacc atcttcatcc  tgggtgatgc  tggggtgggc  aagtccatgc  4620
tgctacagcg gctgcagagc ctctgggcca  cgggccggct  agacgcaggg  gtcaaattct  4680
tcttccactt tcgctgccgc atgttcagct  gcttcaagga  aagtgacagg  ctgtgtctgc  4740
aggacctgct cttcaagcac tactgctacc  agagcgggca  cccgaggag   gtgtttgcct  4800
tcctgctgcg cttccccac  gtggccctct  tcaccttcga  tggcctggac  gagctgcact  4860
cggacttgga cctgagccgc gtgcctgaca  gctcctgccc  ctgggagcct  gcccacccc   4920
tggtcttgct ggccaaccctg ctcagtggga agctgctcaa  ggggctagc   aagctgctca  4980
cagcccgcac aggcatcgag gtcccgcgcc  agttcctgcg  gaagaaggtg  cttctccggg  5040
gcttctcccc cagccaccctg cgcgcctatg  ccaggaggat  gttccccgag  cgggccctgc  5100
aggaccgcct gctgagccag ctggaggcca  accccaacct  ctgcagcctg  tgctctgtgc  5160
ccctcttctg ctggatcatc ttccggtgct  tccagcactt  ccgtgctgcc  tttgaaggct  5220
```

```
caccacagct gcccgactgc acgatgaccc tgacagatgt cttcctcctg gtcactgagg    5280
tccatctgaa caggatgcag cccagcagcc tggtgcagcg aacacacgc agcccagtgg     5340 agaccctcca cgccggccgg gacactctgt gctcgctggg gcaggtggcc caccggggca    5400
tggagaagag cctctttgtc ttcacccagg aggaggtgca ggcctccggg ctgcaggaga    5460
gagacatgca gctgggcttc ctgcgggctt gccggagct gggccccggg ggtgaccagc     5520
agtcctatga gttttccac ctcaccctcc aggccttctt tacagccttc ttcctcgtgc     5580
tggacgacag ggtgggcact caggagctgc tcaggttctt ccaggagtgg atgccccctg    5640
cgggggcagc gaccacgtcc tgctatcctc ccttcctccc gttccagtgc ctgcagggca    5700
gtggtccggc gcgggaagac ctcttcaaga acaaggatca cttccagttc accaacctct    5760
tcctgtgcgg gctgttgtcc aaagccaaac agaaactcct tcggcatctg gtgcccgcgg    5820
cagccctgag gagaaagcgc aaggccctgt gggcacacct gttttccagc ctgcggggct    5880
acctgaagag cctgccccgc gttcaggtcg aaagcttcaa ccaggtgcag gccatgccca    5940
cgttcatctg gatgctgcgc tgcatctacg agacacagag ccagaaggtg gggcagctgg    6000
cggccagggg catctgcgcc aactacctca gctgaccta ctgcaacgcc tgctcggccg     6060
actgcagcgc cctctccttc gtcctgcatc acttccccaa gcggctggcc ctagacctag    6120
acaacaacaa tctcaacgac tacggcgtgc gggagctgca gccctgcttc agccgcctca    6180
ctgttctcag gtgaggctgc caggcaaggg gagcaacagg tgggccgggc gggccaggct    6240
cggagggcat cgggaatggc atcatggacc aggatccccc aggactcatg accatggccc    6300
ttggaatgtc cagaccttt ctttcttagc agggcagagg tcaaggtgca aagcttcgag     6360
gcaggtggac ctggatcagc cacagctggg tgcccttgaa caaagtgctt aactctcaga    6420
gcctccacgc cctcatctgg aaaaagaaga tgctcataat cctatcaatt atggccacag    6480
ggaccaatgt tagttgagaa tgggtgaagt gcattacaaa tattacctaa tggaatgctc    6540
tttacaaccc tgtaacttag gtactgttat tgtctctatt ttggcagata aggaagtaga    6600
ggcacagaga agttaatagc ttgctttagg tcacacagct cagacatagc agtgccagaa    6660
tgcataaaga accttccttt taagattaat gtaaggctcc gagatagccc tcaaaaagtt    6720
tctggaatat gggagctttt attactgcag agaaagcaga ccttgtgcca gttggcactg    6780
gtgactttct gtgatcaacg ctagcagccc ttcacactgc tagagacctc agttaaaatg    6840
ctgactcgtg gttgttttcc tgttccatag tttacgggaa acagagccca gtctgttttc    6900
ttctattagc atttcctatg taaaataaac cttgtaaatc tctacagggg gttaaatttg    6960
ccattacttg actcatgcat ttctaaaaag cagtagggat ttggaactga ctcccagtgc    7020
ctgtcacacc agtgtcagag tgtaaataat tgcatgggga catgggtgc aggggtcga     7080 aggctgccct agcctgggaa ttggaaaacc tggagtctgt tctctgtact ctcagccagt    7140
gactctccct ctgtagcccc aggcagtctc acactcagtg ccaccctctg tccatctttt    7200
ttttttctcc cccaaatgga gtcccgctct gttgcccagg ctggagtgca gtggcgtgat    7260
ctcagctcac tgcaacctcc gcctcctggg ttcaagcgat tctcttgccc cagcctcctg    7320
agtagctggg attacaggca cacgccacca tgtccggcta agtttttgt attttttagta    7380 ggacggggtt tccccatgtt ggccaggctg gtcttgaaat cctgacctca ggtgatccgc    7440
ccgcctcggc cttccaaaat gttggggtta caggcatgag ccgccgcacc cgacccctct    7500
gtccatcttt tcaatgggaa actccacacc agtgtggtgg ccctgccctt cctgctgtcc    7560
```

```
ccaggtgaag ctttccttca caccagtgca agaaaaaaca gcttgtagga aagcagagga    7620
tatgggtaac cacgggaagc acactcagtt ctctggctgc atcagttagg attagtttta    7680
gctgagagcg aaaaccccaa atgttggtga gttacaagct tatttctctc atgtaaaagt    7740
ctagaggtag gtagttcagg actggtatgg agtctccatg accctccgga gcccaggctc    7800
tcttctgcct tcctgttctg ccatcctcac tacccggctt tcccatcttg gcccaagagg    7860
gctgctcaaa ctccagccat ctagtcgaca ctctagctat cagtaagaag gaagggcaaa    7920
gattgagagc atgcctcaat cttttaagaa cacttcttgg ctattactaa ttatattgct    7980
gcttagattt cagaacttaa tggtatgggc agaatttaat gagatgggcc cagctaaaag    8040
atgggggaat ctattgctaa gaaagtatag atattgggaa tgtctagcag cctgtgctgt    8100
cttgggctgg ccatgccatg tacatacaca ctatttccca gcaccaagct ggggactctg    8160
agggaaaggg tccagagtgt ctgacttgat cattttgatg tggcctaaaa atcaagcttt    8220
taattgttca gccttttact tgttatcaag gtcagcttgt gggtctaatt gggcccaagg    8280
cttgtgtttc taagtaaagt tttattggaa cgcagccata cccatttatt tacttactgg    8340
ctgcttcaca ctacacagtt gagtagctgt gacagagacc acatggccca cagagcctaa    8400
aatatttgct gtctgacact ttacagaatg acatgagcag tctcctttga cagtgggact    8460
cacagccttt tccagtgaca aatcaggggt agcccatgtg tttctggatg ggggaagct    8520 gttggcattt tgggtataac agttcttgtg agacctgtcc agcattttgc aggacaccta    8580
acatcattgg ccctgcctgc aagatgacag ggcactccct cctccagtca caaccactaa    8640
aagcagcccc tgacatttcc aaacccatgc cctccaccat acgagaacca ggtacagggt    8700
ctggctgaca cataggtcac acgcaaaggg tggatgtcag aggtggctgg cctcacacgt    8760
cctccctgtg tccttcacgg tcgtgtgagg agccaggggc tgtgctgcag cctcgctcat    8820
gggctggtgc aggatgggtc tggcggcccc acgttggcca ggctttgtaa ggggctattt    8880
ggctgattgc tgtggccatt ctccagggc gtctatacct gagaaaactc cagggcctga    8940
aggcttctgg atctttgtaa gattaatggt ccttcataat gagtgcctgc cctgactcgt    9000
aatttttttg ctgtttttatt tcagactcag cgtaaaccag atcactgacg gtggggtaaa    9060
ggtgctaagc gaagagctga ccaaatacaa aattgtgacc tatttgggt atgtctttct    9120 ccagaacact gggccaacta cctagtaata atacagagct gcagggaatt cacattccca    9180
taggtccctg gatgatcggc acggatggcc cagggctggg aagagcgctg gcccaggagt    9240
tgagagtcct gggttctctt tgtggctcgg ccagtcatga agtcttgctg agcctcagcc    9300
tcctcacctg taaaactggg atcccagtat aggcaagtag gcttacaact ggttattggg    9360
ggatgcaacg agaatataag gggatatatt taataaatgc tagaatcctg tttacatatt    9420
agtctggact attttgggtc cataatccct catccagagc ctttggggca agacccgaat    9480
ggggattctg agtgcatgct atggcatgac gtggccgcag gggtctaagg cagtgcccca    9540
ttttcaaaca ctttcatatt tctcccgcag aatgtatgaa acagtcaaac caagtgtggt    9600
aagaaagact ataagtagct ccacatcagt tgccaaaaga attgtgagaa actttgggca    9660
ttcagagcct ttgaggtttt ggagtctgag agaagggatt gcgggccagc cccacacaac    9720
tggtggctct gcaagctgga gcagttgttc agtttcttgg ggcctcagtg gccttcgatg    9780
ttaatgagga catggacgca aacgaccccg ggccacactc ggctccaggg ctctgtgtgg    9840
ctgtggaacc ctggaagcct gagcttagct gcctttcaac ttccatctgc tgtactattg    9900
aattggcatt gagcggtgag atggctgaaa ggtagacatc gagaagtttt aatattcaga    9960
```

```
atctttctt ctcaagacgc tgaatgtaat cttagttgta aatacccatc acctgccagt    10020
caccgagcac tcatgcacca gggctttgcg ttatgtccta agatcctcat aaccaccctg    10080 caagggact  atcatcatta cctctgtatt acagatggag aaactgaggc acagagaggt    10140
aacgtgactt gtctcaggcc ataaagctgg ggaaagtagt ggagctggtt ttgaacctga    10200
gctgtgagac ctcagagccc taaactctgg tgcctgtgtg ttcccctttc aacccagact    10260
ttggaaatca gtagacacca tatgcttcaa aaaacagggg ctattaaaat gacatcagga    10320
gccagaaagt ctcatggctg tgctttctct tgaagtttat acaacaacca gatcaccgat    10380
gtcggagcca ggtacgtcac caaaatcctg gatgaatgca aaggcctcac gcatcttaag    10440
taagtggggt aggcaccagg ttccttagta tattctcttg atcaccccct tctgttgttc    10500
aaagattaaa tgtcacagta aagagctttc atcctaaagc cttccacttg tcccagggcc    10560
atgttggtca agtaaagata cctctgtgtg atctgtgagg cttggattct ggaagggcct    10620
cccgttattg gtaggggaa  aggttggcat tttgatttca ttaactacta ggccgaagaa    10680
aggactaact ctcacccttt ctggtggtct ttttgcccca agggagtttc ctgtcgggtt    10740
gcaaggaaga gcttgggccc ttgccctgct gtaggtgtgc cctgcgcagg gggtgacagt    10800
gcgccaggct tggagcctct ggtcctgccc tgacagtggc cacataccct gacccttggc    10860
agtcaaagtg ggacctccca ggtctcccga gggaagtcag tgatgctgct gaggtcaatt    10920
agaggacccc agggagggct caggtccctg agcttctgca gagactgtgg accatctcct    10980
ggagaggaac cctgactgac tgtcctcagg gcttcagttc cctccctgac aggaggccca    11040
ggccatggct cttgtggatc ccagaagaaa gtgtacggtt cccaagatgg ggctggaagg    11100
ggctctgtgc tggggaggag ggtgacccac attggagccc ctgcatagct ggaggctgac    11160
tgtgtgtgac tctctctgca gactgggaaa aaacaaaata acaagtgaag gagggaagta    11220
tctcgccctg gctgtgaaga acagcaaatc aatctctgag gttgggtgag tagaaggggga    11280 tggatgtatg tggtacaacc tgctgtgtgt gtgggggggcg ggccttgctg ttcttttcat    11340
acatcagtac accagaagga ccactggggc tcgctgtcgg ggagagatag tggagagctt    11400
tcaccatgct gcgaaactga aaccgtgccc attaagcaat aactccccgg tcccctccc     11460 ccctgcctct tgcagccacc ctgctactta ctctctctat ggttttgact actctacctc    11520
atgtaagtgg aatcatacag tatttgcctt ttggggatgg ctgatttcac tagcatcatg    11580
tcctcaagat tcgtccacat ggaagcatgg gacaggattt ccttttttt  tttttttttt    11640 tttttttttg acagagtctc gctctgttgc ccaggctgga gtgcagtggc atgatctcgg    11700
ctcactgcaa cctctgcctt ctgggttcaa gcgattctct cgcctcagcc acacgagtag    11760
ctgggattat aggcacccgc caccaatccc agctaatttt tgtattttta gtagaggcgg    11820
ggtttcacca tgttggccag gctggtctca aactcctgac ctcaaatgat ccacccacct    11880
cggtctccca aagtgtcagg attataggcg tgagccaccg tgccccgcca ggatttcctt    11940
cttttttaag gctgagtaat actccattgc atggctatgc cacattttgt ttactcattc    12000
atccaagaac agacactggc ttgcttctat gctttggctg ttgtgaataa tgctgctgtg    12060
cacatgggca tacaaatgtc tcttcaagga ctgccttcaa ttctttttt  tttttttttt    12120 tttttttaga ttctttttttt tttttattata ctctaagttt tagggtacat gtgcacattg    12180
tgcaggttag ttacatatgt atacatgtgc catgctggtg cgctgcaccc actaatgtgt    12240
catctagcat taggtatatc tcccaatgct atccctcccc cctccccga  ccccaccaca    12300
```

```
gtccccagag tgtgatattc cccttcctgt gtccatgtga tctcattgtt caattcccac    12360
ctatgagtga gaatatgcgg tgtttggttt tttgttcttg cgatagttta ctgagaatga    12420
tggtttccaa tttcatccat gtccctacaa aggatatgaa ctcatcattt tttatggctg    12480
catagtattc catggtgtat atgtgccaca ttttcttaat ccagtctatc attgttggac    12540
atttggtttg gttccaagtc tttgctattg tgaatagtgc cacaataaac atacgtgtgc    12600
atgtgtcttt atagcagcat gatttatact catttgggta tatacccagt aatgggatgg    12660
ctgggtcaaa tggtatttct agttctagat ccctgaggaa tcgccacact gacttccaca    12720
atggttgaac tagtttacag tcccaccaac agtgtaaaag tgttcctatt tctccgcatc    12780
ctctccagca cctgctgttt cctgactttt taatgattgc cattctaact ggtgtgagat    12840
gatatctcat agtggttttg atttgcattt ctctgatggc cagtgatgat gagcatttct    12900
tcatgtgttt tttggctgca taaatgtctt cttttgagaa gtgtctgttc atgtccttcg    12960
cccacttttt gatggggttg tttgtttttt tcttgtaaat ttgtttgagt tcattgtaga    13020
ttctggatat tagcccttg tcagatgagt aggttgcgaa aatttttctcc catgttgtag    13080
gttgcctgtt cactctgatg gtagtttctt ttgctgtgca gaagctcttt agtttaatta    13140
gatcccattt gtcaattttg tcttttgttg ccattgcttt tggtgttttg gacatgaagt    13200
ccttgcccac gccatgtcc tgaatggtaa tgcctaggtt ttcttctagg ttttttatgg     13260
ttttaggttt aacgtttaaa tctttaatcc atcttgaatt gattttgta taaggtgtaa     13320
ggaagggatc cagtttcagc tttctacata tggctagcca gttttcccag caccatttat    13380
taaataggga atcctttccc cattgcttgt ttttctcagg tttgtcaaag atcagatagt    13440
tgtagatatg cggcattatt tctgagggct ctgttctgtt ccattgatct atatctctgt    13500
tttggtacca gtaccatgct gttttggtta ctgtagcctt gtagtatagt ttgaagtcag    13560
gtagtgtgat gcctccagct ttgttctttt ggcttaggat tgacttggcg atgcgggctc    13620
tttttttggtt ccatatgaac tttaaagtag tttttttccaa ttctgtgaag aaagtcattg   13680
gtagcttgat ggggatggca ttgaatctgt aaattacctt gggcagtatg gccattttca    13740
cgatattgat tcttcctacc catgagcatg gaatgttctt ccatttgttt gtgtcctctt    13800
ttatttcctt gagcagtggt ttgtagttct ccttgaagag gtccttcaca tcccttgtaa    13860
gttggattcc taggtatttt attctctttg aagcaattgt gaatgggagt tcacccatga    13920
tttggctctc tgtttgtctg ttgttggtgt ataagaatgc ttgtgatttt tgtacattga    13980
ttttgtatcc tgagactttg ctgaagttgc ttatcagctt aaggagattt tgggctgaga    14040
cgatggggtt ttctagataa acaatcatgt cgtctgcaaa cagggacaat ttgacttcct    14100
cttttcctaa ttgaataccc tttatttcct tctcctgcct gattgccctg ccagaacttc    14160
ccaacactat gttgaatagg agcggtgaga gagggcatcc ctgtcttgtg ccagttttca    14220
aagggaatgc ttccagtttt tgcccattca gtatgatatt ggctgtgggt ttgtcataga    14280
tagctcttat tattttgaaa tacgtcccat caatacctaa tttattgaga gttttttagca   14340
tgaagggttg ttgaattttg tcaaaggctt tttctgcatc tattgagata atcatgtggt    14400
ttttgtcttt ggctctgttt atatgctgga ttacatttat tgatttgcgt atattgaacc    14460
agccttgcat cccagggatg aagcccactt gatcatggtg gataagcttt tgatgtgct     14520
gctggattcg gtttgccagt attttattga ggatttttgc atcaatgttc atcaaggata    14580
ttggtctaaa attctctttt ttggttgtgt ctctgcccgg ctttggtatc agaatgatgc    14640
tggcctcata aaatgagtta gggaggattc cctctttttc tattgattgg aatagtttca    14700
```

```
gaaggaatgg taccagttcc tccttgtacc tctggtagaa ttcggctgtg aatccatctg    14760
gtcctggact cttttggtt ggtaaactat tgattattgc cacaatttca gagcctgtta    14820
ttggtctatt cagagattca acttcttcct ggtttagtct tgggagagtg tatgtgtcga    14880
ggaatgtatc catttcttct agattttcta gtttatttgc gtagaggtgt ttgtagtatt    14940
ctctgatggt agtttgtatt tctgtgggat cggtggtgat atcccctta tcattttta    15000 ttgtgtctat ttgattcttc tctctttttt tctttattag tcttgctagc ggtctatcaa    15060
ttttgttgat cctttcgaaa aaccagctcc tggattcatt gattttttga agggttttt    15120 gtgtctctat ttccttcagt tctgctctga ttttagttat ttcttgcctt ctgctagctt    15180
ttgaatgtgt ttgctcttgc ttttctagtt cttttaattg tgatgttagg gtgtcaattt    15240
tggatctttc ctgctttctc ttgtaggcat ttagtgctat aaatttccct ctacacactg    15300
ctttgaatgc gtcccagaga ttctggtatg tggtgtcttt gttctcgttg gtttcaaaga    15360 acatcttat ttctgccttc atttcgttat gtacccagta gtcattcagg agcaggttgt    15420
tcagttccca tgtagttgag cggctttgag tgagattctt aatcctgagt tctagtttga    15480
ttgcactgtg gtctgagaga tagtttgtta taatttctgt tcttttacat ttgctgagga    15540
gagctttact tccaactatg tggtcaattt tggaataggt gtggtgtggt gctgaaaaaa    15600
atgtatattc tgttgatttg gggtggagag ttctgtagat gtctattagg tctgcttggt    15660
gcagagctga gttcaattcc tgggtatcct tgttgacttt ctgtctcatt gatctgtcta    15720
atgttgacag tggggtgtta aagtctccca ttattaatgt gtgggagtct aagtctcttt    15780
gtaggtcact gaggacttgc tttatgaatc tgggtgctcc tgtattgggt gcataaatat    15840
ttaggatagt tagctcctct tgttgaattg atccctttac cattatgtaa tggccttctt    15900
tgtctctttt gatctttgtt ggtttaaagt ctgttttatc agagactagg attgcaaccc    15960
ctgccttttt ttgttttcca ttggcttggt agatcttcct ccatccttt attttgagcc    16020 tatgtgtgtc tctgcacgtg agatgggttt cctgaataca gcacactgat gggtcttgac    16080 tcttatcca acttgccagt ctgtgtcttt taattgcaga atttagtcca tttatattta    16140
aagttaatat tgttatgtgt gaatttgatc ctgtcattat gatgttagct ggcgattttg    16200
ctcattagtt gatgcagttt cttcctagtc tcgatggtct ttacattttg gcatgatttt    16260
gcagcggctg gtaccggttg ttcctttcca tgtttaccgc ttccttcagg agctctttta    16320
gggcaggcct ggtggtgaca aaatctctca gcatttgctt gtctataaag tatttttatt    16380
ctccttcact tatgaagctt agtttggctg gatatgaaat tctgggttga aaattctttt    16440
ctttaagaat gttgaatatt ggcccccact ctcttctggc ttgtagggtt ctgccgaga    16500 gatccgctgt tagtctgatg ggctttcctt tgagggtaac ccgaactttc tctctggctg    16560
cccttaacat tttttccttc atttcaactt tggtgaatct gacaattatg tgtcttggag    16620
ttgctcttct cgaggagtat ctttgtggcg ttctctgtat ttcctgaatc tgaacgttgg    16680
cctgccttgc tagattgggg aagttctcct ggataatatc ctgcagagtg ttttccaact    16740
tggttccatt ctccacatca ctttcaggta caccaatcag acgtagattt ggtcttttca    16800
catagtccca tatttcttgg aggctttgct catttctttt tattcttttt tctctaaact    16860
tcccttctcg cttcatttca ttcatttcat cttccattgc tgatacccctt tcttccagtt    16920 gatcgcatcg gctcctgagg cttctgcatt cttcacgtag ttctcgagcc ttggttttca    16980
gctccatcag ctcctttaag cacttctctg tattggttat tctagtttata cattcttcta    17040
```

```
aatttttttc aaagttttca acttctttgc ctttggtttg aatgtcctcc cgtagctcag    17100
agtaatttga tcgtctgaag ccttcttctc tcagctcgtc aaaatcattc tccatccagc    17160
tttgttctgt tgctggtgag gaactgcgtt cctttggagg aggagaggcg ctctgcgttt    17220 tagagttttcc agtttttctg ttctgttttt tccccatctt tgtggtttta tctacttttg    17280
gtctttgatg atggtgatgt acagatgggt tttcagtgta gatgtccttt ctggttgtta    17340
gttttccttc taacagacag gaccctcagc tgcaggtctg ttggaatacc ctgccgtgtg    17400
aggtgtcagt gtgcctctgc tggggggtgc ctcccagtta ggctgctcgg gggtcagggg    17460
tcagggaccc acttgaggag gcagtctgcc cgttctcaga tctccagctg cgtgctggga    17520
gaaccactgc tctcttcaaa gctgtcagac agggacactt aagtctgcag aggttactgc    17580 tgtcttttg tttgtctgtg ccctgcccc agaggtggag cctacagagg caggcaggcc      17640
tccttgagct gtggtgggct ccacccagtt cgagcttccc ggctgctttg tttacctaag    17700
caagcctggg ctatggcggg cgcccctccc ccagcctcgt tgccgccttg cagtttgatc    17760
tcagactgct gtgctagcaa tcagcgagat tccgtgggcg taggaccctc tgagccaggt    17820
gtgggatata gtctcgtggt gcgccgtttc ttaagccggt ctgaaaagcg caatattcgg    17880
gtgggagtga cccgattttc caggtgcgtc cgtcacccct ttctttgact cggaaaggga    17940
actccctgat cccttgcgct tcccaggtga ggcaatgcct cgccctgctt cggctcgcgc    18000
acggtgcgcg cacacactgg cctgcgccca ctgtctggcg ctccctagtg agatgaaccc    18060
ggtacctcag atggaaatgc agaaatcacc cgtcttctgc gtcgctcacg ctgggagctg    18120
tagaccggag ctgttcctat tcggccatct tggctcctcc ctccaattct tttgggtata    18180
tatccagcag tgggattgct ggatcacatg gtaattttta attttttgaa gaatcatcat    18240
actgttttcc acggcagcag caccattta tgttcccacc aacagttcat tctagtttct     18300
ccacatcctt gccaacactt gctattttct cttttgaca gtaccatcc taatgagtgt     18360 gaggtcctgt ctcattgtgg ttttgattct tgaggctttt taaagctttt tgtttcatta    18420 taattttat tggattacaa aaggaacaca ggtaatttta tttggaaact atgaaaaata    18480
ataaaaatta tcttctcaga aaatgattct tgttaacatt taagctcagt taagctctct    18540
cactttctct cccttctctc tctttgtaca acttttaaaa aatatagtag gggtgagact    18600
atatgtatct atactatagt aggggtgaga ctatatgtat ccttccttt tcacttaatc     18660 tcatgccttg agtagctttc cactttatta aaaatgtgat gccattcaat tgtatagtaa    18720
atacatatat gtaagcaaaa cactgaaaac tcttattctg ggttccagca agccatacct    18780
ggaatggtgt aagcaggtag tttgcttggt gtgaacgtgt tgttgaggca gctgccattg    18840
tgttgtgagt gggccacacg aacttgttct gttgtgtgta gacagtgtgt gctgatccta    18900
ttaggaacag ccaacgcttt gtgtgagcca cacacggttc taagtgcttt gcttctgtta    18960
actcagtgaa tcctcacaac tccatgacgg aatgctctaa ttatccccat tttatagatg    19020
gggcaactga ggtccaagag actacataat ttcccgaagt tcacacaggt agcagatggc    19080
agagccgggt caggagtcca ccatcttacc acgcagactt ttttagccag agactctccg    19140
gatctgctgt aggggacaga atacagcttt atcgccgcac ctgtccacca agatggccgt    19200
agccacagag cttggttggg taacgtcctc tttatgtgac aggaacgttg ctgatgggt     19260 ttctgaaggt acttcctgct ctttgtctcc tggaagactg tgtcttcagg aatgtctctg    19320
accctgccca gagttgaacg gatgctggga acccagcacc tgcacacggc cttccctcca    19380
ggactctgcg cacctctgtg ctccacagga gacatgcagg tgctttctct catgagctca    19440
```

```
ggctcctggg ctgacagctc tccgaagctc gtggtgaggc tcggtctcta actgtgccac  19500
ttgccgatgg cctctgttca caaggcttcc cctgctcttc gatcttgcat caccccttga  19560
atttgaaatc cagagcagcc cactcagaga ccagtgtgag gaattagtgt ccaggccaca  19620
gatccaggga ctgggcacaa acatctgcct gttgagtagg aactgagctg tggccattgg  19680
caaaaaagga ggggtgagca tggctgtttc ttggggagct aacattcact atcttgtctc  19740
ctccctcagg atgtggggca atcaagttgg ggatgaagga gcaaaagcct tcgcagaggc  19800
tctgcggaac caccccagct tgaccaccct gaggtaactg tggccctgct gtctccaggg  19860
gccaacctgg tccctcccag ctgctctagg tttgctgggg aagggtgatt cgtgctccta  19920
atagaagagg aatttgcatg tgtgattttc cttactcttg tcaaacctttctttgatgca  19980 taagaggcca tctagtaaag cacattcttc tcttttttta actttaagtt ctgggataca  20040
tgtagaagat gtgcaggttt gttacatagg caaatgcatg ccatggtgat ttgctgcacc  20100
tatcaacctg tcatctaggt tttaagccct gcatgcatta ggtatttgtc ctaatgcttg  20160 ccctccccttgcccccacc cccaacaggc cctggtgtgt gttgttcccc tccatgtgtc  20220
catgtgttct cattgttcaa ctcccactta cgagtgagaa catgcagtgt ttggttttt  20280 gttcctgtgt tagtttgctg agaatgatgg tttccagctt catccatgtg ccagcaaagg  20340
acatgatctc attttttttt atggttgcat agtattccat agtgtgtatg tgccacattt  20400
tctttatcca gtctatcact gatgggcatt tgggttggtt ccaagtcttt gctattgtaa  20460
atagtgctac aataaacata catgtgcttg tgtctttata gcagaatgat ttataatcct  20520
ttgggtaaat acccagtaat gggattgctg ggtcaaatgg tatttctggt tctagatccc  20580
tgaggaatca ccttaagtgt ttattcagct cagtgaattc tgcatgtgtc ccacaccagc  20640
caaccaccac ccccatcaag acagaggaca tttccagccc ctcagccatc cctgcatgtc  20700
ccttgctggt agagggaggg tttcctaagt gcagatgaaa cttaataaga tgctggccag  20760
cagattcctg cccttccttgtcctcagga tgatgctgga aaagagggac tcttcctctc  20820
tataaatggg gatgcaccta cccagccccc gcttaggctg ctggccaaat cttgggacct  20880
tggtatgtcc acggctctgc tgctgttctt cctaccactg aaaagagtc caagaaggtg  20940 gggacagtag cagaagagac tttgccaggt cttgcagatg gggtaccttg atggggccag  21000
cctttagaag acagcttgc caggcctcgc cagcctcctg cccatgtgca gaaacctgag  21060
gtgccgaccc cagcccactg ttgtgtgagc aggctgtgct gatgacccat ttcccgtcca  21120
gcctgccctt gtgctctgtg tgtgggctct ggggcagcag cgcctgggca ctactgctgc  21180 agctgaaacac ttctgcatcc tgccccgagt gagcctgggc tggggccaca gccaggcaga  21240
ggcttcccag ctgttctgat gttgaagcta agattgaatg tagatgtgtc tttaataatt  21300
caccccaagt gtgttccttc ctagtcttgc gtccaacggc atctccacag aaggaggaaa  21360
gagccttgcg agggccctgc agcagaacac gtctctagaa atactgtggt aatagctcga  21420
gtcatttcat ttgtttgttt gtttttctgt gatagggtct tgctttgtcg tccaggcttg  21480
agtgcattgg tgtgatctca gctcactgca gcctccacct cccaggctca ttcgaacctc  21540
ccgccttggc cttccgagtc ctgagactat aggcatgcac caccacccc agttaatttt  21600 aaaattttt gtagagatgg ggttttgcta tgttacccag gctggtcttg aactcctggg  21660
ctcaagcagt tctcctgccc tggcttctca aagcccgggg attgcaggtg tgagccactg  21720
cacctggcac agagtcattt tggagggttt aggtcccagg aattatccca ggggctgcac  21780
```

```
atggcctgga atcttaacag aaaaggtgtc tcccaattgg aaaggctcta ggccttttcag  21840
ttaagttgat aatttcctcc tagagaagag aatagccact tctacaagca taaacaggta   21900
caggaggagg aagtgggctc cgggagcctg gatctgaggc cttggccttc taggccccag   21960
gagaactaga acgctggcca tgcaagctat ccaggtatcc ttggatacct tcagatgtgc   22020
ttagcagagg ccaacttcca cacacttggc tcaaaatttt ctcccttcct cctcttcatc   22080
tgccttcccc caggcagcct cctccttccc caggtcttca catcagggtt tggcctttat   22140
gctccatcca gctcatctgt cacttgtcac ctgaagccca cagtcctcgc tccctctctg   22200
cactctaggg cacttactaa gtggatgtgg cctcctgaga gtgttttttg ttggtgttcc   22260
ctttttatg gccacttaat gttttatttt gctttatttg tatttacatc tctgtatcat    22320
aaattccata caggtggctg ggagcagtga ctcacatctg taatcccagt actttggaag   22380
gctgaggtgg gaggatcgct tgaggccaag agttcgagac tagcctgggc aatatagcga   22440
gaccctctat ctacaaaaaa aaaaaacatt ccttacaggt taagtgaggg agttgtatta   22500
caaccctccc tatcatctac tcagagccca gtgctcattt gatcttgcta aattagttac   22560
tgagaataat gacaatatcc tcttcatgag agagttttga cattaggcct gctgtccagt   22620
aagtgcattt taaattcttt cccctcaaca aatcatttaa catttgaaa agtagtttat    22680
gttttttgga aaaaatgtaa gacactaaag gaggacatga aagtacctcc taaagttcct   22740
gctaaaagga ggaagtgaaa gtacctccct ttgtgttttc caaaataacc tttcctttct   22800
agccttttgt tctatgtatg ttcaaagata tgcaaaacag aatagcattc aagcagtggc   22860
tctaaaaata ttgtaatcac atactttaca tgtctccttt agggtttctc catcttgatg   22920
ctgttgacat tttggtccaa gtgattcttt attatggtag ggctgtcctg tgcatcatag   22980
acggtttagc cgcatctctg ccctgtacct cccagtggtg aggatcaaaa atgcctccgg   23040
acatggccag gtgccccatg gagagtgaaa tcacatggat agtagtaatg tcaacaccta   23100
gaagccctca agtgctgact gcatgccatg tgttattcta cacttttttcc ctgtgttaac  23160
tcactcagcc tcacaaccac tctatacgat ctctactgtt aacgttcacc agtgagaaaa   23220
ctcagaccca aagaacttaa gcctgttgcc cgaggtcacc ctgctggtgg gtgatacaaa   23280
cctgcccagg ctgagtccgg agtagatgtc aatgctgtgt tcttctccct cctcattcta   23340
cctcattctc cctacaagct gcacaacatc tcgaatagat atcacaatat atttcatcag   23400
ttgtttctga tctaaatttg ttcagatttt acattaggat aataccacaa tgcatgctgc   23460
aatgtataaa gctttgtgtg tatatccttg cacactgtag ggtaaatttc tagaagtctg   23520
attgtcttaa aatgaagcac attaaaaatt tgggcaggca catccaaact gcccttcaag   23580
gaattttttt ttttaaatgt tctttctgtt ctattcttct tcctaatgat tctttcgtcc   23640
actggcacaa gtgggtccta ccctgtttac accaaggagc tttggtgctt tatccagacc   23700
acttctggtt ctaaggacca ttgagagact tcctgaactt tcagtcactt aacttgggtc   23760
cctcacaagt taactgagag caaagtactg aacacatttt aatgtgcagt cagtgactgt   23820
ttcaggtctt caaactaact tggataacac actgtcagtg gtgttcaagg gaccctggga   23880
ctagaggaga actgagaagc aggcattggc ccttttgtttt ccgtgggccc ccatcttcca   23940
tgaaatctga gggctcagca aagtggggga gggagggtgg gctcctctac aggtagctgg   24000
gctaagaaat aggagcccag gtacaggatt tgcattaaaa atgagtccca ttgaccttct   24060
gtggggctga caggctgggc ttggagcctg gctgttttct gggttctcag caagtgatca   24120
tctgcatagc tggagagcct tgggctgagc tcccgctcct gtgaactcta aaacaatgtc   24180
```

-continued

```
tgccaagtag gctctcttga gtaaatactt ccttttttt ccttaggctg acccaaaatg    24240
aactcaacga tgaagtggca gagagtttgg cagaaatgtt gaaagtcaac cagacgttaa    24300
agcatttatg gtaactcaga gagccttaca atttcagact gtgctacttt tcaaaagtat    24360
tttttgagat aaaatttaca tactgtaaaa ttcactctct taaagtatac aattcagagg    24420
tttttagtgc aaccatcacc acctaattct agaacatttt cactcctcct ccccactcca    24480
aaaagccctg gtatccatta agcagtcact ccctgtcctc ctccccagac cctggcaacc    24540
actaatccgc tttctgtctc tatggatttg cctactctgg gcatttcata taaatggaat    24600
caagcaatat gtgaccttt gtctctgtgt tctagcatgt ttcattcctt tttatggcta    24660
aatgataatt cactctaagg aaattttgca gtttattaat cagttgatgg gacatttggg    24720
ttgtttctac tttttgacta ttatgcgtaa tgctactgtg aacactcctg ttcatgcttt    24780
tgggtgaaca tatgttttca tctcttttgg gaatatacct gggaatagaa tttctgggtc    24840
atatggcaat tctgtaactt tttgaggagc caccaaactg ttttctaaag tggatgtact    24900
attttacatt ctcgccagca atgtatgtgg attccaattt ctccacatcc tcaccaacac    24960
ttattattgt ccatctttta aaatctagtt atactagtgg atgtgaagta atattgtggt    25020
tttgatttgc atttccctga tgacaacaat gttgaatgtc ttttatgtg cctactggga    25080 gtctgtatag cttctttgga gaaatgtctc catatccttt gcccatttta aaattgggtt    25140
tgtcttctaa tgctgagtta taggggttct ctatatattc tgggtgctag acctttacta    25200
gatacaggtt ttgcaagtat tttctttctt tctgtggagt ttttcctctt tcttgatagt    25260 gaccttaaa ggacaacagt ttttaatttt tgtttttttt gagatggagt cttgctcttg    25320
tcacccagac aggagtgcag tggcatgatc tcagctctct gcaacctcca cctcctgggt    25380
tcaagcgatt cttctgcctc agcctcctga gtagttggga ttacaggcat cagccaccat    25440
gcctgtctca ttttgtattt ttaatagaga tggggtttca ccatttaggc ccaggctggt    25500
cttgaactcc tgacctcagg tgatccacct gcctcagcct cccaaagtgc tgggattaca    25560
ggcgaaaagc cactgcacct ggccaatagt ttttaatttt gatgaagtcc aatttatcta    25620
ttttttcttt tggttgcttg tgctttcagt gtcttatcta agaaatgatt gcctaatcca    25680
agatcacaaa gaactccacc taagttttct gttaagcgtt atagttgttt ccctcacat    25740 ataggtctgc aatccatttt gagttaattt ttgtatagtg taaagtgagg gttaacctca    25800
ttctcttgca cgtggatatc cagctgtccc ggcagcacca cgtgttgaac agattatctt    25860
ttcctattga atggccttga caccctttgtc aaaaatcaat tgaccataaa tgtatgggtt    25920
tatttctgaa ttctctgttc tggtccattg atttatatgt ctctcctatg ccaggaccat    25980
tgctgtagct ttgtgtagta catttttgaaa tcaggaggtg tgagttctac tttgttcttc    26040
tttctcaaga ttgtttagac cattctgggt tcttttgcatt tcttatgaat tcagactcac    26100
cttgtcaatt tctgcaaaaa gactagactc tgctacatat tgttttttct ttccttttta    26160
gcctgcagaa ttatttgatc ccattcccta agtgcaggcc agcctctcca gggagagcag    26220
agctaggaca gggtcagaaa gagagtcttg gctgctttgt gcattcccaa cctgcactgg    26280
ccctagtgaa ggcagcccga gtgggtggat gtgcctggac actgcaggct ttttaggggc    26340
attaggtgct ctccttcctg gcctcctgcc acatcttggt tggaggctgc cttccctgcc    26400
ttcaaaaaag cctaagtggt gactagaaaa cagcagagtg taactgaata cagaacttgg    26460
tgcccacttc ctggttctat ttttgtccct tttgaaaggg aaggtcatta cctctgccat    26520
```

```
tgaacccagg ggccctagcc cttgtggggt atggctggga gcaccagatc ctggctgcag   26580
cccagccacc agtggtcctg tgtgcttggg cagtaacagt gacaagagct cccttccccc   26640
tggacactgt gcctaatacc ctcctcttga aatctcacac acccagtgga tgggggcac   26700 tcttatagtt attctcagtt tacagatgac acaactgagg cacagacaga tgcgtttatt   26760
tcttcaaggt tctgtagctg aacagtgggg agggagggtt taagaggagc tgcacccgct   26820
ctgcaatact gcctctcacg agggagtcct cttcattcat gacagcatag ggccctcgtc   26880
ttcctggtaa gggcttcctt cttgggtcag tgccaggatt ctaagggtc atgtttagca    26940 ggagcctatt ctacaaacag ccaggagcag ggaatgactc tgtgatgaag cggagacact   27000
acagcctctt gatgcattta tttcctggtt gggttagaag cgtagctgcc caagggagca   27060
tttcaggaga ggcctggctt cctagcgata gctgaaaact ttgtttcatt tgaatcactg   27120
ctacccagaa caatggggtg cattctcaga gtccccatta ttaaagcttt tccactgagc   27180
cccatgagaa ctattcatga gaactatttc atggcagcat aactgtttct cctccctccc   27240
tcttgcatgt tggtagcctc ttaacttta aacctgcctt gcctttccct agctacctgg     27300
aaggagacgt cagacttcct gtcccatggt gtgtttctta caatttgttg ttcagattgg    27360
tggtctccca aatatatata aaaatataaa tggagtctca ctctgtcacc caggctggag    27420
tgcagtggca cgatcttggc tcactgcaac ctccacctcc cagttcaagc aattctccta    27480
cctcagtctc ccgagtagct gggagtacag gtgcacacca ccatgcccag ctaatttttt    27540 tgtatttta atagagacag gttggccagg atggtatcga tctcctgagc tcgtgatcca     27600
cccacctcgg cctcccaaag tgctgggatt acaggtgtga gccactgcac ccggcccaa     27660 atattttgat tatgcacctc tgcagtgaaa aatgcaaaca cacacatcag ttcatgtatt    27720
acattatgtt cactataaaa acaaacagaa aatttaaaaa atatcaagct atcctttact    27780
ctagtggatc ttacctggac acttttagcc agatacaaag tcacatggac tcagttcttc    27840
ccctgaccaa cttgtctctt atcccaaaac accttgcaa ctcccttacg aagggtcaa      27900 atttgatcca gtattatgga ttttatacaa gttatgttct tctttcaggc ttatccagaa    27960
tcagatcaca gctaagggga ctgcccagct ggcagatgcg ttacagagca acactggcat   28020
aacagagatt tggtaagatc ccagcgtttg tcacagtaat aacaccagtg actgtttact    28080
caccaccact gactgtgcaa ggcacaacgc agggtggttt ctgtttattc ctccagcaac    28140
cctgcacagt aatggtatta cctctgtttt acagaggtag acagaggccc agaccagtga    28200
aataaggttg cccaaggtca ctacgagaga agctagaatt cagcccagaa tgcctgattc    28260
catattctgt gctctcctgc cctgggcccc cgccctcatc taccttcatt gggtgggatg    28320
ggggaagtgg ccagtgaaat gatttcctag tggaagtaaa tcccctggg actcagcaat     28380 tgagagatga ctgtgttggc caggagtttg gagctcattc ttccccttttt ctgggttccg   28440 taagacattt ccaggctgac ttgaactgac ctgtgctctt tgtctacttc ttttttctgc    28500
tttgagaact tccttatgct aatagaagaa aaaagtttg ctttactgtg acattgagcg     28560
ccatgccact tctttcttgc ctcccataag gcacagacac tccccactca gcagctccct    28620
taacaactta attgcctggg tgacgtggga ctgggtggat gctgggagag gggccttatt    28680
aactatgtcc tcctttcatg actggggaga atttcatagc caattaaaaa aaaacaaaaa    28740
acagctcctt ggccaacaca ggctcctcat acagtgtttt ttaaactttg ctttagaact    28800
tgtttggaac ttgtcataaa atcgatcagt ttggtgaatt gcaaccaaca atatttaaaa    28860
agaaaacaga acagaacaaa atatcaggat gcaatgtgca tggtatgaaa gtatcatttc    28920
```

```
attcatctta gttcatgctt gcatgtgagt gggtgtgtgt ttgcataagt gttggttcac    28980
aacataaaat gtaattctta tttagggttg tagacaaaag gttttttttt aaaaaaaaca    29040
ctgttggcta ggcatggtgg ctcatgcctg taataccagc actttgggag gccaagatgg    29100
gcagatctct tgagcacagg agtttgagac cagcctgggc aacatgcgaa accccgtcac    29160
tacaaaaatt agcccgacat ggtgctatgt gcctgtagtc ccagctactc aggaagctga    29220
tgtgggagga tggatgcatg ggagatcaag gctgcagtga gccaggatca tgccactgca    29280
atccagcctg ggtgccagag accctgtctc aaaaacaaa aagaaaaaa agaaaaacac    29340 catcatagag aatagagccc agatctaaac agacacctgt ggcctgtgtg cctgcgaagc    29400
ccagcctgcc cagcagcctg ggaagcactg gagggcactg gaactgtttg catgggtgtt    29460
tgccctcagg ccactccgtt tctgctgatt cttaagtttt gaggacagca ggcagagggg    29520
gagaggaagg agactgccag actacagaac agtttgcaga gcacagttgg cttccacttt    29580
tctctgtagc tggtcaggcg ggtagtaaag acctacagtt gctttaattc tgtcaagttt    29640
caaaatctgc attgcttccc tcttgagggt caccattcct acacaaggaa ccattttagt    29700
agggccagga gacttcagct tcaaggcctg cacttgtgtc agggtggaga ggggaactgg    29760
ccaccaattc agagagggca ggacaggcgg catgggtgct ggtcttggga gtgtcttcac    29820
ttaggtccct ggcttgttct gggagcctcc agagcatgct cctctgtgtg tgacttcatg    29880
ggactgggct ctgagaaggc tgtggctttg ttggccctgc cagggactgc cacaccaggc    29940
cacagggttg tggttgagct ggccggggag ccacgttcag ggagcagctc tgcttggagc    30000
caacacttac agagtaagcc ttctccttgg acttgttaac tgtactgaca cttatttcta    30060
cctcattcct ttctgaaaat aacttggaag tctgaagtcc cttgatgagt tctgtcttta    30120
agaacagaaa ttagaggtga acaatgaaca ctgtaaatta cagaaatgta tcccactcca    30180
gtataacagc tttctgtgag gctatctcct ccagactgtg gctctgggag ggtgggcct    30240 gagtcaaggt cctagggact agtgctgtgt cttcatttat tccttgaata cgaaacgct    30300 tgagcatcag ggactgtgct agcaccaaaa atccagtggt gaacaacatg gcttcatggg    30360
ttcactgtct agaaagggag aagcacatta agaaaaaat catttgcgta attatttaat    30420
tacaactgtg atgggtacta tcacaaaggg gaaggccaag agggaacctg atttagatga    30480
ggttgcaggg aaggcctctc tgaggaagca gcacttacac taagccatga aggatgaata    30540
ggagctagtc agctgaggtg agtattctgc gtagggaaca gcatgtgcaa agggtctggg    30600
gcaggaggga gtgtggtgtc ctggaagaac tgccagaagc tgctgtgccc cagggttcag    30660
acagtgtgga agaggggact acaggaggct gaggagatag gcagggactg gaccataaaa    30720
gatctgtggg tcatgatgtg cattttggtc tttatcctaa aagtgatgga aagtcagtga    30780
acagtttgaa gcaggagagg catgtgatca gatctgcaat gcaaaaagac caattcttgg    30840
ctcttctagg aaactgaatt ggagaaggcc agagtacgtg gaaatgacct gtcagtagga    30900
cattgtactg atgcagggaa gagatgatgg gtgctcagac caagatggcc ggccaaagac    30960
atagaggttc caggaggca ttctagattc ttaggaatta ggggagaact tgtgataca    31020 aggaacatgg ggatgagaag gaaggtgtcc aggttgaccc ccaggttact aacctgctca    31080
gcaggatgag agtggtccat tcactaagcc aggggaccct aggaggtgtg gctactttga    31140
ggtgtggggg agaggtccaa gtgaggatgc caagcaggta actgcctcca cggacataca    31200
aacaaggccg tggcattgat gagatcgggt ggggaaaagg gcttagcccc aaacctggag    31260
```

-continued

```
gaaatctcag atgtagaggt cacatggagg agaatatagg aaaggaaatt gaagtagagt    31320
gctcagatgc aggagaaaaa tcagcgcata taaccaagcc aaggggaggg agtgcctcaa    31380
gaaggaggga gaggagaggt caggacagcc aaaatcctga gggccaagaa agacaagacc    31440
tggaaaatgt cattaaattc aggcttatgg aggctacagg tgaccttagt gagacccagt    31500
gaacagaggg atggcagctg gagaggatcc atgctaatat gaaggaacta tctgcaaagg    31560
gtatgttcct taatttcagg gatacatgtg tattgtgtga tacacgagtg tgtgctatga    31620
acacaccttg ggaaggagtg tgcgaggatc cttaacattt tacctgtgta cttttgtctt    31680
cctccttttc aacagcctaa atggaaacct gataaaacca gaggaggcca aagtctatga    31740
agatgagaag cggattatct gtttctgaga ggatgctttc ctgttcatgg ggttttttgcc   31800 ctggagcctc agcagcaaat gccactctgg gcagtctttt tgtcagtgt cttaaagggg    31860 cctgcgcagg cgggactatc aggagtccac tgcctccatg atgcaagcca gcttcctgtg    31920
cagaaggtct ggtcggcaaa ctccctaagt acccgctaca attctgcaga aaagaatgt     31980 gtcttgcgag ctgttgtagt tacagtaaat acactgtgaa gagactttat tgcctattat    32040
aa                                                                   32042
```

<210> SEQ ID NO 64
<211> LENGTH: 88
<212> TYPE: PRT
<213> ORGANISM: Homo sapiens

<400> SEQUENCE: 64

```
Ser Thr Pro Ser Glu Ile Ile Glu Arg Glu Arg Lys Lys Leu Leu Glu
  1               5                  10                  15

Ile Leu Gln His Asp Pro Asp Ser Ile Leu Asp Thr Leu Thr Ser Arg
             20                  25                  30

Arg Leu Ile Ser Glu Glu Glu Tyr Glu Thr Leu Glu Asn Val Thr Asp
         35                  40                  45

Leu Leu Lys Lys Ser Arg Lys Leu Leu Ile Leu Val Gln Lys Lys Gly
     50                  55                  60

Glu Ala Thr Cys Gln His Phe Leu Lys Cys Leu Phe Ser Thr Phe Pro
 65                  70                  75                  80

Gln Leu Ala Ala Ile Cys Gly Leu
                 85
```

<210> SEQ ID NO 65
<211> LENGTH: 208
<212> TYPE: PRT
<213> ORGANISM: Rattus rattus

<400> SEQUENCE: 65

```
Pro Val Phe His Gln Thr Pro Val Tyr Met Pro Tyr Pro Ala His Pro
  1               5                  10                  15

Trp Ala Leu Ala Ile Lys Ala Gly Gly Asn Phe Tyr His Val Pro Leu
             20                  25                  30

Asn Ala Pro Trp Leu Trp Ala Pro Thr Leu Asp His Ser Arg Gly Leu
         35                  40                  45

Ser Gly Ser Phe His Ser His Ala Lys Pro Thr His Ser Lys Ala Phe
     50                  55                  60

Gln Ala Asn Cys His His Pro His Pro Ser His Ala Lys Pro Thr His
 65                  70                  75                  80

Val Asn Pro Ser His Ala Asn Pro Thr His Val Gln Pro Cys Met Leu
                 85                  90                  95
```

```
Asn Pro Leu Thr Leu Arg Pro Ser Lys Leu Asn Pro Leu Pro Leu Arg
            100                 105                 110

Pro Leu Gly Ala Lys Leu Thr Ala Ile Met Pro Ile Pro Pro Leu Leu
        115                 120                 125

Asn Pro Leu Ile Arg Ile Pro Leu Met Leu Thr Pro Leu Met Cys Ser
    130                 135                 140

Leu Pro Met Leu Asn Pro Leu Ile Tyr Ser Leu Pro Lys Gln Asn Pro
145                 150                 155                 160

Pro His Pro Asn Leu Leu Gln Phe Thr Ala His Lys Pro Gln Gln Ser
                165                 170                 175

Gln Ser Lys Pro Ser Gln Gln Arg Pro Ser Gln Pro Lys Ser Phe Gln
            180                 185                 190

Thr Lys Pro Ser Gln Ala Arg Ala Cys His Pro Arg Ala Gly Arg Arg
        195                 200                 205

<210> SEQ ID NO 66
<211> LENGTH: 70
<212> TYPE: PRT
<213> ORGANISM: Mus musculus

<400> SEQUENCE: 66

Gly His Phe Val Asp Gln His Arg Gln Ala Leu Ile Ala Arg Val Thr
1               5                   10                  15

Glu Val Asp Gly Val Leu Asp Ala Leu His Gly Ser Val Leu Thr Glu
            20                  25                  30

Gly Gln Tyr Gln Ala Val Arg Ala Glu Thr Thr Ser Gln Asp Lys Met
        35                  40                  45

Arg Lys Leu Phe Ser Phe Val Pro Ser Trp Asn Leu Thr Cys Lys Asp
    50                  55                  60

Ser Leu Leu Gln Ala Leu
65                  70

<210> SEQ ID NO 67
<211> LENGTH: 94
<212> TYPE: PRT
<213> ORGANISM: Artificial Sequence
<220> FEATURE:
<223> OTHER INFORMATION: Consensus sequence

<400> SEQUENCE: 67

Met Ala Glu Asp Glu Arg Arg Leu Leu Lys Lys Asn Arg Val Arg Leu
1               5                   10                  15

Ile Glu Ser Leu Gly Leu Asp Val Leu Asp Glu Leu Leu Asp Val Leu
            20                  25                  30

Leu Glu Lys Asp Val Leu Asn Leu Lys Glu Glu Lys Ile Lys Arg
        35                  40                  45

Ala Gly Ala Lys Leu Glu Asp Asp Lys Ala Arg Glu Leu Val Asp Ser
    50                  55                  60

Leu Gln Arg Arg Gly Ser Gln Ala Phe Asp Ala Phe Ile Asp Ala Leu
65                  70                  75                  80

Glu Asp Thr Gly Gly Ser Tyr Leu Ala Asp Val Leu Glu Leu
            85                  90

<210> SEQ ID NO 68
<211> LENGTH: 25
<212> TYPE: DNA
<213> ORGANISM: Homo sapiens
```

-continued

```
<400> SEQUENCE: 68
taggacctcg gtacccgcgc gcgcg                                           25

<210> SEQ ID NO 69
<211> LENGTH: 25
<212> TYPE: DNA
<213> ORGANISM: Homo sapiens

<400> SEQUENCE: 69
cgccggcccc taggacctcg gtacc                                           25

<210> SEQ ID NO 70
<211> LENGTH: 94
<212> TYPE: PRT
<213> ORGANISM: Homo sapiens

<400> SEQUENCE: 70
```

Met Glu Ala Arg Asp Lys Gln Val Leu Arg Ser Leu Arg Leu Glu Leu
 1               5                  10                  15

Gly Ala Glu Val Leu Val Glu Gly Leu Val Leu Gln Tyr Leu Tyr Gln
                 20                  25                  30

Glu Gly Ile Leu Thr Glu Asn His Ile Gln Glu Ile Asn Ala Gln Thr
             35                  40                  45

Thr Gly Leu Arg Lys Thr Met Leu Leu Leu Asp Ile Leu Pro Ser Arg
         50                  55                  60

Gly Pro Lys Ala Phe Asp Thr Phe Leu Asp Ser Leu Gln Glu Phe Pro
 65                  70                  75                  80

Trp Val Arg Glu Lys Leu Lys Lys Ala Arg Glu Glu Ala Met
                 85                  90

```
<210> SEQ ID NO 71
<211> LENGTH: 109
<212> TYPE: PRT
<213> ORGANISM: Artificial Sequence
<220> FEATURE:
<223> OTHER INFORMATION: Consensus sequence
<221> NAME/KEY: VARIANT
<222> LOCATION: (1)...(109)
<223> OTHER INFORMATION: Xaa = Any Amino Acid

<400> SEQUENCE: 71
```

Xaa Ala Xaa Glu Ser Xaa Gly Ser Glu Ile Ile Asp Gln His Arg Xaa
 1               5                  10                  15

Ala Leu Leu Ala Arg Val Thr Glu Asp Pro Xaa Asp Ser Leu Leu Asp
                 20                  25                  30

Ala Leu Leu Ser Arg Asp Leu Ile Ser Glu Gly Asp Tyr Glu Ala Val
             35                  40                  45

Glu Ala Glu Thr Thr Xaa Leu Ser Lys Val Arg Lys Leu Leu Ile Leu
         50                  55                  60

Val Gln Ser Lys Gly Glu Glu Thr Cys Lys Xaa Phe Leu Lys Cys Leu
 65                  70                  75                  80

Leu Gln Ala Leu Lys Asp Ser Ala Ala Tyr Leu Gly Leu Asp Pro Glu
                 85                  90                  95

Val Xaa Xaa Xaa Xaa Xaa Xaa Xaa Xaa Leu Glu Xaa Ser
            100                 105

I claim:

1. An isolated nucleic acid comprising a nucleotide sequence that encodes a polypeptide comprising amino acid residues 111 to 181 of SEQ ID NO:49, wherein the polypeptide binds to caspase-1.

2. An isolated nucleic acid comprising a nucleotide sequence that encodes a polypeptide comprising the amino acid sequence of SEQ ID NO:49.

3. The nucleic acid of claim 2, wherein the polypeptide consists of the amino acid sequence of SEQ ID NO:49.

4. The nucleic acid of claim 2, wherein the nucleotide sequence comprises SEQ ID NO:48.

5. The nucleic acid of claim 2, wherein the nucleotide sequence comprises SEQ ID NO:50.

6. An isolated nucleic acid comprising a nucleotide sequence encodes a polypeptide comprising an amino acid sequence that is at least 95% identical to the sequence of SEQ ID NO:49, wherein the polypeptide stimulates NF-κB activity.

7. The nucleic acid of claim 6, wherein the amino acid sequence is at least 98% identical to the sequence of SEQ ID NO:49.

8. An isolated nucleic acid comprising a nucleotide sequence that encodes a polpeptide comprising an amino acid sequence that is at least 95% identical to the sequence of SEQ ID NO:49, wherein the polypeptide binds to caspase-1.

9. The nucleic acid of claim 8, wherein the amino acid sequence is at least 98% identical to the sequence of SEQ ID NO:49.

10. An isolated nucleic acid comprising a nucleotide sequence that hybridizes to SEQ ID NO:50 or the complete complement thereof under conditions of hybridization at 45° C. in 6.0×sodium chloride/sodium citrate (SSC) followed by washing in. 0.2×SSC 0.1% sodium dodecyl sulfate (SDS) at 65° C., wherein the nucleotide sequence encodes a polypeptide that stimulates NF-κB activity.

11. The nucleic acid of claim 10, wherein the nucleic acid comprises at least 600 nucleotides.

12. An isolated nucleic acid comprising a nucleotide sequence that hybridizes to SEQ ID NO:50 or the complete complement thereof under conditions of hybridization at 45° C. in 6.0×SSC followed by washing in 0.2×SSC, 0.1% SDS at 65° C., wherein the nucleotide sequence eecodes a polypeptide that binds to caspase-1.

13. The nucleic acid of claim 12, wherein the nucleic acid comprises at least 600 nucleotides.

14. The nucleic acid of claim 1, further comprising a sequence encoding a heterologous polypeptide.

15. The nucleic acid of claim 2, further comprising a sequence encoding a heterologous polypeptide.

16. An expression vector comprising the nucleic acid of claim 1.

17. A host cell comprising the expression vector of claim 16.

18. The host cell of claim 17, which is a mammalian host cell.

19. A method for producing a polypeptide, the method comprising culturing the host cell of claim 18 under conditions in which the nucleic acid is expressed.

20. An expression vector comprising the nucleic acid of claim 6.

21. A host cell comprising the expression vector of claim 20.

22. The host cell of claim 21, which is a mammalian host cell.

23. A method for producing a polypeptide, the method comprising culturing the host cell of claim 22 under conditions in which the nucleic acid is expressed.

24. An expression vector comprising the nucleic acid of claim 8.

25. A host cell comprising the expression vector of claim 24.

26. The host cell of claim 25, which is a mammalian host cell.

27. A method for producing a polypeptide, the method comprising culturing the host cell of claim 26 under conditions in which the nucleic acid is expressed.

28. An isolated nucleic acid selected from the group consisting of:
a) a nucleic acid comprising the cDNA insert of the plasmid EpHC5 deposited with the American Type Culture Collection (ATCC) as Access ion Number PTA-213, or the complete complement of the nucleic acid;
b) a nucleic acid comprising a nucleotide sequence which encodes a polypeptide comprising an amino acid sequence encoded by the cDNA insert of the plasmid EpHC5 deposited with the ATCC as Accession Number PTA-213;
(c) a nucleic acid comprising a nucleotide sequence that hybridizes to the cDNA insert of the plasmid EpHC5 deposied with the ATCC as Accession Number PTA-213 or the complete complement thereof under conditions of hybridization at 45° C. in 6.0×sodium chloride/sodium citrate (SSC) followed by washing in 0.2×SSC, 0.1% sodium dodecyl sulfate (SDS) at 65° C., wherein the nucleotide sequence encodes a polypeptide that stimulates NF-κB activity; and
(d) a nucleic acid comprising a nucleotide sequenece that hybridizes to the cDNA insert of the plasmid EpHC5 deposited with the ATCC as Accession Number PTA-213 or the complete complement thereof under conditions of hybridization at 45° C. in 6.0×sodium chloride/sodium citrate (SSC) followed by washing in 0.2×SSC, 0.1% sodium dodecyl sulfate (SDS) at 65° C., wherein the nucleotide sequence encodes a polypeptide that binds to caspase-1.

29. The nucleic acid of claim 28, wherein the nucleic acid comprises the cDNA insert of the plasmid EpHC5 deposited with the ATCC as Accession Number PTA-213, or the complete complement of the nucleic acid.

30. The nucleic acid of claim 28, wherein the nucleic acid comprises a nucleotide sequence which encodes a polypeptide comprising an amino acid sequence encoded by the cDNA insert of the plasmid EpHC5 deposited with the ATCC as Accession Number PTA-213.

31. The nucleic acid of claim 28, wherein the nucleic acid comprises a nucleotide sequence that hybridizes to the cDNA insert of the plasmid EpHC5 deposited with the ATCC as Accession Number PTA-213 or the complete complement thereof under conditions of hybridization at 45° C. in 6.0×sodium chloride/sodium citrate (SSC) followed by washing in 0.2×SSC, 01% sodium dodecyl sulfate (SDS) at 6500, wherein the nucleotide sequence encodes a polypeptide thai stimulates NE-κB activity.

32. The nucleic acid of claim 28, wherein the nucleic acid comprises a nucleotide sequence that hybridizes to the cDNA insert of the plasmid EpHC5 deposited with the ATCC as Accession Number PTA-213 or the complete complement thereof under conditions of hybridization at 45° C. in 6.0×sodium chloride/sodium citrate (SSC) followed by washing in 0.2×SSC, 04% sodium dodecyl sulfate (SDS) at 65° C., wherein the nucleotide sequence encodes a polypeptide that binds to caspase-1.

* * * * *